(12) United States Patent
Podvent et al.

(10) Patent No.: US 12,100,286 B2
(45) Date of Patent: Sep. 24, 2024

(54) PLATFORM FOR HYGIENE BEHAVIORAL MONITORING AND MODIFICATION

(71) Applicant: HYGIENE IQ, LLC, Los Angeles, CA (US)

(72) Inventors: Sean M. Podvent, Pasadena, CA (US); Richard Adams, Los Angeles, CA (US); Aleksandar Bradic, Palo Alto, CA (US); Vojislav Antonic, Pasadena, CA (US)

(73) Assignee: Hygiene IQ, LLC, Los Angeles, CA (US)

( * ) Notice: Subject to any disclaimer, the term of this patent is extended or adjusted under 35 U.S.C. 154(b) by 119 days.

(21) Appl. No.: 17/778,169

(22) PCT Filed: Nov. 19, 2020

(86) PCT No.: PCT/US2020/061216
§ 371 (c)(1),
(2) Date: May 19, 2022

(87) PCT Pub. No.: WO2021/102103
PCT Pub. Date: May 27, 2021

(65) Prior Publication Data
US 2023/0014548 A1  Jan. 19, 2023

Related U.S. Application Data

(60) Provisional application No. 63/050,524, filed on Jul. 10, 2020, provisional application No. 62/937,376, filed on Nov. 19, 2019.

(51) Int. Cl.
*G08B 21/24* (2006.01)
*G06N 20/00* (2019.01)
(Continued)

(52) U.S. Cl.
CPC .......... *G08B 21/245* (2013.01); *G06N 20/00* (2019.01)

(58) Field of Classification Search
CPC .................................................. G08B 21/245
See application file for complete search history.

(56) References Cited

U.S. PATENT DOCUMENTS

| | | | |
|---|---|---|---|
| 2003/0030562 A1* | 2/2003 | Lane | G16H 40/20 340/573.4 |
| 2008/0103636 A1* | 5/2008 | Glenn | G16H 40/20 705/1.1 |

(Continued)

FOREIGN PATENT DOCUMENTS

| | | | | |
|---|---|---|---|---|
| GB | 2 425 388 | * | 4/2005 | G08B 21/24 |
| JP | 2017-012597 A | | 1/2017 | |

(Continued)

OTHER PUBLICATIONS

Australian Intellectual Property Office, Examination Report No. 1 for Application No. 2020388678, mail date Jun. 1, 2023.
(Continued)

*Primary Examiner* — Joseph H Feild
*Assistant Examiner* — Pameshanand Mahase
(74) *Attorney, Agent, or Firm* — SoCal IP Law Group LLP; Mark Andrew Goldstein

(57) ABSTRACT

A hygienic behavior monitoring system configured to use sensors to detect instances of hygienic behaviors. The hygienic behavior monitoring system includes a presentation unit that presents one or more media items and a processing unit that indexes behavioral instances. An analytic unit calculates instances of one or more hygienic events based at least in part on a fusion of sensor signals including instances of the actions of a sanitary device with instances of detected human presence.

18 Claims, 38 Drawing Sheets

(51) Int. Cl.
*G16H 15/00* (2018.01)
*G16H 40/20* (2018.01)
*G16H 40/63* (2018.01)
*G16H 40/67* (2018.01)

(56) References Cited

U.S. PATENT DOCUMENTS

| | | | | |
|---|---|---|---|---|
| 2009/0267776 | A1* | 10/2009 | Glenn | G16H 40/20 340/573.1 |
| 2012/0212344 | A1 | 8/2012 | Forsberg et al. | |
| 2017/0103592 | A1 | 4/2017 | Buttolo et al. | |
| 2019/0012898 | A1 | 1/2019 | Wittrup | |
| 2019/0228640 | A1* | 7/2019 | Freedman | G08B 21/18 |

FOREIGN PATENT DOCUMENTS

| | | |
|---|---|---|
| KR | 10-0835878 B1 | 6/2008 |
| KR | 10-2017-0114833 A | 10/2017 |

OTHER PUBLICATIONS

Korean Intellectual Property Office/ISA, International Search Report and Written Opinion for PCT Application No. PCT/US2020/061216, mail date Mar. 11, 2021.

\* cited by examiner

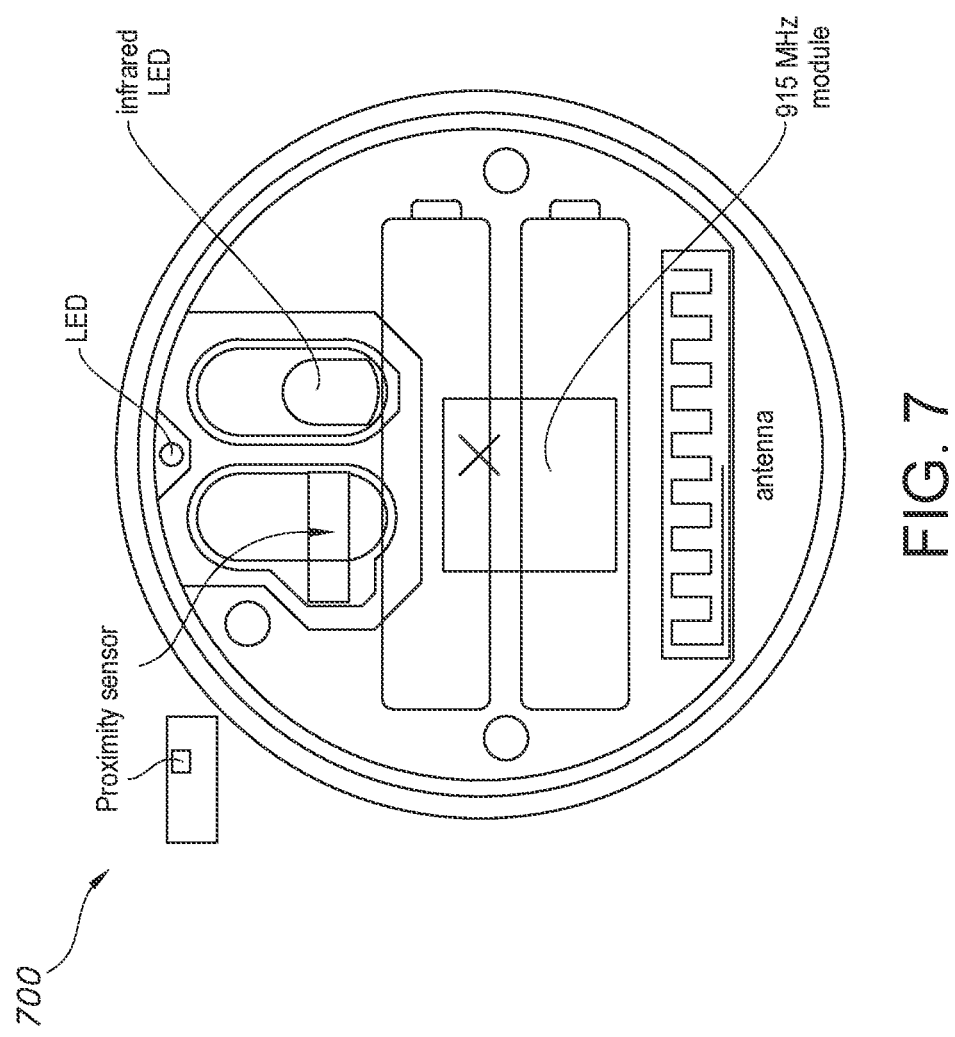

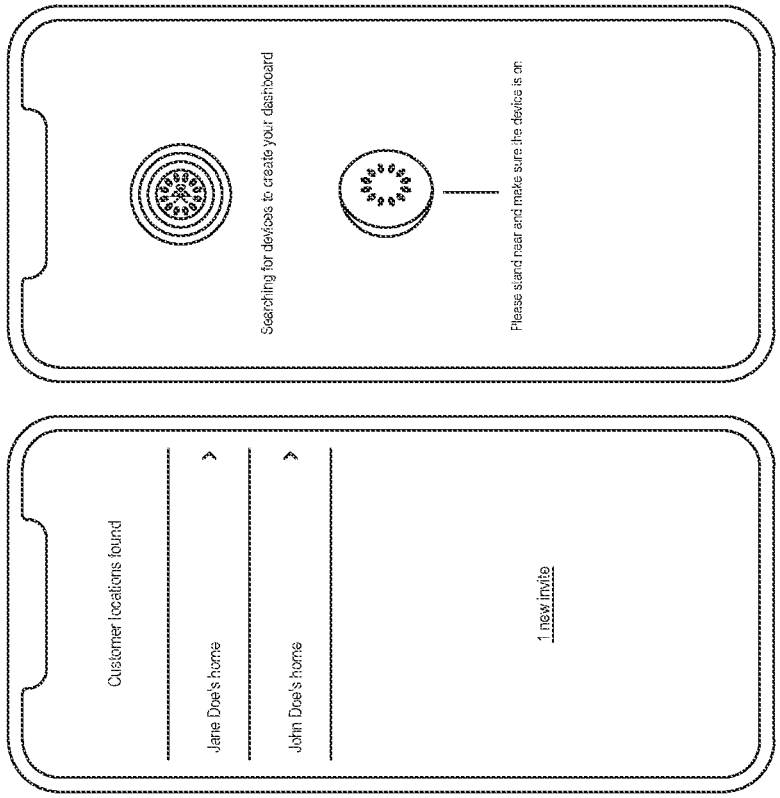
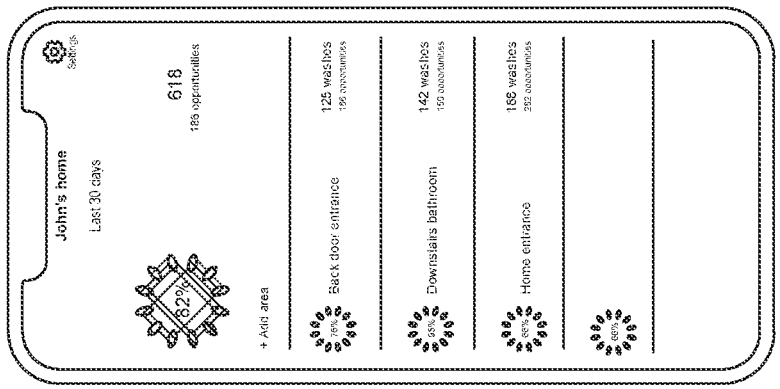
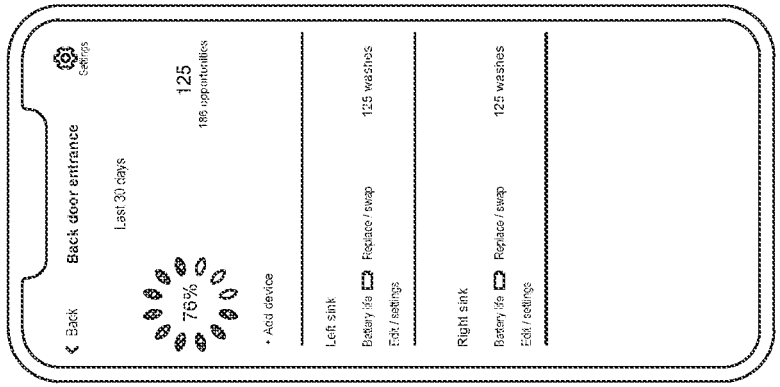
FIG. 22A  FIG. 22B  FIG. 22C  FIG. 22D

PLATFORM FOR HYGIENE BEHAVIORAL MONITORING AND MODIFICATION

This patent claims priority from International PCT Patent Application No. PCT/US2020/061216, filed Nov. 19, 2020, entitled, "PLATFORM FOR HYGIENE BEHAVIORAL MONITORING AND MODIFICATION", which claims priority to U.S. Provisional Application No. 63/050,524, filed Jul. 10, 2020, and U.S. Provisional Application No. 62/937,376, filed Nov. 19, 2019, all of which are incorporated herein by reference in their entirety.

FIELD

This disclosure relates to sensor-based detection of hygiene-related behaviors and a computing platform for the collection, integration, analysis and reporting of hygiene-related information.

BACKGROUND

Basic personal hygiene such as handwashing is a low-cost, proven means of improving public health by reducing the transmission of bacteria, viruses and other pathogens. However, in spite of the prevalence of soap and disinfectants in the home and in public spaces like work or event sites, compliance with proper hygiene protocols remains less than optimal. Even in higher-risk healthcare settings, like hospitals, hygiene compliance can be an ongoing struggle to increase. Applicant, therefore, appreciates that there is a need for methods and systems for monitoring hygienic behaviors and facilitating behavioral modification to improve public health by promoting personal hygienic acts like handwashing.

SUMMARY

A hygienic behavior monitoring system is configured to use a first sensor contained in a housing and positioned to detect instances of said presence of said one or more humans, and a second sensor contained in a housing and configured to determine instances of each action of actions of a vessel able to contain said one or more hygienic substances. The hygienic behavior monitoring system may include a presentation unit that presents one or more media items viewable to said one or more humans upon detection of said presence by the first sensor, and a processing unit that indexes the instances of said presence of said one or more humans based at least in part on data from the first sensor and the instances of the actions of the vessel based at least in part on data from the second sensor. And an analytic unit that calculates instances of one or more hygienic events based at least in part on a fusion of sensor signals including the instances of the actions of the vessel with the instances of said presence detected by the first sensor.

In embodiments, the analytic unit may calculate instances of one or more hygienic events based at least in part on the fusion of sensor signals including a temporal proximity between the instances of the actions of the vessel with the instances of said presence detected by the first sensor.

In embodiments, the housing in which the first sensor is contained may be the same housing in which the second sensor is contained.

In embodiments, the housing in which the first sensor is contained may be different than the housing in which the second sensor is contained.

In embodiments, the housing in which the first sensor is contained may be a different housing than the housing in which the processing unit is contained and a different housing than the housing in which the first sensor is contained.

In embodiments, the housing in which the first sensor is contained may be the same housing in which the presentation unit is contained.

In embodiments, the housing in which the first sensor is contained may be the same housing in which the processing unit is contained.

In embodiments, the housing in which the first sensor is contained may be the same housing in which the analytic unit is contained.

In embodiments, the receipt of sensor data may be wired, wireless or a combination of wired and wireless.

In embodiments, the action of the vessel may be dispensing soap, dispensing a sanitizing liquid, dispensing a sanitizing mist, or dispensing a sanitizing cloth.

In embodiments, the hygienic event may be handwashing.

In embodiments, the first sensor and/or second sensor may be a motion sensor, a passive infrared proximity sensor, or an active infrared proximity sensor.

In embodiments, the analytic unit may include machine learning processing of the data from the plurality of sensors. The machine learning processing may include the data from the plurality of sensors and mobile computing device data.

In embodiments, the mobile computing device data may derive from a smart phone, a smart watch, or a tablet computer.

In embodiments, the media item may be an audio file, an audio-visual file, or a text file.

In embodiments, a hygienic behavior monitoring method is configured to receive data from a first sensor contained in a housing and positioned to detect instances of said presence of said one or more humans, present a media item viewable to said one or more humans upon detection of said presence by the first sensor, wherein the media item relates to promotion of a hygienic behavior, receive data from a second sensor contained in a housing and configured to determine instances of each action of actions of a vessel able to contain said one or more hygienic substances, analyze the received data to calculate a scored variable indicating an instance of one or more hygienic events based at least in part on a fusion of sensor signals including the instances of the actions of the vessel with the instances of said presence detected by the first sensor, store the scored variable, and report the stored variable to a computing platform.

In embodiments, the receipt of sensor data may be wired, wireless or a combination of wired and wireless.

In embodiments, the action of the vessel may be dispensing soap, dispensing a sanitizing liquid, dispensing a sanitizing mist, or dispensing a sanitizing cloth.

In embodiments, the hygienic event may be handwashing.

In embodiments, the first sensor and/or second sensor may be a motion sensor, a passive infrared proximity sensor, or an active infrared proximity sensor.

In embodiments, the computing platform may be a social media website, a company's website, a marketing platform, an email platform, or an SMS platform.

A hygienic behavior monitoring system is configured to use a first sensor contained in a housing and positioned to detect instances of said presence of said one or more humans, and a second sensor contained in a housing and configured to determine instances of each action of actions of a conduit able to deliver said one or more hygienic substances. The hygienic behavior monitoring system may include a presentation unit that presents one or more media items viewable to said one or more humans upon detection of said presence by the first sensor, and a processing unit that indexes the instances of said presence of said one or more humans based at least in part on data from the first sensor and the instances of the actions of the conduit based at least in part on data from the second sensor. And an analytic unit that calculates instances of one or more hygienic events based at least in part on a fusion of sensor signals including the instances of the actions of the conduit with the instances of said presence detected by the first sensor.

In embodiments, a hygienic behavior monitoring method is configured to receive data from a first sensor contained in a housing and positioned to detect instances of said presence of said one or more humans, present a media item viewable to said one or more humans upon detection of said presence by the first sensor, wherein the media item relates to promotion of a hygienic behavior, receive data from a second sensor contained in a housing and configured to determine instances of each action of actions of a conduit able to deliver said one or more hygienic substances, analyze the received data to calculate a scored variable indicating an instance of one or more hygienic events based at least in part on a fusion of sensor signals including the instances of the actions of the conduit with the instances of said presence detected by the first sensor, store the scored variable, and report the stored variable to a computing platform.

BRIEF DESCRIPTION OF THE DRAWINGS

The accompanying drawings, which are included to provide a better understanding of the disclosure, illustrate embodiments of the disclosure and together with the description serve to explain the principle of the disclosure. In the drawings:

FIG. 7 illustrates layout examples of a handwash sensor.

FIG. 22 illustrates examples of the platform application's functionality.

DETAILED DESCRIPTION

Figure 1:
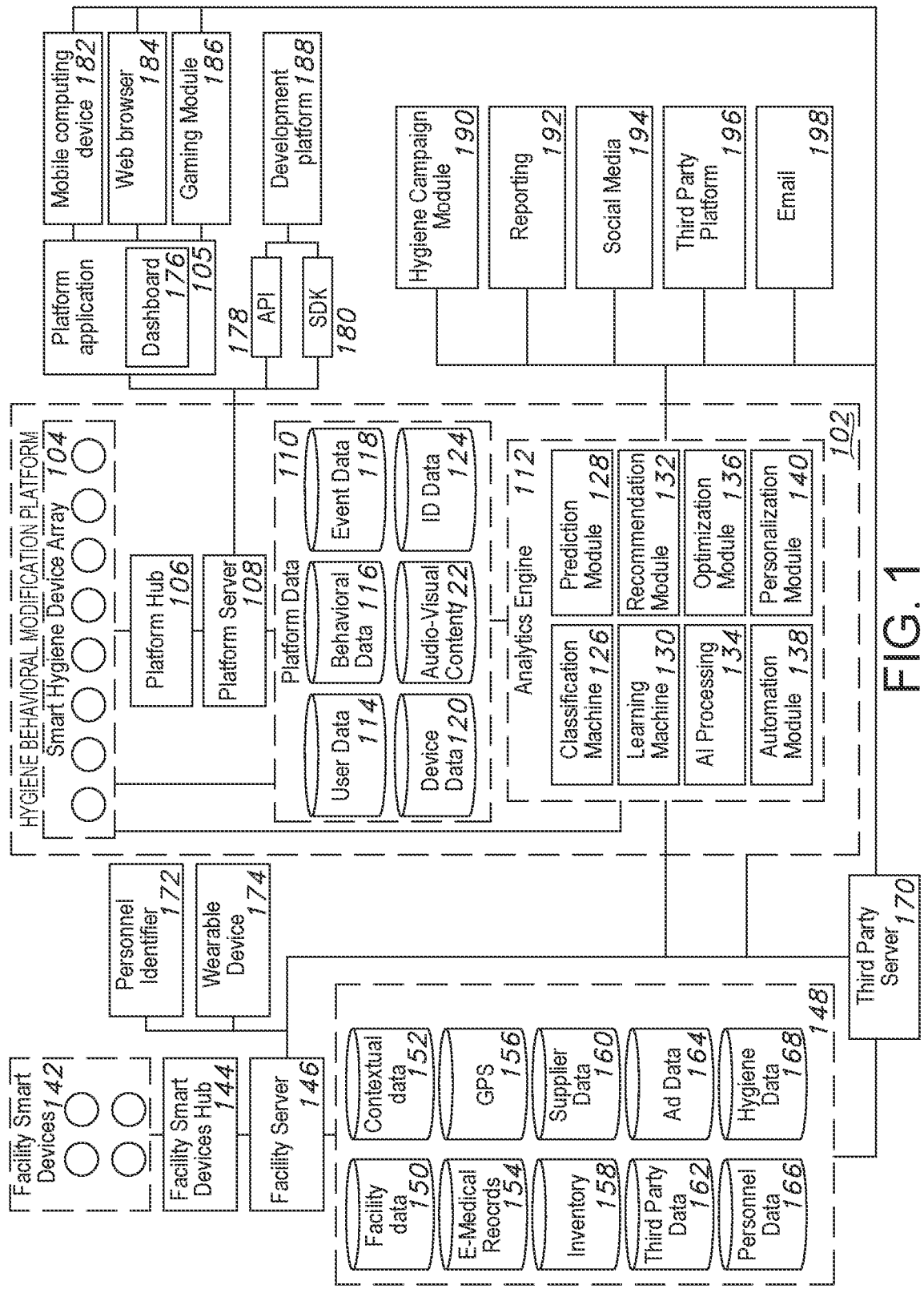
FIG. 1 illustrates a schematic overview of a platform for hygiene behavioral monitoring and modification in accordance with the present disclosure.
Figure 2D:
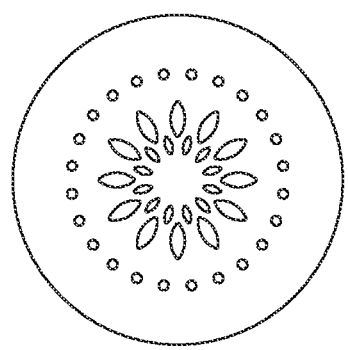
FIGS. 2A, 2B, 2C, and 2D are front, bottom, side and perspective views, respectively, illustrating a platform hub in accordance to the present disclosure.
Figure 2C:
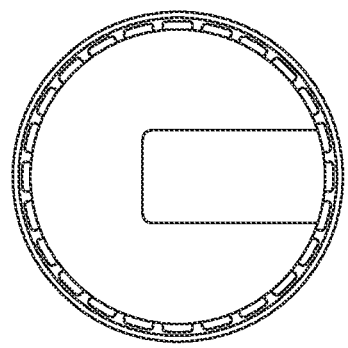
Figure 2B:
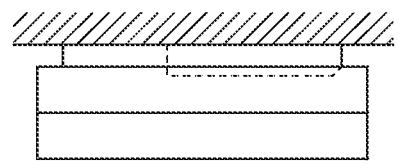
Figure 2A:
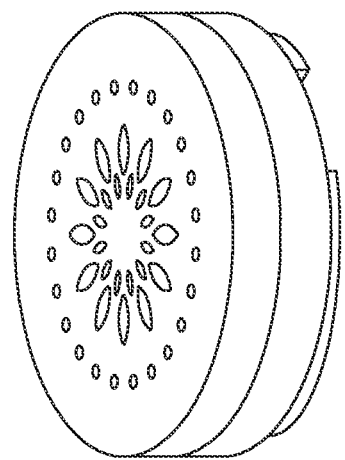

Applicant appreciates the powerful impact that simple hygienic behaviors carried out at the personal level, such as handwashing, may have on community and group health, and reduced pathogen transmission. The incidence of disease, the rate of transmission and other factors may all be more effectively controlled in a population if members of that population practice, for example, consistent and appropriate handwashing techniques.

Unlike therapies to reduce pathogen transmission, such as antibiotic medications, Applicant appreciates that handwashing is low cost, requires no contact with a medical provider, requires only rudimentary skill or knowledge of technique, and can be made consistently and widely available within a population with relatively little risk of misuse that may result in dangerous antimicrobial resistance. Applicant, therefore, can show that handwashing can be deployed to be an inexpensive additional medical therapy that may be deployed directly within environments where antimicrobial, antibacterial and other hygienic activities are particularly effective, and where initial human points of contract with such pathogens is of a higher probability. Such environments include, but are not limited to, kitchens, bathrooms, communal spaces where large numbers of people interact with potentially contaminated surfaces, such as offices (particularly those with an "open office" design), sports venues, music venues, public halls, or some other environment type in which pathogens may be prevalent among a group.

However, in spite of the considerable advantages of low-cost hygiene practices, like handwashing, compliance rates within populations and communities are frequently lower than recommended. Not only might too few people within a population be performing handwashing consistently, but handwashing techniques might be inadequate, such as not applying soap or disinfectants to the hands for a duration that is sufficient to kill pathogens. Given that handwashing is often a private, individual task and activity, Applicant appreciates that the underusage of handwashing and other hygienic activities may be difficult to monitor and measure, making it difficult to know where to deploy public health resources to areas and populations in which intervention is most needed. Applicant appreciates that this has always been an important healthcare issue, but with the coming of events such as the SARS virus and the COVID-19 pandemic, Applicant appreciates that such basic personal hygiene activities have taken on tremendous importance for the health of the entire world population. Applicant, therefore, appreciates that there is a need for automated methods, systems, and devices for actively and prospectively measuring and monitoring hygiene behaviors within a population, inducing proper personal hygiene behaviors, providing incentives for the same, and tracking hygiene behaviors so that effective management of hygiene may be implemented and maintained. The many methods, systems, and devices disclosed herein may be integrated within existing hygiene environments and devices, vessels and conduits, such as soap or other dispensers, and unobtrusively and automatically detect hygiene activities. Data collected using such methods, systems, and devices may be integrated within a platform of data facilities, analytic processing, such as machine learning and artificial intelligence tools, and capable of associating with external resources of a facility in which the platform is deployed or with which it is associated. Reporting tools and other outbound data processing techniques may allow the platform to continuously update managers overseeing hygiene promotion or other public health initiatives. The result may be shown to improve public health and reduce disease incidence and prevalence.

The present disclosure relates to a platform for hygiene behavioral monitoring and modification at platform 102 in FIG. 1. The platform 102 may include a plurality of smart hygiene devices 104. Smart hygiene devices 104 may communicate with a platform hub 106 that is operatively connected to a platform server 108. A plurality of platform data sources, databases and data facilities 110 may be included within and/or associated with the platform 102. Such platform data 110 may include, but is not limited to, user data 114, behavioral data 116, event data 118, device data 120, audio-visual content 122, ID data 124, or some other type of data. The platform 102 includes a data integration system for integrating data across distributed sets of smart hygiene devices.

In embodiments, user data 114 may include, but is not limited to, information pertaining to a person in proximity to a smart hygiene device 104, such as an employee and/or a customer of a business in which smart devices 104 are installed. Behavioral data 116 may include, but is not limited to, information related to users in proximity to smart hygiene devices 104, such as the number and timing of prior uses of a smart hygiene device 104. Event data may include, but is not limited to, actions or occurrences at a facility in which a smart hygiene device 104 is installed, such as a business opening or closing operation for the day. Device data may include, but is not limited to, information contained on or associated with a user's device and/or a device in operation at a facility in which a smart hygiene device is installed, such as a mobile computing device 182, facility smart devices 142, for example cameras, motion detectors or some other type of facility smart devices 142. Audio-visual content 122 may include, but is not limited to, content that may be played to a user in proximity to a smart hygiene device 104, such as a greeting, personalized instruction, or encouragement to engage in hygienic behavior like handwashing. ID data 124 may include, but is not limited to, personal identification information related to users in proximity to smart hygiene devices 104, such as an ID badge or card used to gain entry to a facility or area of a facility.

In embodiments, the platform 102 may include an analytics engine 112. The analytics engine 112 may include, but is not limited to, a classification machine 126, a prediction module 128, a learning machine 130, a recommendation module 132, AI processing 134, an optimization module 136, an automation module 138, a personalization module 140, or some other type of analytic processing module. The analytics engine 112 may intake data that is collected by the platform 102, for example data relating to the usage of smart hygiene devices 104, or data that is obtained by third party data sources 148 that are external to the platform. The analytics engine 112 may build, test and validate machine learning algorithms and models based at least in part on ingested and/or collected data and use such algorithms and models for the purposes of classifying, predicting, recommending, optimizing and/or personalizing the performance of the platform 102 and its utilization of smart hygiene devices 104. The analytic engine may perform AI processing 134 on platform data 110 and/or data from external data sources 148. For example, AI processing 134 may be used to optimize the placement of smart hygiene devices 104 to encourage hygiene behavior modification among a population working at or visiting a facility. Outcomes and actions taken, based at least in part on AI processing, may be automated by the analytics engine 112 of the platform 102.

In embodiments, the platform 102 and the smart hygiene devices 104 associated with the platform 102 may be located at or within a facility, such as a medical facility or business, that includes other facility smart devices 142, that may be operatively connected with at least one facility smart devices hub 144 and facility server 146. The facility server 146 may be further associated with other devices, such as wearable devices 174, personnel identifiers 172, such as login or account information of users, and/or external data sources 148.

In embodiments, external data sources 148 may include, but are not limited to, facility data 150, contextual data 152, medical records 154, GPS data 156, inventory 158 data, supplier data 160, ad data 164, personnel data 166, hygiene data 168, or some other third party data 162. A third party server 170 or plurality of third party servers may also be operatively connected with the platform 102 and facility server(s) 146.

In embodiments, the platform 102 may provide an application programming interface (API) 178 and a software development kit (SDK) 180 to enable developers and development platforms 188 to create applications to interact with the platform 102. An application 105 and dashboard 176 may be associated with the platform 102 and used to configure, operate and/or visualize aspects of the platform's performance. The dashboard 176 may include a set of interfaces and services for operator configuration of a set of timing sequences for behavioral modification stimulus events and types, and for configuration of a set of triggering events and rewards for behavioral modification activities for a set of devices managed by the platform. The dashboard 176 may be viewed on a computing device including, but not limited to, a mobile computing device 182 or web browser 184 and be used to provide a user experience that promotes user awareness of the need to undertake hygienic behavior. The platform 102 may include a set of end user mobile application interfaces configured in the platform for inducing user behavior and for allowing a platform operator to configure a set of parameters of the platform 102. A gaming module 186 may be provided for the gamification of platform data 110.

In embodiments, the platform 102 may include a plurality of outbound data functions including, but not limited to, reporting 192, coordination with a hygiene campaign module 190, social media entities 194 or other third-party platforms 196, and/or general communications platforms such as email 198.

In embodiments, the platform 102 may include a processing unit, the platform hub 106 as shown in FIGS. 2A through 2D, which communicates in real time with a plurality of smart hygiene devices 104, for example smart hygiene devices containing handwash sensors 200, via a long range wide-area network ("LoRa network"), a server via WiFi network and, optionally, a service terminal via LoRa network or via USB port. The platform hub 106 may also contain several internal sensors, for monitoring and acquisition of the physical parameters, including but not limited to, ambient light level in the visible range, air temperature, humidity, air quality or some other physical parameter. It will be appreciated in light of the disclosure that the views of the device contain many protectable ornamental features independent and distinct from the many functional features discussed herein.

In embodiments, the platform 102 may include a battery-operated smart hygiene device 104 that is a handwash sensor having an active infrared proximity sensor 200. The handwash sensor having an active infrared proximity sensor 200 may be separate from a vessel, conduit, and/or soap or disinfectant dispenser, or it may be integrated with a soap or disinfectant dispenser. It may detect a hand hygiene event by detecting a hand in the dispenser area, and wirelessly transmit the information to the platform hub 106. An LED may light up to indicate the detected hand hygiene event. The battery-operated passive infrared motion sensor 200 may be located on a wall, next to a door, or in some other location. The sensor may be used to detect people entering the room. The sensor may detect the direction of the motion and may be programmed to detect only a person's entrance to a room and ignore when the person exits the room. Alternatively, it may be programmed to detect a person's entrance to a room and the person's exit from the room. This information may also be transmitted to the platform hub 106. An LED may light to notify the detected room entrance event.

In embodiments, a platform hub 106 may include the following: 16-bit microcontroller unit PIC24EP512GP806, with 518 Kbytes of program memory and 52 Kbytes of data memory; display unit, with 24 green LED's and 24 blue LED's, automatically dimmable in 256 steps; audio unit that may play pre-recorded sounds or music using the small built-in speaker; USB/UART convertor, used for 5V power supply that may be setup with a service laptop; WiFi module unit ESP12S, which uses 2.4 GHz range to communicate with the server; an antenna may be located on the module itself; LoRa module RFM69HCW, which uses 915 MHz range for data exchange with sensors and service unit; an antenna may be separate from the module, for example located on the main PCB; visible light sensor for ambient light level monitoring; Temperature/humidity sensor (including within a single chip) for temperature and humidity monitoring; air quality sensor for air quality monitoring; DC supply unit, which ensures 3.3V supply voltage for MCU, RF modules and sensors; 5V power. supply (+/−0.25 V) may be driven externally via a USB micro-B connector, for example from a standard 5V USB charger or a service laptop; and peak current consumption may be less than 400 mA.

Figure 3:
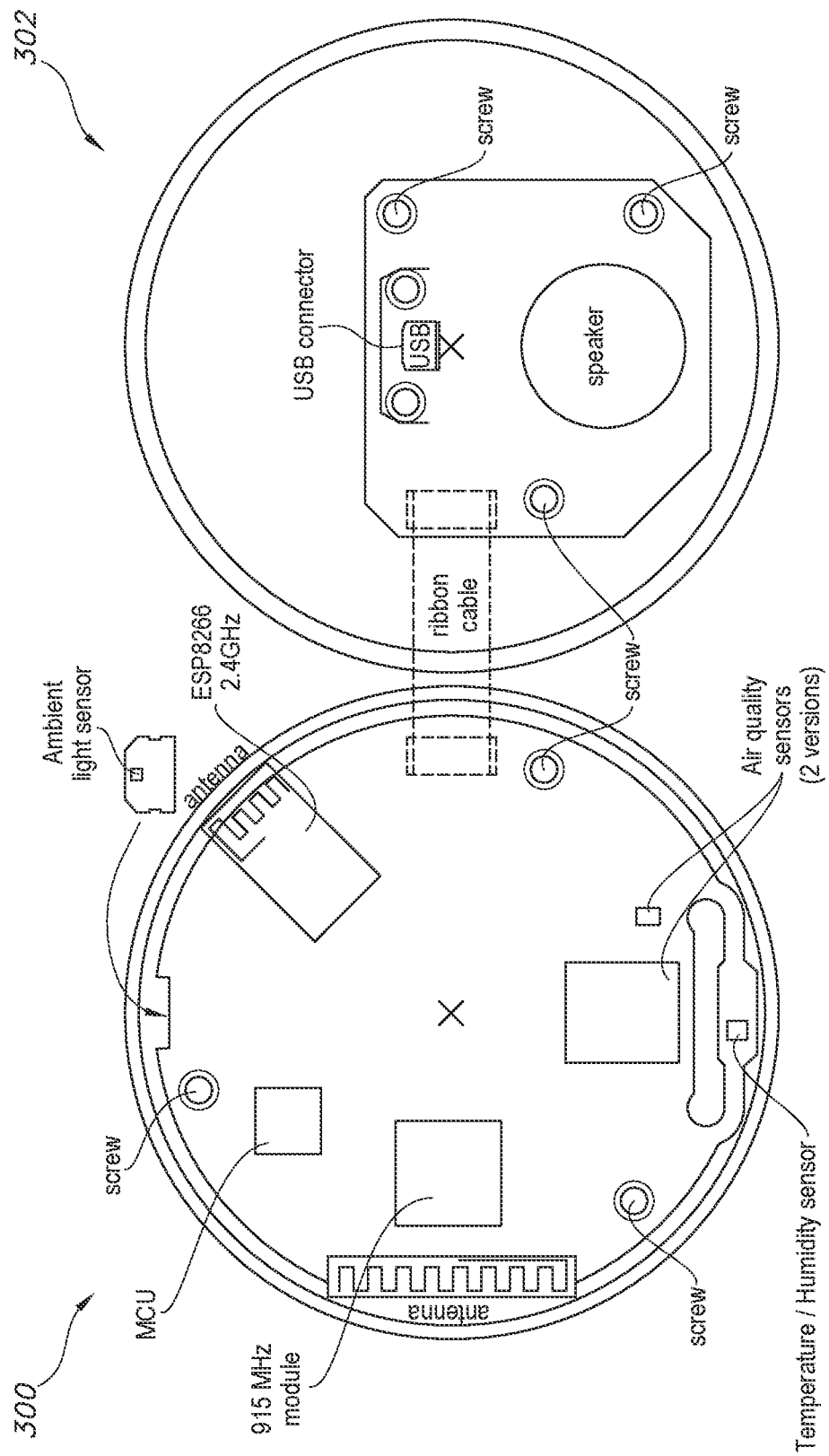
FIG. 3 illustrates an example layout of platform hub components.

FIG. 3 illustrates an example layout of the platform hub 106 components, where the left view 300 shows the top half of the enclosure, and the right view 302 shows the bottom half.

Figure 4:
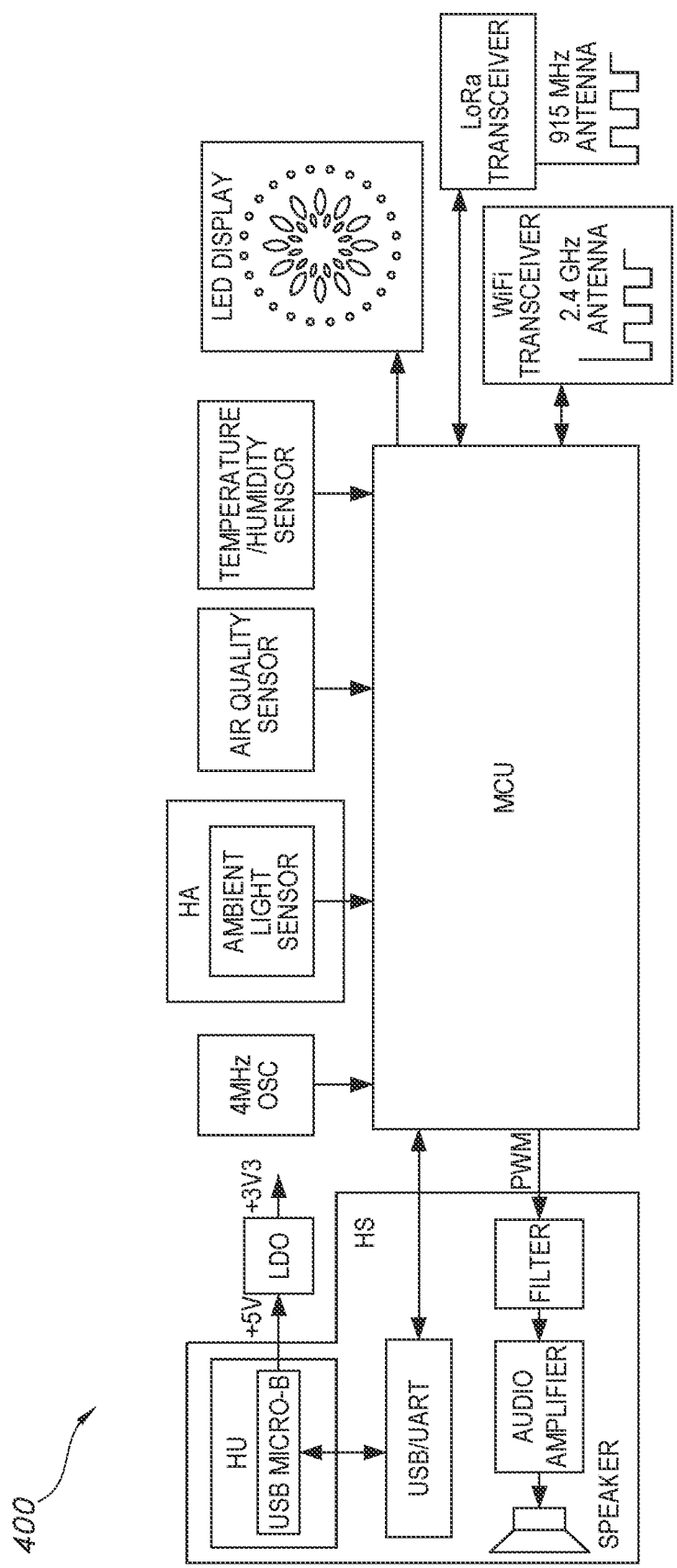
FIG. 4 illustrates a block diagram of a platform hub.
Figure 5A:
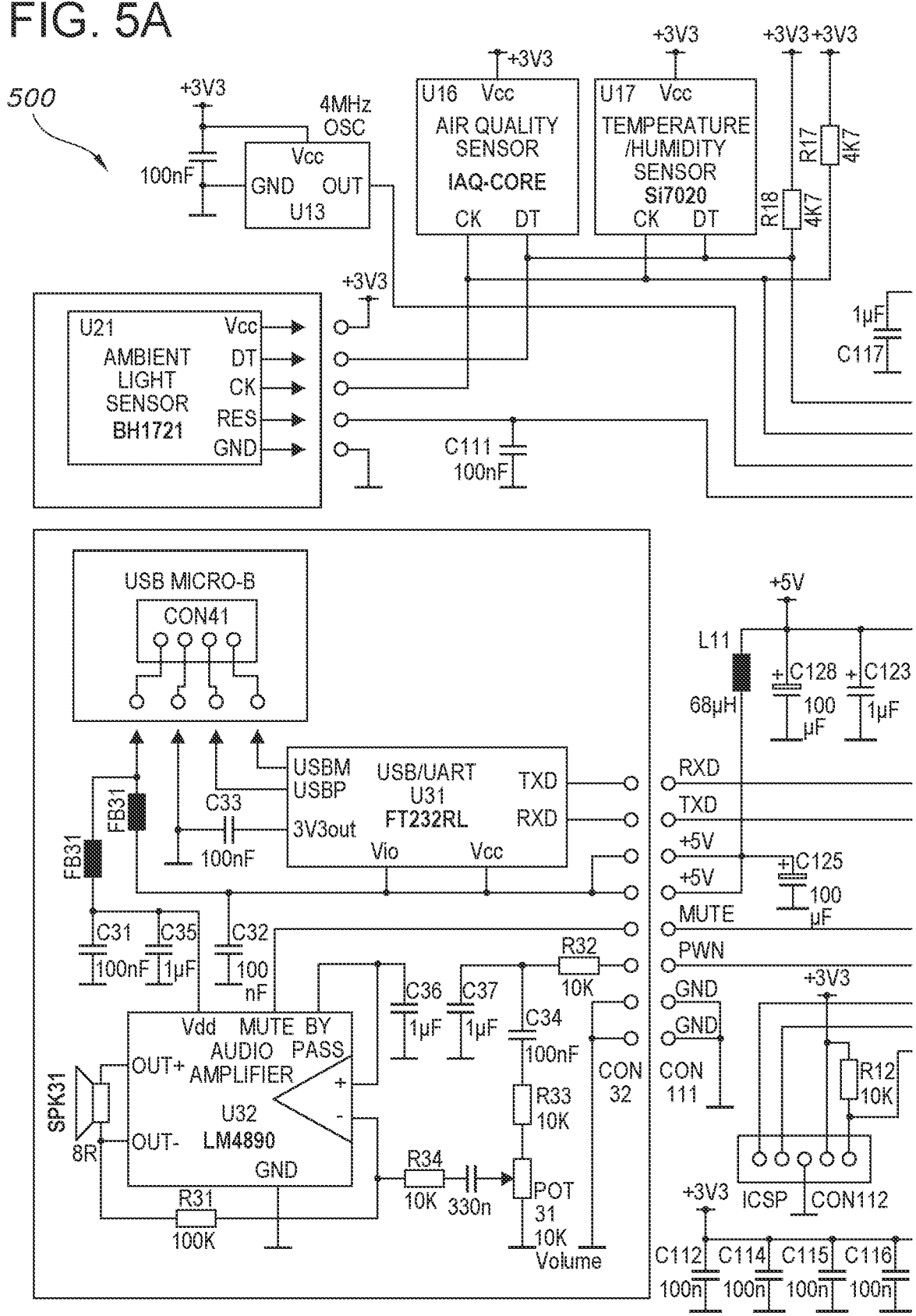
FIG. 5 illustrates a schematic diagram of a platform hub.
Figure 5B:
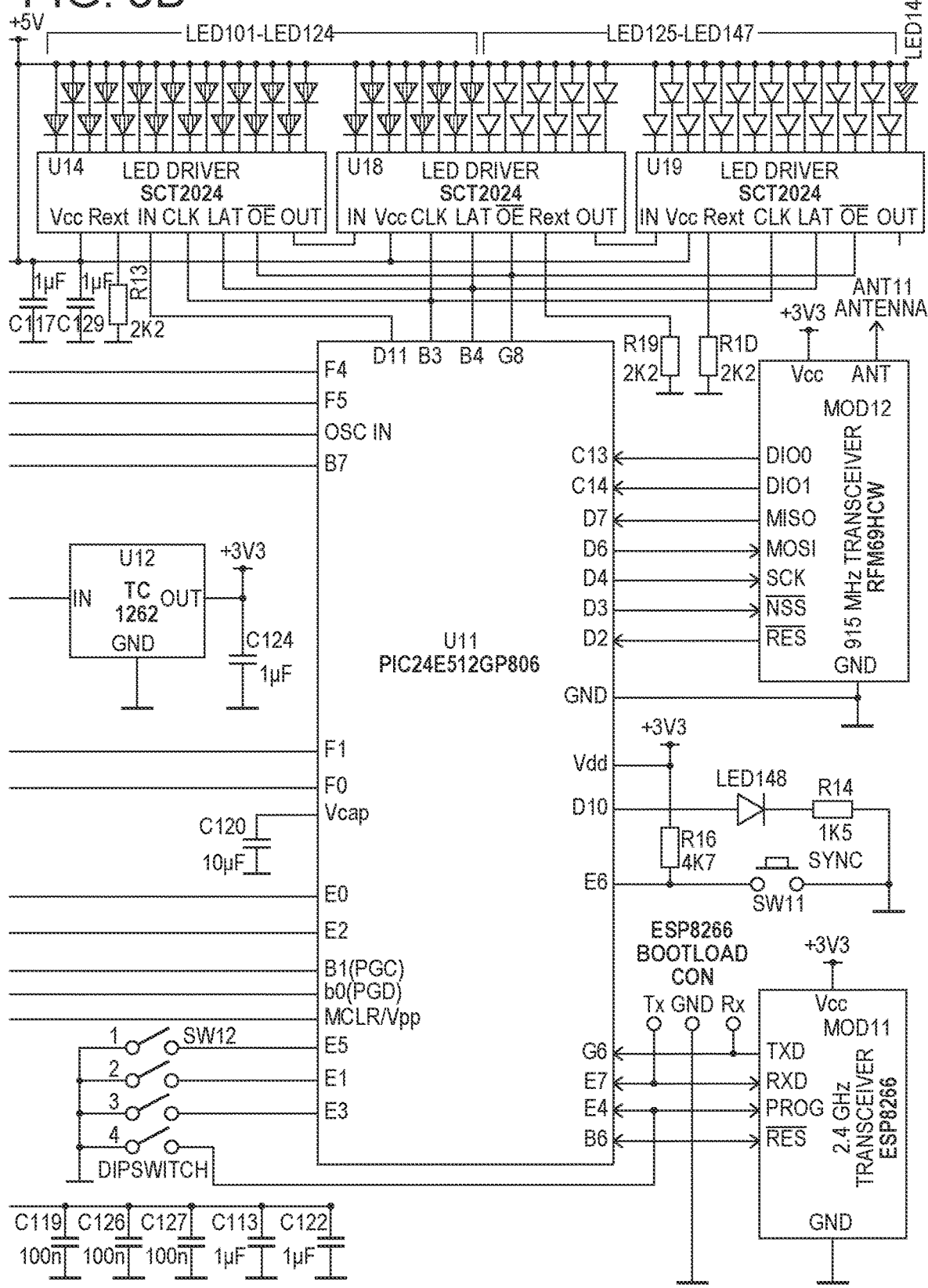

In embodiments, there may be two main PCBs in the platform hub 106. Internal circuits may be located on the main PCB, and an audio amplifier, speaker, USB/UART convertor and USB connector may be located on a separate PCB. The two PCBs may be connected by a ribbon cable and an 8-pole connector. There may be additional PCBs, which may contain an ambient light sensor and be permanently soldered to the main PCB, and a PCB may contain a USB connector. FIG. 4 shows an example block diagram 400 of the platform hub 106, and FIG. 5 shows an example schematic diagram 500 of the platform hub 106.

In embodiments, a handwash sensor 600 may perform the optical monitoring of the space under a soap dispenser or a hand sanitizing unit, vessel or conduit. In an example, there may be windows on the sensors, for example one for a modulated infrared light (~840 nm) transmitter, and the other for an infrared receiver. The handwash sensor may be battery-operated or hard-wired. The sensor may be triggered by the hand or some other reflective object at a distance of, for example, about 12 inches (about 30 centimeters) or closer to the sensor, and at the field of view of the sensor.

Figure 6A:
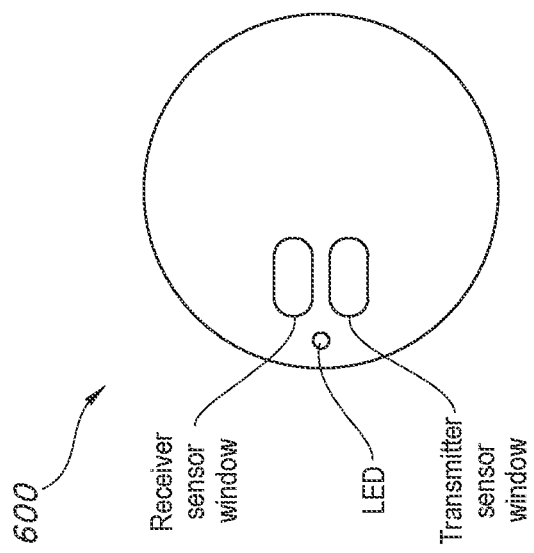
FIGS. 6A, 6B, and 6C are front, side and perspective views, respectively, of a handwash sensor in accordance to the present disclosure.
Figure 6B:
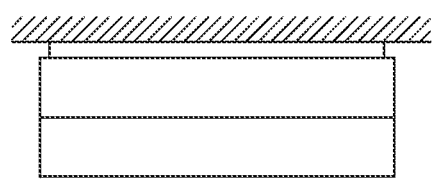
Figure 6C:
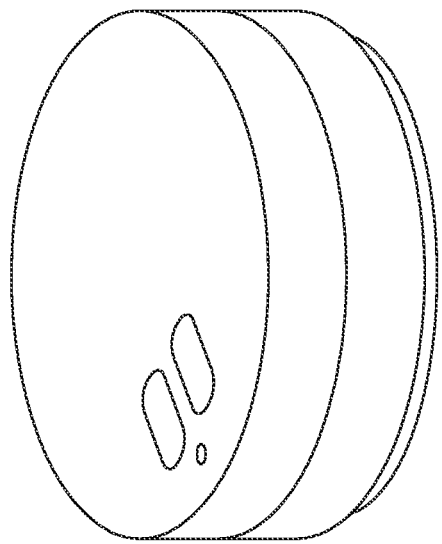

FIGS. 6A through 6C are front, side and perspective views, respectively, of a handwash sensor 600 that may contain internal components, including but not limited to: 8-bit microcontroller unit PIC18LF14K22, with 16 Kbytes of program memory, 512 bytes of data RAM memory and 256 bytes of data EEPROM memory; infrared transmitter, which may be supplied by short bursts of modulated current, emitting bursts of infrared light at ~840 nm at the predetermined period of 100 µs, repeating every 200 ms; infrared receiver, which may detect reflected infrared light, if an object is present; LoRa module RFM69HCW, which may operate at 915 MHz range for data exchange with the platform hub 106; the antenna may be separate from the module, and located on the main PCB; setup button may be located on the main PCB. In an example, this button may be accessible only when the enclosure is opened; LEDs may be used to notify an observer that the sensor is triggered; two 1.5 V alkaline batteries, size AAA for 3V power supply. In an example, the batteries may be accessible only when the enclosure is opened.

FIG. 7 illustrates the layout 700 of the handwash sensor 600 components.

Figure 8:
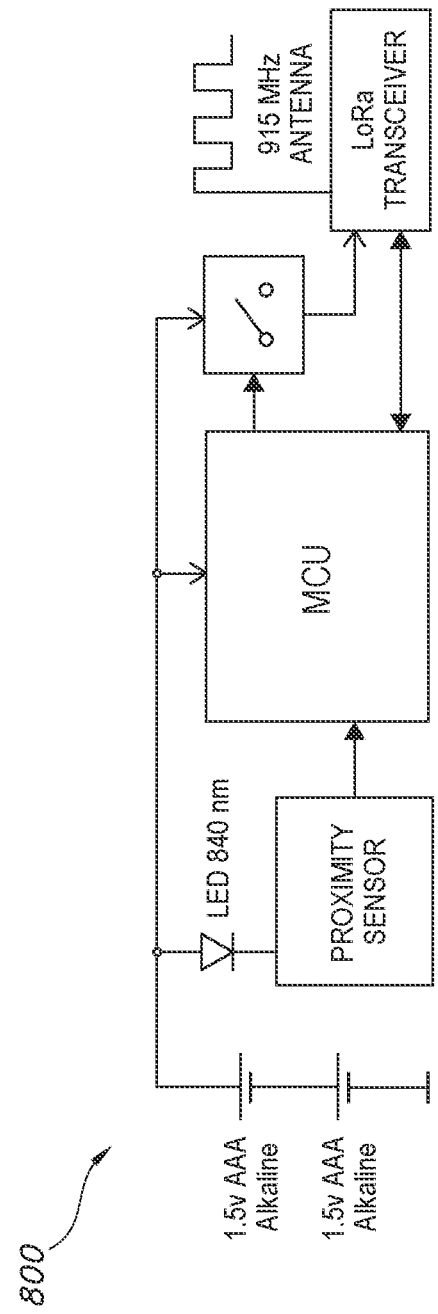
FIG. 8 illustrates a block diagram of a handwash sensor.
Figure 9:
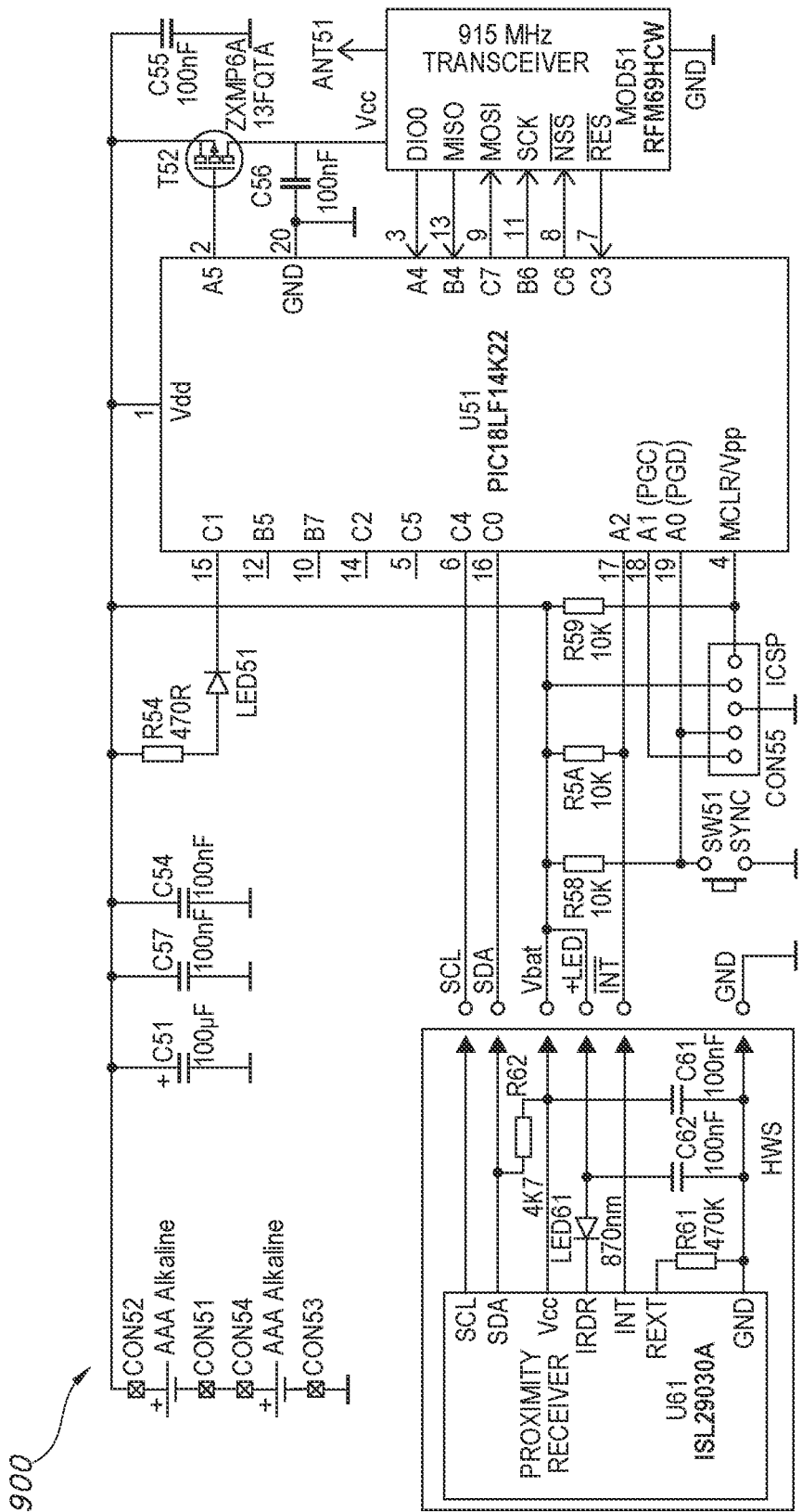
FIG. 9 illustrates a schematic diagram of a handwash sensor.
Figure 10D:
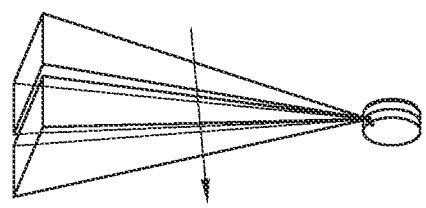
FIGS. 10A, 10B, 10C, and 10D are front, side, and two perspective views, respectively, of a side-monitoring sensor in accordance with the present disclosure.
Figure 10C:
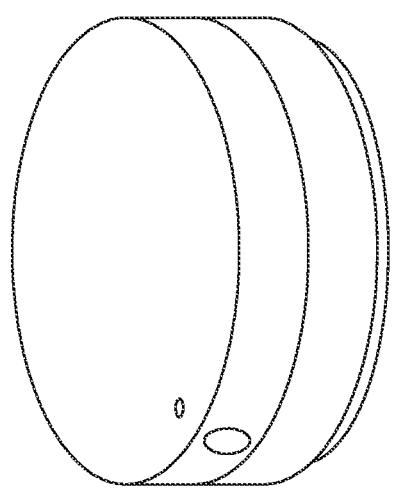
Figure 10B:
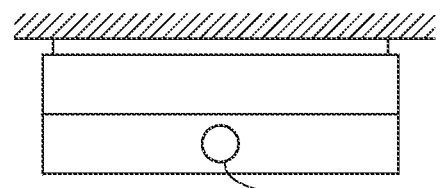
Figure 10A:
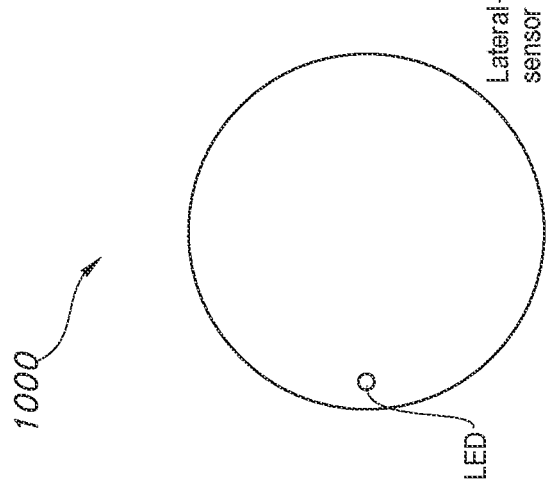
Figure 11A:
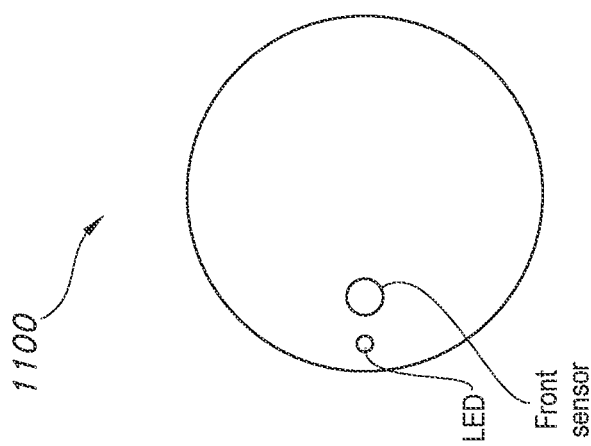
FIGS. 11A, 11B, 11C, and 11D are front, side, and two perspective views, respectively, of a front-monitoring sensor in accordance with the present disclosure.
Figure 11B:
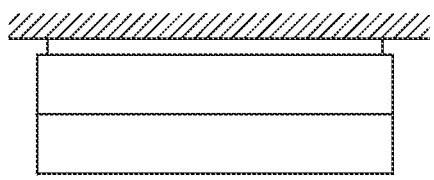
Figure 11C:
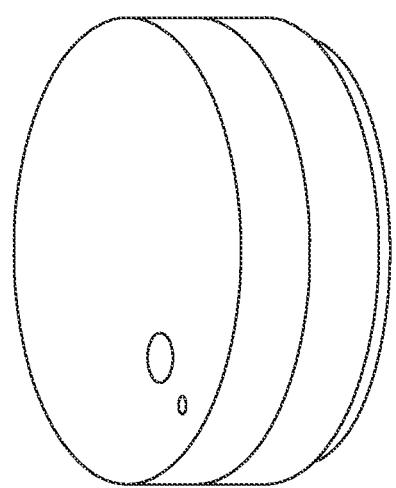
Figure 11D:
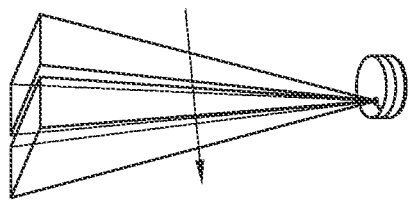

In embodiments, there may be multiple PCBs in the handwash sensor 600. The components, including batteries, which may be located on a main PCB. The infrared transmitter and infrared receiver may be located on a separate PCB. FIG. 8 shows a block diagram 800 of the handwash sensor 600, and FIG. 9 shows a schematic diagram 900 of the handwash sensor 600.

A passive infrared (PIR) sensor may monitor dynamic shifting of infrared radiation (in 5-15 µm range) in defined areas, and detect motion of, for example, a human body. In this example, two independent sensors in the same housing may be used, so that motion may be detected in two areas simultaneously, along with the direction of the sensed motion. In an example, the position of the PIR sensors may allow monitoring the side and the front of the device. FIGS. 10A through 10D show front, side, and two perspective views, respectively, of a side-monitoring sensor 1000. 1000 and FIGS. 11A through 11D show front, side, and two perspective views, respectively, of a front-monitoring sensor 1100. It will be appreciated in light of the disclosure that the views of the device contain many protectable ornamental features independent and distinct from the many functional features discussed herein.

In embodiments, internal components contained in the passive infrared motion sensor may include, but are not limited to: 8-bit microcontroller unit PIC18LF14K22, with 16 Kbytes of program memory, 512 bytes of data RAM memory and 256 bytes of data EEPROM memory; PIR, with a Fresnel lens. The detector may be rearranged in order to detect two separated channels, with two separated fields of view, so that the MCU unit can determine the direction of motion; LoRa module RFM69HCW, which uses 915 MHz range for data exchange with the platform hub 106; the antenna may be separate from the module, and located on the main PCB; setup button may be located on the PCB. This button may be accessible only when the enclosure is opened; LEDs may be used to notify an observer that the sensor is triggered; and two 1.5 V alkaline batteries, size AAA for 3V may supply power. In an example, the batteries may be accessible only when the enclosure is opened.

Figure 12:
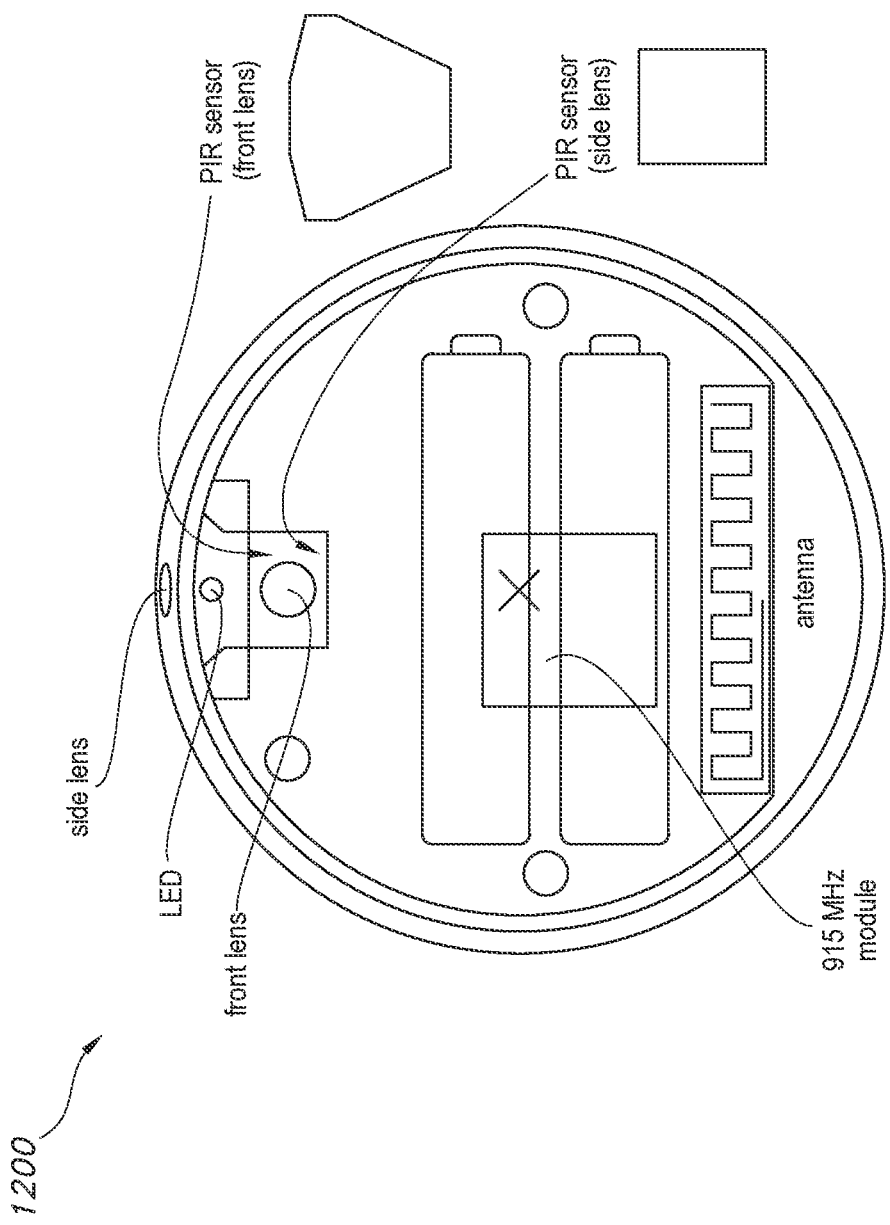
FIG. 12 illustrates an example layout of handwash sensor components.
Figure 13:
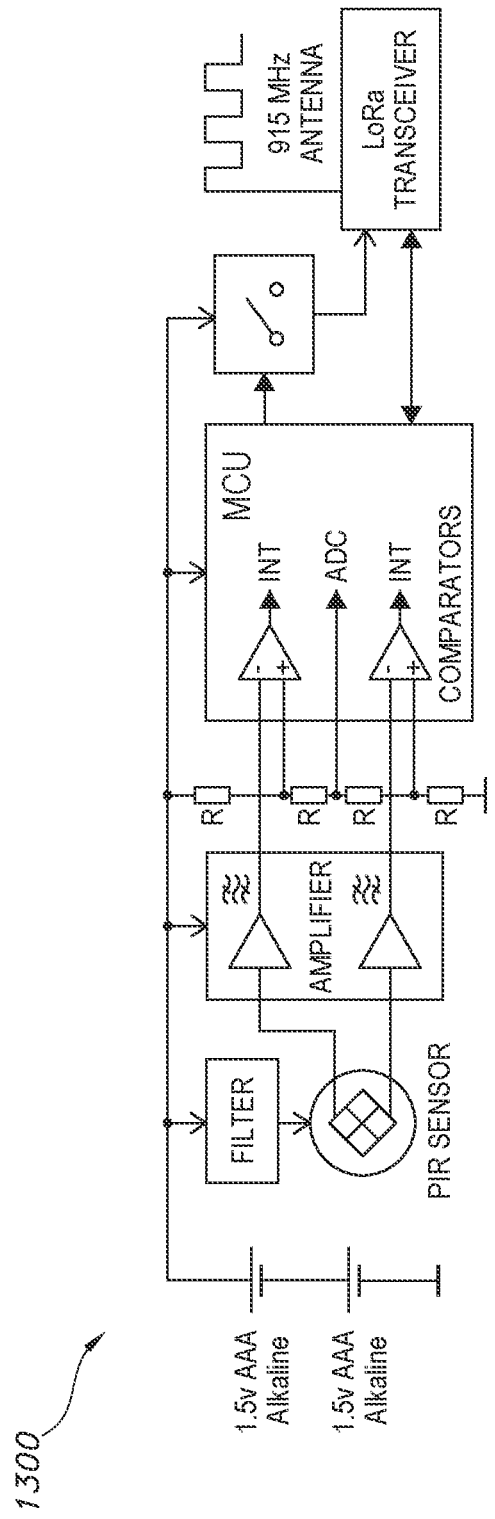
FIG. 13 illustrates a block diagram of a passive infrared sensor.
Figure 14:
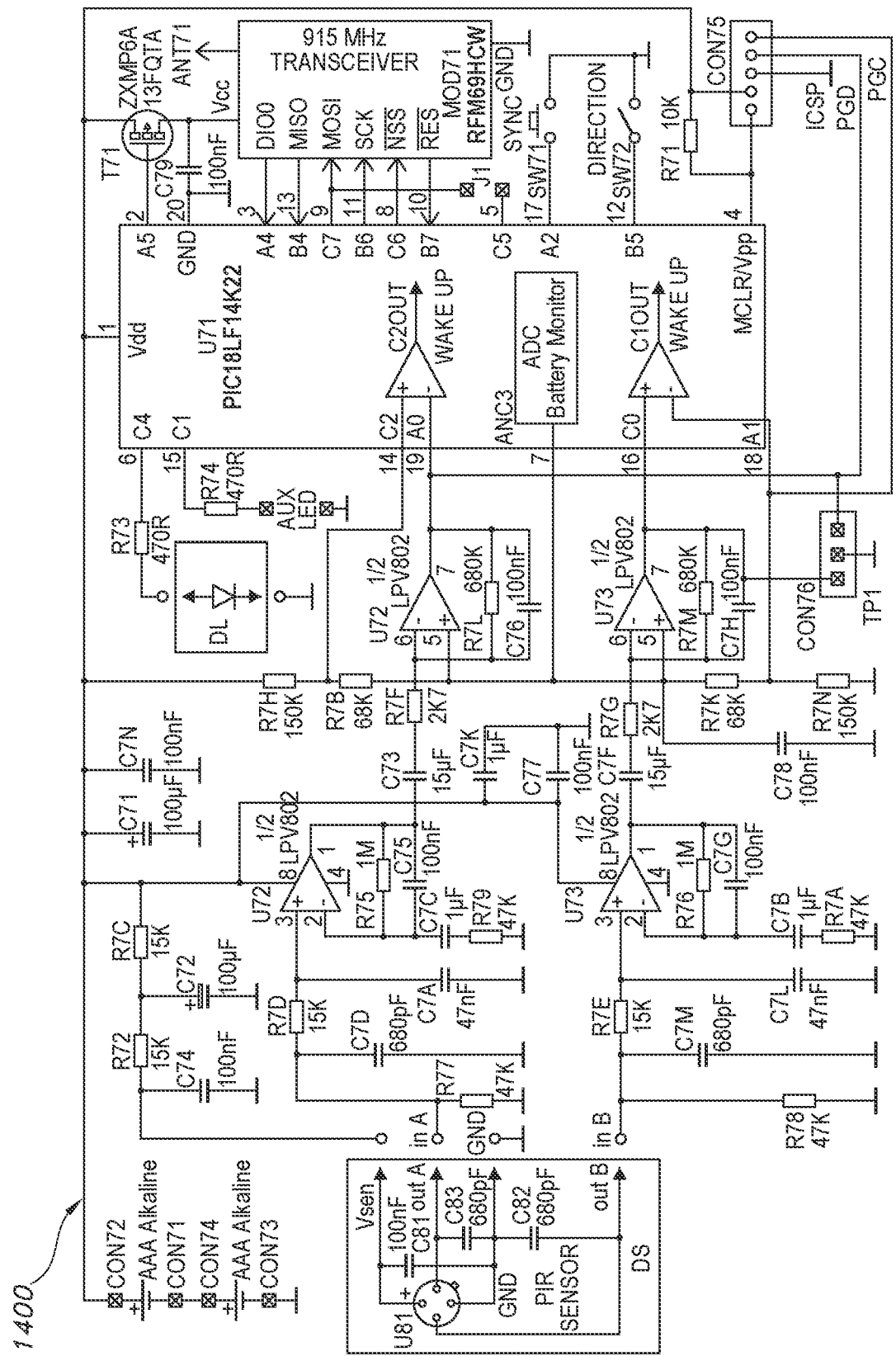
FIG. 14 illustrates a schematic diagram of a passive infrared sensor.

In embodiments, there may be a plurality of PCBs in the PIR sensor. The components, including batteries, may be on the main PCB. FIG. 12 illustrates an example layout 1200 of handwash sensor components (bottom view). The PIR sensor may be on the main PCB, and the LED may be on a separate PCB. FIG. 13 illustrates an example block diagram 1300 of a passive infrared sensor, and FIG. 14 presents an example schematic diagram 1400 of the passive infrared sensor.

Figure 15B:
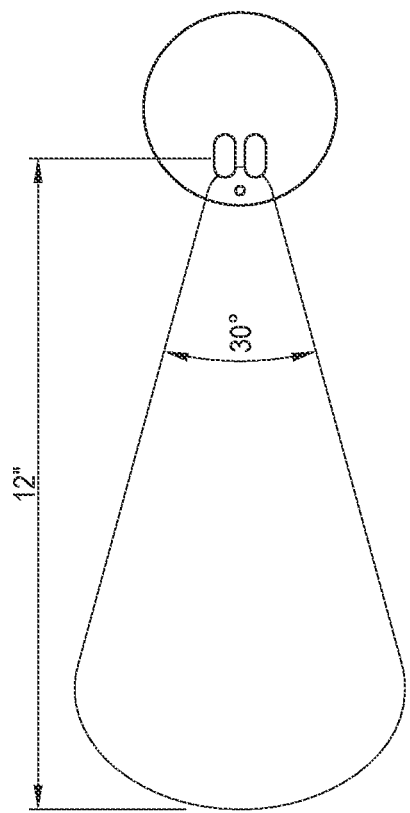
FIGS. 15A and 15B are perspective and front views, respectively, of a handwash sensor's field of view in accordance to the present disclosure.
Figure 15A:
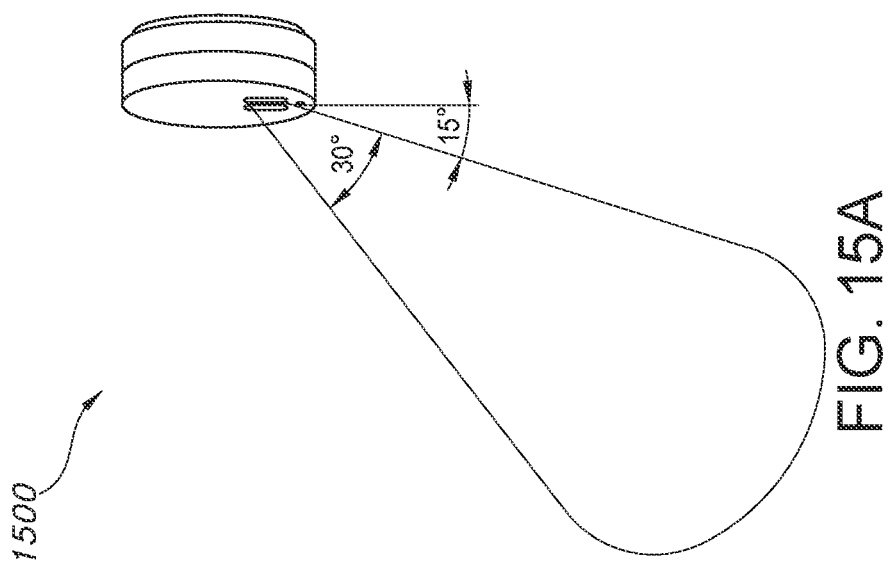
Figure 16:
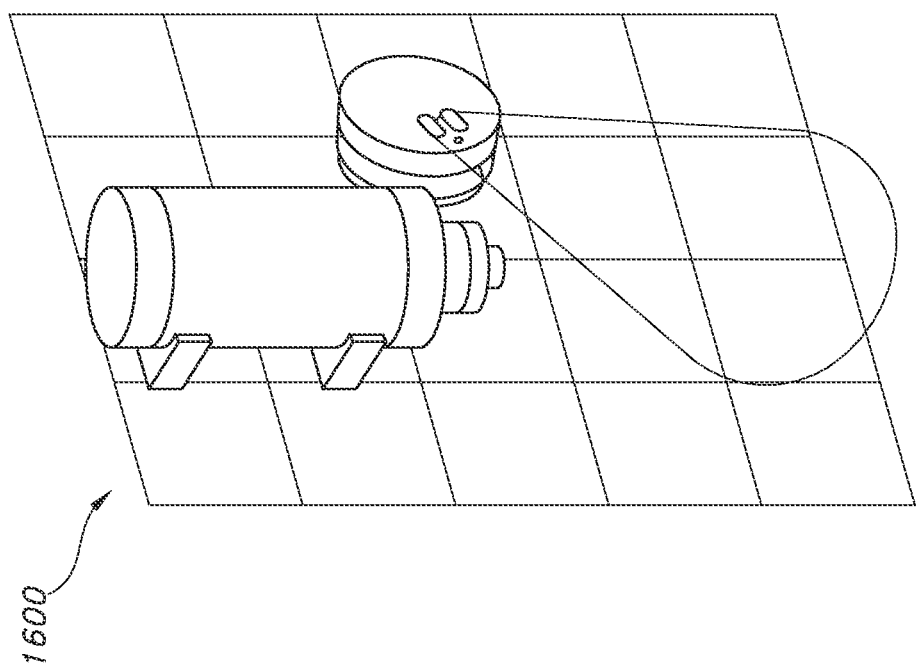
FIG. 16 illustrates an example placement of a handwash sensor.

The field of view of the handwash sensor may be, in one example, a cone with an angle of approximately 30°, which may extend to approximately 12 inches (approximately 30 cm). The approximate position and direction of the cone 1500 may be represented as shown in FIGS. 15A and 15B. The handwash sensor may be placed so that it is triggered by a person's hand, or some other object associated with the person, while the person is using the vessel, conduit, and/or dispenser content. In embodiments, the sensor may be placed so that no other object (dispenser, napkins, bottles, etc.) can trigger it. In examples, a plurality of handwash sensors may be placed in a room that is covered by one platform hub 106. FIG. 16 represents a typical placement of a handwash sensor 1600. In these embodiments, the field of view is not obstructed by any object.

Figure 17B:
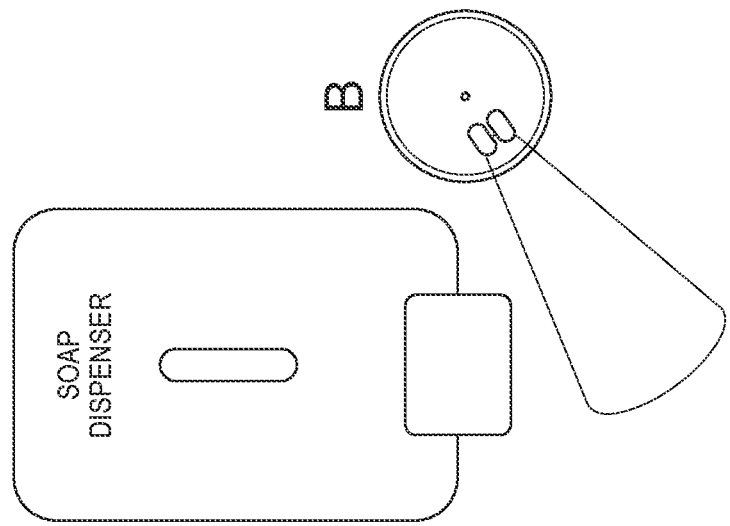
FIGS. 17A and 17B show horizontal and angled fields of view, respectively, of a handwash sensor in accordance to the present disclosure.
Figure 17A:
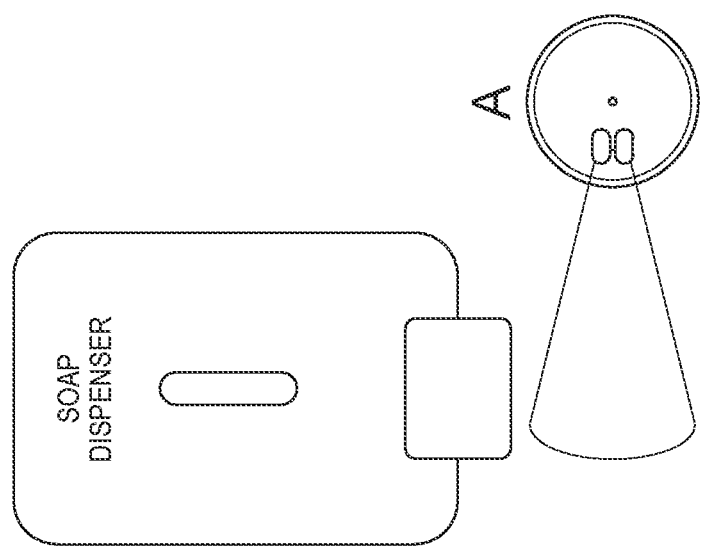
Figure 18B:
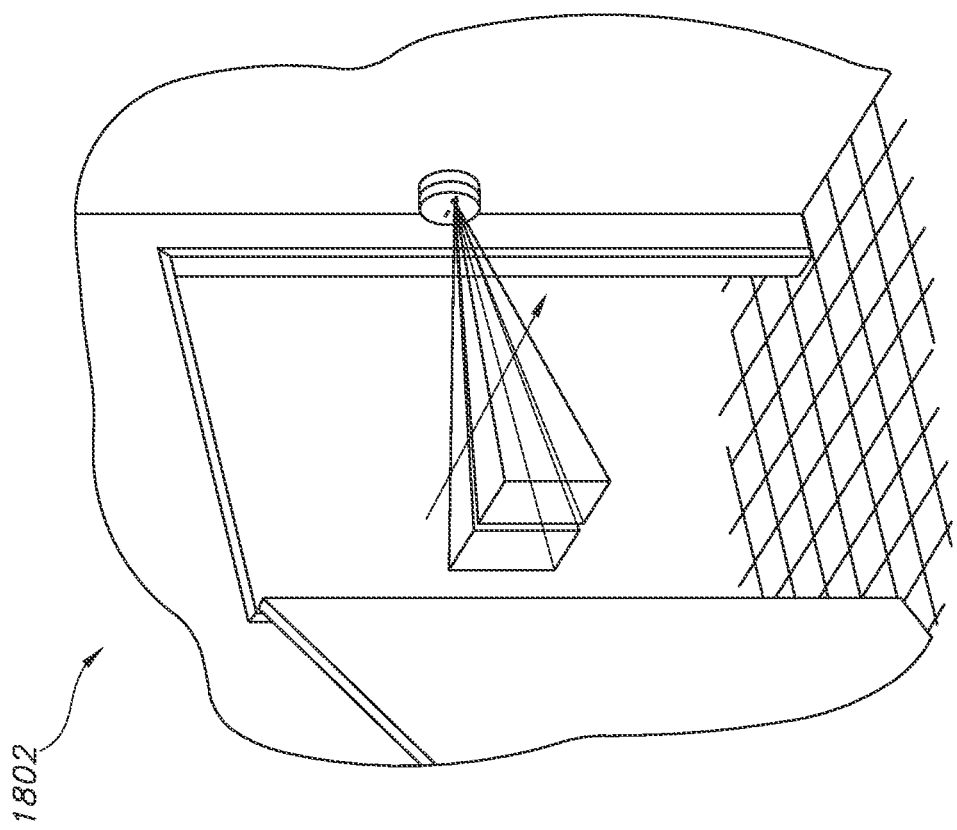
FIGS. 18A and 18B are side-monitoring and front-monitoring views, respectively, of placements of a passive infrared sensor in accordance with the present disclosure.
Figure 18A:
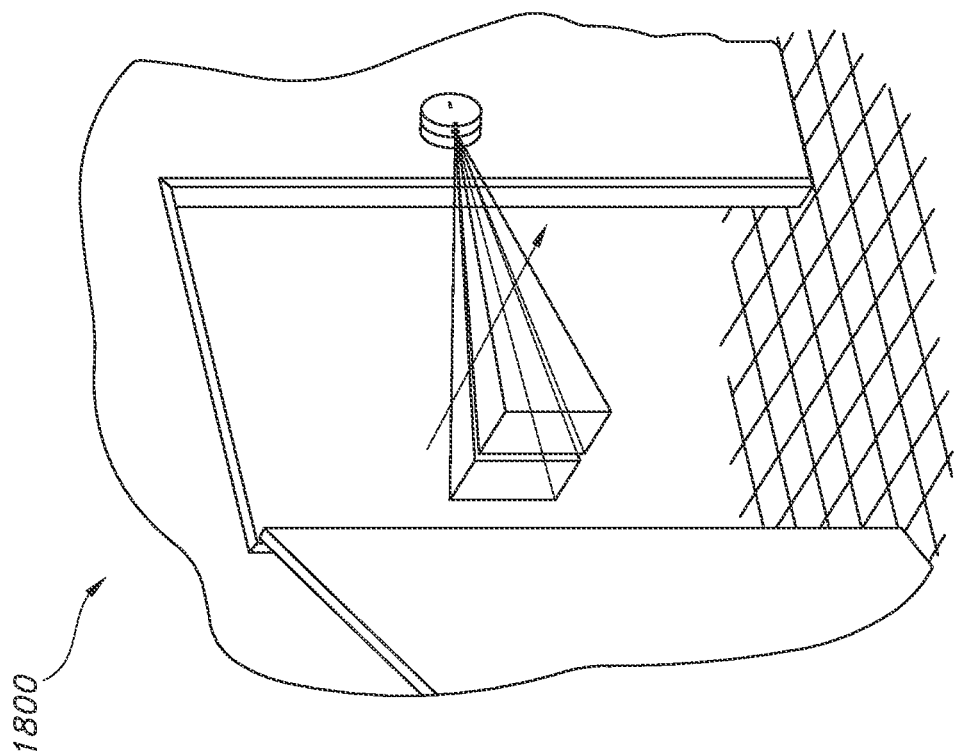

In embodiments, the handwash sensor 600 may be positioned so that its field of view stretches horizontally (FIG. 17A) or at an angle (FIG. 17B) 1700. This may depend on the configuration of objects around the vessel, conduit, and/or dispenser. The PIR sensor may be placed on the wall next to the entrance to the room. In examples, positioning may be represented as in FIG. 18A in the left view 1800, where the side monitoring sensor is used, however in some cases there may not be enough space, making it impossible to attach it to the narrow part of a wall, so the front monitoring sensor may be used. This is represented on the right view 1802 in FIG. 18B.

Figure 19:
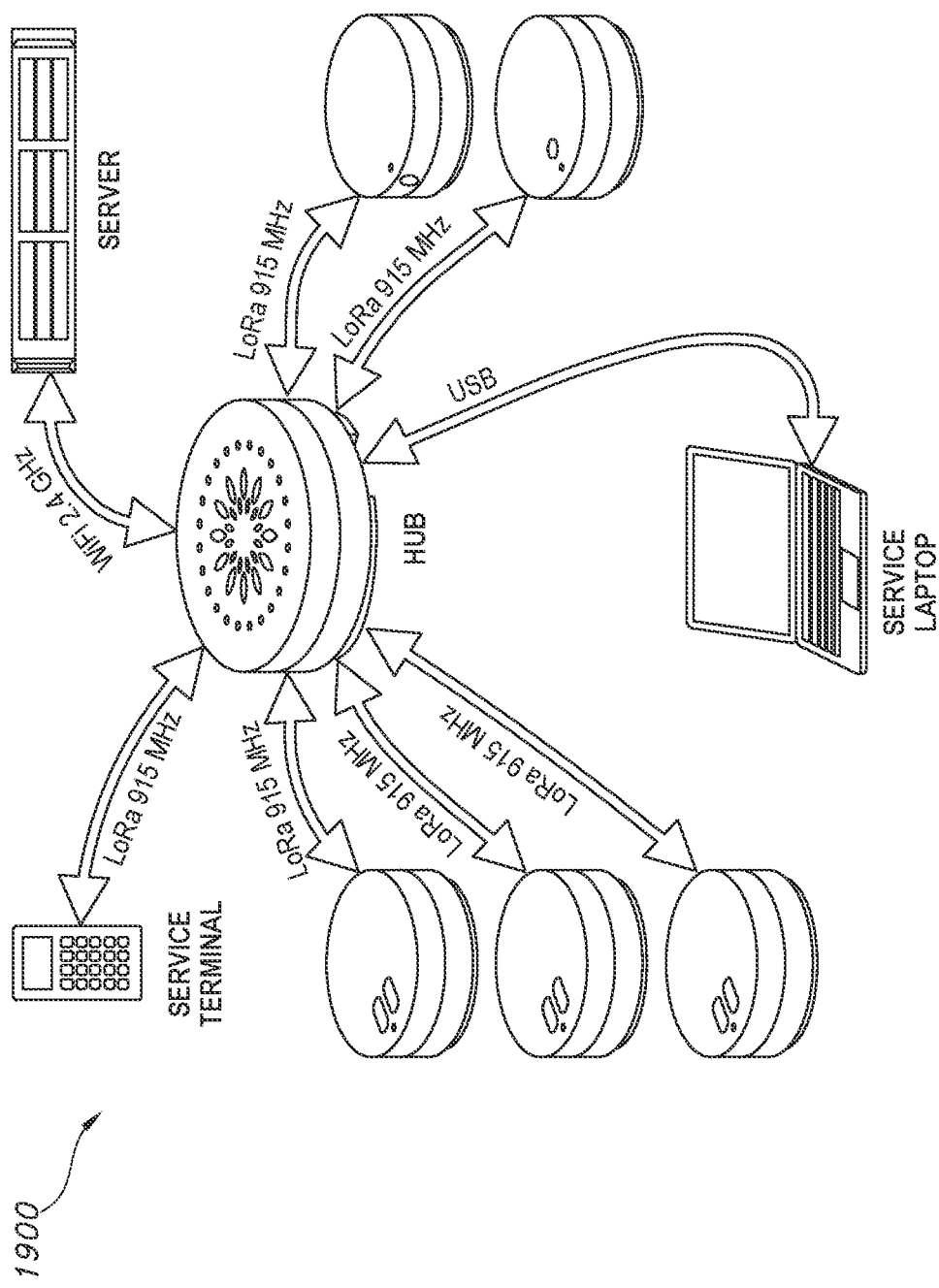
FIG. 19 illustrates a simplified example of an installation of a plurality of smart hygiene devices associated with a platform hub.

In other examples, an optimal vertical position of the PIR sensor may be approximately 50-55 inches above the floor level. Positioning the PIR sensor at a lower position may present functional challenges, as parts of the clothing which are loose and not close to the human body can be too cold and fail to trigger the sensor. The PIR sensor may also be placed above the entrance to a room, on the wall or on the ceiling. In examples, multiple PIR sensors may be placed in a room 1900 that is covered by one platform hub 106, as shown in FIG. 19.

Figure 20B:
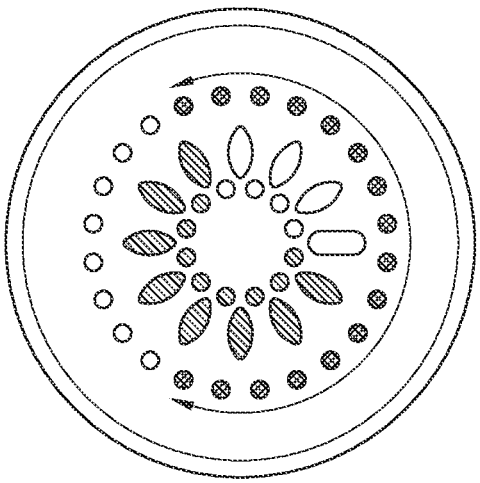
FIGS. 20A, 20B, 20C, and 20D depict animated sequences of LED rings on a smart hygiene device indicating the number of completed handwashes compared to the number of handwash opportunities.
Figure 20D:
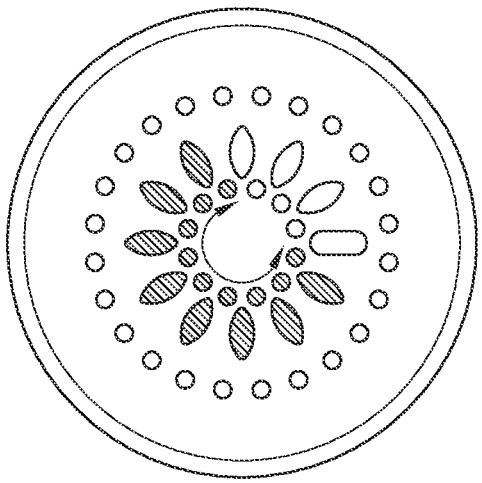
Figure 20A:
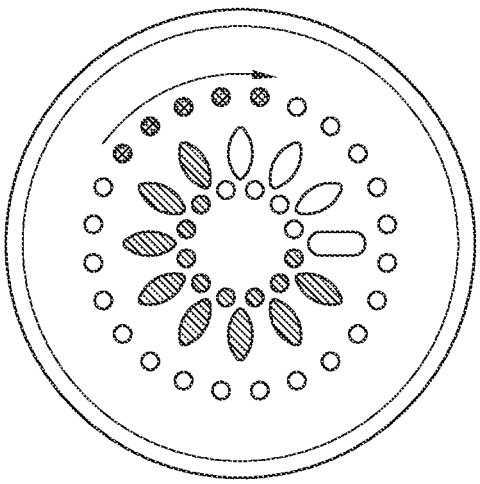
Figure 20C:
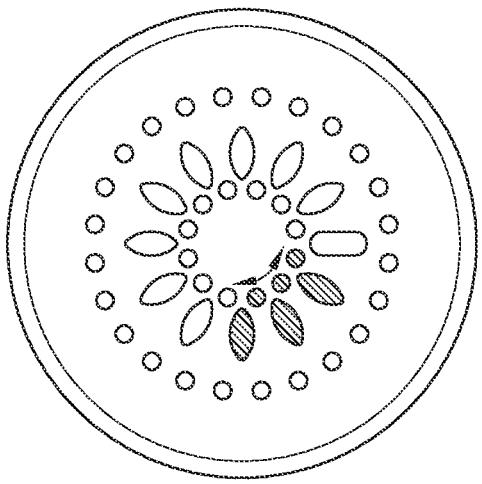

In examples, the platform hub 106 may display the current status of the unit, using, for example, two concentric rings with LEDs. The inner ring may symbolize a leaf, tree, or other object or shape, and the outer ring may remind people who enter the room to wash their hands and display the confirmation after their hands are washed. After a person's entry to a room is detected by a motion sensor, a message may be sent to the platform hub 106. The platform hub 106 may play a prerecorded sound as a reminder and display an animated sequence on the outer LED ring. A portion of LEDs may rotate clockwise, as shown in FIG. 20A. When the person washes their hands, the handwash sensor may trigger, and the platform hub 106 may play another prerecorded sound and display another animated sequence of lights. The left and right halves of the outer ring may simultaneously fill the ring from the bottom to the top, as shown in FIG. 20B. The inner ring represents the number of people who have washed their hands compared to the number that came inside the room. For every person who enters the room and washes their hands, the "tree leaves" (or some other shape formed by the inner ring) may "grow" and for every person who enters the room and doesn't wash their hands, the tree may shed leaves, decreasing in size. The ratio of signals from the handwash sensor and motion sensor may be used to calculate the growth or decline of the tree leaves. FIG. 20C represents relatively poor results (too few visitors washed their hands) and FIG. 20D shows a relatively good result, where the tree is properly "growing" leaves. Such status sequences may be locally controlled by the platform hub 106 but may also be controlled by server software or by an operator. In examples, a preset mode(s) may enable automatic disabling of sound and/or light sequences when the level of ambient light is low, as in, for example, a hospital room when a patient is sleeping and should not be disturbed.

In embodiments, a platform server 108 may monitor and report from a plurality of platform hubs 106 to memory, so all the acquired data is accessible via the Internet, cloud, intranet, or some other network type. In examples, the acquired data may contain the total number of triggers for each motion and handwash sensor, and the temperature, humidity, air quality and ambient light level at a fixed interval. The current battery voltage in each sensor may be read and used by the platform 108 server or remote system to issue warnings when a battery needs replacement.

In embodiments, a plurality of data types may be acquired by the platform 102, including but not limited to: synchronous data: Counter state reading for each sensor monitored by the platform hub 106 (including a plurality of handwash sensors) and state of all internal sensors of the platform hub 106 (e.g., temperature, humidity, air quality and ambient light level). These data may be buffered unconditionally at a predetermined interval asynchronous data: Records each time an event triggers the motion or the handwash sensor and current data: Data written on special request at any time from the server. These data may be buffered in the platform hub 106, safely waiting for a transfer command from the server.

Figure 21:
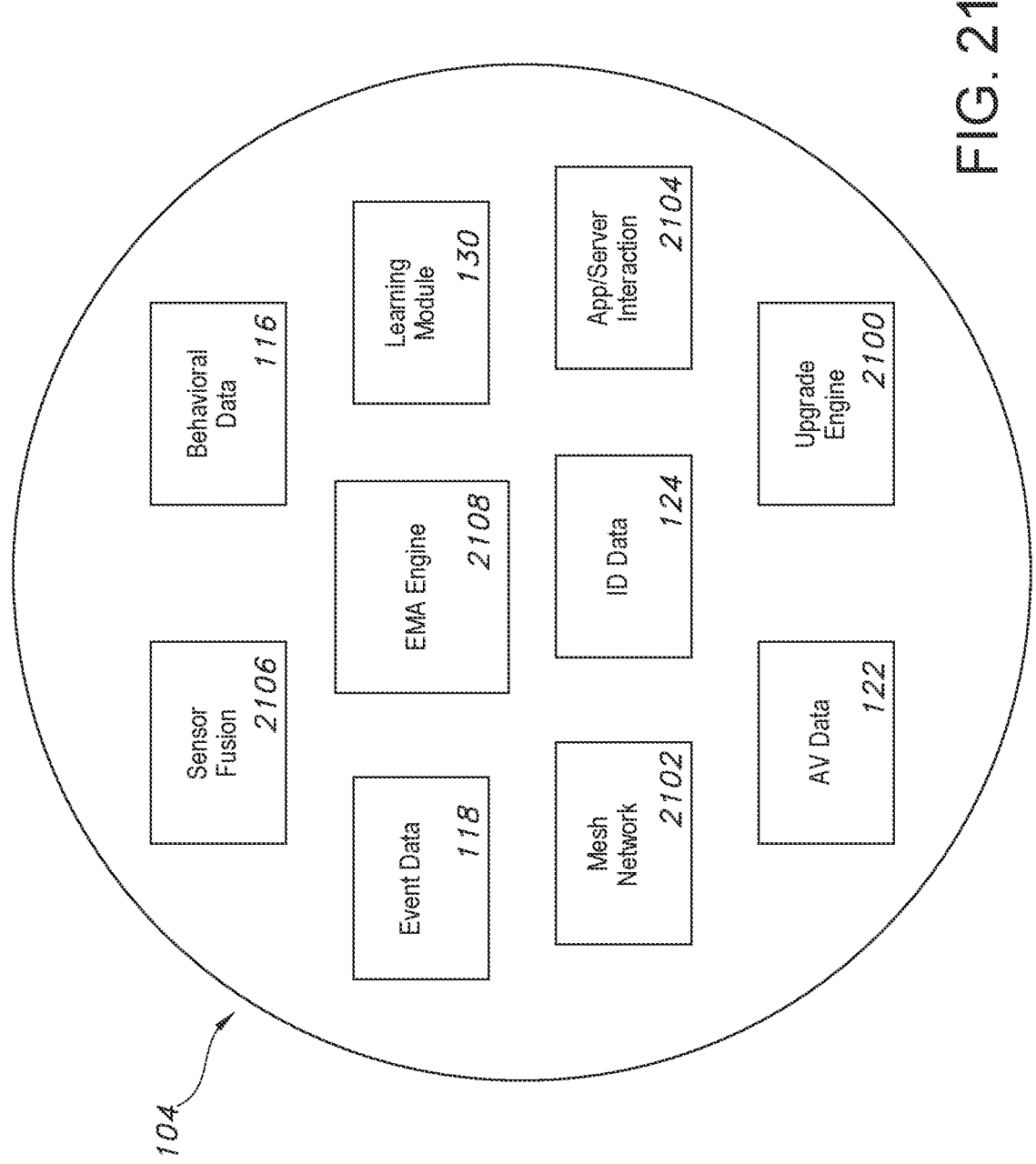
FIG. 21 illustrates a schematic overview of module embodiments of a smart hygiene device in accordance with the present disclosure.

In embodiments, a smart hygiene device 104 may independently operate apart from a platform hub 106 and/or platform server 108, and directly communicate with an application 105 that is associated with the platform 102. As shown in FIG. 21, a smart hygiene device 104 may include modules, functionalities and data that include, but are not limited to, a mesh networking module 2102, application/server interaction module 2104, upgrade engine 2100, sensor fusion 2106, learning module 130, behavioral data 116, event data 118, ID data 124, audio-visual data 122, and an encourage, monitor, and affirm (EMA) engine. The smart hygiene device 104 may include a plurality of sensors and sensor types including, but not limited to, BLE-based sensors to detect mobile computing devices 182 or other BLE-enabled devices, handwash sensors, PIR sensors, or some other sensor type. The smart hygiene device 104, sensors and other data and analytic processing modules may operate in conjunction with an application 105 that is associated with the platform 102 and used to configure the settings of the smart hygiene devices 104. The EMA engine may include models, algorithms or other intelligence analytics that invoke the smart hygiene device's audio-visual capabilities to encourage, monitor and affirm hygiene behaviors of persons in proximity to the smart hygiene device, such as prompting the user to wash their hands, with lighting, sound, or video prompts and/or rewarding handwashing by playing media at the smart hygiene device 104. The mesh networking module 2102 of the smart hygiene devices 104 may allow communication between smart hygiene devices 104, and the application/server interaction module 2104 and upgrade engine 2100 may allow for maintenance of software installed on the smart hygiene devices 104. In examples, the mesh networking module 2102, as described herein, may be a type of cooperative computing module, cluster computing module, or some other type of distributed computing module, other than a mesh network, that may be used for networking cooperative devices.

In embodiments, installation of the platform's 102 smart hygiene devices 104 and related network may include, but is not limited to, the following steps. A user may download the platform application 105. Using the application, the user may set up an account, as shown in FIG. 22A, search for devices 104, as shown in FIG. 22B, define locations and areas within which the smart hygiene devices 104 will be deployed, or perform some other setup operation for the platform 102. For example, the user may configure a first device 104 to only detect persons entering the area using BLE, and a second device may be placed near a sink and configured to detect handwashing only. In embodiments, a smart hygiene device 104 may be configured for a specific purpose or a plurality of purposes. For example, a smart hygiene device 104 may be configured to only detect motion. In another example, a smart hygiene device 104 may be configured to only detect hygiene behaviors, such as handwashing. A smart hygiene device 104 may also be configured to detect multiple events, such as motion in a room, the presence of a mobile computing facility 182, a hygiene event, or some other occurrence or activity. In embodiments, in place of using a motion sensor to detect the presence of a person, a smart hygiene device 104 may use BLE to detect a mobile computing device 182 in proximity to a person, such as a smart phone, smart watch, tablet computer, or some other type of mobile computing device 182. Based at least in part on a learning machine module 130, AI processing 134, classification module 126 and platform data 110 within or associated with a smart hygiene device 104, a smart hygiene device 104 may be able to learn and recognize groups of mobile computing devices 182 that are always or frequently detected together, such as a phone and a watch. This data and intelligence may be used to ascertain and record at the device 104 and/or application 105, that the detection of the watch and phone that are recorded as paired is indicative of only one person being detected and not two unique individuals, one with the watch and another with the phone. In embodiments, using BLE, the smart hygiene devices 104 may be able to detect the number of mobile computing devices 104 present, the distance a mobile computing device 182 is from the smart hygiene device 104, and the type of device it is (e.g., phone versus tablet computer). Smart hygiene devices 104 may also be configured to detect, record and process only one type, or a subset, of BLE-enabled devices, for example only phones or only beacons. This may be useful in certain platform 102 installations, for example where a facility only wants to detect and record hygienic behaviors of its own employees who are outfitted with beacons, and to ignore all mobile computing device 182 detection that may double count employees or be associated with non-employees. The application 105 may also be used to set a range of sensing for each smart hygiene device 104. The application 105 may be used to configure smart hygiene devices 104 to play audio, sound, lighting or video reminders to persons in proximity to the device 104 to wash their hands, and to configure the timing of such reminders (e.g., every 30 minutes, only when a mobile computing device is detected, and so forth). The platform application 105 may present in a dashboard 176 a listing, map or other presentation of where all smart hygiene devices 104 deployed are installed, and include listings of their configurations, purposes, and the like. The platform application 105 may also present summary statistics related to the smart hygiene devices 104 based at least in part on user-defined regions, areas, device clusters and the like, such as a home area, as shown in FIG. 22C, or an entrance to an area, as shown in FIG. 22D. In embodiments, smart hygiene device 104 configurations, settings and the like that are to be shared across a plurality of devices may be configured by a user using the application 105 on only a single device 104, and these settings and configurations may then be distributed and installed on other devices 104 through a mesh network, cooperative network, cluster computing network, or some other type of distributed network, without the user having to individually configure each device 104. In embodiments, a gateway other than the application 105 may be used to configure the platform 102 and the smart hygiene devices 104 including, but not limited to, WiFi, cellular, or some other gateway type.

In embodiments, the smart hygiene devices 104 may communicate with each other through a network including, but not limited to, a mesh network, cooperative network, cluster computing network, or some other type of distributed network. Each device 104 in a network may share, update, upload, download or otherwise transfer data, models, algorithms, artificial intelligence, machine learning, classifications, recommendations and the like, as described herein, so that each device in a network is fully updated and synced with other devices 104 and platform 102 functionalities, as described herein.

In embodiments, the smart hygiene device 104 may contain the elements of the platform 102, as disclosed herein, and may include an analytics engine 112. The analytics engine 112 may include, but is not limited to, a classification machine 126, a prediction module 128, a learning machine 130, a recommendation module 132, AI processing 134, an optimization module 136, an automation module 138, a personalization module 140, or some other type of analytic processing module. The analytics engine 112 may intake data that is collected by smart hygiene devices 104, such as those connected within a mesh network, cooperative network, cluster computing network, or some other type of distributed network, or data that is obtained by third party data sources 148 that are external to the smart hygiene device(s) 104. The analytics engine 112 may build, test and validate machine learning algorithms and models based at least in part on ingested and/or collected data and use such algorithms and models for the purposes of classifying, predicting, recommending, optimizing and/or personalizing the performance and utilization of smart hygiene devices 104. The analytic engine may perform AI processing 134 on platform data 110 and/or data from external data sources 148. For example, AI processing may be used to optimize the media played by a smart hygiene device 104 to encourage hygiene behavior modification among a population working at or visiting a facility.

In embodiments, smart hygiene devices 104 within a mesh network, cooperative network, cluster computing network, or some other type of distributed network, as described herein, may be operatively connected with at least one facility smart devices hub 144 and facility server 146 that are associated with a facility or plurality of facilities at which the smart hygiene devices 104 are deployed. The facility server 146 may be further associated with other devices, such as wearable devices 174, personnel identifiers 172, such as login or account information of users, and/or external data sources 148.

In embodiments, the smart hygiene devices 104 within a mesh network, cooperative network, cluster computing network, or some other type of distributed network, may be associated and operable or controlled by a platform application 105 and/or additional applications that may be developed and/or provided using an application programming interface (API) 178 and a software development kit (SDK) 180 to enable developers and development platforms 188 to create applications to interact with the platform 102, application 105, and smart hygiene devices 105. An application 105 and dashboard 176 may be associated with the platform 102 and used to configure, operate and/or visualize aspects of the platform's performance. The dashboard 176 may include a set of interfaces and services for operator configuration of a set of timing sequences for behavioral modification stimulus events and types, and for configuration of a set of triggering events and rewards for behavioral modification activities for a set of devices managed by the platform. The dashboard 176 may be viewed on a computing device including, but not limited to, a mobile computing device 182 or web browser 184 and be used to provide a user experience that promotes user awareness of the need to undertake hygienic behavior. The application 105 may include a set of end user mobile application interfaces configured in the platform for inducing user behavior and for allowing a platform operator to configure a set of parameters of the platform 102.

In embodiments, the platform 102 and the platform application 105 may include a plurality of outbound data functions including, but not limited to, reporting 192, coordination with a hygiene campaign module 190, social media entities 194 or other third-party platforms 196, and/or general communications platforms such as email 198.

In embodiments, the smart hygiene devices 104 in a mesh network, cooperative network, cluster computing network, or some other type of distributed network, as described herein, may operate, in part, using BLE and may include, a motion sensor, a handwash sensor, a passive infrared proximity sensor, an active infrared proximity sensor 200, or some other type of sensor as described herein. The smart hygiene device 104 in a mesh network, cooperative network, cluster computing network, or some other type of distributed network, may be separate from a vessel, conduit, and/or soap or disinfectant dispenser, or it may be integrated with a soap or disinfectant dispenser. It may detect a hand hygiene event by detecting a hand in the dispenser area and transmit the information to the platform application 105. An LED may light up to indicate a detected hand hygiene event. The battery-operated smart hygiene device 104 may be located on a wall, next to a door, or in some other location. The motion sensor within or associated with the smart hygiene device 104 may be used to detect people entering the room. The sensor may detect the direction of the motion and may be programmed to detect only a person's entrance to a room and ignore when the person exits the room. Alternatively, it may be programmed to detect a person's entrance to a room and the person's exit from the room using BLE detection of mobile computing devices 182 on or in proximity to persons near the smart hygiene devices 104. This information may also be transmitted to other of the platform's or facilities infrastructure, such as servers, databases and the like.

Figure 23:
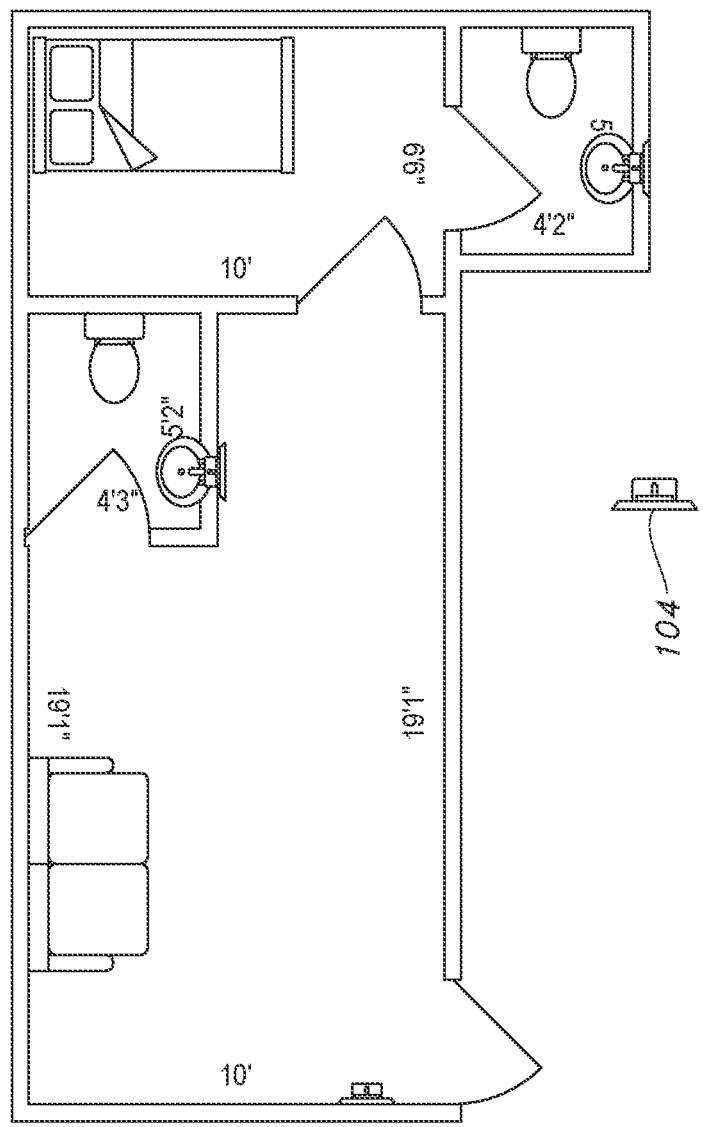
FIG. 23 illustrates examples of a deployment of smart hygiene devices in a network within a residence.

In embodiments, and referring to FIG. 23, smart hygiene devices 104 may be located within a residence like a house or apartment and interconnected within a mesh network, cooperative network, cluster computing network, or some other type of distributed network. In examples, a plurality of smart hygiene devices 104 may be distributed across locations of the residence, such as near an entrance and within bathrooms positioned near sinks where handwashing may occur. Each device in this example is configured for a similar monitoring purpose. Upon entering the residence, the first smart hygiene device may detect the mobile computing facility 182 of the person entering the room. Data and analytics within the mesh network, cooperative network, cluster computing network, or some other type of distributed network, of the smart hygiene devices 104, as described herein, may enable the network to identify the user based on prior encounters the user has had with the networked devices 104. Based at least in part on this knowledge of the person within the network, a recommended media selection, such as a sound, song, video, or text may be presented, such as media encouraging or reminding the person to perform some hygienic act like handwashing. Other smart hygiene devices 104 in the network, for example those located near sinks, may detect, record and transmit data regarding handwashing such as the occurrence or absence of a handwash during the person's visit to a bathroom.

Figure 24:
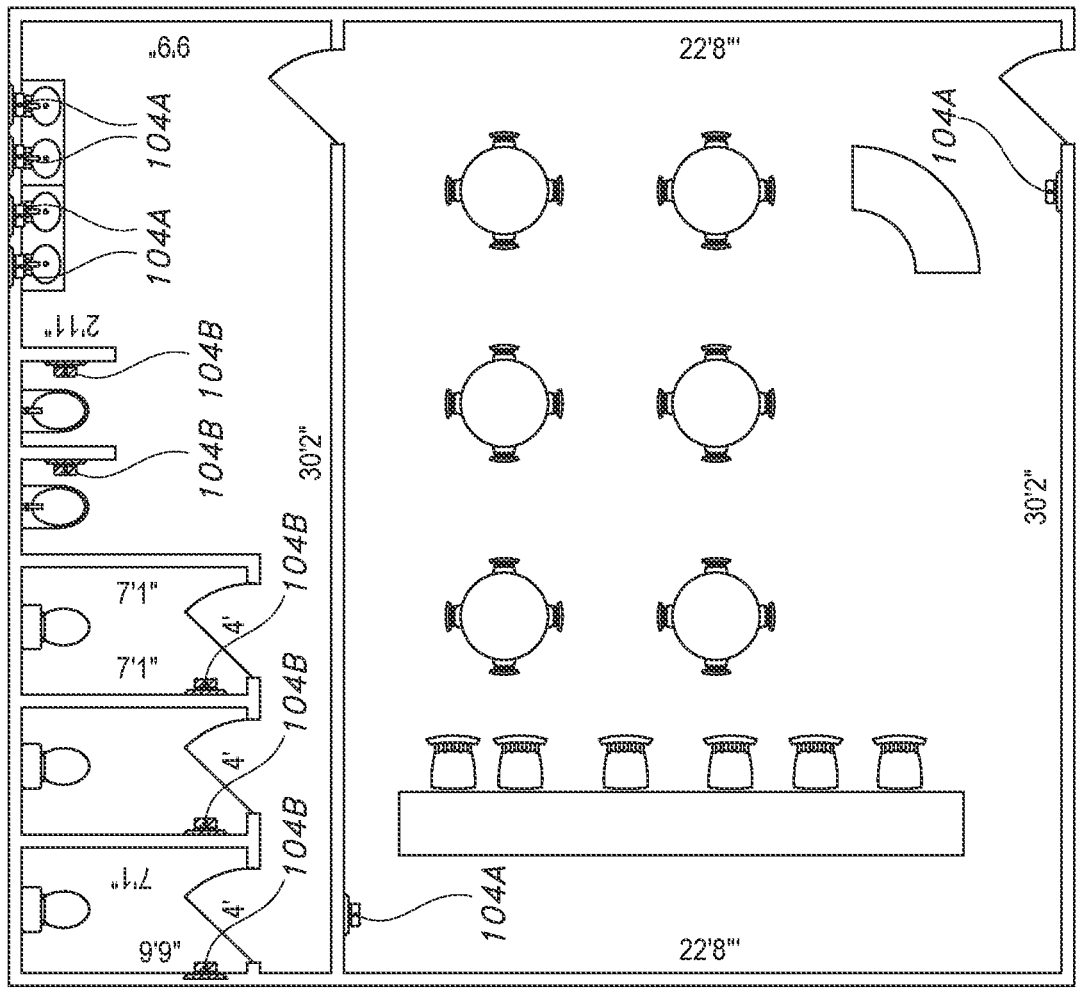
FIG. 24 illustrates examples of a deployment of smart hygiene devices in a network within an office space.

In another example, as shown in FIG. 24, devices 104A and 104B within a mesh network, cooperative network, cluster computing network, or some other type of distributed network, may be configured for specific and differing purposes. For example, devices 104B in common areas, such as a conference room in an office, may be configured to detect persons present in the room based on detection of mobile computing devices 182 present, as described herein, and devices 104A in private areas, such as restrooms, may be configured to detect the occurrence or absence of handwashing. Additional devices in the restroom may also be configured to detect persons present in the room based on detection of mobile computing devices 182 present, so that unique individuals may be paired with each handwashing opportunity, and each handwashing occurrence or absence. Summary data and analytics may be shared across the platform 102 and provided to a platform application 105 where the data may be viewed within a dashboard 176.

Figure 25:
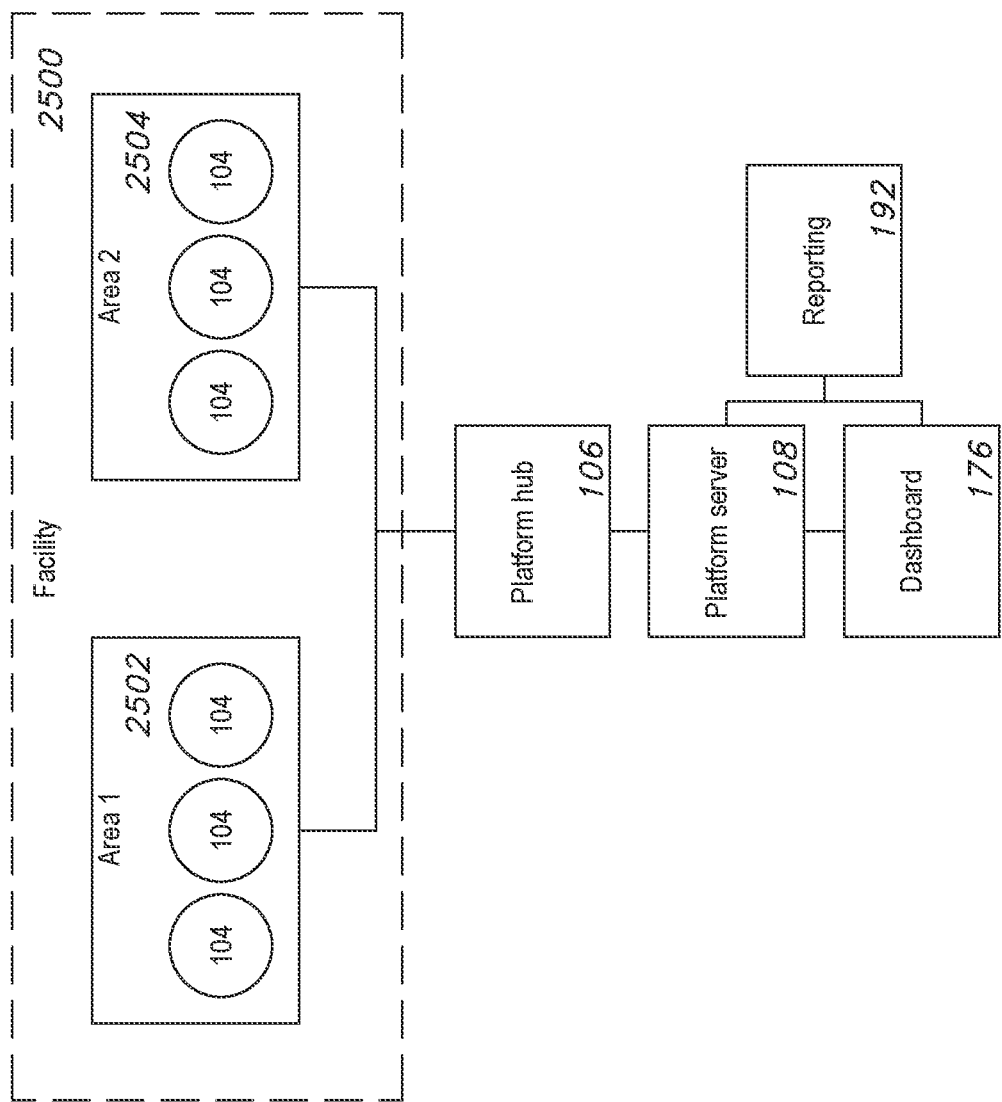
FIG. 25 illustrates a multi-area deployment of smart hygiene devices across a facility and an associated reporting process.

In embodiments, the platform 102 may include an API system 178 that manages one or more APIs of the platform 102 and exposes the APIs to one or more related applications or third-party systems. An SDK 180 may be further associated with the platform 102 and used to develop software applications that may be used to configure the smart hygiene devices 104, facilitate communications with the platform 102 and among the devices 104, networks, hubs 106 and servers 108 of the platform 102, as well as facility smart devices 142, hubs 144, servers 146 and the like that are external to the platform 102. Such software may also be configured to monitor, track, and report on smart hygiene device 104 activity, and to configure a set of services for integration with the platform 102. Monitoring may be used to oversee levels of smart hygiene device 104 usage, for example relative to a stated goal of a business. Independent arrays of smart hygiene devices 104, including arrays of smart hygiene devices 104 connected within a mesh network, cooperative network, cluster computing network, or some other type of distributed network, may be associated with defined units of a facility and their usage monitored and compared as part of, for example, a hygiene campaign or initiative. Referring to FIG. 25, a facility 2500 may define areas within it such as an Area 1 at 2502 and an Area 2 at 2504, each with a smart hygiene device array 104. These areas might conform to a physical space such as a room like a bathroom, but they may also be multi-room domains that are defined by a function of the facility, such as "Kitchen" "Storerooms" "Offices." As employees, customers, and others visit the areas (2502, 2504), the smart hygiene devices 104 may monitor hygienic opportunities and completed hygienic activities and communicate with a platform application 105, mesh network, cooperative network, cluster computing network, or some other type of distributed network, platform hub 106, or plurality of platform hubs 106, that coordinates with each smart hygiene device array 104 in the facility 2500. The platform application 105, device 104 networks, and/or platform hubs 106 may communicate with a platform server 108, or plurality of platform servers 108, and populate platform data 110 and/or external data sources 148 with the hygiene behavior information. As a hygiene campaign progresses, a manager may use the platform application 105 and an associated dashboard 176 to identify behavioral or environmental modifications needed to increase compliance, such as more handwashing by employees. The parameters of full compliance may be specified within the platform application 105, and iteratively reporting 192 on (e.g., daily) within a facility, and alerts may be sent out as regards the performance of persons at the facility in meeting such parameters.

The platform 102 may be deployed in association with a plurality of facilities and may be particularly relevant for facilities and industries where personal hygiene is emphasized or required, for example, in healthcare, hospitality, education, travel, fitness and/or sports, government, entertainment, personal services, and also within the "smart home" or enterprise.

The platform 102 may include a set of services configured to induce hygiene-promoting behavior in a hospitality environment, including a set of hospitality entity data integration and information technology services.

The platform 102 may include a set of services configured to induce hygiene-promoting behavior in an education environment, including a set of hospitality entity data integration and information technology services.

The platform 102 may include a set of services configured to induce hygiene-promoting behavior in a travel environment and a set of services for tracking hygiene behaviors and/or encouraging the modification of hygiene behaviors in a mobility service travel environment.

The platform may include a set of services configured to induce hygiene-promoting behavior in a travel environment, including a set of travel data integration and information technology services.

The platform 102 may include a set of services configured to induce hygiene-promoting behavior in a smart home environment, including a set of smart home data integration and information technology services.

The platform 102 may include a set of services configured to induce hygiene-promoting behavior in an entertainment environment, including a set of entertainment data integration and information technology services.

The platform 102 may include a set of services configured to induce hygiene-promoting behavior in an enterprise environment, including a set of enterprise data integration and information technology services.

The platform 102 may include a set of services configured to induce hygiene-promoting behavior in a fitness/sports environment, including a set of fitness/sports data integration and information technology services.

The platform 102 may include a set of services configured to induce hygiene-promoting behavior in a personal services environment, including a set of personal services data integration and information technology services.

The platform 102 may include a set of services configured to induce hygiene-promoting behavior in a government environment, including a set of government data integration and information technology services.

In embodiments, a user may communicate with the platform 102 using a mobile computing device 182, such as a smart phone, tablet, watch, or some other type of mobile computing device. In examples, such communication may be through Bluetooth Low Energy (BLE), near field communication (NFC), or some other communications protocol. A software application 105 associated with the platform 102 may include a dashboard 176 that is presented to the user on a mobile computing device 182. The application 105 and dashboard 176 allow a user to monitor and configure the devices 104 within a facility. The dashboard may be used to present a user with summaries of handwashing or other hygienic events, such as hygienic behaviors in relation to a stated facility goal, department goal, and/or personal goal. The dashboard may present a mapping functionality to indicate the current locations of deployed devices 104 and the usage statistics that are associated with devices. "Heat maps" and other visual presentations may be used to graphically show a user, like a facility manager, where hygienic behaviors are in compliance with stated parameters and where they are not. This may be presented for regions of a facility, across an entire facility, and/or across a set of facilities.

Figure 26:
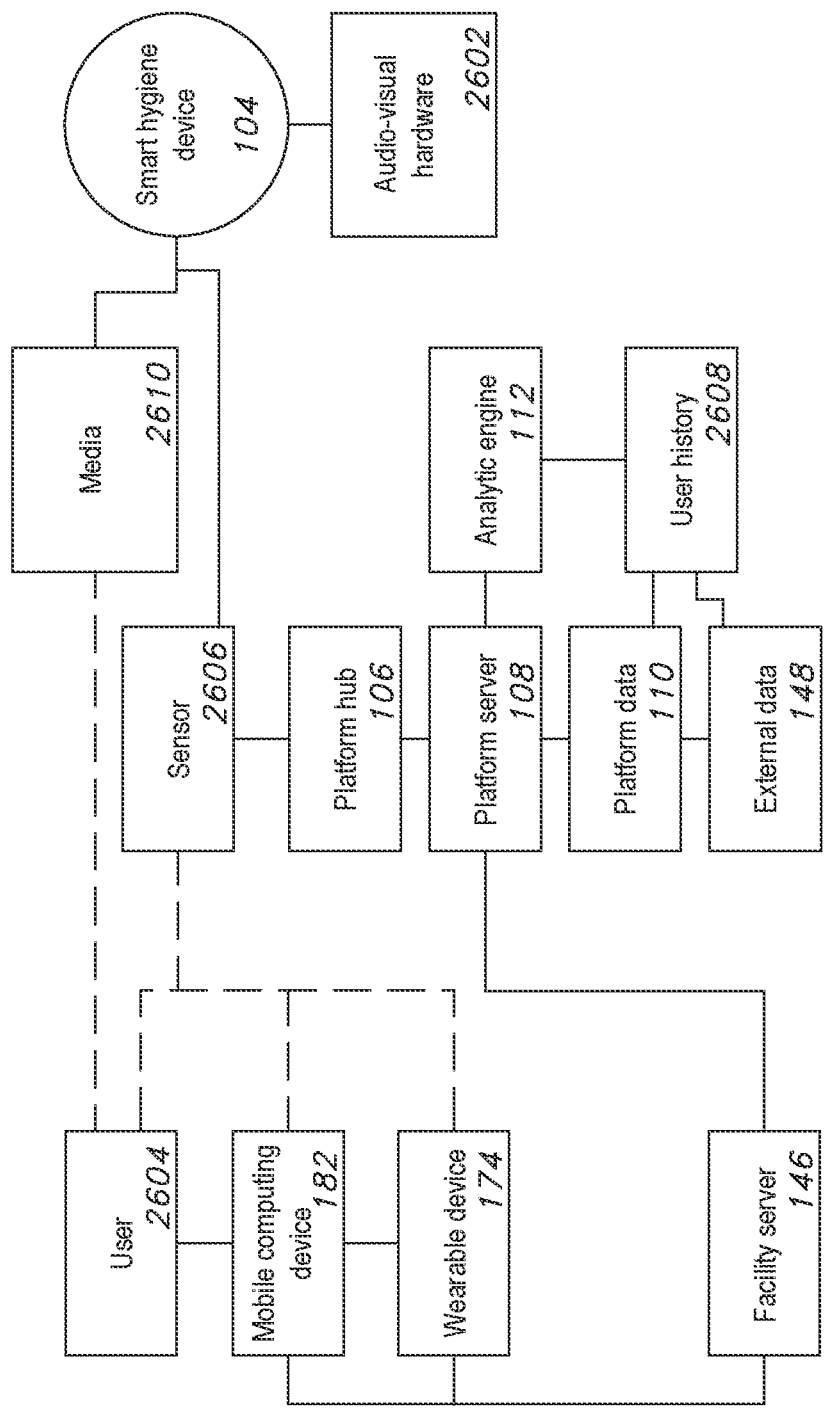
FIG. 26 illustrates a simplified process flow for presenting personalized media to a user using smart hygiene devices.

In embodiments, and referring to FIG. 26, the smart hygiene devices 104 of the platform 102 may include or be associated with audio-visual hardware, software and content. Such audio-visual hardware 2602 may include, but is not limited to, LEDs or other lighting, speakers, and/or a screen, such as an OLED screen for presenting media 2610 to users. Upon entering a room in which smart hygiene devices 104 are located, the motion of a user 2604 may be identified by smart hygiene devices 104 connected with a mesh network, cooperative network, cluster computing network, or some other type of distributed network, a sensor 2606 of the platform 102, for example using a PIR sensor as described herein. The platform 102 may detect the user 2604 based at least in part upon information that is associated with a mobile computing device 182. The user 2604 may be identified as a specific individual, or alternatively simply identified as an anonymous, unique individual. Upon detection of personally identifiable information (PII) pertaining to a person in proximity to a smart hygiene device 104, the platform may present an informed consent request to a mobile computing device associated with the person to obtain their consent for the collection of the person's PII. This information may be used by the platform 102 analytics engine 112 to locate other platform data 110 or external data sources 148 about the user 2604, for example prior hygiene events 2608 of the user 2604 such as a handwashing event, or a missed handwashing opportunity. Continuing the example, as the user 2604 enters the room in which the smart hygiene devices 104 of the platform 102 are located, the devices 104 may present an LED array that indicates the number of opportunities that users have had to, for example, wash their hands, along with other lights indicating the number that successfully completed handwashing. A speaker may also play personalized audio content for the user entering the room, such as an informative message on how to properly wash hands and/or a personalized message to encourage compliance, such as "Hello, the Kitchen Department is targeting 100% handwashing compliance for the month of June. Please do your part." Identification of the user may also be made based in part on external data sources 148, such as a personal identifier 172 or wearable device 174 data stored by the facility and accessible to the platform 102 from, for example, a facility server 146. The smart hygiene devices 104 of the platform 102 may also present media 2610 such as audio-visual content on a screen, such as photographs, graphics and/or videos. Such screens may be used to present summary data, analogous to that described above using LEDs, regarding handwashing or other hygienic events occurring on the platform 102. Lighting or sound may also be used by the smart hygiene devices 104 of the platform 102 to attract the attention of a person in proximity to a smart hygiene device 104 and serve as a means of reminding the person to wash their hands or perform some other type of hygienic act. Sound may also be provided in the form of music or a song. In an example the music may be played for the duration that one should wash one's hands in order to properly sanitize. Lighting may be used by the smart hygiene devices 104 in a similar manner to indicate the proper duration of an activity like handwashing. The platform may include a system for providing an audio-visual experience for the promotion of hygiene behaviors having a system for facilitating progressive reminders as a person crosses an environment and passes one or more points of reference. The progressive reminders may continue to play until the wanted hygiene event is performed, such as hand washing.

Figure 27:
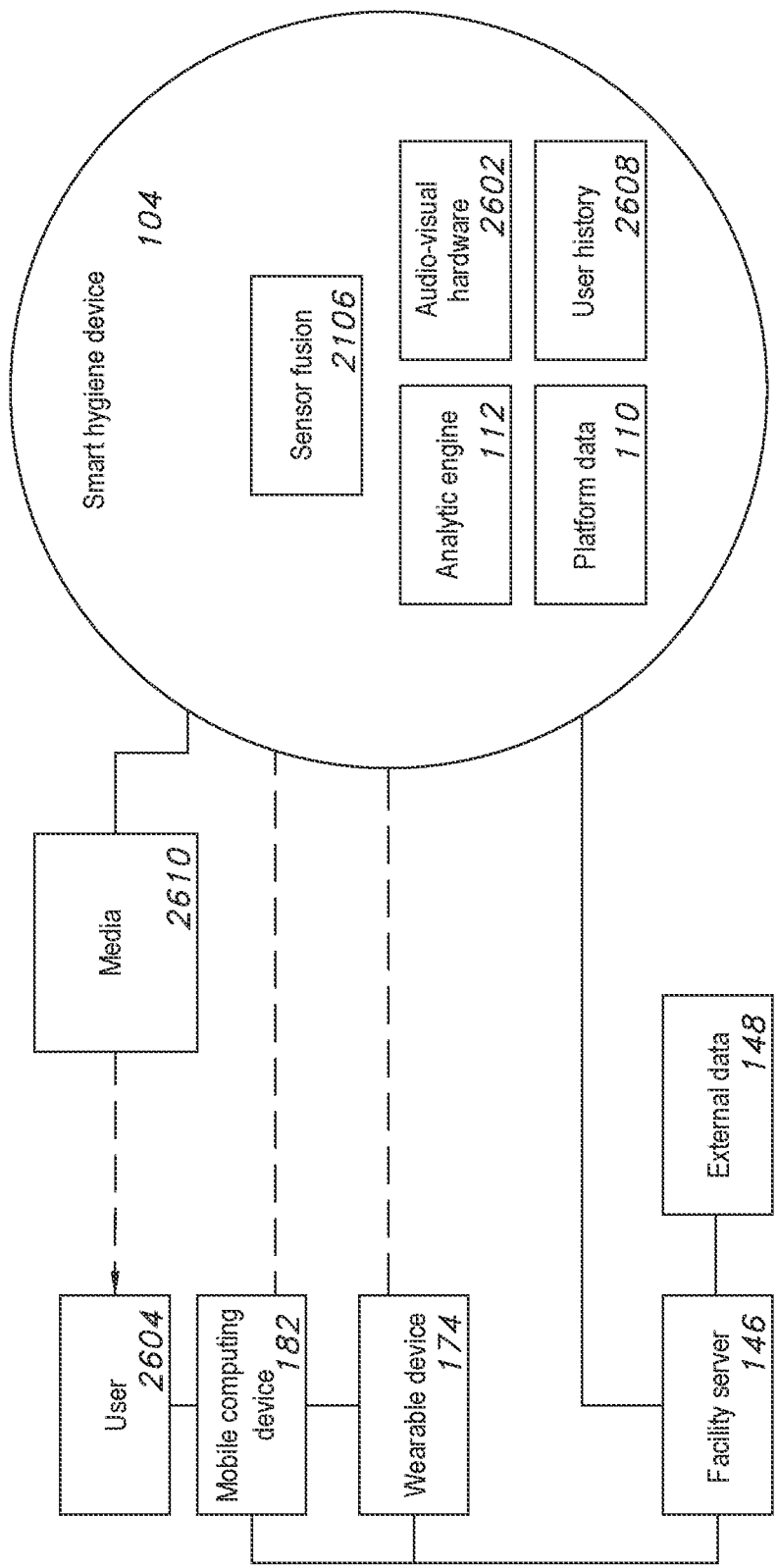
FIG. 27 illustrates a simplified process flow for presenting personalized media to a user using smart hygiene devices within a network.

In embodiments, and referring to FIG. 27, a smart hygiene device 104 may be connected with other devices in a mesh network, cooperative network, cluster computing network, or some other type of distributed network, and include, within the device, audio-visual hardware, software and content. Such audio-visual hardware 2602 may include, but is not limited to, LEDs or other lighting, speakers, and/or a screen, such as an OLED screen for presenting media 2610 to users. Upon entering a room in which smart hygiene devices 104 of a network are located, a user's 2604 mobile computing facility 182 may be detected by a smart hygiene device sensor 104 using BLE, as described herein. The device 104 may detect the user 2604 based at least in part upon information that is associated with the mobile computing device 182. This information may be used by the device 104 to locate other platform data 110 or external data sources 148 about the user 2604, for example prior hygiene events 2608 of the user 2604 such as a handwashing event, or a missed handwashing opportunity. As the user 2604 enters the room in which the smart hygiene devices 104 of the network are located, the devices 104 may present personalized media 2610 to the user. For example, a speaker may play a preferred song for the user entering the room. Identification of the user may also be made based in part on external data sources 148, such as a personal identifier or wearable device 174 data stored by the facility and accessible to the platform 102 from, for example, a facility server 146.

In embodiments, the platform may include a system for providing an audio-visual experience for promotion of hygiene behaviors wherein the audiovisual experience includes an advertisement that plays during the recommended duration of a handwashing event.

In embodiments, the platform 102 may have a network connectivity system for enabling network entities to connect to the platform. This may include a gateway system and a peer-to-peer configuration system for enabling peer-to-peer communication among a set of hygiene-promoting devices, and for providing network connectivity between a set of hygiene promoting devices and another system.

In embodiments, the platform 102 may have a cloud platform for receiving data and other inputs collected in one or more environments and transmitted to the cloud platform over one or more networks. A set of services may be deployed on a cloud platform for receiving data and other inputs collected in one or more environments and transmitted to the cloud platform over one or more networks. The platform 102 may include a set of services and interfaces configurable to encourage hygiene-promoting behavior for a user environment, where the services are configured in a microservices architecture.

Figure 28:
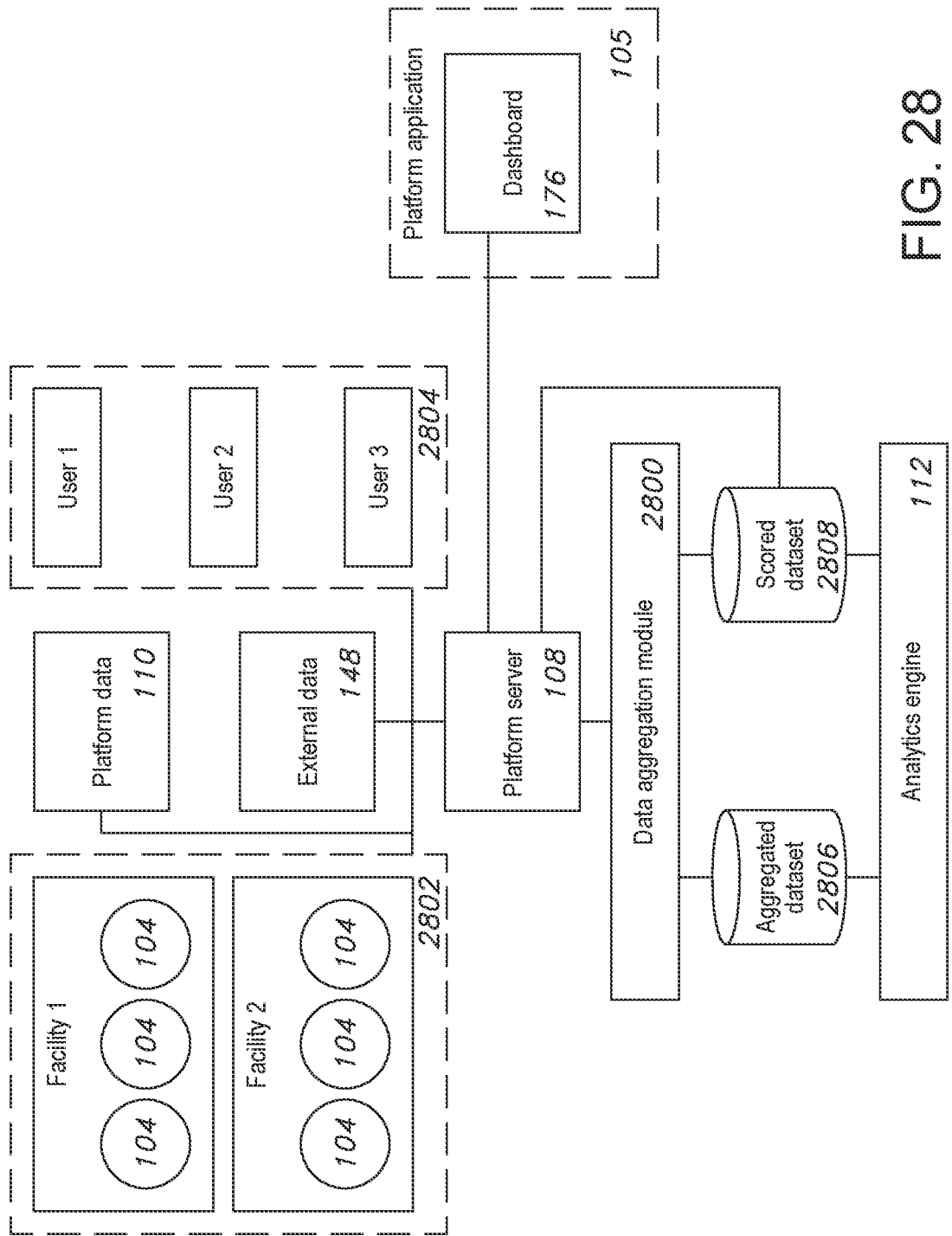
FIG. 28 illustrates a simplified view of a data aggregation and scoring process.
Figure 29:
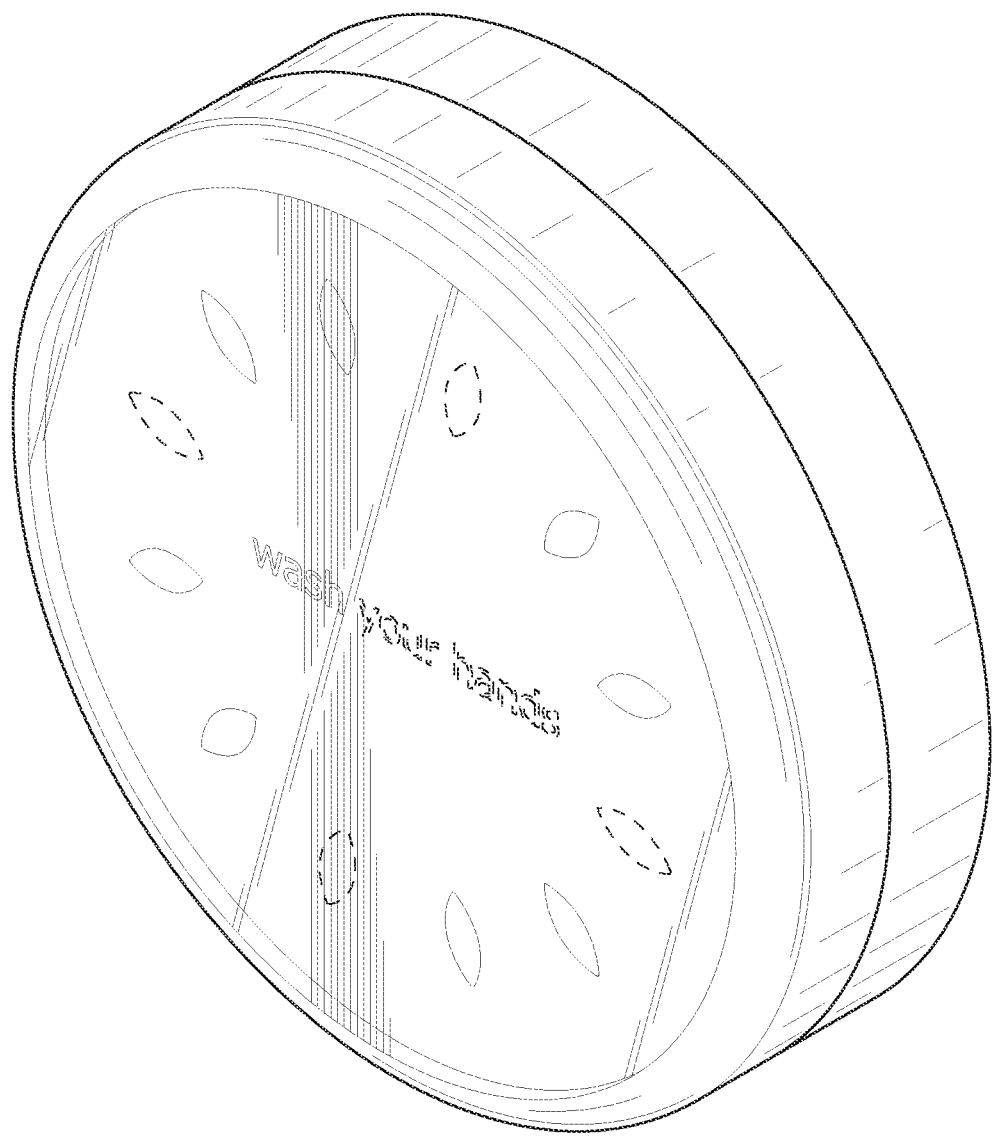
FIGS. 29 through 37 illustrate examples of smart hygiene device form factors.
Figure 30:
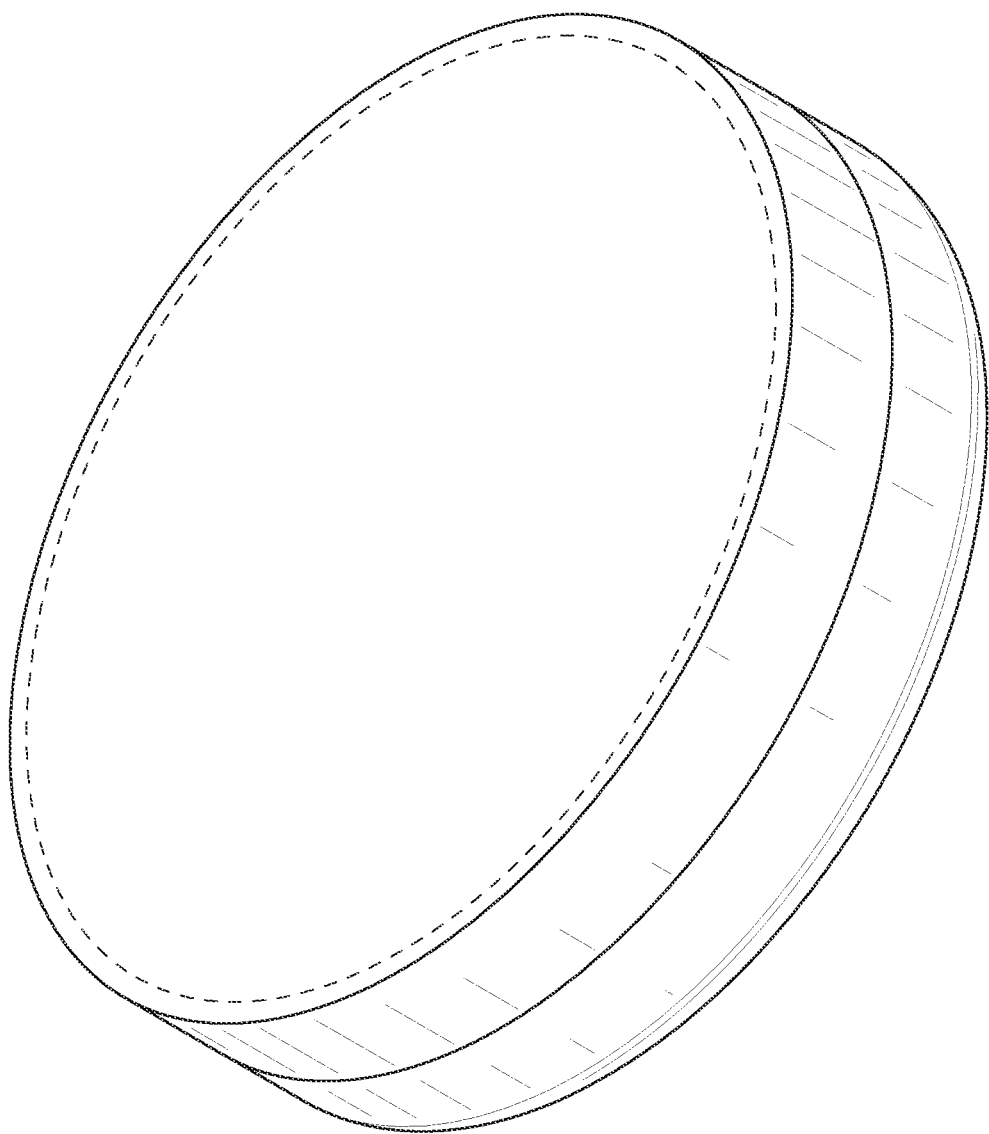
Figure 31:
Figure 32:
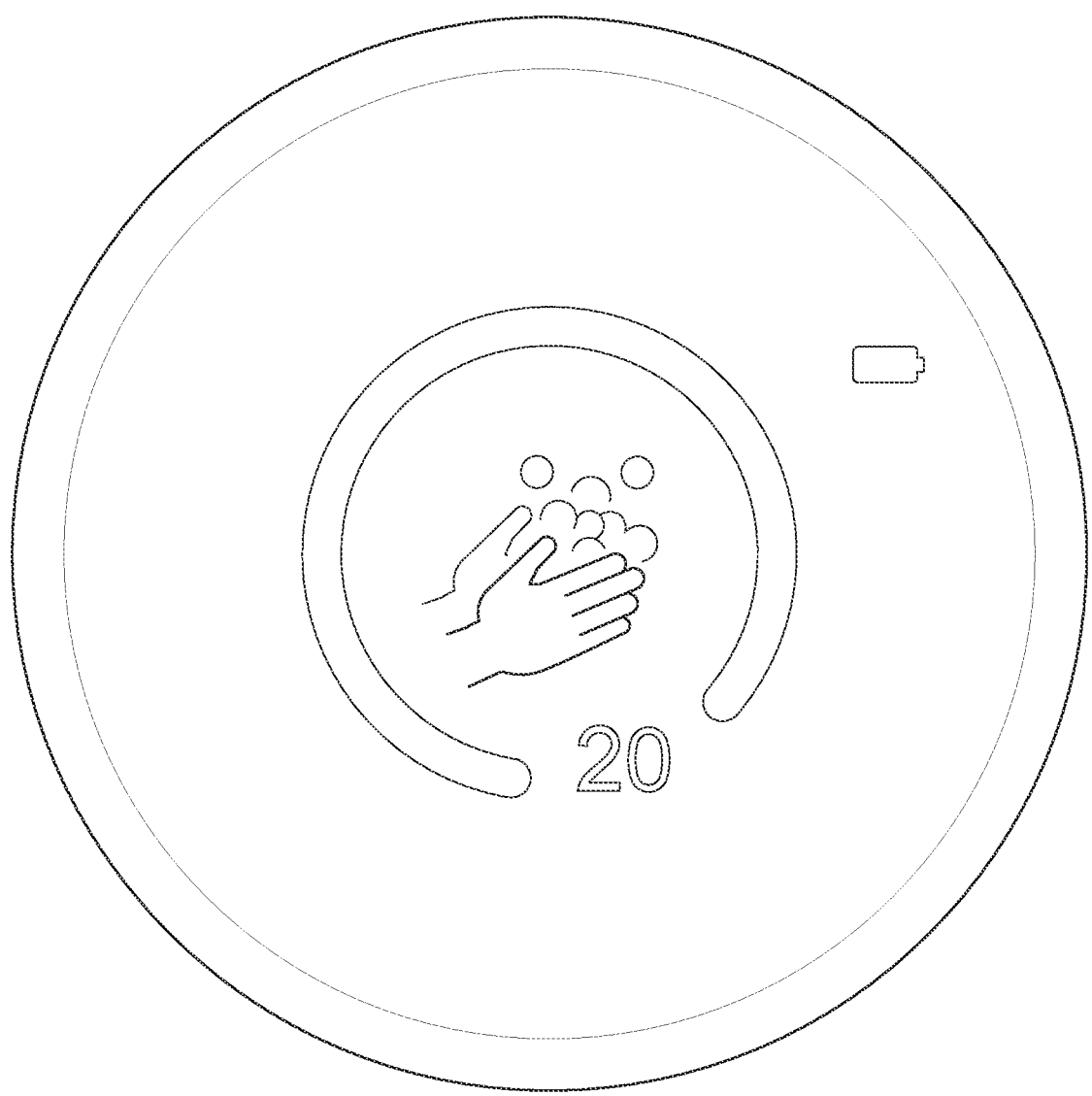
Figure 33:
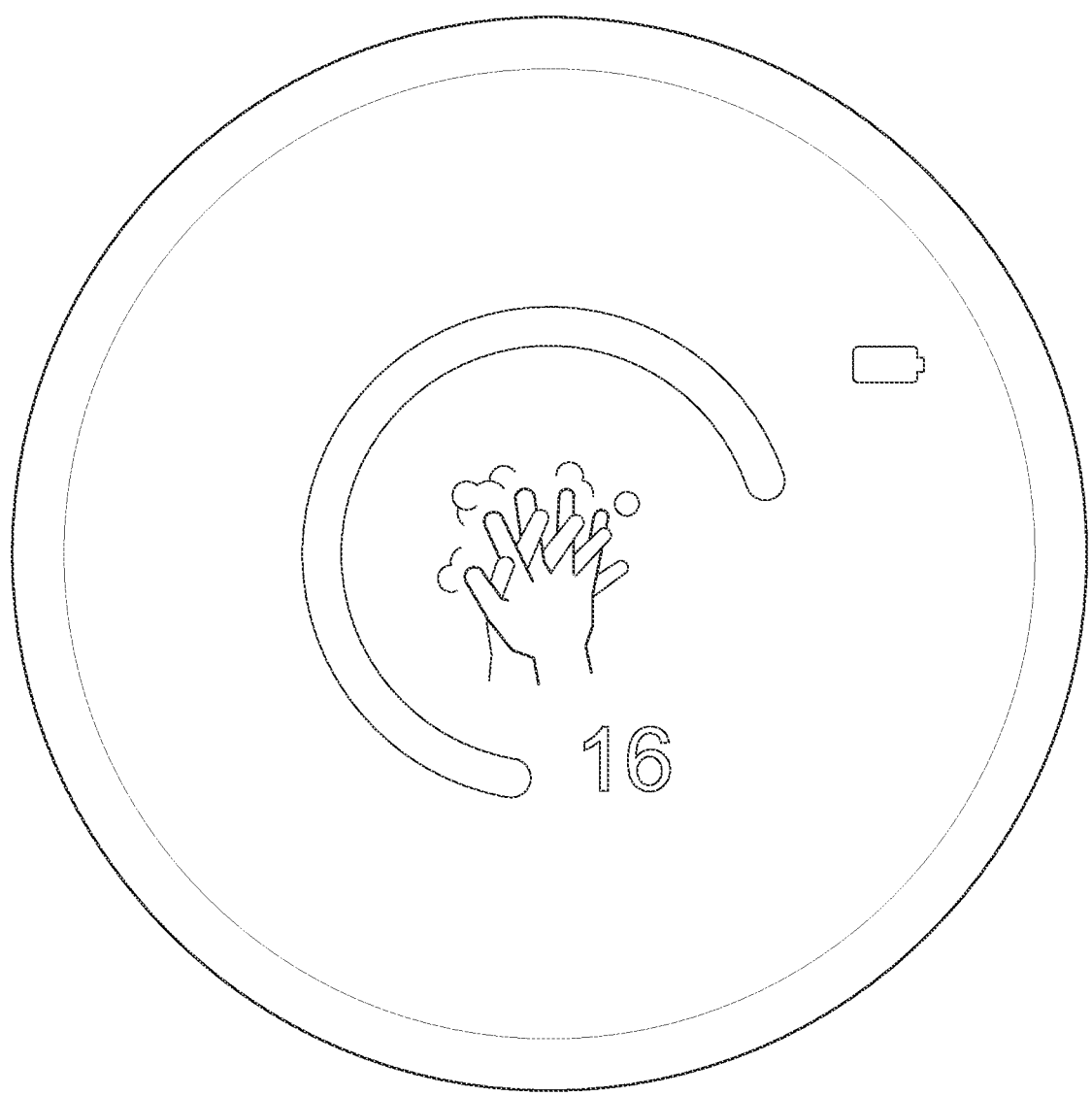
Figure 34:
Figure 35:
Figure 36:
Figure 37:
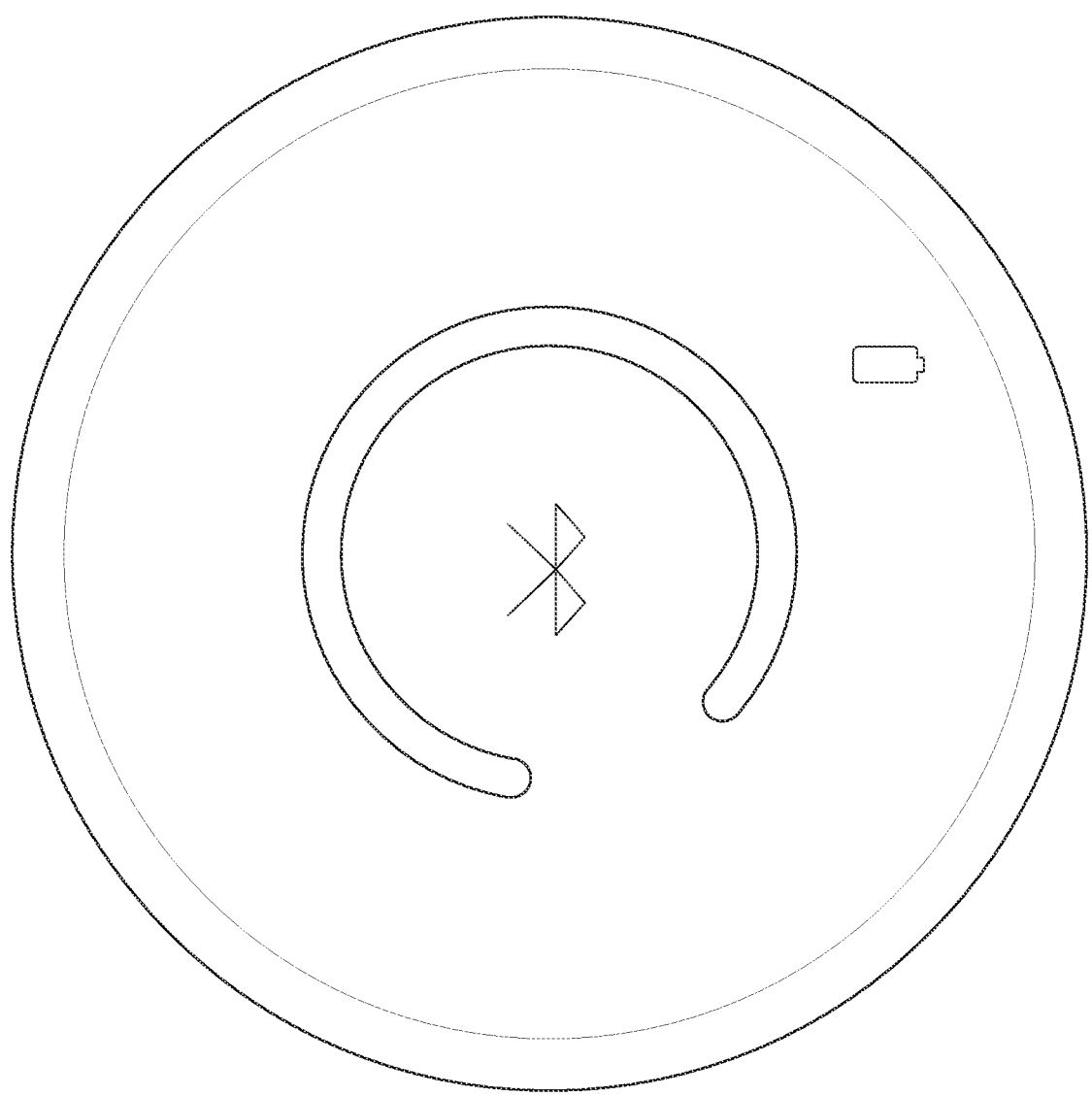

In embodiments, and referring to FIG. 28, the platform 102 may have an analytics engine 112 for performing analytics related to hygiene behavior. The platform 102 may have platform data 110 and a data aggregation system 2800 for aggregating hygiene behavioral data. The data aggregation system 2800 may be used for aggregating hygiene behavioral data 2806 across a set of devices 104, a set of locations or facilities 2802, and/or a population of individuals 2804. In examples, the analytics engine 112 may perform scoring actions including a community score system for generating a community score 2808 based on handwashing behavior compliance in an environment such as a community score 2808 that is calculated based on the proportion of people entering the environment that wash their hands. The community score 2808 may be present to a user in, for example, a dashboard 176 associated with the platform 102. In other examples, a community score system may be provided by the analytics engine 112 for generating a community score 2808 based on handwashing behavior compliance in an environment, where the community score 2808 is calculated based on the proportion of people entering the environment washing their hands and the proportion of people washing their hands for a recommended duration of time. The platform 102 may include a community score system for generating a community score 2808 for an enterprise across multiple locations based on hand washing behavior in one or more environments of the multiple locations, wherein the community score 2808 is calculated based on the proportion of people entering an environment that wash their hands. In other examples, the platform's analytics engine 112 may also provide a rating system for rating environments according to hygiene behavior compliance, such as according to the community score for the environment.

In embodiments, the platform 102 may include a system for creating personal profiles with accompanying personal data structures for storing personal information.

In embodiments, the platform 102 may include an analytics system for performing an analytic operation to produce an analytic measure related to hygiene behavior and having analytics indicating hygiene performance levels relevant to a particular individual.

In embodiments, the platform 102 may include an analytics system for performing an analytic operation to produce an analytic measure related to hygiene behavior and having analytics indicating hygiene performance levels relevant to a population of individuals.

In embodiments, the platform 102 may include an analytics system for performing an analytic operation to produce an analytic measure related to hygiene behavior and having analytics indicating hygiene performance levels relevant to a location of a business.

In embodiments, the platform 102 may include an analytics system for performing an analytic operation to produce an analytic measure related to hygiene behavior and having analytics indicating hygiene performance levels relevant to a brand across multiple locations.

In embodiments, the platform 102 may include an analytics system for performing an analytic operation to produce an analytic measure related to hygiene behavior and having analytics indicating hygiene performance levels relevant to the effectiveness of hygiene stimulus measures.

In embodiments, the platform 102 may include an analytics system for performing an analytic operation to produce an analytic measure related to hygiene behavior and having analytics indicating hygiene performance levels relevant to the effectiveness of arrangements of hygiene stimulus devices.

In embodiments, the platform 102 may use BLE proximity sensing, passive infrared sensors, and/or active infrared sensors for detecting the presence of one or more persons. Such sensing may be performed by one or more smart hygiene devices 104 configured to attach to, for example, a vessel, conduit, and/or soap dispenser. In an alternate embodiment, such sensing may be performed by one or more smart hygiene devices 104 embedded within a vessel, conduit, and/or soap dispenser. A smart hygiene device 104 may be provided in a plurality of form factors including, but not limited to shapes such as a disc, a puck, a sphere, cube or rectangular box, or asymmetric form. Non-limiting examples of smart hygiene device form factors are shown in FIGS. 29 through 37. The form factor may house a BLE chipset, multiple PCBs, sensors and other electronics enabling cross-device communications. BLE may also be used by the platform 102 to detect cohorts. For example, in a hospital environment doctors and nurses may wear BLE beacons and the platform 102 may use the beacons to detect which cohorts are in proximity to the smart hygiene devices 104. Similar detection may be carried out in other facility spaces, such as conference rooms, schools, and/or a home where people carry phones. For example, the platform 102 may detect cohorts from handset signatures to obtain a representation of how many people are present in a room. This rudimentary count may then be used by the platform 102 to compare the number of persons present in a room or space to the number of handwashes performed.

In embodiments, passive IR may be blended with active IR. Passive IR may detect a warm body very well but may lack accuracy and be unable to distinguish two people versus what may appear to be one large warm region that is in fact populated by the two people. The platform 102 may use passive IR alongside active IR that sends an IR light source and reads the reflection. This may provide more accuracy for short range detection of handwashing. BLE combined with passive IR and active IR may enable the platform 102 to determine an entire room's "dynamics" in terms of number of people present during a time duration and the number of events, such as handwashing. This greater accuracy can be shown, in turn, to improve the accuracy of the platform's analytics and reporting 192.

In embodiments, the platform 102 may provide BLE proximity sensing, passive infrared sensors, and active infrared sensors for detecting the presence of one or more people, where the smart hygiene device is configured to attach to a vessel, conduit, and/or hand sanitizer dispenser and/or sanitizing wipe dispenser.

In embodiments, the platform 102 may provide BLE proximity sensing, passive infrared sensors, and active infrared sensors for detecting the presence of one or more people, where the smart hygiene device is configured to attach to a vessel, conduit, and/or soap dispenser, where the smart hygiene device has a lighting system and wherein the lighting system is configured to activate upon detection of the one or more people.

In embodiments, the platform 102 may provide BLE proximity sensing, passive infrared sensors, and active infrared sensors for detecting the presence of one or more people, where the smart hygiene device is configured to attach to a vessel, conduit, and/or soap dispenser and where the smart hygiene device 104 has a sound system that is configured to activate upon detection of the one or more people.

In embodiments, the platform 102 may provide BLE proximity sensing, passive infrared sensors, and active infrared sensors for detecting the presence of one or more people, where the smart hygiene device 104 is configured to attach to a vessel, conduit, and/or soap dispenser and the smart hygiene device 104 is in communication with one or more hand wash sensors that are configured to detect whether a human washed their hands and/or hand washing time.

In embodiments, the platform 102 may provide BLE proximity sensing, passive infrared sensors, and active infrared sensors for detecting the presence of one or more people, where the smart hygiene device 104 is configured as a vessel, conduit, and/or soap dispenser.

In embodiments, the platform 102 may provide BLE proximity sensing, passive infrared sensors, and active infrared sensors for detecting the presence of one or more people, where the smart hygiene device 104 is configured as a vessel, conduit, and/or hand sanitizer dispenser.

In embodiments, the platform 102 may include a sensor fusion system configured to combine data from sensors of at least two types, where the fused sensor data is processed to produce an indicator of hygiene behavior and the sensor fusion system combines data from a mobile phone and a hygiene promoting device that is fixed in an environment.

In embodiments, the platform 102 may include a sensor fusion system configured to combine data from sensors of at least two types, where the fused sensor data is processed to produce an indicator of hygiene behavior and the sensor fusion system combines data from multiple fixed hygiene promoting devices.

In embodiments, the platform 102 may include a sensor fusion system configured to combine data from sensors of at least two types, where the fused sensor data is processed to produce an indicator of hygiene behavior and the sensor fusion system combines data from an edge network and a fixed hygiene promoting device.

In embodiments, the platform 102 may include a data integration system for integrating data across distributed sets of smart hygiene devices 104.

In embodiments, the platform 102 may include a sensor fusion system configured to combine data from sensors, where the data is related to hygiene behavior activity.

In embodiments, the platform 102 may provide BLE proximity sensing, passive infrared sensors, and active infrared sensors for detecting the presence of one or more people and having a sensor fusion system and wherein the smart hygiene device 104 is configured to attach to a vessel, conduit, and/or soap dispenser and is in communication with one or more handwash sensors that are configured to detect whether a person washed their hands and/or hand washing time, and the smart hygiene device 104 has a lighting system and/or a sound system configured to activate upon detection of the one or more people.

In embodiments, the platform 102 may provide BLE proximity sensing, passive infrared sensors, and active infrared sensors for detecting the presence of one or more people and having a sensor fusion system, where the smart hygiene device 104 is configured as a vessel, conduit, and/or soap dispenser and wherein the smart hygiene device 104 is in communication with one or more handwash sensors that are configured to detect whether a person washed their hands and/or hand washing time, and the smart hygiene device 104 has a lighting system and/or a sound system configured to activate upon detection of the one or more people.

In embodiments, the platform 102 may include a machine learning and/or artificial intelligence system configured to optimize an audiovisual experience of a smart hygiene device 104 to encourage hygiene behavior modification.

In embodiments, the platform 102 may include a machine learning and/or artificial intelligence system configured to optimize the placement of a smart hygiene device 104 to encourage hygiene behavior modification.

In embodiments, the platform 102 may include a machine learning and/or artificial intelligence system configured to classify hygiene-related activities.

In embodiments, the platform 102 may include a machine learning and/or artificial intelligence system configured to classify hygiene-related activities as compliant or non-compliant.

In embodiments, the platform 102 may include a machine learning and/or artificial intelligence system configured to classify activities that require hygiene responses.

In embodiments, the platform 102 may include a machine learning and/or artificial intelligence system configured to classify people as employees or customers.

In embodiments, the platform 102 may include a machine learning and/or artificial intelligence system configured to generate a context-sensitive prediction of hygiene behavior.

In embodiments, the platform 102 may include a machine learning and/or artificial intelligence system configured to automate control of a hygiene behavioral modification experience.

In embodiments, the platform 102 may include a machine learning and/or artificial intelligence system configured to generate a recommendation related to washing hands and/or hand sanitizing.

In an example embodiment of a deployment of the platform 102 within a hospital, smart hygiene devices 104 may be arrayed and associated with specific units, departments or regions of a hospital, with each smart device array 104 in communication within a mesh network, cooperative network, cluster computing network, or some other type of distributed network, or with at least one platform hub 106 and platform server 108. For example, each care unit of the hospital (e.g., Intensive Care Unit, Pediatrics, Outpatient Surgery, Administrative offices, and so forth) may have an array of devices dedicated solely to it in order for a manager of the care unit to monitor the hygiene practices of persons within the unit. Based at least in part on platform data 110 relating to similar facilities and modeling done within the analytics engine on this data using machine learning and artificial intelligence tools, the platform 102 may make recommendations on the number of smart hygiene devices, the physical positioning of their placement in the care unit, or some other characteristic in order to optimize and promote hygienic behaviors. Smart hygiene devices 104 may be placed within the care unit as devices that are independent of vessels, conduits, and/or dispensers, such as soap, disinfectant, wipes, towels or other sanitary products, or alternatively the smart hygiene devices 104 may be embedded within the vessels, conduits, and/or dispensers. A manager overseeing a hygiene promotion initiative using the platform 102 may login to the platform using a mobile computing device 182, web browser 184 or other device to access the dashboard 176. The manager may also utilize an application 105 that the hospital or other entity has used to customize utilization of the platform 102 using a development platform 188, SDK 180, API 178 and the like. Within the dashboard the manager may access the analytics engine 112 and platform data 110 to specify parameters and goals for the hygiene promotion initiative. This might be expressed as a target number for total number of persons washing hands during a shift, a target percentage of handwashes completed of the total handwashing opportunities, or some other target metric of interest to the manager. Using these metrics the manager may also use the dashboard 176 to specify the nature and timing of alerts and other communications the platform 102 will deliver based on the hygienic performance of a care unit. For example, the manager may specify a target of 90% of all handwashing opportunities resulting in a completed handwashing. She may also specify a completion rate of 79% or lower as necessitating an alert be sent from the platform 102. A hygiene campaign module 190 may be in communication with the platform 102 to receive this data on a rolling basis and update, for example, a website presentation so that all persons working in a given facility or care unit may see how they are performing and/or how all persons on the care unit are performing relative to the stated hygiene goal. Other alerts may be sent via email 198, third party platform 196 or other reporting 192 means.

Continuing the example, as employees of the care unit come in proximity to a smart hygiene device 104, the device may detect their presence based on a passive IR, active IR, or monitoring sensor as described herein, and provide an audio, visual or audio-visual cue to the person, such as a light, sound, a song, a taped message or video, as described herein. This may serve to remind the person of the presence of a vessel, conduit, and/or dispenser, such as a soap dispenser, and the need for handwashing. The facility may have personnel identifiers 172 stored, for example employee badges, passes or other identification that may be used or required to enter a secured area. This may be used to identify the person and personalize audio-visual content presented by a smart hygiene device 104. For example, the device may inform the person how long it has been since they last washed their hands, or provide information that is relevant to the user, based on their position, shift, patient care or some other factor that is associated with the personnel identifier of the person. Alternatively, the person's wearable device 174 or mobile computing device 182, such as a smart phone, may identify the person. This may also be used to simply identify "a unique person," but anonymously with no personally identifiable information provided to the platform 102. As described herein, upon detection of PII pertaining to a person in proximity to a smart hygiene device 104, the platform may present an informed consent request to a mobile computing device associated with the person to obtain their consent for the collection of the person's PII.

In this example, as the person approaches the smart hygiene device 104 the handwash sensor, as described herein, may detect the hand or other component associated with the person in proximity to a vessel, conduit, and/or dispenser. In other examples, upon detecting the hand or other component associated with the person in proximity to the vessel, conduit, and/or dispenser the platform 102 may initiate dispensing soap, disinfectant, a sanitary wipe or some other hygiene product. The smart hygiene device 104 may be separate from or embedded in a vessel, conduit, and/or dispenser. A dispenser that is associated with the platform 102 may have a plurality of interior compartments for holding different types of disinfectants. The platform 102 may use platform data 110, external data sources 148 and/or personnel identifiers 172 to select which material should be dispensed based on the individual, his occupation or role, data about the care unit or region of the care unit in which the vessel, conduit, and/or dispenser is located, or some other data.

Still continuing the example, as the handwash is occurring, the smart hygiene device 104 may display a light, sound, play a some and/or display audio-visual content and media to the user. This may be a display of the duration for which a proper handwash should occur. Alternatively, it may be instructional material, such as a video informing the user on proper technique, or material updating the user on the performance of the care unit relative to a hygiene campaign goal stored by the platform 102. The duration of the handwashing may be recorded and the platform may use this and other data collected as a marker of the quality of each handwash, which may be shared with a hygiene manager. When the quality and performance of an individual, group or care unit falls below a goal that is stored by the platform, alerts may be distributed to key personnel. Alerts may be provided by text, email, phone call, website posting, or some other means. Alerts, data summaries and other material and reporting 192 from the platform 102 may also be shared with, for example, third party platforms 196 and social media entities 194. For example, a ratings website may receive data for publicly posting that summarizes that all care units of the facility are fully compliant with an industry hygiene standard. This may serve as effective marketing and give facilities reporting such data a competitive advantage in the market.

As the platform records and stores information such as the number and duration of handwashing events, the type of soap or disinfectant dispensed, the duration of each dispense, and the like, this information may be stored as platform data 110 and provided to the analytic engine for the purpose of tracking the volume of disinfectant product usage. This data may be shared with managers to track inventory 158 of disinfectants and automate the scheduling of ordering disinfectant from suppliers based on real time usage data provided by the platform 102. This data may also be used by a manager to spot areas of a facility in which the proportion of proper handwashing durations, soap amounts and the like is unacceptably low. This may assist a manager in allocating resources, such as training, to focus on those areas of a facility with employees who are not fully compliant with a hygiene policy.

In embodiments, the platform 102 may include a system for integrating with a smart home system.

In embodiments, the platform 102 may include a system for integrating with a human resources system.

In embodiments, the platform 102 may include a system for integrating with a smart lighting system.

In embodiments, the platform 102 may include a system for integrating with a machine vision system.

In embodiments, the platform 102 may include a system for integrating with an adenosine triphosphate (ATP) monitoring system/meter.

In embodiments, the platform 102 may include a system for integrating with a smart toilet.

In embodiments, the platform 102 may include a system for integrating with a smart garbage disposal system.

In embodiments, the platform 102 may include a system for integrating with a smart faucet system.

In embodiments, the platform 102 may include a system for integrating with a vessel, conduit, and/or soap dispenser system.

In embodiments, the platform 102 may include a system for integrating with a hand sanitizer dispensing system.

In embodiments, the platform 102 may include a system for integrating with a sanitizing wipe dispensing system.

In embodiments, the platform 102 may include a system for integrating with a smart faucet system.

In embodiments, the platform 102 may include a system for integrating with a wearable device.

In embodiments, the platform 102 may include a system for integrating with an online rating/review system.

In embodiments, the platform 102 may include a system for integrating with a mobility application.

In embodiments, the platform 102 may include a system for integrating with a customer and/or location tracking system.

In embodiments, the platform 102 may include a system for integrating with a social media system.

In embodiments, the platform 102 may include a system for integrating with a location/business check-in system.

In embodiments, the smart hygiene device 104 may be positioned in a vehicle, including but not limited to a car, van, bus, train, plane, or other transportation means, so that its field of view, for example, covers an interior space occupied by passengers. The smart hygiene device 104 may be placed in an area next to, or within, the entrance to a vehicle, on the back of a seat, or some other location on, in, or associated with a vehicle (e.g., including an area exterior to a vehicle such as a cab stand, bus stop or other area). The smart hygiene device 104 may be battery-powered (or hard wired if located on a wall, next to a door, or in some other location exterior to the vehicle). The motion sensor within or associated with the smart hygiene device 104 may be used to detect people entering the vehicle. The sensor may detect the direction of the motion and may be programmed to detect only a person's entrance to a vehicle and ignore when the person exits the vehicle. Alternatively, it may be programmed to detect a person's entrance to a vehicle and the person's exit from the vehicle using, for example, BLE detection of mobile computing devices 182 on or in proximity to persons near the smart hygiene device 104. This information may also be transmitted to other of the platform's or facilities infrastructure, such as servers, databases and the like, including infrastructure of entities associated with a vehicle, such as a ride-share service, taxi service, public transit service, airline, or some other transportation-related service.

In examples, the smart hygiene device 104 may display the current status of the unit, using, for example, LEDs, or other lighting or media, as described herein. After a person's entry to a vehicle is detected by a motion sensor, a message may be sent to the platform 106. The platform 106 may play a prerecorded sound as a reminder and display an animated sequence on an LED or other media. When a person washes their hands, such as by dispensing hand sanitizer, the handwash sensor may trigger, and the platform 106 may play another pre-recorded sound, video, or some other media item, and, for example, display another animated sequence of lights. For every person who enters the vehicle and washes their hands, the smart hygiene device 104 may record an indicate if, for example, the prior occupant of the vehicle washed their hands and/or present a cumulative measure of handwashing occurring in the vehicle over a defined time period. In an embodiment, for every person who enters the vehicle and doesn't wash their hands, the smart hygiene device 104 may present or send an alert to the vehicle user or next user of the vehicle, the operator of the vehicle, the owner of the vehicle, or some other party. The ratio of signals from the smart hygiene device 104 may be used to calculate a sanitary rating for the vehicle. This sanitary rating may be directly communicated with an application 105 that is associated with the platform 102, and/or including, but not limited to, a ride-share company's application, taxi service application, public transit service application or some other transportation-related service application. Such sanitary status sequences may be locally controlled by the platform 102 but may also be controlled by server software or by an operator. In examples, a preset mode(s) may enable automatic disabling of sound and/or light sequences when the level of ambient light is low, as in, for example, an ambulance, overnight flight, when an occupant should not be disturbed.

In embodiments, a platform server 108 may monitor and report from a plurality of devices to memory, so all vehicle-based data acquired is accessible via the Internet, cloud, intranet, or some other network type. In examples, the acquired data may contain the total number of triggers for each motion and handwash sensor, and the temperature, humidity, air quality and ambient light level at a fixed interval. The current battery voltage in each device may be read and used by the platform server or remote system to issue warnings when a battery needs replacement.

In embodiments, a smart hygiene device 104 may independently operate apart from a platform hub 106 and/or platform server 108, and directly communicate with an application 105 that is associated with the platform 102, including but not limited to a ride-share company's application, taxi service application, public transit service application or some other transportation-related service application.

In embodiments, a vehicle user may communicate with the platform 102 using a mobile computing device 182, such as a smart phone, tablet, watch, or some other type of mobile computing device. In examples, such communication may be through Bluetooth Low Energy (BLE), near field communication (NFC), or some other communications protocol. A software application 105 associated with the platform 102 may include a dashboard 176 that is presented to the vehicle user on a mobile computing device 182. The application 105 and dashboard 176 may allow a user to monitor devices 104 within a vehicle. The dashboard may be used to present a vehicle user with summaries of handwashing or other hygienic events, such as hygienic behaviors in relation to a stated goal or minimum requirement (e.g., as specified by a vehicle user), department goal, and/or other goal. The dashboard may present a mapping functionality to indicate the current locations of deployed vehicles, such as taxis or ride-share vehicles, and the usage and sanitary ratings that are associated with vehicles. Visual presentations may be used to graphically show a user, like a person about to hire a ride-share vehicle, which vehicles' sanitary ratings are in compliance with user-stated requirements and which are not. This may be presented for regions in proximity to a user and/or selected by a user in advance, for example, a user on an airplane that is scheduling a ride-share from the airport upon her future arrival may select among a ride-share company's vehicle options based at least in part on their sanitary ratings.

In embodiments, a smart hygiene device 104 may be connected with other devices in a mesh network, cooperative network, cluster computing network, or some other type of distributed and/or smart or IoT network, including but not limited to a toilet, refrigerator, faucet, garbage can, or some other smart device, and include, within the device, audio-visual hardware, software and content. Such audio-visual hardware 2602 may include, but is not limited to, LEDs or other lighting, speakers, and/or a screen, such as an OLED screen for presenting media 2610 to users. A smart hygiene device 104 may initiate an action based at least in part on an occurrence at another smart devices of a network. For example, upon a flush of a toilet, an opening of a garbage can, the opening of a refrigerator, or use of a faucet, or some other smart device activity, an audio and/or visual reminder to wash hands may be presented on a smart hygiene device 104 or plurality of smart hygiene devices 104. The device 104 may detect the user 2604 based at least in part upon information detected by another smart device. This information may be used by the smart hygiene device 104 and/or platform 102 to locate other platform data 110 or external data sources 148 about the user 2604, for example prior hygiene events 2608 of the user 2604 such as a handwashing event, or a missed handwashing opportunity. As the user 2604 uses a smart device, like a garbage can, in which the smart hygiene devices 104 of the network are located, the devices 104 may present personalized media 2610 to the user based at least in part on prior hygiene events 2608 and smart device usage. For example, if a user has used the garbage can twice but not washed hands, a rule could be invoked to require a smart hygiene device 104 to present a reminder to wash hands. Identification of the user may also be made based in part on external data sources 148, such as a personal identifier or wearable device 174 data stored by the facility and accessible to the platform 102 from, for example, a facility server 146.

In embodiments, the platform 102 analytics engine 112 may perform analytics, such as machine learning, algorithmic modeling and the like, related to scoring, rating, and/or modeling the hygiene behavior occurring at a location, region, within a facility, or some other area. The platform 102 may have platform data 110 and a data aggregation system 2800 for aggregating hygiene behavioral data of, for example, a facility of an entity like a retail store location. The data aggregation system 2800 may be used for aggregating hygiene behavioral data 2806 across a set of devices 104, a set of locations or facilities 2802, and/or a population of individuals 2804. In examples, the analytic engines 112 may perform scoring actions including a rating system for generating ratings based on handwashing behavior compliance in an environment such as a rating that is calculated based on the proportion of people entering the environment, like a retail store, that wash their hands. The rating may be presented to customer of a store in, for example, a dashboard 176 associated with the platform 102. In other examples, a rating system may be provided by the analytics engine 112 for generating a rating based on handwashing behavior compliance in an environment, where the rating is calculated based on the proportion of people entering the environment washing their hands and the proportion of people washing their hands for a recommended duration of time. The platform 102 may include a rating system for generating a rating for an enterprise across multiple locations, for example all of a company's retail stores in a specified region, based on hand washing behavior in one or more environments of the multiple locations, wherein the rating is calculated based on the proportion of people entering an environment that wash their hands. In other examples, the platform's analytics engine 112 may also provide a rating system for rating environments according to hygiene behavior compliance, such as according to a goal, public health standard or other criterion. The rating system may inform an entity's advertising, social media or other public outreach, as a type of hygiene and/or marketing campaign. Such communications may be updated by the platform 102 on a rolling basis and automatically updated to, for example, social media websites or some other type of website or other presentation so that the public may see how a location, facility or entity is performing. Alerts may also be sent via email 198, third party platform 196 or other reporting 192 means in real time.

While only a few embodiments of the present disclosure have been shown and described, it will be obvious to those skilled in the art that many changes and modifications may be made thereunto without departing from the spirit and scope of the present disclosure as described in the following claims. All patent applications and patents, both foreign and domestic, and all other publications referenced herein are incorporated herein in their entireties to the full extent permitted by law.

In embodiments, provided herein is a hygiene behavioral modification platform having a set of services and interfaces configurable to encourage hygiene-promoting behavior for a user environment. In embodiments, provided herein is a hygiene behavioral modification platform having a set of services and interfaces configurable to encourage hygiene-promoting behavior for a user environment and having a set of services deployed on a cloud platform for receiving data and other inputs collected in one or more environments and transmitted to the cloud platform over one or more networks. In embodiments, provided herein is a hygiene behavioral modification platform having a set of services and interfaces configurable to encourage hygiene-promoting behavior for a user environment and having a data integration system for integrating data across distributed sets of smart hygiene devices. In embodiments, provided herein is a hygiene behavioral modification platform having a set of services and interfaces configurable to encourage hygiene-promoting behavior for a user environment and having a set of interfaces and services for operator configuration of a set of behavioral modification parameters for a set of devices managed by the platform. In embodiments, provided herein is a hygiene behavioral modification platform having a set of services and interfaces configurable to encourage hygiene-promoting behavior for a user environment and having a set of services configured to induce hygiene-promoting behavior within a healthcare environment. In embodiments, provided herein is a hygiene behavioral modification platform having a set of services and interfaces configurable to encourage hygiene-promoting behavior for a user environment and having a set of services configured to induce hygiene-promoting behavior in a hospitality environment. In embodiments, provided herein is a hygiene behavioral modification platform having a set of services and interfaces configurable to encourage hygiene-promoting behavior for a user environment and having a set of services configured to induce hygiene-promoting behavior in an education environment. In embodiments, provided herein is a hygiene behavioral modification platform having a set of services and interfaces configurable to encourage hygiene-promoting behavior for a user environment and having a set of services configured to induce hygiene-promoting behavior in a travel environment. In embodiments, provided herein is a hygiene behavioral modification platform having a set of services and interfaces configurable to encourage hygiene-promoting behavior for a user environment and having a set of services configured to induce hygiene-promoting behavior in a smart home environment. In embodiments, provided herein is a hygiene behavioral modification platform having a set of services and interfaces configurable to encourage hygiene-promoting behavior for a user environment and having a set of services configured to induce hygiene-promoting behavior in a government environment. In embodiments, provided herein is a hygiene behavioral modification platform having a set of services and interfaces configurable to encourage hygiene-promoting behavior for a user environment and having a mobile application integrated with the platform for enabling mobile access to the platform. In embodiments, provided herein is a hygiene behavioral modification platform having a set of services and interfaces configurable to encourage hygiene-promoting behavior for a user environment and having a dashboard system for representing status information regarding hygiene behavior modification for an environment. In embodiments, provided herein is a hygiene behavioral modification platform having a set of services and interfaces configurable to encourage hygiene-promoting behavior for a user environment and having a handwashing compliance dashboard system. In embodiments, provided herein is a hygiene behavioral modification platform having a set of services and interfaces configurable to encourage hygiene-promoting behavior for a user environment and having a reporting system for providing reporting of hygiene behavioral monitoring data. In embodiments, provided herein is a hygiene behavioral modification platform having a set of services and interfaces configurable to encourage hygiene-promoting behavior for a user environment and having a user interface providing a user experience that promotes user awareness of the need to undertake hygiene behavior. In embodiments, provided herein is a hygiene behavioral modification platform having a set of services and interfaces configurable to encourage hygiene-promoting behavior for a user environment and having a digital tree leaf pattern wherein the digital tree leaf pattern's growth is based on community hygiene behaviors. In embodiments, provided herein is a hygiene behavioral modification platform having a set of services and interfaces configurable to encourage hygiene-promoting behavior for a user environment and having a system for providing audiovisual experiences for the promotion of hygiene behaviors. In embodiments, provided herein is a hygiene behavioral modification platform having a set of services and interfaces configurable to encourage hygiene-promoting behavior for a user environment and having a system for providing an audiovisual experience for the promotion of hygiene behaviors wherein the audiovisual experience includes a lighting display event. In embodiments, provided herein is a hygiene behavioral modification platform having a set of services and interfaces configurable to encourage hygiene-promoting behavior for a user environment and having a system for providing an audiovisual experience for the promotion of hygiene behaviors wherein the audiovisual experience includes a sound event. In embodiments, provided herein is a hygiene behavioral modification platform having a set of services and interfaces configurable to encourage hygiene-promoting behavior for a user environment and having a system for providing an audiovisual experience for the promotion of hygiene behaviors wherein the audiovisual experience includes an audio reminder to wash hands. In embodiments, provided herein is a hygiene behavioral modification platform having a set of services and interfaces configurable to encourage hygiene-promoting behavior for a user environment and having a system for providing an audiovisual experience for the promotion of hygiene behaviors having a system for facilitating progressive reminders as an individual moves through transits an environment and passes one or more points of reference. In embodiments, provided herein is a hygiene behavioral modification platform having a set of services and interfaces configurable to encourage hygiene-promoting behavior for a user environment and having a system for providing an audiovisual experience for the promotion of hygiene behaviors wherein the audiovisual experience includes an advertisement that plays during the recommended duration of a handwashing event. In embodiments, provided herein is a hygiene behavioral modification platform having a set of services and interfaces configurable to encourage hygiene-promoting behavior for a user environment and having a peer-to-peer configuration system for enabling peer-to-peer communication among a set of hygiene-promoting devices. In embodiments, provided herein is a hygiene behavioral modification platform having a set of services and interfaces configurable to encourage hygiene-promoting behavior for a user environment and having a data aggregation system for aggregating hygiene behavioral data across a set of devices, a set of locations and/or a population of individuals. In embodiments, provided herein is a hygiene behavioral modification platform having a set of services and interfaces configurable to encourage hygiene-promoting behavior for a user environment and having an analytics system for performing an analytic operation to produce analytic measures related to hygiene behavior. In embodiments, provided herein is a hygiene behavioral modification platform having a set of services and interfaces configurable to encourage hygiene-promoting behavior for a user environment and having an analytics system for performing an analytic operation to produce an analytic measure related to hygiene behavior and having analytics indicating hygiene performance levels relevant to a particular individual. In embodiments, provided herein is a hygiene behavioral modification platform having a set of services and interfaces configurable to encourage hygiene-promoting behavior for a user environment and having an analytics system for performing an analytic operation to produce an analytic measure related to hygiene behavior and having analytics indicating hygiene performance levels relevant to a population of individuals. In embodiments, provided herein is a hygiene behavioral modification platform having a set of services and interfaces configurable to encourage hygiene-promoting behavior for a user environment and having an analytics system for performing an analytic operation to produce an analytic measure related to hygiene behavior and having analytics indicating hygiene performance levels relevant to a location of a business. In embodiments, provided herein is a hygiene behavioral modification platform having a set of services and interfaces configurable to encourage hygiene-promoting behavior for a user environment and having a community score system for generating a community score based on handwashing behavior compliance in an environment, and wherein the community score is calculated based on the proportion of humans entering the environment that wash their hands. In embodiments, provided herein is a hygiene behavioral modification platform having a set of services and interfaces configurable to encourage hygiene-promoting behavior for a user environment and for promoting hygiene behavioral modification having Bluetooth Low Energy proximity sensing, passive infrared sensors, and active infrared sensors for detecting the presence of one or more humans, and wherein the smart hygiene device is configured to attach to a soap dispenser. In embodiments, provided herein is a hygiene behavioral modification platform having a set of services and interfaces configurable to encourage hygiene-promoting behavior for a user environment and having Bluetooth Low Energy proximity sensing, passive infrared sensors, and active infrared sensors for detecting the presence of one or more humans. In embodiments, provided herein is a hygiene behavioral modification platform having a set of services and interfaces configurable to encourage hygiene-promoting behavior for a user environment and for promoting hygiene behavioral modification having Bluetooth Low Energy proximity sensing, passive infrared sensors, and active infrared sensors for detecting the presence of one or more humans and wherein the smart hygiene device is configured as a soap dispenser. In embodiments, provided herein is a hygiene behavioral modification platform having a set of services and interfaces configurable to encourage hygiene-promoting behavior for a user environment and having a system for detecting activities related to hygiene and reporting a set of indicators of hygiene behaviors. In embodiments, provided herein is a hygiene behavioral modification platform having a set of services and interfaces configurable to encourage hygiene-promoting behavior for a user environment and having a system for detecting handwashing activity. In embodiments, provided herein is a hygiene behavioral modification platform having a set of services and interfaces configurable to encourage hygiene-promoting behavior for a user environment and having a system for detecting handwashing activity and producing a measure of duration and timing of the handwashing activity. In embodiments, provided herein is a hygiene behavioral modification platform having a set of services and interfaces configurable to encourage hygiene-promoting behavior for a user environment and having a sensor fusion system configured to combine data from sensors of at least two types, wherein the fused sensor data is processed to produce an indicator related to hygiene behavior activity. In embodiments, provided herein is a hygiene behavioral modification platform having a set of services and interfaces configurable to encourage hygiene-promoting behavior for a user environment and having a machine learning and/or artificial intelligence system configured to classify humans as employees or customers. In embodiments, provided herein is a hygiene behavioral modification platform having a set of services and interfaces configurable to encourage hygiene-promoting behavior for a user environment and having a system for integrating a set of detected indicators of hygiene behavior for a location and/or entity with an online rating/review system for the location and/or entity. In embodiments, provided herein is a hygiene behavioral modification platform having a set of services and interfaces configurable to encourage hygiene-promoting behavior for a user environment and having a machine learning and/or artificial intelligence system configured to generate a recommendation related to washing hands and/or hand sanitizing. In embodiments, provided herein is a hygiene behavioral modification platform having a set of services and interfaces configurable to encourage hygiene-promoting behavior for a user environment and having a machine learning and/or artificial intelligence system configured to generate a recommendation related to the duration of handwashing. In embodiments, provided herein is a hygiene behavioral modification platform having a set of services and interfaces configurable to encourage hygiene-promoting behavior for a user environment and having personal profiles with accompanying personal data structures for storing personal information. In embodiments, provided herein is a hygiene behavioral modification platform having a set of services and interfaces configurable to encourage hygiene-promoting behavior for a user environment and having workforce profiles with accompanying workforce structures for storing workforce information.

In embodiments, provided herein is a hygiene behavioral modification platform having a set of services deployed on a cloud platform for receiving data and other inputs collected in one or more environments and transmitted to the cloud platform over one or more networks. In embodiments, provided herein is a hygiene behavioral modification platform having a set of services deployed on a cloud platform for receiving data and other inputs collected in one or more environments and transmitted to the cloud platform over one or more networks and having a data integration system for integrating data across distributed sets of smart hygiene devices. In embodiments, provided herein is a hygiene behavioral modification platform having a set of services deployed on a cloud platform for receiving data and other inputs collected in one or more environments and transmitted to the cloud platform over one or more networks and having a set of interfaces and services for operator configuration of a set of behavioral modification parameters for a set of devices managed by the platform. In embodiments, provided herein is a hygiene behavioral modification platform having a set of services deployed on a cloud platform for receiving data and other inputs collected in one or more environments and transmitted to the cloud platform over one or more networks and having a set of services configured to induce hygiene-promoting behavior within a healthcare environment. In embodiments, provided herein is a hygiene behavioral modification platform having a set of services deployed on a cloud platform for receiving data and other inputs collected in one or more environments and transmitted to the cloud platform over one or more networks and having a set of services configured to induce hygiene-promoting behavior in a hospitality environment. In embodiments, provided herein is a hygiene behavioral modification platform having a set of services deployed on a cloud platform for receiving data and other inputs collected in one or more environments and transmitted to the cloud platform over one or more networks and having a set of services configured to induce hygiene-promoting behavior in an education environment. In embodiments, provided herein is a hygiene behavioral modification platform having a set of services deployed on a cloud platform for receiving data and other inputs collected in one or more environments and transmitted to the cloud platform over one or more networks and having a set of services configured to induce hygiene-promoting behavior in a travel environment. In embodiments, provided herein is a hygiene behavioral modification platform having a set of services deployed on a cloud platform for receiving data and other inputs collected in one or more environments and transmitted to the cloud platform over one or more networks and having a set of services configured to induce hygiene-promoting behavior in a smart home environment. In embodiments, provided herein is a hygiene behavioral modification platform having a set of services deployed on a cloud platform for receiving data and other inputs collected in one or more environments and transmitted to the cloud platform over one or more networks and having a set of services configured to induce hygiene-promoting behavior in a government environment. In embodiments, provided herein is a hygiene behavioral modification platform having a set of services deployed on a cloud platform for receiving data and other inputs collected in one or more environments and transmitted to the cloud platform over one or more networks and having a mobile application integrated with the platform for enabling mobile access to the platform. In embodiments, provided herein is a hygiene behavioral modification platform having a set of services deployed on a cloud platform for receiving data and other inputs collected in one or more environments and transmitted to the cloud platform over one or more networks and having a dashboard system for representing status information regarding hygiene behavior modification for an environment. In embodiments, provided herein is a hygiene behavioral modification platform having a set of services deployed on a cloud platform for receiving data and other inputs collected in one or more environments and transmitted to the cloud platform over one or more networks and having a handwashing compliance dashboard system. In embodiments, provided herein is a hygiene behavioral modification platform having a set of services deployed on a cloud platform for receiving data and other inputs collected in one or more environments and transmitted to the cloud platform over one or more networks and having a reporting system for providing reporting of hygiene behavioral monitoring data. In embodiments, provided herein is a hygiene behavioral modification platform having a set of services deployed on a cloud platform for receiving data and other inputs collected in one or more environments and transmitted to the cloud platform over one or more networks and having a user interface providing a user experience that promotes user awareness of the need to undertake hygiene behavior. In embodiments, provided herein is a hygiene behavioral modification platform having a set of services deployed on a cloud platform for receiving data and other inputs collected in one or more environments and transmitted to the cloud platform over one or more networks and having a digital tree leaf pattern wherein the digital tree leaf pattern's growth is based on community hygiene behaviors. In embodiments, provided herein is a hygiene behavioral modification platform having a set of services deployed on a cloud platform for receiving data and other inputs collected in one or more environments and transmitted to the cloud platform over one or more networks and having a system for providing audiovisual experiences for the promotion of hygiene behaviors. In embodiments, provided herein is a hygiene behavioral modification platform having a set of services deployed on a cloud platform for receiving data and other inputs collected in one or more environments and transmitted to the cloud platform over one or more networks and having a system for providing an audiovisual experience for the promotion of hygiene behaviors wherein the audiovisual experience includes a lighting display event. In embodiments, provided herein is a hygiene behavioral modification platform having a set of services deployed on a cloud platform for receiving data and other inputs collected in one or more environments and transmitted to the cloud platform over one or more networks and having a system for providing an audiovisual experience for the promotion of hygiene behaviors wherein the audiovisual experience includes a sound event. In embodiments, provided herein is a hygiene behavioral modification platform having a set of services deployed on a cloud platform for receiving data and other inputs collected in one or more environments and transmitted to the cloud platform over one or more networks and having a system for providing an audiovisual experience for the promotion of hygiene behaviors wherein the audiovisual experience includes an audio reminder to wash hands. In embodiments, provided herein is a hygiene behavioral modification platform having a set of services deployed on a cloud platform for receiving data and other inputs collected in one or more environments and transmitted to the cloud platform over one or more networks and having a system for providing an audiovisual experience for the promotion of hygiene behaviors having a system for facilitating progressive reminders as an individual moves through transits an environment and passes one or more points of reference. In embodiments, provided herein is a hygiene behavioral modification platform having a set of services deployed on a cloud platform for receiving data and other inputs collected in one or more environments and transmitted to the cloud platform over one or more networks and having a system for providing an audiovisual experience for the promotion of hygiene behaviors wherein the audiovisual experience includes an advertisement that plays during the recommended duration of a handwashing event. In embodiments, provided herein is a hygiene behavioral modification platform having a set of services deployed on a cloud platform for receiving data and other inputs collected in one or more environments and transmitted to the cloud platform over one or more networks and having a peer-to-peer configuration system for enabling peer-to-peer communication among a set of hygiene-promoting devices. In embodiments, provided herein is a hygiene behavioral modification platform having a set of services deployed on a cloud platform for receiving data and other inputs collected in one or more environments and transmitted to the cloud platform over one or more networks and having a data aggregation system for aggregating hygiene behavioral data across a set of devices, a set of locations and/or a population of individuals. In embodiments, provided herein is a hygiene behavioral modification platform having a set of services deployed on a cloud platform for receiving data and other inputs collected in one or more environments and transmitted to the cloud platform over one or more networks and having an analytics system for performing an analytic operation to produce analytic measures related to hygiene behavior. In embodiments, provided herein is a hygiene behavioral modification platform having a set of services deployed on a cloud platform for receiving data and other inputs collected in one or more environments and transmitted to the cloud platform over one or more networks and having an analytics system for performing an analytic operation to produce an analytic measure related to hygiene behavior and having analytics indicating hygiene performance levels relevant to a particular individual. In embodiments, provided herein is a hygiene behavioral modification platform having a set of services deployed on a cloud platform for receiving data and other inputs collected in one or more environments and transmitted to the cloud platform over one or more networks and having an analytics system for performing an analytic operation to produce an analytic measure related to hygiene behavior and having analytics indicating hygiene performance levels relevant to a population of individuals. In embodiments, provided herein is a hygiene behavioral modification platform having a set of services deployed on a cloud platform for receiving data and other inputs collected in one or more environments and transmitted to the cloud platform over one or more networks and having an analytics system for performing an analytic operation to produce an analytic measure related to hygiene behavior and having analytics indicating hygiene performance levels relevant to a location of a business. In embodiments, provided herein is a hygiene behavioral modification platform having a set of services deployed on a cloud platform for receiving data and other inputs collected in one or more environments and transmitted to the cloud platform over one or more networks and having a community score system for generating a community score based on handwashing behavior compliance in an environment, and wherein the community score is calculated based on the proportion of humans entering the environment that wash their hands. In embodiments, provided herein is a hygiene behavioral modification platform having a set of services deployed on a cloud platform for receiving data and other inputs collected in one or more environments and transmitted to the cloud platform over one or more networks and for promoting hygiene behavioral modification having Bluetooth Low Energy proximity sensing, passive infrared sensors, and active infrared sensors for detecting the presence of one or more humans, and wherein the smart hygiene device is configured to attach to a soap dispenser. In embodiments, provided herein is a hygiene behavioral modification platform having a set of services deployed on a cloud platform for receiving data and other inputs collected in one or more environments and transmitted to the cloud platform over one or more networks and having Bluetooth Low Energy proximity sensing, passive infrared sensors, and active infrared sensors for detecting the presence of one or more humans. In embodiments, provided herein is a hygiene behavioral modification platform having a set of services deployed on a cloud platform for receiving data and other inputs collected in one or more environments and transmitted to the cloud platform over one or more networks and for promoting hygiene behavioral modification having Bluetooth Low Energy proximity sensing, passive infrared sensors, and active infrared sensors for detecting the presence of one or more humans and wherein the smart hygiene device is configured as a soap dispenser. In embodiments, provided herein is a hygiene behavioral modification platform having a set of services deployed on a cloud platform for receiving data and other inputs collected in one or more environments and transmitted to the cloud platform over one or more networks and having a system for detecting activities related to hygiene and reporting a set of indicators of hygiene behaviors. In embodiments, provided herein is a hygiene behavioral modification platform having a set of services deployed on a cloud platform for receiving data and other inputs collected in one or more environments and transmitted to the cloud platform over one or more networks and having a system for detecting handwashing activity. In embodiments, provided herein is a hygiene behavioral modification platform having a set of services deployed on a cloud platform for receiving data and other inputs collected in one or more environments and transmitted to the cloud platform over one or more networks and having a system for detecting handwashing activity and producing a measure of duration and timing of the handwashing activity. In embodiments, provided herein is a hygiene behavioral modification platform having a set of services deployed on a cloud platform for receiving data and other inputs collected in one or more environments and transmitted to the cloud platform over one or more networks and having a sensor fusion system configured to combine data from sensors of at least two types, wherein the fused sensor data is processed to produce an indicator related to hygiene behavior activity. In embodiments, provided herein is a hygiene behavioral modification platform having a set of services deployed on a cloud platform for receiving data and other inputs collected in one or more environments and transmitted to the cloud platform over one or more networks and having a machine learning and/or artificial intelligence system configured to classify humans as employees or customers. In embodiments, provided herein is a hygiene behavioral modification platform having a set of services deployed on a cloud platform for receiving data and other inputs collected in one or more environments and transmitted to the cloud platform over one or more networks and having a system for integrating a set of detected indicators of hygiene behavior for a location and/or entity with an online rating/review system for the location and/or entity. In embodiments, provided herein is a hygiene behavioral modification platform having a set of services deployed on a cloud platform for receiving data and other inputs collected in one or more environments and transmitted to the cloud platform over one or more networks and having a machine learning and/or artificial intelligence system configured to generate a recommendation related to washing hands and/or hand sanitizing. In embodiments, provided herein is a hygiene behavioral modification platform having a set of services deployed on a cloud platform for receiving data and other inputs collected in one or more environments and transmitted to the cloud platform over one or more networks and having a machine learning and/or artificial intelligence system configured to generate a recommendation related to the duration of handwashing. In embodiments, provided herein is a hygiene behavioral modification platform having a set of services deployed on a cloud platform for receiving data and other inputs collected in one or more environments and transmitted to the cloud platform over one or more networks and having personal profiles with accompanying personal data structures for storing personal information. In embodiments, provided herein is a hygiene behavioral modification platform having a set of services deployed on a cloud platform for receiving data and other inputs collected in one or more environments and transmitted to the cloud platform over one or more networks and having workforce profiles with accompanying workforce structures for storing workforce information.

In embodiments, provided herein is a hygiene behavioral modification platform having a data integration system for integrating data across distributed sets of smart hygiene devices. In embodiments, provided herein is a hygiene behavioral modification platform having a data integration system for integrating data across distributed sets of smart hygiene devices and having a set of interfaces and services for operator configuration of a set of behavioral modification parameters for a set of devices managed by the platform. In embodiments, provided herein is a hygiene behavioral modification platform having a data integration system for integrating data across distributed sets of smart hygiene devices and having a set of services configured to induce hygiene-promoting behavior within a healthcare environment. In embodiments, provided herein is a hygiene behavioral modification platform having a data integration system for integrating data across distributed sets of smart hygiene devices and having a set of services configured to induce hygiene-promoting behavior in a hospitality environment. In embodiments, provided herein is a hygiene behavioral modification platform having a data integration system for integrating data across distributed sets of smart hygiene devices and having a set of services configured to induce hygiene-promoting behavior in an education environment. In embodiments, provided herein is a hygiene behavioral modification platform having a data integration system for integrating data across distributed sets of smart hygiene devices and having a set of services configured to induce hygiene-promoting behavior in a travel environment. In embodiments, provided herein is a hygiene behavioral modification platform having a data integration system for integrating data across distributed sets of smart hygiene devices and having a set of services configured to induce hygiene-promoting behavior in a smart home environment. In embodiments, provided herein is a hygiene behavioral modification platform having a data integration system for integrating data across distributed sets of smart hygiene devices and having a set of services configured to induce hygiene-promoting behavior in a government environment. In embodiments, provided herein is a hygiene behavioral modification platform having a data integration system for integrating data across distributed sets of smart hygiene devices and having a mobile application integrated with the platform for enabling mobile access to the platform. In embodiments, provided herein is a hygiene behavioral modification platform having a data integration system for integrating data across distributed sets of smart hygiene devices and having a dashboard system for representing status information regarding hygiene behavior modification for an environment. In embodiments, provided herein is a hygiene behavioral modification platform having a data integration system for integrating data across distributed sets of smart hygiene devices and having a handwashing compliance dashboard system. In embodiments, provided herein is a hygiene behavioral modification platform having a data integration system for integrating data across distributed sets of smart hygiene devices and having a reporting system for providing reporting of hygiene behavioral monitoring data. In embodiments, provided herein is a hygiene behavioral modification platform having a data integration system for integrating data across distributed sets of smart hygiene devices and having a user interface providing a user experience that promotes user awareness of the need to undertake hygiene behavior. In embodiments, provided herein is a hygiene behavioral modification platform having a data integration system for integrating data across distributed sets of smart hygiene devices and having a digital tree leaf pattern wherein the digital tree leaf pattern's growth is based on community hygiene behaviors. In embodiments, provided herein is a hygiene behavioral modification platform having a data integration system for integrating data across distributed sets of smart hygiene devices and having a system for providing audiovisual experiences for the promotion of hygiene behaviors. In embodiments, provided herein is a hygiene behavioral modification platform having a data integration system for integrating data across distributed sets of smart hygiene devices and having a system for providing an audiovisual experience for the promotion of hygiene behaviors wherein the audiovisual experience includes a lighting display event. In embodiments, provided herein is a hygiene behavioral modification platform having a data integration system for integrating data across distributed sets of smart hygiene devices and having a system for providing an audiovisual experience for the promotion of hygiene behaviors wherein the audiovisual experience includes a sound event. In embodiments, provided herein is a hygiene behavioral modification platform having a data integration system for integrating data across distributed sets of smart hygiene devices and having a system for providing an audiovisual experience for the promotion of hygiene behaviors wherein the audiovisual experience includes an audio reminder to wash hands. In embodiments, provided herein is a hygiene behavioral modification platform having a data integration system for integrating data across distributed sets of smart hygiene devices and having a system for providing an audiovisual experience for the promotion of hygiene behaviors having a system for facilitating progressive reminders as an individual moves through transits an environment and passes one or more points of reference. In embodiments, provided herein is a hygiene behavioral modification platform having a data integration system for integrating data across distributed sets of smart hygiene devices and having a system for providing an audiovisual experience for the promotion of hygiene behaviors wherein the audiovisual experience includes an advertisement that plays during the recommended duration of a handwashing event. In embodiments, provided herein is a hygiene behavioral modification platform having a data integration system for integrating data across distributed sets of smart hygiene devices and having a peer-to-peer configuration system for enabling peer-to-peer communication among a set of hygiene-promoting devices. In embodiments, provided herein is a hygiene behavioral modification platform having a data integration system for integrating data across distributed sets of smart hygiene devices and having a data aggregation system for aggregating hygiene behavioral data across a set of devices, a set of locations and/or a population of individuals. In embodiments, provided herein is a hygiene behavioral modification platform having a data integration system for integrating data across distributed sets of smart hygiene devices and having an analytics system for performing an analytic operation to produce analytic measures related to hygiene behavior. In embodiments, provided herein is a hygiene behavioral modification platform having a data integration system for integrating data across distributed sets of smart hygiene devices and having an analytics system for performing an analytic operation to produce an analytic measure related to hygiene behavior and having analytics indicating hygiene performance levels relevant to a particular individual. In embodiments, provided herein is a hygiene behavioral modification platform having a data integration system for integrating data across distributed sets of smart hygiene devices and having an analytics system for performing an analytic operation to produce an analytic measure related to hygiene behavior and having analytics indicating hygiene performance levels relevant to a population of individuals. In embodiments, provided herein is a hygiene behavioral modification platform having a data integration system for integrating data across distributed sets of smart hygiene devices and having an analytics system for performing an analytic operation to produce an analytic measure related to hygiene behavior and having analytics indicating hygiene performance levels relevant to a location of a business. In embodiments, provided herein is a hygiene behavioral modification platform having a data integration system for integrating data across distributed sets of smart hygiene devices and having a community score system for generating a community score based on handwashing behavior compliance in an environment, and wherein the community score is calculated based on the proportion of humans entering the environment that wash their hands. In embodiments, provided herein is a hygiene behavioral modification platform having a data integration system for integrating data across distributed sets of smart hygiene devices and for promoting hygiene behavioral modification having Bluetooth Low Energy proximity sensing, passive infrared sensors, and active infrared sensors for detecting the presence of one or more humans, and wherein the smart hygiene device is configured to attach to a soap dispenser. In embodiments, provided herein is a hygiene behavioral modification platform having a data integration system for integrating data across distributed sets of smart hygiene devices and having Bluetooth Low Energy proximity sensing, passive infrared sensors, and active infrared sensors for detecting the presence of one or more humans. In embodiments, provided herein is a hygiene behavioral modification platform having a data integration system for integrating data across distributed sets of smart hygiene devices and for promoting hygiene behavioral modification having Bluetooth Low Energy proximity sensing, passive infrared sensors, and active infrared sensors for detecting the presence of one or more humans and wherein the smart hygiene device is configured as a soap dispenser. In embodiments, provided herein is a hygiene behavioral modification platform having a data integration system for integrating data across distributed sets of smart hygiene devices and having a system for detecting activities related to hygiene and reporting a set of indicators of hygiene behaviors. In embodiments, provided herein is a hygiene behavioral modification platform having a data integration system for integrating data across distributed sets of smart hygiene devices and having a system for detecting handwashing activity. In embodiments, provided herein is a hygiene behavioral modification platform having a data integration system for integrating data across distributed sets of smart hygiene devices and having a system for detecting handwashing activity and producing a measure of duration and timing of the handwashing activity. In embodiments, provided herein is a hygiene behavioral modification platform having a data integration system for integrating data across distributed sets of smart hygiene devices and having a sensor fusion system configured to combine data from sensors of at least two types, wherein the fused sensor data is processed to produce an indicator related to hygiene behavior activity. In embodiments, provided herein is a hygiene behavioral modification platform having a data integration system for integrating data across distributed sets of smart hygiene devices and having a machine learning and/or artificial intelligence system configured to classify humans as employees or customers. In embodiments, provided herein is a hygiene behavioral modification platform having a data integration system for integrating data across distributed sets of smart hygiene devices and having a system for integrating a set of detected indicators of hygiene behavior for a location and/or entity with an online rating/review system for the location and/or entity. In embodiments, provided herein is a hygiene behavioral modification platform having a data integration system for integrating data across distributed sets of smart hygiene devices and having a machine learning and/or artificial intelligence system configured to generate a recommendation related to washing hands and/or hand sanitizing. In embodiments, provided herein is a hygiene behavioral modification platform having a data integration system for integrating data across distributed sets of smart hygiene devices and having a machine learning and/or artificial intelligence system configured to generate a recommendation related to the duration of handwashing. In embodiments, provided herein is a hygiene behavioral modification platform having a data integration system for integrating data across distributed sets of smart hygiene devices and having personal profiles with accompanying personal data structures for storing personal information. In embodiments, provided herein is a hygiene behavioral modification platform having a data integration system for integrating data across distributed sets of smart hygiene devices and having workforce profiles with accompanying workforce structures for storing workforce information.

In embodiments, provided herein is a hygiene behavioral platform having a set of interfaces and services for operator configuration of a set of behavioral modification parameters for a set of devices managed by the platform. In embodiments, provided herein is a hygiene behavioral platform having a set of interfaces and services for operator configuration of a set of behavioral modification parameters for a set of devices managed by the platform and having a set of services configured to induce hygiene-promoting behavior within a healthcare environment. In embodiments, provided herein is a hygiene behavioral platform having a set of interfaces and services for operator configuration of a set of behavioral modification parameters for a set of devices managed by the platform and having a set of services configured to induce hygiene-promoting behavior in a hospitality environment. In embodiments, provided herein is a hygiene behavioral platform having a set of interfaces and services for operator configuration of a set of behavioral modification parameters for a set of devices managed by the platform and having a set of services configured to induce hygiene-promoting behavior in an education environment. In embodiments, provided herein is a hygiene behavioral platform having a set of interfaces and services for operator configuration of a set of behavioral modification parameters for a set of devices managed by the platform and having a set of services configured to induce hygiene-promoting behavior in a travel environment. In embodiments, provided herein is a hygiene behavioral platform having a set of interfaces and services for operator configuration of a set of behavioral modification parameters for a set of devices managed by the platform and having a set of services configured to induce hygiene-promoting behavior in a smart home environment. In embodiments, provided herein is a hygiene behavioral platform having a set of interfaces and services for operator configuration of a set of behavioral modification parameters for a set of devices managed by the platform and having a set of services configured to induce hygiene-promoting behavior in a government environment. In embodiments, provided herein is a hygiene behavioral platform having a set of interfaces and services for operator configuration of a set of behavioral modification parameters for a set of devices managed by the platform and having a mobile application integrated with the platform for enabling mobile access to the platform. In embodiments, provided herein is a hygiene behavioral platform having a set of interfaces and services for operator configuration of a set of behavioral modification parameters for a set of devices managed by the platform and having a dashboard system for representing status information regarding hygiene behavior modification for an environment. In embodiments, provided herein is a hygiene behavioral platform having a set of interfaces and services for operator configuration of a set of behavioral modification parameters for a set of devices managed by the platform and having a handwashing compliance dashboard system. In embodiments, provided herein is a hygiene behavioral platform having a set of interfaces and services for operator configuration of a set of behavioral modification parameters for a set of devices managed by the platform and having a reporting system for providing reporting of hygiene behavioral monitoring data. In embodiments, provided herein is a hygiene behavioral platform having a set of interfaces and services for operator configuration of a set of behavioral modification parameters for a set of devices managed by the platform and having a user interface providing a user experience that promotes user awareness of the need to undertake hygiene behavior. In embodiments, provided herein is a hygiene behavioral platform having a set of interfaces and services for operator configuration of a set of behavioral modification parameters for a set of devices managed by the platform and having a digital tree leaf pattern wherein the digital tree leaf pattern's growth is based on community hygiene behaviors. In embodiments, provided herein is a hygiene behavioral platform having a set of interfaces and services for operator configuration of a set of behavioral modification parameters for a set of devices managed by the platform and having a system for providing audiovisual experiences for the promotion of hygiene behaviors. In embodiments, provided herein is a hygiene behavioral platform having a set of interfaces and services for operator configuration of a set of behavioral modification parameters for a set of devices managed by the platform and having a system for providing an audiovisual experience for the promotion of hygiene behaviors wherein the audiovisual experience includes a lighting display event. In embodiments, provided herein is a hygiene behavioral platform having a set of interfaces and services for operator configuration of a set of behavioral modification parameters for a set of devices managed by the platform and having a system for providing an audiovisual experience for the promotion of hygiene behaviors wherein the audiovisual experience includes a sound event. In embodiments, provided herein is a hygiene behavioral platform having a set of interfaces and services for operator configuration of a set of behavioral modification parameters for a set of devices managed by the platform and having a system for providing an audiovisual experience for the promotion of hygiene behaviors wherein the audiovisual experience includes an audio reminder to wash hands. In embodiments, provided herein is a hygiene behavioral platform having a set of interfaces and services for operator configuration of a set of behavioral modification parameters for a set of devices managed by the platform and having a system for providing an audiovisual experience for the promotion of hygiene behaviors having a system for facilitating progressive reminders as an individual moves through transits an environment and passes one or more points of reference. In embodiments, provided herein is a hygiene behavioral platform having a set of interfaces and services for operator configuration of a set of behavioral modification parameters for a set of devices managed by the platform and having a system for providing an audiovisual experience for the promotion of hygiene behaviors wherein the audiovisual experience includes an advertisement that plays during the recommended duration of a handwashing event. In embodiments, provided herein is a hygiene behavioral platform having a set of interfaces and services for operator configuration of a set of behavioral modification parameters for a set of devices managed by the platform and having a peer-to-peer configuration system for enabling peer-to-peer communication among a set of hygiene-promoting devices. In embodiments, provided herein is a hygiene behavioral platform having a set of interfaces and services for operator configuration of a set of behavioral modification parameters for a set of devices managed by the platform and having a data aggregation system for aggregating hygiene behavioral data across a set of devices, a set of locations and/or a population of individuals. In embodiments, provided herein is a hygiene behavioral platform having a set of interfaces and services for operator configuration of a set of behavioral modification parameters for a set of devices managed by the platform and having an analytics system for performing an analytic operation to produce analytic measures related to hygiene behavior. In embodiments, provided herein is a hygiene behavioral platform having a set of interfaces and services for operator configuration of a set of behavioral modification parameters for a set of devices managed by the platform and having an analytics system for performing an analytic operation to produce an analytic measure related to hygiene behavior and having analytics indicating hygiene performance levels relevant to a particular individual. In embodiments, provided herein is a hygiene behavioral platform having a set of interfaces and services for operator configuration of a set of behavioral modification parameters for a set of devices managed by the platform and having an analytics system for performing an analytic operation to produce an analytic measure related to hygiene behavior and having analytics indicating hygiene performance levels relevant to a population of individuals. In embodiments, provided herein is a hygiene behavioral platform having a set of interfaces and services for operator configuration of a set of behavioral modification parameters for a set of devices managed by the platform and having an analytics system for performing an analytic operation to produce an analytic measure related to hygiene behavior and having analytics indicating hygiene performance levels relevant to a location of a business. In embodiments, provided herein is a hygiene behavioral platform having a set of interfaces and services for operator configuration of a set of behavioral modification parameters for a set of devices managed by the platform and having a community score system for generating a community score based on handwashing behavior compliance in an environment, and wherein the community score is calculated based on the proportion of humans entering the environment that wash their hands. In embodiments, provided herein is a hygiene behavioral platform having a set of interfaces and services for operator configuration of a set of behavioral modification parameters for a set of devices managed by the platform and for promoting hygiene behavioral modification having Bluetooth Low Energy proximity sensing, passive infrared sensors, and active infrared sensors for detecting the presence of one or more humans, and wherein the smart hygiene device is configured to attach to a soap dispenser. In embodiments, provided herein is a hygiene behavioral platform having a set of interfaces and services for operator configuration of a set of behavioral modification parameters for a set of devices managed by the platform and having Bluetooth Low Energy proximity sensing, passive infrared sensors, and active infrared sensors for detecting the presence of one or more humans. In embodiments, provided herein is a hygiene behavioral platform having a set of interfaces and services for operator configuration of a set of behavioral modification parameters for a set of devices managed by the platform and for promoting hygiene behavioral modification having Bluetooth Low Energy proximity sensing, passive infrared sensors, and active infrared sensors for detecting the presence of one or more humans and wherein the smart hygiene device is configured as a soap dispenser. In embodiments, provided herein is a hygiene behavioral platform having a set of interfaces and services for operator configuration of a set of behavioral modification parameters for a set of devices managed by the platform and having a system for detecting activities related to hygiene and reporting a set of indicators of hygiene behaviors. In embodiments, provided herein is a hygiene behavioral platform having a set of interfaces and services for operator configuration of a set of behavioral modification parameters for a set of devices managed by the platform and having a system for detecting handwashing activity. In embodiments, provided herein is a hygiene behavioral platform having a set of interfaces and services for operator configuration of a set of behavioral modification parameters for a set of devices managed by the platform and having a system for detecting handwashing activity and producing a measure of duration and timing of the handwashing activity. In embodiments, provided herein is a hygiene behavioral platform having a set of interfaces and services for operator configuration of a set of behavioral modification parameters for a set of devices managed by the platform and having a sensor fusion system configured to combine data from sensors of at least two types, wherein the fused sensor data is processed to produce an indicator related to hygiene behavior activity. In embodiments, provided herein is a hygiene behavioral platform having a set of interfaces and services for operator configuration of a set of behavioral modification parameters for a set of devices managed by the platform and having a machine learning and/or artificial intelligence system configured to classify humans as employees or customers. In embodiments, provided herein is a hygiene behavioral platform having a set of interfaces and services for operator configuration of a set of behavioral modification parameters for a set of devices managed by the platform and having a system for integrating a set of detected indicators of hygiene behavior for a location and/or entity with an online rating/review system for the location and/or entity. In embodiments, provided herein is a hygiene behavioral platform having a set of interfaces and services for operator configuration of a set of behavioral modification parameters for a set of devices managed by the platform and having a machine learning and/or artificial intelligence system configured to generate a recommendation related to washing hands and/or hand sanitizing. In embodiments, provided herein is a hygiene behavioral platform having a set of interfaces and services for operator configuration of a set of behavioral modification parameters for a set of devices managed by the platform and having a machine learning and/or artificial intelligence system configured to generate a recommendation related to the duration of handwashing. In embodiments, provided herein is a hygiene behavioral platform having a set of interfaces and services for operator configuration of a set of behavioral modification parameters for a set of devices managed by the platform and having personal profiles with accompanying personal data structures for storing personal information. In embodiments, provided herein is a hygiene behavioral platform having a set of interfaces and services for operator configuration of a set of behavioral modification parameters for a set of devices managed by the platform and having workforce profiles with accompanying workforce structures for storing workforce information.

In embodiments, provided herein is a hygiene behavioral modification platform having a set of services configured to induce hygiene-promoting behavior within a healthcare environment. In embodiments, provided herein is a hygiene behavioral modification platform having a set of services configured to induce hygiene-promoting behavior within a healthcare environment and having a set of services configured to induce hygiene-promoting behavior in a hospitality environment. In embodiments, provided herein is a hygiene behavioral modification platform having a set of services configured to induce hygiene-promoting behavior within a healthcare environment and having a set of services configured to induce hygiene-promoting behavior in an education environment. In embodiments, provided herein is a hygiene behavioral modification platform having a set of services configured to induce hygiene-promoting behavior within a healthcare environment and having a set of services configured to induce hygiene-promoting behavior in a travel environment. In embodiments, provided herein is a hygiene behavioral modification platform having a set of services configured to induce hygiene-promoting behavior within a healthcare environment and having a set of services configured to induce hygiene-promoting behavior in a smart home environment. In embodiments, provided herein is a hygiene behavioral modification platform having a set of services configured to induce hygiene-promoting behavior within a healthcare environment and having a set of services configured to induce hygiene-promoting behavior in a government environment. In embodiments, provided herein is a hygiene behavioral modification platform having a set of services configured to induce hygiene-promoting behavior within a healthcare environment and having a mobile application integrated with the platform for enabling mobile access to the platform. In embodiments, provided herein is a hygiene behavioral modification platform having a set of services configured to induce hygiene-promoting behavior within a healthcare environment and having a dashboard system for representing status information regarding hygiene behavior modification for an environment. In embodiments, provided herein is a hygiene behavioral modification platform having a set of services configured to induce hygiene-promoting behavior within a healthcare environment and having a handwashing compliance dashboard system. In embodiments, provided herein is a hygiene behavioral modification platform having a set of services configured to induce hygiene-promoting behavior within a healthcare environment and having a reporting system for providing reporting of hygiene behavioral monitoring data. In embodiments, provided herein is a hygiene behavioral modification platform having a set of services configured to induce hygiene-promoting behavior within a healthcare environment and having a user interface providing a user experience that promotes user awareness of the need to undertake hygiene behavior. In embodiments, provided herein is a hygiene behavioral modification platform having a set of services configured to induce hygiene-promoting behavior within a healthcare environment and having a digital tree leaf pattern wherein the digital tree leaf pattern's growth is based on community hygiene behaviors. In embodiments, provided herein is a hygiene behavioral modification platform having a set of services configured to induce hygiene-promoting behavior within a healthcare environment and having a system for providing audiovisual experiences for the promotion of hygiene behaviors. In embodiments, provided herein is a hygiene behavioral modification platform having a set of services configured to induce hygiene-promoting behavior within a healthcare environment and having a system for providing an audiovisual experience for the promotion of hygiene behaviors wherein the audiovisual experience includes a lighting display event. In embodiments, provided herein is a hygiene behavioral modification platform having a set of services configured to induce hygiene-promoting behavior within a healthcare environment and having a system for providing an audiovisual experience for the promotion of hygiene behaviors wherein the audiovisual experience includes a sound event. In embodiments, provided herein is a hygiene behavioral modification platform having a set of services configured to induce hygiene-promoting behavior within a healthcare environment and having a system for providing an audiovisual experience for the promotion of hygiene behaviors wherein the audiovisual experience includes an audio reminder to wash hands. In embodiments, provided herein is a hygiene behavioral modification platform having a set of services configured to induce hygiene-promoting behavior within a healthcare environment and having a system for providing an audiovisual experience for the promotion of hygiene behaviors having a system for facilitating progressive reminders as an individual moves through transits an environment and passes one or more points of reference. In embodiments, provided herein is a hygiene behavioral modification platform having a set of services configured to induce hygiene-promoting behavior within a healthcare environment and having a system for providing an audiovisual experience for the promotion of hygiene behaviors wherein the audiovisual experience includes an advertisement that plays during the recommended duration of a handwashing event. In embodiments, provided herein is a hygiene behavioral modification platform having a set of services configured to induce hygiene-promoting behavior within a healthcare environment and having a peer-to-peer configuration system for enabling peer-to-peer communication among a set of hygiene-promoting devices. In embodiments, provided herein is a hygiene behavioral modification platform having a set of services configured to induce hygiene-promoting behavior within a healthcare environment and having a data aggregation system for aggregating hygiene behavioral data across a set of devices, a set of locations and/or a population of individuals. In embodiments, provided herein is a hygiene behavioral modification platform having a set of services configured to induce hygiene-promoting behavior within a healthcare environment and having an analytics system for performing an analytic operation to produce analytic measures related to hygiene behavior. In embodiments, provided herein is a hygiene behavioral modification platform having a set of services configured to induce hygiene-promoting behavior within a healthcare environment and having an analytics system for performing an analytic operation to produce an analytic measure related to hygiene behavior and having analytics indicating hygiene performance levels relevant to a particular individual. In embodiments, provided herein is a hygiene behavioral modification platform having a set of services configured to induce hygiene-promoting behavior within a healthcare environment and having an analytics system for performing an analytic operation to produce an analytic measure related to hygiene behavior and having analytics indicating hygiene performance levels relevant to a population of individuals. In embodiments, provided herein is a hygiene behavioral modification platform having a set of services configured to induce hygiene-promoting behavior within a healthcare environment and having an analytics system for performing an analytic operation to produce an analytic measure related to hygiene behavior and having analytics indicating hygiene performance levels relevant to a location of a business. In embodiments, provided herein is a hygiene behavioral modification platform having a set of services configured to induce hygiene-promoting behavior within a healthcare environment and having a community score system for generating a community score based on handwashing behavior compliance in an environment, and wherein the community score is calculated based on the proportion of humans entering the environment that wash their hands. In embodiments, provided herein is a hygiene behavioral modification platform having a set of services configured to induce hygiene-promoting behavior within a healthcare environment and for promoting hygiene behavioral modification having Bluetooth Low Energy proximity sensing, passive infrared sensors, and active infrared sensors for detecting the presence of one or more humans, and wherein the smart hygiene device is configured to attach to a soap dispenser. In embodiments, provided herein is a hygiene behavioral modification platform having a set of services configured to induce hygiene-promoting behavior within a healthcare environment and having Bluetooth Low Energy proximity sensing, passive infrared sensors, and active infrared sensors for detecting the presence of one or more humans. In embodiments, provided herein is a hygiene behavioral modification platform having a set of services configured to induce hygiene-promoting behavior within a healthcare environment and for promoting hygiene behavioral modification having Bluetooth Low Energy proximity sensing, passive infrared sensors, and active infrared sensors for detecting the presence of one or more humans and wherein the smart hygiene device is configured as a soap dispenser. In embodiments, provided herein is a hygiene behavioral modification platform having a set of services configured to induce hygiene-promoting behavior within a healthcare environment and having a system for detecting activities related to hygiene and reporting a set of indicators of hygiene behaviors. In embodiments, provided herein is a hygiene behavioral modification platform having a set of services configured to induce hygiene-promoting behavior within a healthcare environment and having a system for detecting handwashing activity. In embodiments, provided herein is a hygiene behavioral modification platform having a set of services configured to induce hygiene-promoting behavior within a healthcare environment and having a system for detecting handwashing activity and producing a measure of duration and timing of the handwashing activity. In embodiments, provided herein is a hygiene behavioral modification platform having a set of services configured to induce hygiene-promoting behavior within a healthcare environment and having a sensor fusion system configured to combine data from sensors of at least two types, wherein the fused sensor data is processed to produce an indicator related to hygiene behavior activity. In embodiments, provided herein is a hygiene behavioral modification platform having a set of services configured to induce hygiene-promoting behavior within a healthcare environment and having a machine learning and/or artificial intelligence system configured to classify humans as employees or customers. In embodiments, provided herein is a hygiene behavioral modification platform having a set of services configured to induce hygiene-promoting behavior within a healthcare environment and having a system for integrating a set of detected indicators of hygiene behavior for a location and/or entity with an online rating/review system for the location and/or entity. In embodiments, provided herein is a hygiene behavioral modification platform having a set of services configured to induce hygiene-promoting behavior within a healthcare environment and having a machine learning and/or artificial intelligence system configured to generate a recommendation related to washing hands and/or hand sanitizing. In embodiments, provided herein is a hygiene behavioral modification platform having a set of services configured to induce hygiene-promoting behavior within a healthcare environment and having a machine learning and/or artificial intelligence system configured to generate a recommendation related to the duration of handwashing. In embodiments, provided herein is a hygiene behavioral modification platform having a set of services configured to induce hygiene-promoting behavior within a healthcare environment and having personal profiles with accompanying personal data structures for storing personal information. In embodiments, provided herein is a hygiene behavioral modification platform having a set of services configured to induce hygiene-promoting behavior within a healthcare environment and having workforce profiles with accompanying workforce structures for storing workforce information.

In embodiments, provided herein is a hygiene behavioral modification platform having a set of services configured to induce hygiene-promoting behavior in a hospitality environment. In embodiments, provided herein is a hygiene behavioral modification platform having a set of services configured to induce hygiene-promoting behavior in a hospitality environment and having a set of services configured to induce hygiene-promoting behavior in an education environment. In embodiments, provided herein is a hygiene behavioral modification platform having a set of services configured to induce hygiene-promoting behavior in a hospitality environment and having a set of services configured to induce hygiene-promoting behavior in a travel environment. In embodiments, provided herein is a hygiene behavioral modification platform having a set of services configured to induce hygiene-promoting behavior in a hospitality environment and having a set of services configured to induce hygiene-promoting behavior in a smart home environment. In embodiments, provided herein is a hygiene behavioral modification platform having a set of services configured to induce hygiene-promoting behavior in a hospitality environment and having a set of services configured to induce hygiene-promoting behavior in a government environment. In embodiments, provided herein is a hygiene behavioral modification platform having a set of services configured to induce hygiene-promoting behavior in a hospitality environment and having a mobile application integrated with the platform for enabling mobile access to the platform. In embodiments, provided herein is a hygiene behavioral modification platform having a set of services configured to induce hygiene-promoting behavior in a hospitality environment and having a dashboard system for representing status information regarding hygiene behavior modification for an environment. In embodiments, provided herein is a hygiene behavioral modification platform having a set of services configured to induce hygiene-promoting behavior in a hospitality environment and having a handwashing compliance dashboard system. In embodiments, provided herein is a hygiene behavioral modification platform having a set of services configured to induce hygiene-promoting behavior in a hospitality environment and having a reporting system for providing reporting of hygiene behavioral monitoring data. In embodiments, provided herein is a hygiene behavioral modification platform having a set of services configured to induce hygiene-promoting behavior in a hospitality environment and having a user interface providing a user experience that promotes user awareness of the need to undertake hygiene behavior. In embodiments, provided herein is a hygiene behavioral modification platform having a set of services configured to induce hygiene-promoting behavior in a hospitality environment and having a digital tree leaf pattern wherein the digital tree leaf pattern's growth is based on community hygiene behaviors. In embodiments, provided herein is a hygiene behavioral modification platform having a set of services configured to induce hygiene-promoting behavior in a hospitality environment and having a system for providing audiovisual experiences for the promotion of hygiene behaviors. In embodiments, provided herein is a hygiene behavioral modification platform having a set of services configured to induce hygiene-promoting behavior in a hospitality environment and having a system for providing an audiovisual experience for the promotion of hygiene behaviors wherein the audiovisual experience includes a lighting display event. In embodiments, provided herein is a hygiene behavioral modification platform having a set of services configured to induce hygiene-promoting behavior in a hospitality environment and having a system for providing an audiovisual experience for the promotion of hygiene behaviors wherein the audiovisual experience includes a sound event. In embodiments, provided herein is a hygiene behavioral modification platform having a set of services configured to induce hygiene-promoting behavior in a hospitality environment and having a system for providing an audiovisual experience for the promotion of hygiene behaviors wherein the audiovisual experience includes an audio reminder to wash hands. In embodiments, provided herein is a hygiene behavioral modification platform having a set of services configured to induce hygiene-promoting behavior in a hospitality environment and having a system for providing an audiovisual experience for the promotion of hygiene behaviors having a system for facilitating progressive reminders as an individual moves through transits an environment and passes one or more points of reference. In embodiments, provided herein is a hygiene behavioral modification platform having a set of services configured to induce hygiene-promoting behavior in a hospitality environment and having a system for providing an audiovisual experience for the promotion of hygiene behaviors wherein the audiovisual experience includes an advertisement that plays during the recommended duration of a handwashing event. In embodiments, provided herein is a hygiene behavioral modification platform having a set of services configured to induce hygiene-promoting behavior in a hospitality environment and having a peer-to-peer configuration system for enabling peer-to-peer communication among a set of hygiene-promoting devices. In embodiments, provided herein is a hygiene behavioral modification platform having a set of services configured to induce hygiene-promoting behavior in a hospitality environment and having a data aggregation system for aggregating hygiene behavioral data across a set of devices, a set of locations and/or a population of individuals. In embodiments, provided herein is a hygiene behavioral modification platform having a set of services configured to induce hygiene-promoting behavior in a hospitality environment and having an analytics system for performing an analytic operation to produce analytic measures related to hygiene behavior. In embodiments, provided herein is a hygiene behavioral modification platform having a set of services configured to induce hygiene-promoting behavior in a hospitality environment and having an analytics system for performing an analytic operation to produce an analytic measure related to hygiene behavior and having analytics indicating hygiene performance levels relevant to a particular individual. In embodiments, provided herein is a hygiene behavioral modification platform having a set of services configured to induce hygiene-promoting behavior in a hospitality environment and having an analytics system for performing an analytic operation to produce an analytic measure related to hygiene behavior and having analytics indicating hygiene performance levels relevant to a population of individuals. In embodiments, provided herein is a hygiene behavioral modification platform having a set of services configured to induce hygiene-promoting behavior in a hospitality environment and having an analytics system for performing an analytic operation to produce an analytic measure related to hygiene behavior and having analytics indicating hygiene performance levels relevant to a location of a business. In embodiments, provided herein is a hygiene behavioral modification platform having a set of services configured to induce hygiene-promoting behavior in a hospitality environment and having a community score system for generating a community score based on handwashing behavior compliance in an environment, and wherein the community score is calculated based on the proportion of humans entering the environment that wash their hands. In embodiments, provided herein is a hygiene behavioral modification platform having a set of services configured to induce hygiene-promoting behavior in a hospitality environment and for promoting hygiene behavioral modification having Bluetooth Low Energy proximity sensing, passive infrared sensors, and active infrared sensors for detecting the presence of one or more humans, and wherein the smart hygiene device is configured to attach to a soap dispenser. In embodiments, provided herein is a hygiene behavioral modification platform having a set of services configured to induce hygiene-promoting behavior in a hospitality environment and having Bluetooth Low Energy proximity sensing, passive infrared sensors, and active infrared sensors for detecting the presence of one or more humans. In embodiments, provided herein is a hygiene behavioral modification platform having a set of services configured to induce hygiene-promoting behavior in a hospitality environment and for promoting hygiene behavioral modification having Bluetooth Low Energy proximity sensing, passive infrared sensors, and active infrared sensors for detecting the presence of one or more humans and wherein the smart hygiene device is configured as a soap dispenser. In embodiments, provided herein is a hygiene behavioral modification platform having a set of services configured to induce hygiene-promoting behavior in a hospitality environment and having a system for detecting activities related to hygiene and reporting a set of indicators of hygiene behaviors. In embodiments, provided herein is a hygiene behavioral modification platform having a set of services configured to induce hygiene-promoting behavior in a hospitality environment and having a system for detecting handwashing activity. In embodiments, provided herein is a hygiene behavioral modification platform having a set of services configured to induce hygiene-promoting behavior in a hospitality environment and having a system for detecting handwashing activity and producing a measure of duration and timing of the handwashing activity. In embodiments, provided herein is a hygiene behavioral modification platform having a set of services configured to induce hygiene-promoting behavior in a hospitality environment and having a sensor fusion system configured to combine data from sensors of at least two types, wherein the fused sensor data is processed to produce an indicator related to hygiene behavior activity. In embodiments, provided herein is a hygiene behavioral modification platform having a set of services configured to induce hygiene-promoting behavior in a hospitality environment and having a machine learning and/or artificial intelligence system configured to classify humans as employees or customers. In embodiments, provided herein is a hygiene behavioral modification platform having a set of services configured to induce hygiene-promoting behavior in a hospitality environment and having a system for integrating a set of detected indicators of hygiene behavior for a location and/or entity with an online rating/review system for the location and/or entity. In embodiments, provided herein is a hygiene behavioral modification platform having a set of services configured to induce hygiene-promoting behavior in a hospitality environment and having a machine learning and/or artificial intelligence system configured to generate a recommendation related to washing hands and/or hand sanitizing. In embodiments, provided herein is a hygiene behavioral modification platform having a set of services configured to induce hygiene-promoting behavior in a hospitality environment and having a machine learning and/or artificial intelligence system configured to generate a recommendation related to the duration of handwashing. In embodiments, provided herein is a hygiene behavioral modification platform having a set of services configured to induce hygiene-promoting behavior in a hospitality environment and having personal profiles with accompanying personal data structures for storing personal information. In embodiments, provided herein is a hygiene behavioral modification platform having a set of services configured to induce hygiene-promoting behavior in a hospitality environment and having workforce profiles with accompanying workforce structures for storing workforce information.

In embodiments, provided herein is a hygiene behavioral modification platform having a set of services configured to induce hygiene-promoting behavior in an education environment. In embodiments, provided herein is a hygiene behavioral modification platform having a set of services configured to induce hygiene-promoting behavior in an education environment and having a set of services configured to induce hygiene-promoting behavior in a travel environment. In embodiments, provided herein is a hygiene behavioral modification platform having a set of services configured to induce hygiene-promoting behavior in an education environment and having a set of services configured to induce hygiene-promoting behavior in a smart home environment. In embodiments, provided herein is a hygiene behavioral modification platform having a set of services configured to induce hygiene-promoting behavior in an education environment and having a set of services configured to induce hygiene-promoting behavior in a government environment. In embodiments, provided herein is a hygiene behavioral modification platform having a set of services configured to induce hygiene-promoting behavior in an education environment and having a mobile application integrated with the platform for enabling mobile access to the platform. In embodiments, provided herein is a hygiene behavioral modification platform having a set of services configured to induce hygiene-promoting behavior in an education environment and having a dashboard system for representing status information regarding hygiene behavior modification for an environment. In embodiments, provided herein is a hygiene behavioral modification platform having a set of services configured to induce hygiene-promoting behavior in an education environment and having a handwashing compliance dashboard system. In embodiments, provided herein is a hygiene behavioral modification platform having a set of services configured to induce hygiene-promoting behavior in an education environment and having a reporting system for providing reporting of hygiene behavioral monitoring data. In embodiments, provided herein is a hygiene behavioral modification platform having a set of services configured to induce hygiene-promoting behavior in an education environment and having a user interface providing a user experience that promotes user awareness of the need to undertake hygiene behavior. In embodiments, provided herein is a hygiene behavioral modification platform having a set of services configured to induce hygiene-promoting behavior in an education environment and having a digital tree leaf pattern wherein the digital tree leaf pattern's growth is based on community hygiene behaviors. In embodiments, provided herein is a hygiene behavioral modification platform having a set of services configured to induce hygiene-promoting behavior in an education environment and having a system for providing audiovisual experiences for the promotion of hygiene behaviors. In embodiments, provided herein is a hygiene behavioral modification platform having a set of services configured to induce hygiene-promoting behavior in an education environment and having a system for providing an audiovisual experience for the promotion of hygiene behaviors wherein the audiovisual experience includes a lighting display event. In embodiments, provided herein is a hygiene behavioral modification platform having a set of services configured to induce hygiene-promoting behavior in an education environment and having a system for providing an audiovisual experience for the promotion of hygiene behaviors wherein the audiovisual experience includes a sound event. In embodiments, provided herein is a hygiene behavioral modification platform having a set of services configured to induce hygiene-promoting behavior in an education environment and having a system for providing an audiovisual experience for the promotion of hygiene behaviors wherein the audiovisual experience includes an audio reminder to wash hands. In embodiments, provided herein is a hygiene behavioral modification platform having a set of services configured to induce hygiene-promoting behavior in an education environment and having a system for providing an audiovisual experience for the promotion of hygiene behaviors having a system for facilitating progressive reminders as an individual moves through transits an environment and passes one or more points of reference. In embodiments, provided herein is a hygiene behavioral modification platform having a set of services configured to induce hygiene-promoting behavior in an education environment and having a system for providing an audiovisual experience for the promotion of hygiene behaviors wherein the audiovisual experience includes an advertisement that plays during the recommended duration of a handwashing event. In embodiments, provided herein is a hygiene behavioral modification platform having a set of services configured to induce hygiene-promoting behavior in an education environment and having a peer-to-peer configuration system for enabling peer-to-peer communication among a set of hygiene-promoting devices. In embodiments, provided herein is a hygiene behavioral modification platform having a set of services configured to induce hygiene-promoting behavior in an education environment and having a data aggregation system for aggregating hygiene behavioral data across a set of devices, a set of locations and/or a population of individuals. In embodiments, provided herein is a hygiene behavioral modification platform having a set of services configured to induce hygiene-promoting behavior in an education environment and having an analytics system for performing an analytic operation to produce analytic measures related to hygiene behavior. In embodiments, provided herein is a hygiene behavioral modification platform having a set of services configured to induce hygiene-promoting behavior in an education environment and having an analytics system for performing an analytic operation to produce an analytic measure related to hygiene behavior and having analytics indicating hygiene performance levels relevant to a particular individual. In embodiments, provided herein is a hygiene behavioral modification platform having a set of services configured to induce hygiene-promoting behavior in an education environment and having an analytics system for performing an analytic operation to produce an analytic measure related to hygiene behavior and having analytics indicating hygiene performance levels relevant to a population of individuals. In embodiments, provided herein is a hygiene behavioral modification platform having a set of services configured to induce hygiene-promoting behavior in an education environment and having an analytics system for performing an analytic operation to produce an analytic measure related to hygiene behavior and having analytics indicating hygiene performance levels relevant to a location of a business. In embodiments, provided herein is a hygiene behavioral modification platform having a set of services configured to induce hygiene-promoting behavior in an education environment and having a community score system for generating a community score based on handwashing behavior compliance in an environment, and wherein the community score is calculated based on the proportion of humans entering the environment that wash their hands. In embodiments, provided herein is a hygiene behavioral modification platform having a set of services configured to induce hygiene-promoting behavior in an education environment and for promoting hygiene behavioral modification having Bluetooth Low Energy proximity sensing, passive infrared sensors, and active infrared sensors for detecting the presence of one or more humans, and wherein the smart hygiene device is configured to attach to a soap dispenser. In embodiments, provided herein is a hygiene behavioral modification platform having a set of services configured to induce hygiene-promoting behavior in an education environment and having Bluetooth Low Energy proximity sensing, passive infrared sensors, and active infrared sensors for detecting the presence of one or more humans. In embodiments, provided herein is a hygiene behavioral modification platform having a set of services configured to induce hygiene-promoting behavior in an education environment and for promoting hygiene behavioral modification having Bluetooth Low Energy proximity sensing, passive infrared sensors, and active infrared sensors for detecting the presence of one or more humans and wherein the smart hygiene device is configured as a soap dispenser. In embodiments, provided herein is a hygiene behavioral modification platform having a set of services configured to induce hygiene-promoting behavior in an education environment and having a system for detecting activities related to hygiene and reporting a set of indicators of hygiene behaviors. In embodiments, provided herein is a hygiene behavioral modification platform having a set of services configured to induce hygiene-promoting behavior in an education environment and having a system for detecting handwashing activity. In embodiments, provided herein is a hygiene behavioral modification platform having a set of services configured to induce hygiene-promoting behavior in an education environment and having a system for detecting handwashing activity and producing a measure of duration and timing of the handwashing activity. In embodiments, provided herein is a hygiene behavioral modification platform having a set of services configured to induce hygiene-promoting behavior in an education environment and having a sensor fusion system configured to combine data from sensors of at least two types, wherein the fused sensor data is processed to produce an indicator related to hygiene behavior activity. In embodiments, provided herein is a hygiene behavioral modification platform having a set of services configured to induce hygiene-promoting behavior in an education environment and having a machine learning and/or artificial intelligence system configured to classify humans as employees or customers. In embodiments, provided herein is a hygiene behavioral modification platform having a set of services configured to induce hygiene-promoting behavior in an education environment and having a system for integrating a set of detected indicators of hygiene behavior for a location and/or entity with an online rating/review system for the location and/or entity. In embodiments, provided herein is a hygiene behavioral modification platform having a set of services configured to induce hygiene-promoting behavior in an education environment and having a machine learning and/or artificial intelligence system configured to generate a recommendation related to washing hands and/or hand sanitizing. In embodiments, provided herein is a hygiene behavioral modification platform having a set of services configured to induce hygiene-promoting behavior in an education environment and having a machine learning and/or artificial intelligence system configured to generate a recommendation related to the duration of handwashing. In embodiments, provided herein is a hygiene behavioral modification platform having a set of services configured to induce hygiene-promoting behavior in an education environment and having personal profiles with accompanying personal data structures for storing personal information. In embodiments, provided herein is a hygiene behavioral modification platform having a set of services configured to induce hygiene-promoting behavior in an education environment and having workforce profiles with accompanying workforce structures for storing workforce information.

In embodiments, provided herein is a hygiene behavioral modification platform having a set of services configured to induce hygiene-promoting behavior in a travel environment. In embodiments, provided herein is a hygiene behavioral modification platform having a set of services configured to induce hygiene-promoting behavior in a travel environment and having a set of services configured to induce hygiene-promoting behavior in a smart home environment. In embodiments, provided herein is a hygiene behavioral modification platform having a set of services configured to induce hygiene-promoting behavior in a travel environment and having a set of services configured to induce hygiene-promoting behavior in a government environment. In embodiments, provided herein is a hygiene behavioral modification platform having a set of services configured to induce hygiene-promoting behavior in a travel environment and having a mobile application integrated with the platform for enabling mobile access to the platform. In embodiments, provided herein is a hygiene behavioral modification platform having a set of services configured to induce hygiene-promoting behavior in a travel environment and having a dashboard system for representing status information regarding hygiene behavior modification for an environment. In embodiments, provided herein is a hygiene behavioral modification platform having a set of services configured to induce hygiene-promoting behavior in a travel environment and having a handwashing compliance dashboard system. In embodiments, provided herein is a hygiene behavioral modification platform having a set of services configured to induce hygiene-promoting behavior in a travel environment and having a reporting system for providing reporting of hygiene behavioral monitoring data. In embodiments, provided herein is a hygiene behavioral modification platform having a set of services configured to induce hygiene-promoting behavior in a travel environment and having a user interface providing a user experience that promotes user awareness of the need to undertake hygiene behavior. In embodiments, provided herein is a hygiene behavioral modification platform having a set of services configured to induce hygiene-promoting behavior in a travel environment and having a digital tree leaf pattern wherein the digital tree leaf pattern's growth is based on community hygiene behaviors. In embodiments, provided herein is a hygiene behavioral modification platform having a set of services configured to induce hygiene-promoting behavior in a travel environment and having a system for providing audiovisual experiences for the promotion of hygiene behaviors. In embodiments, provided herein is a hygiene behavioral modification platform having a set of services configured to induce hygiene-promoting behavior in a travel environment and having a system for providing an audiovisual experience for the promotion of hygiene behaviors wherein the audiovisual experience includes a lighting display event. In embodiments, provided herein is a hygiene behavioral modification platform having a set of services configured to induce hygiene-promoting behavior in a travel environment and having a system for providing an audiovisual experience for the promotion of hygiene behaviors wherein the audiovisual experience includes a sound event. In embodiments, provided herein is a hygiene behavioral modification platform having a set of services configured to induce hygiene-promoting behavior in a travel environment and having a system for providing an audiovisual experience for the promotion of hygiene behaviors wherein the audiovisual experience includes an audio reminder to wash hands. In embodiments, provided herein is a hygiene behavioral modification platform having a set of services configured to induce hygiene-promoting behavior in a travel environment and having a system for providing an audiovisual experience for the promotion of hygiene behaviors having a system for facilitating progressive reminders as an individual moves through transits an environment and passes one or more points of reference. In embodiments, provided herein is a hygiene behavioral modification platform having a set of services configured to induce hygiene-promoting behavior in a travel environment and having a system for providing an audiovisual experience for the promotion of hygiene behaviors wherein the audiovisual experience includes an advertisement that plays during the recommended duration of a handwashing event. In embodiments, provided herein is a hygiene behavioral modification platform having a set of services configured to induce hygiene-promoting behavior in a travel environment and having a peer-to-peer configuration system for enabling peer-to-peer communication among a set of hygiene-promoting devices. In embodiments, provided herein is a hygiene behavioral modification platform having a set of services configured to induce hygiene-promoting behavior in a travel environment and having a data aggregation system for aggregating hygiene behavioral data across a set of devices, a set of locations and/or a population of individuals. In embodiments, provided herein is a hygiene behavioral modification platform having a set of services configured to induce hygiene-promoting behavior in a travel environment and having an analytics system for performing an analytic operation to produce analytic measures related to hygiene behavior. In embodiments, provided herein is a hygiene behavioral modification platform having a set of services configured to induce hygiene-promoting behavior in a travel environment and having an analytics system for performing an analytic operation to produce an analytic measure related to hygiene behavior and having analytics indicating hygiene performance levels relevant to a particular individual. In embodiments, provided herein is a hygiene behavioral modification platform having a set of services configured to induce hygiene-promoting behavior in a travel environment and having an analytics system for performing an analytic operation to produce an analytic measure related to hygiene behavior and having analytics indicating hygiene performance levels relevant to a population of individuals. In embodiments, provided herein is a hygiene behavioral modification platform having a set of services configured to induce hygiene-promoting behavior in a travel environment and having an analytics system for performing an analytic operation to produce an analytic measure related to hygiene behavior and having analytics indicating hygiene performance levels relevant to a location of a business. In embodiments, provided herein is a hygiene behavioral modification platform having a set of services configured to induce hygiene-promoting behavior in a travel environment and having a community score system for generating a community score based on handwashing behavior compliance in an environment, and wherein the community score is calculated based on the proportion of humans entering the environment that wash their hands. In embodiments, provided herein is a hygiene behavioral modification platform having a set of services configured to induce hygiene-promoting behavior in a travel environment and for promoting hygiene behavioral modification having Bluetooth Low Energy proximity sensing, passive infrared sensors, and active infrared sensors for detecting the presence of one or more humans, and wherein the smart hygiene device is configured to attach to a soap dispenser. In embodiments, provided herein is a hygiene behavioral modification platform having a set of services configured to induce hygiene-promoting behavior in a travel environment and having Bluetooth Low Energy proximity sensing, passive infrared sensors, and active infrared sensors for detecting the presence of one or more humans. In embodiments, provided herein is a hygiene behavioral modification platform having a set of services configured to induce hygiene-promoting behavior in a travel environment and for promoting hygiene behavioral modification having Bluetooth Low Energy proximity sensing, passive infrared sensors, and active infrared sensors for detecting the presence of one or more humans and wherein the smart hygiene device is configured as a soap dispenser. In embodiments, provided herein is a hygiene behavioral modification platform having a set of services configured to induce hygiene-promoting behavior in a travel environment and having a system for detecting activities related to hygiene and reporting a set of indicators of hygiene behaviors. In embodiments, provided herein is a hygiene behavioral modification platform having a set of services configured to induce hygiene-promoting behavior in a travel environment and having a system for detecting handwashing activity. In embodiments, provided herein is a hygiene behavioral modification platform having a set of services configured to induce hygiene-promoting behavior in a travel environment and having a system for detecting handwashing activity and producing a measure of duration and timing of the handwashing activity. In embodiments, provided herein is a hygiene behavioral modification platform having a set of services configured to induce hygiene-promoting behavior in a travel environment and having a sensor fusion system configured to combine data from sensors of at least two types, wherein the fused sensor data is processed to produce an indicator related to hygiene behavior activity. In embodiments, provided herein is a hygiene behavioral modification platform having a set of services configured to induce hygiene-promoting behavior in a travel environment and having a machine learning and/or artificial intelligence system configured to classify humans as employees or customers. In embodiments, provided herein is a hygiene behavioral modification platform having a set of services configured to induce hygiene-promoting behavior in a travel environment and having a system for integrating a set of detected indicators of hygiene behavior for a location and/or entity with an online rating/review system for the location and/or entity. In embodiments, provided herein is a hygiene behavioral modification platform having a set of services configured to induce hygiene-promoting behavior in a travel environment and having a machine learning and/or artificial intelligence system configured to generate a recommendation related to washing hands and/or hand sanitizing. In embodiments, provided herein is a hygiene behavioral modification platform having a set of services configured to induce hygiene-promoting behavior in a travel environment and having a machine learning and/or artificial intelligence system configured to generate a recommendation related to the duration of handwashing. In embodiments, provided herein is a hygiene behavioral modification platform having a set of services configured to induce hygiene-promoting behavior in a travel environment and having personal profiles with accompanying personal data structures for storing personal information. In embodiments, provided herein is a hygiene behavioral modification platform having a set of services configured to induce hygiene-promoting behavior in a travel environment and having workforce profiles with accompanying workforce structures for storing workforce information.

In embodiments, provided herein is a hygiene behavioral modification platform having a set of services configured to induce hygiene-promoting behavior in a smart home environment. In embodiments, provided herein is a hygiene behavioral modification platform having a set of services configured to induce hygiene-promoting behavior in a smart home environment and having a set of services configured to induce hygiene-promoting behavior in a government environment. In embodiments, provided herein is a hygiene behavioral modification platform having a set of services configured to induce hygiene-promoting behavior in a smart home environment and having a mobile application integrated with the platform for enabling mobile access to the platform. In embodiments, provided herein is a hygiene behavioral modification platform having a set of services configured to induce hygiene-promoting behavior in a smart home environment and having a dashboard system for representing status information regarding hygiene behavior modification for an environment. In embodiments, provided herein is a hygiene behavioral modification platform having a set of services configured to induce hygiene-promoting behavior in a smart home environment and having a handwashing compliance dashboard system. In embodiments, provided herein is a hygiene behavioral modification platform having a set of services configured to induce hygiene-promoting behavior in a smart home environment and having a reporting system for providing reporting of hygiene behavioral monitoring data. In embodiments, provided herein is a hygiene behavioral modification platform having a set of services configured to induce hygiene-promoting behavior in a smart home environment and having a user interface providing a user experience that promotes user awareness of the need to undertake hygiene behavior. In embodiments, provided herein is a hygiene behavioral modification platform having a set of services configured to induce hygiene-promoting behavior in a smart home environment and having a digital tree leaf pattern wherein the digital tree leaf pattern's growth is based on community hygiene behaviors. In embodiments, provided herein is a hygiene behavioral modification platform having a set of services configured to induce hygiene-promoting behavior in a smart home environment and having a system for providing audiovisual experiences for the promotion of hygiene behaviors. In embodiments, provided herein is a hygiene behavioral modification platform having a set of services configured to induce hygiene-promoting behavior in a smart home environment and having a system for providing an audiovisual experience for the promotion of hygiene behaviors wherein the audiovisual experience includes a lighting display event. In embodiments, provided herein is a hygiene behavioral modification platform having a set of services configured to induce hygiene-promoting behavior in a smart home environment and having a system for providing an audiovisual experience for the promotion of hygiene behaviors wherein the audiovisual experience includes a sound event. In embodiments, provided herein is a hygiene behavioral modification platform having a set of services configured to induce hygiene-promoting behavior in a smart home environment and having a system for providing an audiovisual experience for the promotion of hygiene behaviors wherein the audiovisual experience includes an audio reminder to wash hands. In embodiments, provided herein is a hygiene behavioral modification platform having a set of services configured to induce hygiene-promoting behavior in a smart home environment and having a system for providing an audiovisual experience for the promotion of hygiene behaviors having a system for facilitating progressive reminders as an individual moves through transits an environment and passes one or more points of reference. In embodiments, provided herein is a hygiene behavioral modification platform having a set of services configured to induce hygiene-promoting behavior in a smart home environment and having a system for providing an audiovisual experience for the promotion of hygiene behaviors wherein the audiovisual experience includes an advertisement that plays during the recommended duration of a handwashing event. In embodiments, provided herein is a hygiene behavioral modification platform having a set of services configured to induce hygiene-promoting behavior in a smart home environment and having a peer-to-peer configuration system for enabling peer-to-peer communication among a set of hygiene-promoting devices. In embodiments, provided herein is a hygiene behavioral modification platform having a set of services configured to induce hygiene-promoting behavior in a smart home environment and having a data aggregation system for aggregating hygiene behavioral data across a set of devices, a set of locations and/or a population of individuals. In embodiments, provided herein is a hygiene behavioral modification platform having a set of services configured to induce hygiene-promoting behavior in a smart home environment and having an analytics system for performing an analytic operation to produce analytic measures related to hygiene behavior. In embodiments, provided herein is a hygiene behavioral modification platform having a set of services configured to induce hygiene-promoting behavior in a smart home environment and having an analytics system for performing an analytic operation to produce an analytic measure related to hygiene behavior and having analytics indicating hygiene performance levels relevant to a particular individual. In embodiments, provided herein is a hygiene behavioral modification platform having a set of services configured to induce hygiene-promoting behavior in a smart home environment and having an analytics system for performing an analytic operation to produce an analytic measure related to hygiene behavior and having analytics indicating hygiene performance levels relevant to a population of individuals. In embodiments, provided herein is a hygiene behavioral modification platform having a set of services configured to induce hygiene-promoting behavior in a smart home environment and having an analytics system for performing an analytic operation to produce an analytic measure related to hygiene behavior and having analytics indicating hygiene performance levels relevant to a location of a business. In embodiments, provided herein is a hygiene behavioral modification platform having a set of services configured to induce hygiene-promoting behavior in a smart home environment and having a community score system for generating a community score based on handwashing behavior compliance in an environment, and wherein the community score is calculated based on the proportion of humans entering the environment that wash their hands. In embodiments, provided herein is a hygiene behavioral modification platform having a set of services configured to induce hygiene-promoting behavior in a smart home environment and for promoting hygiene behavioral modification having Bluetooth Low Energy proximity sensing, passive infrared sensors, and active infrared sensors for detecting the presence of one or more humans, and wherein the smart hygiene device is configured to attach to a soap dispenser. In embodiments, provided herein is a hygiene behavioral modification platform having a set of services configured to induce hygiene-promoting behavior in a smart home environment and having Bluetooth Low Energy proximity sensing, passive infrared sensors, and active infrared sensors for detecting the presence of one or more humans. In embodiments, provided herein is a hygiene behavioral modification platform having a set of services configured to induce hygiene-promoting behavior in a smart home environment and for promoting hygiene behavioral modification having Bluetooth Low Energy proximity sensing, passive infrared sensors, and active infrared sensors for detecting the presence of one or more humans and wherein the smart hygiene device is configured as a soap dispenser. In embodiments, provided herein is a hygiene behavioral modification platform having a set of services configured to induce hygiene-promoting behavior in a smart home environment and having a system for detecting activities related to hygiene and reporting a set of indicators of hygiene behaviors. In embodiments, provided herein is a hygiene behavioral modification platform having a set of services configured to induce hygiene-promoting behavior in a smart home environment and having a system for detecting handwashing activity. In embodiments, provided herein is a hygiene behavioral modification platform having a set of services configured to induce hygiene-promoting behavior in a smart home environment and having a system for detecting handwashing activity and producing a measure of duration and timing of the handwashing activity. In embodiments, provided herein is a hygiene behavioral modification platform having a set of services configured to induce hygiene-promoting behavior in a smart home environment and having a sensor fusion system configured to combine data from sensors of at least two types, wherein the fused sensor data is processed to produce an indicator related to hygiene behavior activity. In embodiments, provided herein is a hygiene behavioral modification platform having a set of services configured to induce hygiene-promoting behavior in a smart home environment and having a machine learning and/or artificial intelligence system configured to classify humans as employees or customers. In embodiments, provided herein is a hygiene behavioral modification platform having a set of services configured to induce hygiene-promoting behavior in a smart home environment and having a system for integrating a set of detected indicators of hygiene behavior for a location and/or entity with an online rating/review system for the location and/or entity. In embodiments, provided herein is a hygiene behavioral modification platform having a set of services configured to induce hygiene-promoting behavior in a smart home environment and having a machine learning and/or artificial intelligence system configured to generate a recommendation related to washing hands and/or hand sanitizing. In embodiments, provided herein is a hygiene behavioral modification platform having a set of services configured to induce hygiene-promoting behavior in a smart home environment and having a machine learning and/or artificial intelligence system configured to generate a recommendation related to the duration of handwashing. In embodiments, provided herein is a hygiene behavioral modification platform having a set of services configured to induce hygiene-promoting behavior in a smart home environment and having personal profiles with accompanying personal data structures for storing personal information. In embodiments, provided herein is a hygiene behavioral modification platform having a set of services configured to induce hygiene-promoting behavior in a smart home environment and having workforce profiles with accompanying workforce structures for storing workforce information.

In embodiments, provided herein is a hygiene behavioral modification platform having a set of services configured to induce hygiene-promoting behavior in a government environment. In embodiments, provided herein is a hygiene behavioral modification platform having a set of services configured to induce hygiene-promoting behavior in a government environment and having a mobile application integrated with the platform for enabling mobile access to the platform. In embodiments, provided herein is a hygiene behavioral modification platform having a set of services configured to induce hygiene-promoting behavior in a government environment and having a dashboard system for representing status information regarding hygiene behavior modification for an environment. In embodiments, provided herein is a hygiene behavioral modification platform having a set of services configured to induce hygiene-promoting behavior in a government environment and having a handwashing compliance dashboard system. In embodiments, provided herein is a hygiene behavioral modification platform having a set of services configured to induce hygiene-promoting behavior in a government environment and having a reporting system for providing reporting of hygiene behavioral monitoring data. In embodiments, provided herein is a hygiene behavioral modification platform having a set of services configured to induce hygiene-promoting behavior in a government environment and having a user interface providing a user experience that promotes user awareness of the need to undertake hygiene behavior. In embodiments, provided herein is a hygiene behavioral modification platform having a set of services configured to induce hygiene-promoting behavior in a government environment and having a digital tree leaf pattern wherein the digital tree leaf pattern's growth is based on community hygiene behaviors. In embodiments, provided herein is a hygiene behavioral modification platform having a set of services configured to induce hygiene-promoting behavior in a government environment and having a system for providing audiovisual experiences for the promotion of hygiene behaviors. In embodiments, provided herein is a hygiene behavioral modification platform having a set of services configured to induce hygiene-promoting behavior in a government environment and having a system for providing an audiovisual experience for the promotion of hygiene behaviors wherein the audiovisual experience includes a lighting display event. In embodiments, provided herein is a hygiene behavioral modification platform having a set of services configured to induce hygiene-promoting behavior in a government environment and having a system for providing an audiovisual experience for the promotion of hygiene behaviors wherein the audiovisual experience includes a sound event. In embodiments, provided herein is a hygiene behavioral modification platform having a set of services configured to induce hygiene-promoting behavior in a government environment and having a system for providing an audiovisual experience for the promotion of hygiene behaviors wherein the audiovisual experience includes an audio reminder to wash hands. In embodiments, provided herein is a hygiene behavioral modification platform having a set of services configured to induce hygiene-promoting behavior in a government environment and having a system for providing an audiovisual experience for the promotion of hygiene behaviors having a system for facilitating progressive reminders as an individual moves through transits an environment and passes one or more points of reference. In embodiments, provided herein is a hygiene behavioral modification platform having a set of services configured to induce hygiene-promoting behavior in a government environment and having a system for providing an audiovisual experience for the promotion of hygiene behaviors wherein the audiovisual experience includes an advertisement that plays during the recommended duration of a handwashing event. In embodiments, provided herein is a hygiene behavioral modification platform having a set of services configured to induce hygiene-promoting behavior in a government environment and having a peer-to-peer configuration system for enabling peer-to-peer communication among a set of hygiene-promoting devices. In embodiments, provided herein is a hygiene behavioral modification platform having a set of services configured to induce hygiene-promoting behavior in a government environment and having a data aggregation system for aggregating hygiene behavioral data across a set of devices, a set of locations and/or a population of individuals. In embodiments, provided herein is a hygiene behavioral modification platform having a set of services configured to induce hygiene-promoting behavior in a government environment and having an analytics system for performing an analytic operation to produce analytic measures related to hygiene behavior. In embodiments, provided herein is a hygiene behavioral modification platform having a set of services configured to induce hygiene-promoting behavior in a government environment and having an analytics system for performing an analytic operation to produce an analytic measure related to hygiene behavior and having analytics indicating hygiene performance levels relevant to a particular individual. In embodiments, provided herein is a hygiene behavioral modification platform having a set of services configured to induce hygiene-promoting behavior in a government environment and having an analytics system for performing an analytic operation to produce an analytic measure related to hygiene behavior and having analytics indicating hygiene performance levels relevant to a population of individuals. In embodiments, provided herein is a hygiene behavioral modification platform having a set of services configured to induce hygiene-promoting behavior in a government environment and having an analytics system for performing an analytic operation to produce an analytic measure related to hygiene behavior and having analytics indicating hygiene performance levels relevant to a location of a business. In embodiments, provided herein is a hygiene behavioral modification platform having a set of services configured to induce hygiene-promoting behavior in a government environment and having a community score system for generating a community score based on handwashing behavior compliance in an environment, and wherein the community score is calculated based on the proportion of humans entering the environment that wash their hands. In embodiments, provided herein is a hygiene behavioral modification platform having a set of services configured to induce hygiene-promoting behavior in a government environment and for promoting hygiene behavioral modification having Bluetooth Low Energy proximity sensing, passive infrared sensors, and active infrared sensors for detecting the presence of one or more humans, and wherein the smart hygiene device is configured to attach to a soap dispenser. In embodiments, provided herein is a hygiene behavioral modification platform having a set of services configured to induce hygiene-promoting behavior in a government environment and having Bluetooth Low Energy proximity sensing, passive infrared sensors, and active infrared sensors for detecting the presence of one or more humans. In embodiments, provided herein is a hygiene behavioral modification platform having a set of services configured to induce hygiene-promoting behavior in a government environment and for promoting hygiene behavioral modification having Bluetooth Low Energy proximity sensing, passive infrared sensors, and active infrared sensors for detecting the presence of one or more humans and wherein the smart hygiene device is configured as a soap dispenser. In embodiments, provided herein is a hygiene behavioral modification platform having a set of services configured to induce hygiene-promoting behavior in a government environment and having a system for detecting activities related to hygiene and reporting a set of indicators of hygiene behaviors. In embodiments, provided herein is a hygiene behavioral modification platform having a set of services configured to induce hygiene-promoting behavior in a government environment and having a system for detecting handwashing activity. In embodiments, provided herein is a hygiene behavioral modification platform having a set of services configured to induce hygiene-promoting behavior in a government environment and having a system for detecting handwashing activity and producing a measure of duration and timing of the handwashing activity. In embodiments, provided herein is a hygiene behavioral modification platform having a set of services configured to induce hygiene-promoting behavior in a government environment and having a sensor fusion system configured to combine data from sensors of at least two types, wherein the fused sensor data is processed to produce an indicator related to hygiene behavior activity. In embodiments, provided herein is a hygiene behavioral modification platform having a set of services configured to induce hygiene-promoting behavior in a government environment and having a machine learning and/or artificial intelligence system configured to classify humans as employees or customers. In embodiments, provided herein is a hygiene behavioral modification platform having a set of services configured to induce hygiene-promoting behavior in a government environment and having a system for integrating a set of detected indicators of hygiene behavior for a location and/or entity with an online rating/review system for the location and/or entity. In embodiments, provided herein is a hygiene behavioral modification platform having a set of services configured to induce hygiene-promoting behavior in a government environment and having a machine learning and/or artificial intelligence system configured to generate a recommendation related to washing hands and/or hand sanitizing. In embodiments, provided herein is a hygiene behavioral modification platform having a set of services configured to induce hygiene-promoting behavior in a government environment and having a machine learning and/or artificial intelligence system configured to generate a recommendation related to the duration of handwashing. In embodiments, provided herein is a hygiene behavioral modification platform having a set of services configured to induce hygiene-promoting behavior in a government environment and having personal profiles with accompanying personal data structures for storing personal information. In embodiments, provided herein is a hygiene behavioral modification platform having a set of services configured to induce hygiene-promoting behavior in a government environment and having workforce profiles with accompanying workforce structures for storing workforce information.

In embodiments, provided herein is a hygiene behavioral modification platform having a mobile application integrated with the platform for enabling mobile access to the platform. In embodiments, provided herein is a hygiene behavioral modification platform having a mobile application integrated with the platform for enabling mobile access to the platform and having a dashboard system for representing status information regarding hygiene behavior modification for an environment. In embodiments, provided herein is a hygiene behavioral modification platform having a mobile application integrated with the platform for enabling mobile access to the platform and having a handwashing compliance dashboard system. In embodiments, provided herein is a hygiene behavioral modification platform having a mobile application integrated with the platform for enabling mobile access to the platform and having a reporting system for providing reporting of hygiene behavioral monitoring data. In embodiments, provided herein is a hygiene behavioral modification platform having a mobile application integrated with the platform for enabling mobile access to the platform and having a user interface providing a user experience that promotes user awareness of the need to undertake hygiene behavior. In embodiments, provided herein is a hygiene behavioral modification platform having a mobile application integrated with the platform for enabling mobile access to the platform and having a digital tree leaf pattern wherein the digital tree leaf pattern's growth is based on community hygiene behaviors. In embodiments, provided herein is a hygiene behavioral modification platform having a mobile application integrated with the platform for enabling mobile access to the platform and having a system for providing audiovisual experiences for the promotion of hygiene behaviors. In embodiments, provided herein is a hygiene behavioral modification platform having a mobile application integrated with the platform for enabling mobile access to the platform and having a system for providing an audiovisual experience for the promotion of hygiene behaviors wherein the audiovisual experience includes a lighting display event. In embodiments, provided herein is a hygiene behavioral modification platform having a mobile application integrated with the platform for enabling mobile access to the platform and having a system for providing an audiovisual experience for the promotion of hygiene behaviors wherein the audiovisual experience includes a sound event. In embodiments, provided herein is a hygiene behavioral modification platform having a mobile application integrated with the platform for enabling mobile access to the platform and having a system for providing an audiovisual experience for the promotion of hygiene behaviors wherein the audiovisual experience includes an audio reminder to wash hands. In embodiments, provided herein is a hygiene behavioral modification platform having a mobile application integrated with the platform for enabling mobile access to the platform and having a system for providing an audiovisual experience for the promotion of hygiene behaviors having a system for facilitating progressive reminders as an individual moves through transits an environment and passes one or more points of reference. In embodiments, provided herein is a hygiene behavioral modification platform having a mobile application integrated with the platform for enabling mobile access to the platform and having a system for providing an audiovisual experience for the promotion of hygiene behaviors wherein the audiovisual experience includes an advertisement that plays during the recommended duration of a handwashing event. In embodiments, provided herein is a hygiene behavioral modification platform having a mobile application integrated with the platform for enabling mobile access to the platform and having a peer-to-peer configuration system for enabling peer-to-peer communication among a set of hygiene-promoting devices. In embodiments, provided herein is a hygiene behavioral modification platform having a mobile application integrated with the platform for enabling mobile access to the platform and having a data aggregation system for aggregating hygiene behavioral data across a set of devices, a set of locations and/or a population of individuals. In embodiments, provided herein is a hygiene behavioral modification platform having a mobile application integrated with the platform for enabling mobile access to the platform and having an analytics system for performing an analytic operation to produce analytic measures related to hygiene behavior. In embodiments, provided herein is a hygiene behavioral modification platform having a mobile application integrated with the platform for enabling mobile access to the platform and having an analytics system for performing an analytic operation to produce an analytic measure related to hygiene behavior and having analytics indicating hygiene performance levels relevant to a particular individual. In embodiments, provided herein is a hygiene behavioral modification platform having a mobile application integrated with the platform for enabling mobile access to the platform and having an analytics system for performing an analytic operation to produce an analytic measure related to hygiene behavior and having analytics indicating hygiene performance levels relevant to a population of individuals. In embodiments, provided herein is a hygiene behavioral modification platform having a mobile application integrated with the platform for enabling mobile access to the platform and having an analytics system for performing an analytic operation to produce an analytic measure related to hygiene behavior and having analytics indicating hygiene performance levels relevant to a location of a business. In embodiments, provided herein is a hygiene behavioral modification platform having a mobile application integrated with the platform for enabling mobile access to the platform and having a community score system for generating a community score based on handwashing behavior compliance in an environment, and wherein the community score is calculated based on the proportion of humans entering the environment that wash their hands. In embodiments, provided herein is a hygiene behavioral modification platform having a mobile application integrated with the platform for enabling mobile access to the platform and for promoting hygiene behavioral modification having Bluetooth Low Energy proximity sensing, passive infrared sensors, and active infrared sensors for detecting the presence of one or more humans, and wherein the smart hygiene device is configured to attach to a soap dispenser. In embodiments, provided herein is a hygiene behavioral modification platform having a mobile application integrated with the platform for enabling mobile access to the platform and having Bluetooth Low Energy proximity sensing, passive infrared sensors, and active infrared sensors for detecting the presence of one or more humans. In embodiments, provided herein is a hygiene behavioral modification platform having a mobile application integrated with the platform for enabling mobile access to the platform and for promoting hygiene behavioral modification having Bluetooth Low Energy proximity sensing, passive infrared sensors, and active infrared sensors for detecting the presence of one or more humans and wherein the smart hygiene device is configured as a soap dispenser. In embodiments, provided herein is a hygiene behavioral modification platform having a mobile application integrated with the platform for enabling mobile access to the platform and having a system for detecting activities related to hygiene and reporting a set of indicators of hygiene behaviors. In embodiments, provided herein is a hygiene behavioral modification platform having a mobile application integrated with the platform for enabling mobile access to the platform and having a system for detecting handwashing activity. In embodiments, provided herein is a hygiene behavioral modification platform having a mobile application integrated with the platform for enabling mobile access to the platform and having a system for detecting handwashing activity and producing a measure of duration and timing of the handwashing activity. In embodiments, provided herein is a hygiene behavioral modification platform having a mobile application integrated with the platform for enabling mobile access to the platform and having a sensor fusion system configured to combine data from sensors of at least two types, wherein the fused sensor data is processed to produce an indicator related to hygiene behavior activity. In embodiments, provided herein is a hygiene behavioral modification platform having a mobile application integrated with the platform for enabling mobile access to the platform and having a machine learning and/or artificial intelligence system configured to classify humans as employees or customers. In embodiments, provided herein is a hygiene behavioral modification platform having a mobile application integrated with the platform for enabling mobile access to the platform and having a system for integrating a set of detected indicators of hygiene behavior for a location and/or entity with an online rating/review system for the location and/or entity. In embodiments, provided herein is a hygiene behavioral modification platform having a mobile application integrated with the platform for enabling mobile access to the platform and having a machine learning and/or artificial intelligence system configured to generate a recommendation related to washing hands and/or hand sanitizing. In embodiments, provided herein is a hygiene behavioral modification platform having a mobile application integrated with the platform for enabling mobile access to the platform and having a machine learning and/or artificial intelligence system configured to generate a recommendation related to the duration of handwashing. In embodiments, provided herein is a hygiene behavioral modification platform having a mobile application integrated with the platform for enabling mobile access to the platform and having personal profiles with accompanying personal data structures for storing personal information. In embodiments, provided herein is a hygiene behavioral modification platform having a mobile application integrated with the platform for enabling mobile access to the platform and having workforce profiles with accompanying workforce structures for storing workforce information.

In embodiments, provided herein is a hygiene behavioral modification platform having a dashboard system for representing status information regarding hygiene behavior modification for an environment. In embodiments, provided herein is a hygiene behavioral modification platform having a dashboard system for representing status information regarding hygiene behavior modification for an environment and having a handwashing compliance dashboard system. In embodiments, provided herein is a hygiene behavioral modification platform having a dashboard system for representing status information regarding hygiene behavior modification for an environment and having a reporting system for providing reporting of hygiene behavioral monitoring data. In embodiments, provided herein is a hygiene behavioral modification platform having a dashboard system for representing status information regarding hygiene behavior modification for an environment and having a user interface providing a user experience that promotes user awareness of the need to undertake hygiene behavior. In embodiments, provided herein is a hygiene behavioral modification platform having a dashboard system for representing status information regarding hygiene behavior modification for an environment and having a digital tree leaf pattern wherein the digital tree leaf pattern's growth is based on community hygiene behaviors. In embodiments, provided herein is a hygiene behavioral modification platform having a dashboard system for representing status information regarding hygiene behavior modification for an environment and having a system for providing audiovisual experiences for the promotion of hygiene behaviors. In embodiments, provided herein is a hygiene behavioral modification platform having a dashboard system for representing status information regarding hygiene behavior modification for an environment and having a system for providing an audiovisual experience for the promotion of hygiene behaviors wherein the audiovisual experience includes a lighting display event. In embodiments, provided herein is a hygiene behavioral modification platform having a dashboard system for representing status information regarding hygiene behavior modification for an environment and having a system for providing an audiovisual experience for the promotion of hygiene behaviors wherein the audiovisual experience includes a sound event. In embodiments, provided herein is a hygiene behavioral modification platform having a dashboard system for representing status information regarding hygiene behavior modification for an environment and having a system for providing an audiovisual experience for the promotion of hygiene behaviors wherein the audiovisual experience includes an audio reminder to wash hands. In embodiments, provided herein is a hygiene behavioral modification platform having a dashboard system for representing status information regarding hygiene behavior modification for an environment and having a system for providing an audiovisual experience for the promotion of hygiene behaviors having a system for facilitating progressive reminders as an individual moves through transits an environment and passes one or more points of reference. In embodiments, provided herein is a hygiene behavioral modification platform having a dashboard system for representing status information regarding hygiene behavior modification for an environment and having a system for providing an audiovisual experience for the promotion of hygiene behaviors wherein the audiovisual experience includes an advertisement that plays during the recommended duration of a handwashing event. In embodiments, provided herein is a hygiene behavioral modification platform having a dashboard system for representing status information regarding hygiene behavior modification for an environment and having a peer-to-peer configuration system for enabling peer-to-peer communication among a set of hygiene-promoting devices. In embodiments, provided herein is a hygiene behavioral modification platform having a dashboard system for representing status information regarding hygiene behavior modification for an environment and having a data aggregation system for aggregating hygiene behavioral data across a set of devices, a set of locations and/or a population of individuals. In embodiments, provided herein is a hygiene behavioral modification platform having a dashboard system for representing status information regarding hygiene behavior modification for an environment and having an analytics system for performing an analytic operation to produce analytic measures related to hygiene behavior. In embodiments, provided herein is a hygiene behavioral modification platform having a dashboard system for representing status information regarding hygiene behavior modification for an environment and having an analytics system for performing an analytic operation to produce an analytic measure related to hygiene behavior and having analytics indicating hygiene performance levels relevant to a particular individual. In embodiments, provided herein is a hygiene behavioral modification platform having a dashboard system for representing status information regarding hygiene behavior modification for an environment and having an analytics system for performing an analytic operation to produce an analytic measure related to hygiene behavior and having analytics indicating hygiene performance levels relevant to a population of individuals. In embodiments, provided herein is a hygiene behavioral modification platform having a dashboard system for representing status information regarding hygiene behavior modification for an environment and having an analytics system for performing an analytic operation to produce an analytic measure related to hygiene behavior and having analytics indicating hygiene performance levels relevant to a location of a business. In embodiments, provided herein is a hygiene behavioral modification platform having a dashboard system for representing status information regarding hygiene behavior modification for an environment and having a community score system for generating a community score based on handwashing behavior compliance in an environment, and wherein the community score is calculated based on the proportion of humans entering the environment that wash their hands. In embodiments, provided herein is a hygiene behavioral modification platform having a dashboard system for representing status information regarding hygiene behavior modification for an environment and for promoting hygiene behavioral modification having Bluetooth Low Energy proximity sensing, passive infrared sensors, and active infrared sensors for detecting the presence of one or more humans, and wherein the smart hygiene device is configured to attach to a soap dispenser. In embodiments, provided herein is a hygiene behavioral modification platform having a dashboard system for representing status information regarding hygiene behavior modification for an environment and having Bluetooth Low Energy proximity sensing, passive infrared sensors, and active infrared sensors for detecting the presence of one or more humans. In embodiments, provided herein is a hygiene behavioral modification platform having a dashboard system for representing status information regarding hygiene behavior modification for an environment and for promoting hygiene behavioral modification having Bluetooth Low Energy proximity sensing, passive infrared sensors, and active infrared sensors for detecting the presence of one or more humans and wherein the smart hygiene device is configured as a soap dispenser. In embodiments, provided herein is a hygiene behavioral modification platform having a dashboard system for representing status information regarding hygiene behavior modification for an environment and having a system for detecting activities related to hygiene and reporting a set of indicators of hygiene behaviors. In embodiments, provided herein is a hygiene behavioral modification platform having a dashboard system for representing status information regarding hygiene behavior modification for an environment and having a system for detecting handwashing activity. In embodiments, provided herein is a hygiene behavioral modification platform having a dashboard system for representing status information regarding hygiene behavior modification for an environment and having a system for detecting handwashing activity and producing a measure of duration and timing of the handwashing activity. In embodiments, provided herein is a hygiene behavioral modification platform having a dashboard system for representing status information regarding hygiene behavior modification for an environment and having a sensor fusion system configured to combine data from sensors of at least two types, wherein the fused sensor data is processed to produce an indicator related to hygiene behavior activity. In embodiments, provided herein is a hygiene behavioral modification platform having a dashboard system for representing status information regarding hygiene behavior modification for an environment and having a machine learning and/or artificial intelligence system configured to classify humans as employees or customers. In embodiments, provided herein is a hygiene behavioral modification platform having a dashboard system for representing status information regarding hygiene behavior modification for an environment and having a system for integrating a set of detected indicators of hygiene behavior for a location and/or entity with an online rating/review system for the location and/or entity. In embodiments, provided herein is a hygiene behavioral modification platform having a dashboard system for representing status information regarding hygiene behavior modification for an environment and having a machine learning and/or artificial intelligence system configured to generate a recommendation related to washing hands and/or hand sanitizing. In embodiments, provided herein is a hygiene behavioral modification platform having a dashboard system for representing status information regarding hygiene behavior modification for an environment and having a machine learning and/or artificial intelligence system configured to generate a recommendation related to the duration of handwashing. In embodiments, provided herein is a hygiene behavioral modification platform having a dashboard system for representing status information regarding hygiene behavior modification for an environment and having personal profiles with accompanying personal data structures for storing personal information. In embodiments, provided herein is a hygiene behavioral modification platform having a dashboard system for representing status information regarding hygiene behavior modification for an environment and having workforce profiles with accompanying workforce structures for storing workforce information.

In embodiments, provided herein is a hygiene behavioral modification platform having a handwashing compliance dashboard system. In embodiments, provided herein is a hygiene behavioral modification platform having a handwashing compliance dashboard system and having a reporting system for providing reporting of hygiene behavioral monitoring data. In embodiments, provided herein is a hygiene behavioral modification platform having a handwashing compliance dashboard system and having a user interface providing a user experience that promotes user awareness of the need to undertake hygiene behavior. In embodiments, provided herein is a hygiene behavioral modification platform having a handwashing compliance dashboard system and having a digital tree leaf pattern wherein the digital tree leaf pattern's growth is based on community hygiene behaviors. In embodiments, provided herein is a hygiene behavioral modification platform having a handwashing compliance dashboard system and having a system for providing audiovisual experiences for the promotion of hygiene behaviors. In embodiments, provided herein is a hygiene behavioral modification platform having a handwashing compliance dashboard system and having a system for providing an audiovisual experience for the promotion of hygiene behaviors wherein the audiovisual experience includes a lighting display event. In embodiments, provided herein is a hygiene behavioral modification platform having a handwashing compliance dashboard system and having a system for providing an audiovisual experience for the promotion of hygiene behaviors wherein the audiovisual experience includes a sound event. In embodiments, provided herein is a hygiene behavioral modification platform having a handwashing compliance dashboard system and having a system for providing an audiovisual experience for the promotion of hygiene behaviors wherein the audiovisual experience includes an audio reminder to wash hands. In embodiments, provided herein is a hygiene behavioral modification platform having a handwashing compliance dashboard system and having a system for providing an audiovisual experience for the promotion of hygiene behaviors having a system for facilitating progressive reminders as an individual moves through transits an environment and passes one or more points of reference. In embodiments, provided herein is a hygiene behavioral modification platform having a handwashing compliance dashboard system and having a system for providing an audiovisual experience for the promotion of hygiene behaviors wherein the audiovisual experience includes an advertisement that plays during the recommended duration of a handwashing event. In embodiments, provided herein is a hygiene behavioral modification platform having a handwashing compliance dashboard system and having a peer-to-peer configuration system for enabling peer-to-peer communication among a set of hygiene-promoting devices. In embodiments, provided herein is a hygiene behavioral modification platform having a handwashing compliance dashboard system and having a data aggregation system for aggregating hygiene behavioral data across a set of devices, a set of locations and/or a population of individuals. In embodiments, provided herein is a hygiene behavioral modification platform having a handwashing compliance dashboard system and having an analytics system for performing an analytic operation to produce analytic measures related to hygiene behavior. In embodiments, provided herein is a hygiene behavioral modification platform having a handwashing compliance dashboard system and having an analytics system for performing an analytic operation to produce an analytic measure related to hygiene behavior and having analytics indicating hygiene performance levels relevant to a particular individual. In embodiments, provided herein is a hygiene behavioral modification platform having a handwashing compliance dashboard system and having an analytics system for performing an analytic operation to produce an analytic measure related to hygiene behavior and having analytics indicating hygiene performance levels relevant to a population of individuals. In embodiments, provided herein is a hygiene behavioral modification platform having a handwashing compliance dashboard system and having an analytics system for performing an analytic operation to produce an analytic measure related to hygiene behavior and having analytics indicating hygiene performance levels relevant to a location of a business. In embodiments, provided herein is a hygiene behavioral modification platform having a handwashing compliance dashboard system and having a community score system for generating a community score based on handwashing behavior compliance in an environment, and wherein the community score is calculated based on the proportion of humans entering the environment that wash their hands. In embodiments, provided herein is a hygiene behavioral modification platform having a handwashing compliance dashboard system and for promoting hygiene behavioral modification having Bluetooth Low Energy proximity sensing, passive infrared sensors, and active infrared sensors for detecting the presence of one or more humans, and wherein the smart hygiene device is configured to attach to a soap dispenser. In embodiments, provided herein is a hygiene behavioral modification platform having a handwashing compliance dashboard system and having Bluetooth Low Energy proximity sensing, passive infrared sensors, and active infrared sensors for detecting the presence of one or more humans. In embodiments, provided herein is a hygiene behavioral modification platform having a handwashing compliance dashboard system and for promoting hygiene behavioral modification having Bluetooth Low Energy proximity sensing, passive infrared sensors, and active infrared sensors for detecting the presence of one or more humans and wherein the smart hygiene device is configured as a soap dispenser. In embodiments, provided herein is a hygiene behavioral modification platform having a handwashing compliance dashboard system and having a system for detecting activities related to hygiene and reporting a set of indicators of hygiene behaviors. In embodiments, provided herein is a hygiene behavioral modification platform having a handwashing compliance dashboard system and having a system for detecting handwashing activity. In embodiments, provided herein is a hygiene behavioral modification platform having a handwashing compliance dashboard system and having a system for detecting handwashing activity and producing a measure of duration and timing of the handwashing activity. In embodiments, provided herein is a hygiene behavioral modification platform having a handwashing compliance dashboard system and having a sensor fusion system configured to combine data from sensors of at least two types, wherein the fused sensor data is processed to produce an indicator related to hygiene behavior activity. In embodiments, provided herein is a hygiene behavioral modification platform having a handwashing compliance dashboard system and having a machine learning and/or artificial intelligence system configured to classify humans as employees or customers. In embodiments, provided herein is a hygiene behavioral modification platform having a handwashing compliance dashboard system and having a system for integrating a set of detected indicators of hygiene behavior for a location and/or entity with an online rating/review system for the location and/or entity. In embodiments, provided herein is a hygiene behavioral modification platform having a handwashing compliance dashboard system and having a machine learning and/or artificial intelligence system configured to generate a recommendation related to washing hands and/or hand sanitizing. In embodiments, provided herein is a hygiene behavioral modification platform having a handwashing compliance dashboard system and having a machine learning and/or artificial intelligence system configured to generate a recommendation related to the duration of handwashing. In embodiments, provided herein is a hygiene behavioral modification platform having a handwashing compliance dashboard system and having personal profiles with accompanying personal data structures for storing personal information. In embodiments, provided herein is a hygiene behavioral modification platform having a handwashing compliance dashboard system and having workforce profiles with accompanying workforce structures for storing workforce information.

In embodiments, provided herein is a hygiene behavioral modification platform having a reporting system for providing reporting of hygiene behavioral monitoring data. In embodiments, provided herein is a hygiene behavioral modification platform having a reporting system for providing reporting of hygiene behavioral monitoring data and having a user interface providing a user experience that promotes user awareness of the need to undertake hygiene behavior. In embodiments, provided herein is a hygiene behavioral modification platform having a reporting system for providing reporting of hygiene behavioral monitoring data and having a digital tree leaf pattern wherein the digital tree leaf pattern's growth is based on community hygiene behaviors. In embodiments, provided herein is a hygiene behavioral modification platform having a reporting system for providing reporting of hygiene behavioral monitoring data and having a system for providing audiovisual experiences for the promotion of hygiene behaviors. In embodiments, provided herein is a hygiene behavioral modification platform having a reporting system for providing reporting of hygiene behavioral monitoring data and having a system for providing an audiovisual experience for the promotion of hygiene behaviors wherein the audiovisual experience includes a lighting display event. In embodiments, provided herein is a hygiene behavioral modification platform having a reporting system for providing reporting of hygiene behavioral monitoring data and having a system for providing an audiovisual experience for the promotion of hygiene behaviors wherein the audiovisual experience includes a sound event. In embodiments, provided herein is a hygiene behavioral modification platform having a reporting system for providing reporting of hygiene behavioral monitoring data and having a system for providing an audiovisual experience for the promotion of hygiene behaviors wherein the audiovisual experience includes an audio reminder to wash hands. In embodiments, provided herein is a hygiene behavioral modification platform having a reporting system for providing reporting of hygiene behavioral monitoring data and having a system for providing an audiovisual experience for the promotion of hygiene behaviors having a system for facilitating progressive reminders as an individual moves through transits an environment and passes one or more points of reference. In embodiments, provided herein is a hygiene behavioral modification platform having a reporting system for providing reporting of hygiene behavioral monitoring data and having a system for providing an audiovisual experience for the promotion of hygiene behaviors wherein the audiovisual experience includes an advertisement that plays during the recommended duration of a handwashing event. In embodiments, provided herein is a hygiene behavioral modification platform having a reporting system for providing reporting of hygiene behavioral monitoring data and having a peer-to-peer configuration system for enabling peer-to-peer communication among a set of hygiene-promoting devices. In embodiments, provided herein is a hygiene behavioral modification platform having a reporting system for providing reporting of hygiene behavioral monitoring data and having a data aggregation system for aggregating hygiene behavioral data across a set of devices, a set of locations and/or a population of individuals. In embodiments, provided herein is a hygiene behavioral modification platform having a reporting system for providing reporting of hygiene behavioral monitoring data and having an analytics system for performing an analytic operation to produce analytic measures related to hygiene behavior. In embodiments, provided herein is a hygiene behavioral modification platform having a reporting system for providing reporting of hygiene behavioral monitoring data and having an analytics system for performing an analytic operation to produce an analytic measure related to hygiene behavior and having analytics indicating hygiene performance levels relevant to a particular individual. In embodiments, provided herein is a hygiene behavioral modification platform having a reporting system for providing reporting of hygiene behavioral monitoring data and having an analytics system for performing an analytic operation to produce an analytic measure related to hygiene behavior and having analytics indicating hygiene performance levels relevant to a population of individuals. In embodiments, provided herein is a hygiene behavioral modification platform having a reporting system for providing reporting of hygiene behavioral monitoring data and having an analytics system for performing an analytic operation to produce an analytic measure related to hygiene behavior and having analytics indicating hygiene performance levels relevant to a location of a business. In embodiments, provided herein is a hygiene behavioral modification platform having a reporting system for providing reporting of hygiene behavioral monitoring data and having a community score system for generating a community score based on handwashing behavior compliance in an environment, and wherein the community score is calculated based on the proportion of humans entering the environment that wash their hands. In embodiments, provided herein is a hygiene behavioral modification platform having a reporting system for providing reporting of hygiene behavioral monitoring data and for promoting hygiene behavioral modification having Bluetooth Low Energy proximity sensing, passive infrared sensors, and active infrared sensors for detecting the presence of one or more humans, and wherein the smart hygiene device is configured to attach to a soap dispenser. In embodiments, provided herein is a hygiene behavioral modification platform having a reporting system for providing reporting of hygiene behavioral monitoring data and having Bluetooth Low Energy proximity sensing, passive infrared sensors, and active infrared sensors for detecting the presence of one or more humans. In embodiments, provided herein is a hygiene behavioral modification platform having a reporting system for providing reporting of hygiene behavioral monitoring data and for promoting hygiene behavioral modification having Bluetooth Low Energy proximity sensing, passive infrared sensors, and active infrared sensors for detecting the presence of one or more humans and wherein the smart hygiene device is configured as a soap dispenser. In embodiments, provided herein is a hygiene behavioral modification platform having a reporting system for providing reporting of hygiene behavioral monitoring data and having a system for detecting activities related to hygiene and reporting a set of indicators of hygiene behaviors. In embodiments, provided herein is a hygiene behavioral modification platform having a reporting system for providing reporting of hygiene behavioral monitoring data and having a system for detecting handwashing activity. In embodiments, provided herein is a hygiene behavioral modification platform having a reporting system for providing reporting of hygiene behavioral monitoring data and having a system for detecting handwashing activity and producing a measure of duration and timing of the handwashing activity. In embodiments, provided herein is a hygiene behavioral modification platform having a reporting system for providing reporting of hygiene behavioral monitoring data and having a sensor fusion system configured to combine data from sensors of at least two types, wherein the fused sensor data is processed to produce an indicator related to hygiene behavior activity. In embodiments, provided herein is a hygiene behavioral modification platform having a reporting system for providing reporting of hygiene behavioral monitoring data and having a machine learning and/or artificial intelligence system configured to classify humans as employees or customers. In embodiments, provided herein is a hygiene behavioral modification platform having a reporting system for providing reporting of hygiene behavioral monitoring data and having a system for integrating a set of detected indicators of hygiene behavior for a location and/or entity with an online rating/review system for the location and/or entity. In embodiments, provided herein is a hygiene behavioral modification platform having a reporting system for providing reporting of hygiene behavioral monitoring data and having a machine learning and/or artificial intelligence system configured to generate a recommendation related to washing hands and/or hand sanitizing. In embodiments, provided herein is a hygiene behavioral modification platform having a reporting system for providing reporting of hygiene behavioral monitoring data and having a machine learning and/or artificial intelligence system configured to generate a recommendation related to the duration of handwashing. In embodiments, provided herein is a hygiene behavioral modification platform having a reporting system for providing reporting of hygiene behavioral monitoring data and having personal profiles with accompanying personal data structures for storing personal information. In embodiments, provided herein is a hygiene behavioral modification platform having a reporting system for providing reporting of hygiene behavioral monitoring data and having workforce profiles with accompanying workforce structures for storing workforce information.

In embodiments, provided herein is a hygiene behavioral modification platform having a user interface providing a user experience that promotes user awareness of the need to undertake hygiene behavior. In embodiments, provided herein is a hygiene behavioral modification platform having a user interface providing a user experience that promotes user awareness of the need to undertake hygiene behavior and having a digital tree leaf pattern wherein the digital tree leaf pattern's growth is based on community hygiene behaviors. In embodiments, provided herein is a hygiene behavioral modification platform having a user interface providing a user experience that promotes user awareness of the need to undertake hygiene behavior and having a system for providing audiovisual experiences for the promotion of hygiene behaviors. In embodiments, provided herein is a hygiene behavioral modification platform having a user interface providing a user experience that promotes user awareness of the need to undertake hygiene behavior and having a system for providing an audiovisual experience for the promotion of hygiene behaviors wherein the audiovisual experience includes a lighting display event. In embodiments, provided herein is a hygiene behavioral modification platform having a user interface providing a user experience that promotes user awareness of the need to undertake hygiene behavior and having a system for providing an audiovisual experience for the promotion of hygiene behaviors wherein the audiovisual experience includes a sound event. In embodiments, provided herein is a hygiene behavioral modification platform having a user interface providing a user experience that promotes user awareness of the need to undertake hygiene behavior and having a system for providing an audiovisual experience for the promotion of hygiene behaviors wherein the audiovisual experience includes an audio reminder to wash hands. In embodiments, provided herein is a hygiene behavioral modification platform having a user interface providing a user experience that promotes user awareness of the need to undertake hygiene behavior and having a system for providing an audiovisual experience for the promotion of hygiene behaviors having a system for facilitating progressive reminders as an individual moves through transits an environment and passes one or more points of reference. In embodiments, provided herein is a hygiene behavioral modification platform having a user interface providing a user experience that promotes user awareness of the need to undertake hygiene behavior and having a system for providing an audiovisual experience for the promotion of hygiene behaviors wherein the audiovisual experience includes an advertisement that plays during the recommended duration of a handwashing event. In embodiments, provided herein is a hygiene behavioral modification platform having a user interface providing a user experience that promotes user awareness of the need to undertake hygiene behavior and having a peer-to-peer configuration system for enabling peer-to-peer communication among a set of hygiene-promoting devices. In embodiments, provided herein is a hygiene behavioral modification platform having a user interface providing a user experience that promotes user awareness of the need to undertake hygiene behavior and having a data aggregation system for aggregating hygiene behavioral data across a set of devices, a set of locations and/or a population of individuals. In embodiments, provided herein is a hygiene behavioral modification platform having a user interface providing a user experience that promotes user awareness of the need to undertake hygiene behavior and having an analytics system for performing an analytic operation to produce analytic measures related to hygiene behavior. In embodiments, provided herein is a hygiene behavioral modification platform having a user interface providing a user experience that promotes user awareness of the need to undertake hygiene behavior and having an analytics system for performing an analytic operation to produce an analytic measure related to hygiene behavior and having analytics indicating hygiene performance levels relevant to a particular individual. In embodiments, provided herein is a hygiene behavioral modification platform having a user interface providing a user experience that promotes user awareness of the need to undertake hygiene behavior and having an analytics system for performing an analytic operation to produce an analytic measure related to hygiene behavior and having analytics indicating hygiene performance levels relevant to a population of individuals. In embodiments, provided herein is a hygiene behavioral modification platform having a user interface providing a user experience that promotes user awareness of the need to undertake hygiene behavior and having an analytics system for performing an analytic operation to produce an analytic measure related to hygiene behavior and having analytics indicating hygiene performance levels relevant to a location of a business. In embodiments, provided herein is a hygiene behavioral modification platform having a user interface providing a user experience that promotes user awareness of the need to undertake hygiene behavior and having a community score system for generating a community score based on handwashing behavior compliance in an environment, and wherein the community score is calculated based on the proportion of humans entering the environment that wash their hands. In embodiments, provided herein is a hygiene behavioral modification platform having a user interface providing a user experience that promotes user awareness of the need to undertake hygiene behavior and for promoting hygiene behavioral modification having Bluetooth Low Energy proximity sensing, passive infrared sensors, and active infrared sensors for detecting the presence of one or more humans, and wherein the smart hygiene device is configured to attach to a soap dispenser. In embodiments, provided herein is a hygiene behavioral modification platform having a user interface providing a user experience that promotes user awareness of the need to undertake hygiene behavior and having Bluetooth Low Energy proximity sensing, passive infrared sensors, and active infrared sensors for detecting the presence of one or more humans. In embodiments, provided herein is a hygiene behavioral modification platform having a user interface providing a user experience that promotes user awareness of the need to undertake hygiene behavior and for promoting hygiene behavioral modification having Bluetooth Low Energy proximity sensing, passive infrared sensors, and active infrared sensors for detecting the presence of one or more humans and wherein the smart hygiene device is configured as a soap dispenser. In embodiments, provided herein is a hygiene behavioral modification platform having a user interface providing a user experience that promotes user awareness of the need to undertake hygiene behavior and having a system for detecting activities related to hygiene and reporting a set of indicators of hygiene behaviors. In embodiments, provided herein is a hygiene behavioral modification platform having a user interface providing a user experience that promotes user awareness of the need to undertake hygiene behavior and having a system for detecting handwashing activity. In embodiments, provided herein is a hygiene behavioral modification platform having a user interface providing a user experience that promotes user awareness of the need to undertake hygiene behavior and having a system for detecting handwashing activity and producing a measure of duration and timing of the handwashing activity. In embodiments, provided herein is a hygiene behavioral modification platform having a user interface providing a user experience that promotes user awareness of the need to undertake hygiene behavior and having a sensor fusion system configured to combine data from sensors of at least two types, wherein the fused sensor data is processed to produce an indicator related to hygiene behavior activity. In embodiments, provided herein is a hygiene behavioral modification platform having a user interface providing a user experience that promotes user awareness of the need to undertake hygiene behavior and having a machine learning and/or artificial intelligence system configured to classify humans as employees or customers. In embodiments, provided herein is a hygiene behavioral modification platform having a user interface providing a user experience that promotes user awareness of the need to undertake hygiene behavior and having a system for integrating a set of detected indicators of hygiene behavior for a location and/or entity with an online rating/review system for the location and/or entity. In embodiments, provided herein is a hygiene behavioral modification platform having a user interface providing a user experience that promotes user awareness of the need to undertake hygiene behavior and having a machine learning and/or artificial intelligence system configured to generate a recommendation related to washing hands and/or hand sanitizing. In embodiments, provided herein is a hygiene behavioral modification platform having a user interface providing a user experience that promotes user awareness of the need to undertake hygiene behavior and having a machine learning and/or artificial intelligence system configured to generate a recommendation related to the duration of handwashing. In embodiments, provided herein is a hygiene behavioral modification platform having a user interface providing a user experience that promotes user awareness of the need to undertake hygiene behavior and having personal profiles with accompanying personal data structures for storing personal information. In embodiments, provided herein is a hygiene behavioral modification platform having a user interface providing a user experience that promotes user awareness of the need to undertake hygiene behavior and having workforce profiles with accompanying workforce structures for storing workforce information.

In embodiments, provided herein is a hygiene behavioral modification platform having a digital tree leaf pattern wherein the digital tree leaf pattern's growth is based on community hygiene behaviors. In embodiments, provided herein is a hygiene behavioral modification platform having a digital tree leaf pattern wherein the digital tree leaf pattern's growth is based on community hygiene behaviors and having a system for providing audiovisual experiences for the promotion of hygiene behaviors. In embodiments, provided herein is a hygiene behavioral modification platform having a digital tree leaf pattern wherein the digital tree leaf pattern's growth is based on community hygiene behaviors and having a system for providing an audiovisual experience for the promotion of hygiene behaviors wherein the audiovisual experience includes a lighting display event. In embodiments, provided herein is a hygiene behavioral modification platform having a digital tree leaf pattern wherein the digital tree leaf pattern's growth is based on community hygiene behaviors and having a system for providing an audiovisual experience for the promotion of hygiene behaviors wherein the audiovisual experience includes a sound event. In embodiments, provided herein is a hygiene behavioral modification platform having a digital tree leaf pattern wherein the digital tree leaf pattern's growth is based on community hygiene behaviors and having a system for providing an audiovisual experience for the promotion of hygiene behaviors wherein the audiovisual experience includes an audio reminder to wash hands. In embodiments, provided herein is a hygiene behavioral modification platform having a digital tree leaf pattern wherein the digital tree leaf pattern's growth is based on community hygiene behaviors and having a system for providing an audiovisual experience for the promotion of hygiene behaviors having a system for facilitating progressive reminders as an individual moves through transits an environment and passes one or more points of reference. In embodiments, provided herein is a hygiene behavioral modification platform having a digital tree leaf pattern wherein the digital tree leaf pattern's growth is based on community hygiene behaviors and having a system for providing an audiovisual experience for the promotion of hygiene behaviors wherein the audiovisual experience includes an advertisement that plays during the recommended duration of a handwashing event. In embodiments, provided herein is a hygiene behavioral modification platform having a digital tree leaf pattern wherein the digital tree leaf pattern's growth is based on community hygiene behaviors and having a peer-to-peer configuration system for enabling peer-to-peer communication among a set of hygiene-promoting devices. In embodiments, provided herein is a hygiene behavioral modification platform having a digital tree leaf pattern wherein the digital tree leaf pattern's growth is based on community hygiene behaviors and having a data aggregation system for aggregating hygiene behavioral data across a set of devices, a set of locations and/or a population of individuals. In embodiments, provided herein is a hygiene behavioral modification platform having a digital tree leaf pattern wherein the digital tree leaf pattern's growth is based on community hygiene behaviors and having an analytics system for performing an analytic operation to produce analytic measures related to hygiene behavior. In embodiments, provided herein is a hygiene behavioral modification platform having a digital tree leaf pattern wherein the digital tree leaf pattern's growth is based on community hygiene behaviors and having an analytics system for performing an analytic operation to produce an analytic measure related to hygiene behavior and having analytics indicating hygiene performance levels relevant to a particular individual. In embodiments, provided herein is a hygiene behavioral modification platform having a digital tree leaf pattern wherein the digital tree leaf pattern's growth is based on community hygiene behaviors and having an analytics system for performing an analytic operation to produce an analytic measure related to hygiene behavior and having analytics indicating hygiene performance levels relevant to a population of individuals. In embodiments, provided herein is a hygiene behavioral modification platform having a digital tree leaf pattern wherein the digital tree leaf pattern's growth is based on community hygiene behaviors and having an analytics system for performing an analytic operation to produce an analytic measure related to hygiene behavior and having analytics indicating hygiene performance levels relevant to a location of a business. In embodiments, provided herein is a hygiene behavioral modification platform having a digital tree leaf pattern wherein the digital tree leaf pattern's growth is based on community hygiene behaviors and having a community score system for generating a community score based on handwashing behavior compliance in an environment, and wherein the community score is calculated based on the proportion of humans entering the environment that wash their hands. In embodiments, provided herein is a hygiene behavioral modification platform having a digital tree leaf pattern wherein the digital tree leaf pattern's growth is based on community hygiene behaviors and for promoting hygiene behavioral modification having Bluetooth Low Energy proximity sensing, passive infrared sensors, and active infrared sensors for detecting the presence of one or more humans, and wherein the smart hygiene device is configured to attach to a soap dispenser. In embodiments, provided herein is a hygiene behavioral modification platform having a digital tree leaf pattern wherein the digital tree leaf pattern's growth is based on community hygiene behaviors and having Bluetooth Low Energy proximity sensing, passive infrared sensors, and active infrared sensors for detecting the presence of one or more humans. In embodiments, provided herein is a hygiene behavioral modification platform having a digital tree leaf pattern wherein the digital tree leaf pattern's growth is based on community hygiene behaviors and for promoting hygiene behavioral modification having Bluetooth Low Energy proximity sensing, passive infrared sensors, and active infrared sensors for detecting the presence of one or more humans and wherein the smart hygiene device is configured as a soap dispenser. In embodiments, provided herein is a hygiene behavioral modification platform having a digital tree leaf pattern wherein the digital tree leaf pattern's growth is based on community hygiene behaviors and having a system for detecting activities related to hygiene and reporting a set of indicators of hygiene behaviors. In embodiments, provided herein is a hygiene behavioral modification platform having a digital tree leaf pattern wherein the digital tree leaf pattern's growth is based on community hygiene behaviors and having a system for detecting handwashing activity. In embodiments, provided herein is a hygiene behavioral modification platform having a digital tree leaf pattern wherein the digital tree leaf pattern's growth is based on community hygiene behaviors and having a system for detecting handwashing activity and producing a measure of duration and timing of the handwashing activity. In embodiments, provided herein is a hygiene behavioral modification platform having a digital tree leaf pattern wherein the digital tree leaf pattern's growth is based on community hygiene behaviors and having a sensor fusion system configured to combine data from sensors of at least two types, wherein the fused sensor data is processed to produce an indicator related to hygiene behavior activity. In embodiments, provided herein is a hygiene behavioral modification platform having a digital tree leaf pattern wherein the digital tree leaf pattern's growth is based on community hygiene behaviors and having a machine learning and/or artificial intelligence system configured to classify humans as employees or customers. In embodiments, provided herein is a hygiene behavioral modification platform having a digital tree leaf pattern wherein the digital tree leaf pattern's growth is based on community hygiene behaviors and having a system for integrating a set of detected indicators of hygiene behavior for a location and/or entity with an online rating/review system for the location and/or entity. In embodiments, provided herein is a hygiene behavioral modification platform having a digital tree leaf pattern wherein the digital tree leaf pattern's growth is based on community hygiene behaviors and having a machine learning and/or artificial intelligence system configured to generate a recommendation related to washing hands and/or hand sanitizing. In embodiments, provided herein is a hygiene behavioral modification platform having a digital tree leaf pattern wherein the digital tree leaf pattern's growth is based on community hygiene behaviors and having a machine learning and/or artificial intelligence system configured to generate a recommendation related to the duration of handwashing. In embodiments, provided herein is a hygiene behavioral modification platform having a digital tree leaf pattern wherein the digital tree leaf pattern's growth is based on community hygiene behaviors and having personal profiles with accompanying personal data structures for storing personal information. In embodiments, provided herein is a hygiene behavioral modification platform having a digital tree leaf pattern wherein the digital tree leaf pattern's growth is based on community hygiene behaviors and having workforce profiles with accompanying workforce structures for storing workforce information.

In embodiments, provided herein is a hygiene behavioral modification platform having a system for providing audiovisual experiences for the promotion of hygiene behaviors. In embodiments, provided herein is a hygiene behavioral modification platform having a system for providing audiovisual experiences for the promotion of hygiene behaviors and having a system for providing an audiovisual experience for the promotion of hygiene behaviors wherein the audiovisual experience includes a lighting display event. In embodiments, provided herein is a hygiene behavioral modification platform having a system for providing audiovisual experiences for the promotion of hygiene behaviors and having a system for providing an audiovisual experience for the promotion of hygiene behaviors wherein the audiovisual experience includes a sound event. In embodiments, provided herein is a hygiene behavioral modification platform having a system for providing audiovisual experiences for the promotion of hygiene behaviors and having a system for providing an audiovisual experience for the promotion of hygiene behaviors wherein the audiovisual experience includes an audio reminder to wash hands. In embodiments, provided herein is a hygiene behavioral modification platform having a system for providing audiovisual experiences for the promotion of hygiene behaviors and having a system for providing an audiovisual experience for the promotion of hygiene behaviors having a system for facilitating progressive reminders as an individual moves through transits an environment and passes one or more points of reference. In embodiments, provided herein is a hygiene behavioral modification platform having a system for providing audiovisual experiences for the promotion of hygiene behaviors and having a system for providing an audiovisual experience for the promotion of hygiene behaviors wherein the audiovisual experience includes an advertisement that plays during the recommended duration of a handwashing event. In embodiments, provided herein is a hygiene behavioral modification platform having a system for providing audiovisual experiences for the promotion of hygiene behaviors and having a peer-to-peer configuration system for enabling peer-to-peer communication among a set of hygiene-promoting devices. In embodiments, provided herein is a hygiene behavioral modification platform having a system for providing audiovisual experiences for the promotion of hygiene behaviors and having a data aggregation system for aggregating hygiene behavioral data across a set of devices, a set of locations and/or a population of individuals. In embodiments, provided herein is a hygiene behavioral modification platform having a system for providing audiovisual experiences for the promotion of hygiene behaviors and having an analytics system for performing an analytic operation to produce analytic measures related to hygiene behavior. In embodiments, provided herein is a hygiene behavioral modification platform having a system for providing audiovisual experiences for the promotion of hygiene behaviors and having an analytics system for performing an analytic operation to produce an analytic measure related to hygiene behavior and having analytics indicating hygiene performance levels relevant to a particular individual. In embodiments, provided herein is a hygiene behavioral modification platform having a system for providing audiovisual experiences for the promotion of hygiene behaviors and having an analytics system for performing an analytic operation to produce an analytic measure related to hygiene behavior and having analytics indicating hygiene performance levels relevant to a population of individuals. In embodiments, provided herein is a hygiene behavioral modification platform having a system for providing audiovisual experiences for the promotion of hygiene behaviors and having an analytics system for performing an analytic operation to produce an analytic measure related to hygiene behavior and having analytics indicating hygiene performance levels relevant to a location of a business. In embodiments, provided herein is a hygiene behavioral modification platform having a system for providing audiovisual experiences for the promotion of hygiene behaviors and having a community score system for generating a community score based on handwashing behavior compliance in an environment, and wherein the community score is calculated based on the proportion of humans entering the environment that wash their hands. In embodiments, provided herein is a hygiene behavioral modification platform having a system for providing audiovisual experiences for the promotion of hygiene behaviors and for promoting hygiene behavioral modification having Bluetooth Low Energy proximity sensing, passive infrared sensors, and active infrared sensors for detecting the presence of one or more humans, and wherein the smart hygiene device is configured to attach to a soap dispenser. In embodiments, provided herein is a hygiene behavioral modification platform having a system for providing audiovisual experiences for the promotion of hygiene behaviors and having Bluetooth Low Energy proximity sensing, passive infrared sensors, and active infrared sensors for detecting the presence of one or more humans. In embodiments, provided herein is a hygiene behavioral modification platform having a system for providing audiovisual experiences for the promotion of hygiene behaviors and for promoting hygiene behavioral modification having Bluetooth Low Energy proximity sensing, passive infrared sensors, and active infrared sensors for detecting the presence of one or more humans and wherein the smart hygiene device is configured as a soap dispenser. In embodiments, provided herein is a hygiene behavioral modification platform having a system for providing audiovisual experiences for the promotion of hygiene behaviors and having a system for detecting activities related to hygiene and reporting a set of indicators of hygiene behaviors. In embodiments, provided herein is a hygiene behavioral modification platform having a system for providing audiovisual experiences for the promotion of hygiene behaviors and having a system for detecting handwashing activity. In embodiments, provided herein is a hygiene behavioral modification platform having a system for providing audiovisual experiences for the promotion of hygiene behaviors and having a system for detecting handwashing activity and producing a measure of duration and timing of the handwashing activity. In embodiments, provided herein is a hygiene behavioral modification platform having a system for providing audiovisual experiences for the promotion of hygiene behaviors and having a sensor fusion system configured to combine data from sensors of at least two types, wherein the fused sensor data is processed to produce an indicator related to hygiene behavior activity. In embodiments, provided herein is a hygiene behavioral modification platform having a system for providing audiovisual experiences for the promotion of hygiene behaviors and having a machine learning and/or artificial intelligence system configured to classify humans as employees or customers. In embodiments, provided herein is a hygiene behavioral modification platform having a system for providing audiovisual experiences for the promotion of hygiene behaviors and having a system for integrating a set of detected indicators of hygiene behavior for a location and/or entity with an online rating/review system for the location and/or entity. In embodiments, provided herein is a hygiene behavioral modification platform having a system for providing audiovisual experiences for the promotion of hygiene behaviors and having a machine learning and/or artificial intelligence system configured to generate a recommendation related to washing hands and/or hand sanitizing. In embodiments, provided herein is a hygiene behavioral modification platform having a system for providing audiovisual experiences for the promotion of hygiene behaviors and having a machine learning and/or artificial intelligence system configured to generate a recommendation related to the duration of handwashing. In embodiments, provided herein is a hygiene behavioral modification platform having a system for providing audiovisual experiences for the promotion of hygiene behaviors and having personal profiles with accompanying personal data structures for storing personal information. In embodiments, provided herein is a hygiene behavioral modification platform having a system for providing audiovisual experiences for the promotion of hygiene behaviors and having workforce profiles with accompanying workforce structures for storing workforce information.

In embodiments, provided herein is a hygiene behavioral modification platform having a system for providing an audiovisual experience for the promotion of hygiene behaviors wherein the audiovisual experience includes a lighting display event. In embodiments, provided herein is a hygiene behavioral modification platform having a system for providing an audiovisual experience for the promotion of hygiene behaviors wherein the audiovisual experience includes a lighting display event and having a system for providing an audiovisual experience for the promotion of hygiene behaviors wherein the audiovisual experience includes a sound event. In embodiments, provided herein is a hygiene behavioral modification platform having a system for providing an audiovisual experience for the promotion of hygiene behaviors wherein the audiovisual experience includes a lighting display event and having a system for providing an audiovisual experience for the promotion of hygiene behaviors wherein the audiovisual experience includes an audio reminder to wash hands. In embodiments, provided herein is a hygiene behavioral modification platform having a system for providing an audiovisual experience for the promotion of hygiene behaviors wherein the audiovisual experience includes a lighting display event and having a system for providing an audiovisual experience for the promotion of hygiene behaviors having a system for facilitating progressive reminders as an individual moves through transits an environment and passes one or more points of reference. In embodiments, provided herein is a hygiene behavioral modification platform having a system for providing an audiovisual experience for the promotion of hygiene behaviors wherein the audiovisual experience includes a lighting display event and having a system for providing an audiovisual experience for the promotion of hygiene behaviors wherein the audiovisual experience includes an advertisement that plays during the recommended duration of a handwashing event. In embodiments, provided herein is a hygiene behavioral modification platform having a system for providing an audiovisual experience for the promotion of hygiene behaviors wherein the audiovisual experience includes a lighting display event and having a peer-to-peer configuration system for enabling peer-to-peer communication among a set of hygiene-promoting devices. In embodiments, provided herein is a hygiene behavioral modification platform having a system for providing an audiovisual experience for the promotion of hygiene behaviors wherein the audiovisual experience includes a lighting display event and having a data aggregation system for aggregating hygiene behavioral data across a set of devices, a set of locations and/or a population of individuals. In embodiments, provided herein is a hygiene behavioral modification platform having a system for providing an audiovisual experience for the promotion of hygiene behaviors wherein the audiovisual experience includes a lighting display event and having an analytics system for performing an analytic operation to produce analytic measures related to hygiene behavior. In embodiments, provided herein is a hygiene behavioral modification platform having a system for providing an audiovisual experience for the promotion of hygiene behaviors wherein the audiovisual experience includes a lighting display event and having an analytics system for performing an analytic operation to produce an analytic measure related to hygiene behavior and having analytics indicating hygiene performance levels relevant to a particular individual. In embodiments, provided herein is a hygiene behavioral modification platform having a system for providing an audiovisual experience for the promotion of hygiene behaviors wherein the audiovisual experience includes a lighting display event and having an analytics system for performing an analytic operation to produce an analytic measure related to hygiene behavior and having analytics indicating hygiene performance levels relevant to a population of individuals. In embodiments, provided herein is a hygiene behavioral modification platform having a system for providing an audiovisual experience for the promotion of hygiene behaviors wherein the audiovisual experience includes a lighting display event and having an analytics system for performing an analytic operation to produce an analytic measure related to hygiene behavior and having analytics indicating hygiene performance levels relevant to a location of a business. In embodiments, provided herein is a hygiene behavioral modification platform having a system for providing an audiovisual experience for the promotion of hygiene behaviors wherein the audiovisual experience includes a lighting display event and having a community score system for generating a community score based on handwashing behavior compliance in an environment, and wherein the community score is calculated based on the proportion of humans entering the environment that wash their hands. In embodiments, provided herein is a hygiene behavioral modification platform having a system for providing an audiovisual experience for the promotion of hygiene behaviors wherein the audiovisual experience includes a lighting display event and for promoting hygiene behavioral modification having Bluetooth Low Energy proximity sensing, passive infrared sensors, and active infrared sensors for detecting the presence of one or more humans, and wherein the smart hygiene device is configured to attach to a soap dispenser. In embodiments, provided herein is a hygiene behavioral modification platform having a system for providing an audiovisual experience for the promotion of hygiene behaviors wherein the audiovisual experience includes a lighting display event and having Bluetooth Low Energy proximity sensing, passive infrared sensors, and active infrared sensors for detecting the presence of one or more humans. In embodiments, provided herein is a hygiene behavioral modification platform having a system for providing an audiovisual experience for the promotion of hygiene behaviors wherein the audiovisual experience includes a lighting display event and for promoting hygiene behavioral modification having Bluetooth Low Energy proximity sensing, passive infrared sensors, and active infrared sensors for detecting the presence of one or more humans and wherein the smart hygiene device is configured as a soap dispenser. In embodiments, provided herein is a hygiene behavioral modification platform having a system for providing an audiovisual experience for the promotion of hygiene behaviors wherein the audiovisual experience includes a lighting display event and having a system for detecting activities related to hygiene and reporting a set of indicators of hygiene behaviors. In embodiments, provided herein is a hygiene behavioral modification platform having a system for providing an audiovisual experience for the promotion of hygiene behaviors wherein the audiovisual experience includes a lighting display event and having a system for detecting handwashing activity. In embodiments, provided herein is a hygiene behavioral modification platform having a system for providing an audiovisual experience for the promotion of hygiene behaviors wherein the audiovisual experience includes a lighting display event and having a system for detecting handwashing activity and producing a measure of duration and timing of the handwashing activity. In embodiments, provided herein is a hygiene behavioral modification platform having a system for providing an audiovisual experience for the promotion of hygiene behaviors wherein the audiovisual experience includes a lighting display event and having a sensor fusion system configured to combine data from sensors of at least two types, wherein the fused sensor data is processed to produce an indicator related to hygiene behavior activity. In embodiments, provided herein is a hygiene behavioral modification platform having a system for providing an audiovisual experience for the promotion of hygiene behaviors wherein the audiovisual experience includes a lighting display event and having a machine learning and/or artificial intelligence system configured to classify humans as employees or customers. In embodiments, provided herein is a hygiene behavioral modification platform having a system for providing an audiovisual experience for the promotion of hygiene behaviors wherein the audiovisual experience includes a lighting display event and having a system for integrating a set of detected indicators of hygiene behavior for a location and/or entity with an online rating/review system for the location and/or entity. In embodiments, provided herein is a hygiene behavioral modification platform having a system for providing an audiovisual experience for the promotion of hygiene behaviors wherein the audiovisual experience includes a lighting display event and having a machine learning and/or artificial intelligence system configured to generate a recommendation related to washing hands and/or hand sanitizing. In embodiments, provided herein is a hygiene behavioral modification platform having a system for providing an audiovisual experience for the promotion of hygiene behaviors wherein the audiovisual experience includes a lighting display event and having a machine learning and/or artificial intelligence system configured to generate a recommendation related to the duration of handwashing. In embodiments, provided herein is a hygiene behavioral modification platform having a system for providing an audiovisual experience for the promotion of hygiene behaviors wherein the audiovisual experience includes a lighting display event and having personal profiles with accompanying personal data structures for storing personal information. In embodiments, provided herein is a hygiene behavioral modification platform having a system for providing an audiovisual experience for the promotion of hygiene behaviors wherein the audiovisual experience includes a lighting display event and having workforce profiles with accompanying workforce structures for storing workforce information.

In embodiments, provided herein is a hygiene behavioral modification platform having a system for providing an audiovisual experience for the promotion of hygiene behaviors wherein the audiovisual experience includes a sound event. In embodiments, provided herein is a hygiene behavioral modification platform having a system for providing an audiovisual experience for the promotion of hygiene behaviors wherein the audiovisual experience includes a sound event and having a system for providing an audiovisual experience for the promotion of hygiene behaviors wherein the audiovisual experience includes an audio reminder to wash hands. In embodiments, provided herein is a hygiene behavioral modification platform having a system for providing an audiovisual experience for the promotion of hygiene behaviors wherein the audiovisual experience includes a sound event and having a system for providing an audiovisual experience for the promotion of hygiene behaviors having a system for facilitating progressive reminders as an individual moves through transits an environment and passes one or more points of reference. In embodiments, provided herein is a hygiene behavioral modification platform having a system for providing an audiovisual experience for the promotion of hygiene behaviors wherein the audiovisual experience includes a sound event and having a system for providing an audiovisual experience for the promotion of hygiene behaviors wherein the audiovisual experience includes an advertisement that plays during the recommended duration of a handwashing event. In embodiments, provided herein is a hygiene behavioral modification platform having a system for providing an audiovisual experience for the promotion of hygiene behaviors wherein the audiovisual experience includes a sound event and having a peer-to-peer configuration system for enabling peer-to-peer communication among a set of hygiene-promoting devices. In embodiments, provided herein is a hygiene behavioral modification platform having a system for providing an audiovisual experience for the promotion of hygiene behaviors wherein the audiovisual experience includes a sound event and having a data aggregation system for aggregating hygiene behavioral data across a set of devices, a set of locations and/or a population of individuals. In embodiments, provided herein is a hygiene behavioral modification platform having a system for providing an audiovisual experience for the promotion of hygiene behaviors wherein the audiovisual experience includes a sound event and having an analytics system for performing an analytic operation to produce analytic measures related to hygiene behavior. In embodiments, provided herein is a hygiene behavioral modification platform having a system for providing an audiovisual experience for the promotion of hygiene behaviors wherein the audiovisual experience includes a sound event and having an analytics system for performing an analytic operation to produce an analytic measure related to hygiene behavior and having analytics indicating hygiene performance levels relevant to a particular individual. In embodiments, provided herein is a hygiene behavioral modification platform having a system for providing an audiovisual experience for the promotion of hygiene behaviors wherein the audiovisual experience includes a sound event and having an analytics system for performing an analytic operation to produce an analytic measure related to hygiene behavior and having analytics indicating hygiene performance levels relevant to a population of individuals. In embodiments, provided herein is a hygiene behavioral modification platform having a system for providing an audiovisual experience for the promotion of hygiene behaviors wherein the audiovisual experience includes a sound event and having an analytics system for performing an analytic operation to produce an analytic measure related to hygiene behavior and having analytics indicating hygiene performance levels relevant to a location of a business. In embodiments, provided herein is a hygiene behavioral modification platform having a system for providing an audiovisual experience for the promotion of hygiene behaviors wherein the audiovisual experience includes a sound event and having a community score system for generating a community score based on handwashing behavior compliance in an environment, and wherein the community score is calculated based on the proportion of humans entering the environment that wash their hands. In embodiments, provided herein is a hygiene behavioral modification platform having a system for providing an audiovisual experience for the promotion of hygiene behaviors wherein the audiovisual experience includes a sound event and for promoting hygiene behavioral modification having Bluetooth Low Energy proximity sensing, passive infrared sensors, and active infrared sensors for detecting the presence of one or more humans, and wherein the smart hygiene device is configured to attach to a soap dispenser. In embodiments, provided herein is a hygiene behavioral modification platform having a system for providing an audiovisual experience for the promotion of hygiene behaviors wherein the audiovisual experience includes a sound event and having Bluetooth Low Energy proximity sensing, passive infrared sensors, and active infrared sensors for detecting the presence of one or more humans. In embodiments, provided herein is a hygiene behavioral modification platform having a system for providing an audiovisual experience for the promotion of hygiene behaviors wherein the audiovisual experience includes a sound event and for promoting hygiene behavioral modification having Bluetooth Low Energy proximity sensing, passive infrared sensors, and active infrared sensors for detecting the presence of one or more humans and wherein the smart hygiene device is configured as a soap dispenser. In embodiments, provided herein is a hygiene behavioral modification platform having a system for providing an audiovisual experience for the promotion of hygiene behaviors wherein the audiovisual experience includes a sound event and having a system for detecting activities related to hygiene and reporting a set of indicators of hygiene behaviors. In embodiments, provided herein is a hygiene behavioral modification platform having a system for providing an audiovisual experience for the promotion of hygiene behaviors wherein the audiovisual experience includes a sound event and having a system for detecting handwashing activity. In embodiments, provided herein is a hygiene behavioral modification platform having a system for providing an audiovisual experience for the promotion of hygiene behaviors wherein the audiovisual experience includes a sound event and having a system for detecting handwashing activity and producing a measure of duration and timing of the handwashing activity. In embodiments, provided herein is a hygiene behavioral modification platform having a system for providing an audiovisual experience for the promotion of hygiene behaviors wherein the audiovisual experience includes a sound event and having a sensor fusion system configured to combine data from sensors of at least two types, wherein the fused sensor data is processed to produce an indicator related to hygiene behavior activity. In embodiments, provided herein is a hygiene behavioral modification platform having a system for providing an audiovisual experience for the promotion of hygiene behaviors wherein the audiovisual experience includes a sound event and having a machine learning and/or artificial intelligence system configured to classify humans as employees or customers. In embodiments, provided herein is a hygiene behavioral modification platform having a system for providing an audiovisual experience for the promotion of hygiene behaviors wherein the audiovisual experience includes a sound event and having a system for integrating a set of detected indicators of hygiene behavior for a location and/or entity with an online rating/review system for the location and/or entity. In embodiments, provided herein is a hygiene behavioral modification platform having a system for providing an audiovisual experience for the promotion of hygiene behaviors wherein the audiovisual experience includes a sound event and having a machine learning and/or artificial intelligence system configured to generate a recommendation related to washing hands and/or hand sanitizing. In embodiments, provided herein is a hygiene behavioral modification platform having a system for providing an audiovisual experience for the promotion of hygiene behaviors wherein the audiovisual experience includes a sound event and having a machine learning and/or artificial intelligence system configured to generate a recommendation related to the duration of handwashing. In embodiments, provided herein is a hygiene behavioral modification platform having a system for providing an audiovisual experience for the promotion of hygiene behaviors wherein the audiovisual experience includes a sound event and having personal profiles with accompanying personal data structures for storing personal information. In embodiments, provided herein is a hygiene behavioral modification platform having a system for providing an audiovisual experience for the promotion of hygiene behaviors wherein the audiovisual experience includes a sound event and having workforce profiles with accompanying workforce structures for storing workforce information.

In embodiments, provided herein is a hygiene behavioral modification platform having a system for providing an audiovisual experience for the promotion of hygiene behaviors wherein the audiovisual experience includes an audio reminder to wash hands. In embodiments, provided herein is a hygiene behavioral modification platform having a system for providing an audiovisual experience for the promotion of hygiene behaviors wherein the audiovisual experience includes an audio reminder to wash hands and having a system for providing an audiovisual experience for the promotion of hygiene behaviors having a system for facilitating progressive reminders as an individual moves through transits an environment and passes one or more points of reference. In embodiments, provided herein is a hygiene behavioral modification platform having a system for providing an audiovisual experience for the promotion of hygiene behaviors wherein the audiovisual experience includes an audio reminder to wash hands and having a system for providing an audiovisual experience for the promotion of hygiene behaviors wherein the audiovisual experience includes an advertisement that plays during the recommended duration of a handwashing event. In embodiments, provided herein is a hygiene behavioral modification platform having a system for providing an audiovisual experience for the promotion of hygiene behaviors wherein the audiovisual experience includes an audio reminder to wash hands and having a peer-to-peer configuration system for enabling peer-to-peer communication among a set of hygiene-promoting devices. In embodiments, provided herein is a hygiene behavioral modification platform having a system for providing an audiovisual experience for the promotion of hygiene behaviors wherein the audiovisual experience includes an audio reminder to wash hands and having a data aggregation system for aggregating hygiene behavioral data across a set of devices, a set of locations and/or a population of individuals. In embodiments, provided herein is a hygiene behavioral modification platform having a system for providing an audiovisual experience for the promotion of hygiene behaviors wherein the audiovisual experience includes an audio reminder to wash hands and having an analytics system for performing an analytic operation to produce analytic measures related to hygiene behavior. In embodiments, provided herein is a hygiene behavioral modification platform having a system for providing an audiovisual experience for the promotion of hygiene behaviors wherein the audiovisual experience includes an audio reminder to wash hands and having an analytics system for performing an analytic operation to produce an analytic measure related to hygiene behavior and having analytics indicating hygiene performance levels relevant to a particular individual. In embodiments, provided herein is a hygiene behavioral modification platform having a system for providing an audiovisual experience for the promotion of hygiene behaviors wherein the audiovisual experience includes an audio reminder to wash hands and having an analytics system for performing an analytic operation to produce an analytic measure related to hygiene behavior and having analytics indicating hygiene performance levels relevant to a population of individuals. In embodiments, provided herein is a hygiene behavioral modification platform having a system for providing an audiovisual experience for the promotion of hygiene behaviors wherein the audiovisual experience includes an audio reminder to wash hands and having an analytics system for performing an analytic operation to produce an analytic measure related to hygiene behavior and having analytics indicating hygiene performance levels relevant to a location of a business. In embodiments, provided herein is a hygiene behavioral modification platform having a system for providing an audiovisual experience for the promotion of hygiene behaviors wherein the audiovisual experience includes an audio reminder to wash hands and having a community score system for generating a community score based on handwashing behavior compliance in an environment, and wherein the community score is calculated based on the proportion of humans entering the environment that wash their hands. In embodiments, provided herein is a hygiene behavioral modification platform having a system for providing an audiovisual experience for the promotion of hygiene behaviors wherein the audiovisual experience includes an audio reminder to wash hands and for promoting hygiene behavioral modification having Bluetooth Low Energy proximity sensing, passive infrared sensors, and active infrared sensors for detecting the presence of one or more humans, and wherein the smart hygiene device is configured to attach to a soap dispenser. In embodiments, provided herein is a hygiene behavioral modification platform having a system for providing an audiovisual experience for the promotion of hygiene behaviors wherein the audiovisual experience includes an audio reminder to wash hands and having Bluetooth Low Energy proximity sensing, passive infrared sensors, and active infrared sensors for detecting the presence of one or more humans. In embodiments, provided herein is a hygiene behavioral modification platform having a system for providing an audiovisual experience for the promotion of hygiene behaviors wherein the audiovisual experience includes an audio reminder to wash hands and for promoting hygiene behavioral modification having Bluetooth Low Energy proximity sensing, passive infrared sensors, and active infrared sensors for detecting the presence of one or more humans and wherein the smart hygiene device is configured as a soap dispenser. In embodiments, provided herein is a hygiene behavioral modification platform having a system for providing an audiovisual experience for the promotion of hygiene behaviors wherein the audiovisual experience includes an audio reminder to wash hands and having a system for detecting activities related to hygiene and reporting a set of indicators of hygiene behaviors. In embodiments, provided herein is a hygiene behavioral modification platform having a system for providing an audiovisual experience for the promotion of hygiene behaviors wherein the audiovisual experience includes an audio reminder to wash hands and having a system for detecting handwashing activity. In embodiments, provided herein is a hygiene behavioral modification platform having a system for providing an audiovisual experience for the promotion of hygiene behaviors wherein the audiovisual experience includes an audio reminder to wash hands and having a system for detecting handwashing activity and producing a measure of duration and timing of the handwashing activity. In embodiments, provided herein is a hygiene behavioral modification platform having a system for providing an audiovisual experience for the promotion of hygiene behaviors wherein the audiovisual experience includes an audio reminder to wash hands and having a sensor fusion system configured to combine data from sensors of at least two types, wherein the fused sensor data is processed to produce an indicator related to hygiene behavior activity. In embodiments, provided herein is a hygiene behavioral modification platform having a system for providing an audiovisual experience for the promotion of hygiene behaviors wherein the audiovisual experience includes an audio reminder to wash hands and having a machine learning and/or artificial intelligence system configured to classify humans as employees or customers. In embodiments, provided herein is a hygiene behavioral modification platform having a system for providing an audiovisual experience for the promotion of hygiene behaviors wherein the audiovisual experience includes an audio reminder to wash hands and having a system for integrating a set of detected indicators of hygiene behavior for a location and/or entity with an online rating/review system for the location and/or entity. In embodiments, provided herein is a hygiene behavioral modification platform having a system for providing an audiovisual experience for the promotion of hygiene behaviors wherein the audiovisual experience includes an audio reminder to wash hands and having a machine learning and/or artificial intelligence system configured to generate a recommendation related to washing hands and/or hand sanitizing. In embodiments, provided herein is a hygiene behavioral modification platform having a system for providing an audiovisual experience for the promotion of hygiene behaviors wherein the audiovisual experience includes an audio reminder to wash hands and having a machine learning and/or artificial intelligence system configured to generate a recommendation related to the duration of handwashing. In embodiments, provided herein is a hygiene behavioral modification platform having a system for providing an audiovisual experience for the promotion of hygiene behaviors wherein the audiovisual experience includes an audio reminder to wash hands and having personal profiles with accompanying personal data structures for storing personal information. In embodiments, provided herein is a hygiene behavioral modification platform having a system for providing an audiovisual experience for the promotion of hygiene behaviors wherein the audiovisual experience includes an audio reminder to wash hands and having workforce profiles with accompanying workforce structures for storing workforce information.

In embodiments, provided herein is a hygiene behavioral modification platform having a system for providing an audiovisual experience for the promotion of hygiene behaviors having a system for facilitating progressive reminders as an individual moves through transits an environment and passes one or more points of reference. In embodiments, provided herein is a hygiene behavioral modification platform having a system for providing an audiovisual experience for the promotion of hygiene behaviors having a system for facilitating progressive reminders as an individual moves through transits an environment and passes one or more points of reference and having a system for providing an audiovisual experience for the promotion of hygiene behaviors wherein the audiovisual experience includes an advertisement that plays during the recommended duration of a handwashing event. In embodiments, provided herein is a hygiene behavioral modification platform having a system for providing an audiovisual experience for the promotion of hygiene behaviors having a system for facilitating progressive reminders as an individual moves through transits an environment and passes one or more points of reference and having a peer-to-peer configuration system for enabling peer-to-peer communication among a set of hygiene-promoting devices. In embodiments, provided herein is a hygiene behavioral modification platform having a system for providing an audiovisual experience for the promotion of hygiene behaviors having a system for facilitating progressive reminders as an individual moves through transits an environment and passes one or more points of reference and having a data aggregation system for aggregating hygiene behavioral data across a set of devices, a set of locations and/or a population of individuals. In embodiments, provided herein is a hygiene behavioral modification platform having a system for providing an audiovisual experience for the promotion of hygiene behaviors having a system for facilitating progressive reminders as an individual moves through transits an environment and passes one or more points of reference and having an analytics system for performing an analytic operation to produce analytic measures related to hygiene behavior. In embodiments, provided herein is a hygiene behavioral modification platform having a system for providing an audiovisual experience for the promotion of hygiene behaviors having a system for facilitating progressive reminders as an individual moves through transits an environment and passes one or more points of reference and having an analytics system for performing an analytic operation to produce an analytic measure related to hygiene behavior and having analytics indicating hygiene performance levels relevant to a particular individual. In embodiments, provided herein is a hygiene behavioral modification platform having a system for providing an audiovisual experience for the promotion of hygiene behaviors having a system for facilitating progressive reminders as an individual moves through transits an environment and passes one or more points of reference and having an analytics system for performing an analytic operation to produce an analytic measure related to hygiene behavior and having analytics indicating hygiene performance levels relevant to a population of individuals. In embodiments, provided herein is a hygiene behavioral modification platform having a system for providing an audiovisual experience for the promotion of hygiene behaviors having a system for facilitating progressive reminders as an individual moves through transits an environment and passes one or more points of reference and having an analytics system for performing an analytic operation to produce an analytic measure related to hygiene behavior and having analytics indicating hygiene performance levels relevant to a location of a business. In embodiments, provided herein is a hygiene behavioral modification platform having a system for providing an audiovisual experience for the promotion of hygiene behaviors having a system for facilitating progressive reminders as an individual moves through transits an environment and passes one or more points of reference and having a community score system for generating a community score based on handwashing behavior compliance in an environment, and wherein the community score is calculated based on the proportion of humans entering the environment that wash their hands. In embodiments, provided herein is a hygiene behavioral modification platform having a system for providing an audiovisual experience for the promotion of hygiene behaviors having a system for facilitating progressive reminders as an individual moves through transits an environment and passes one or more points of reference and for promoting hygiene behavioral modification having Bluetooth Low Energy proximity sensing, passive infrared sensors, and active infrared sensors for detecting the presence of one or more humans, and wherein the smart hygiene device is configured to attach to a soap dispenser. In embodiments, provided herein is a hygiene behavioral modification platform having a system for providing an audiovisual experience for the promotion of hygiene behaviors having a system for facilitating progressive reminders as an individual moves through transits an environment and passes one or more points of reference and having Bluetooth Low Energy proximity sensing, passive infrared sensors, and active infrared sensors for detecting the presence of one or more humans. In embodiments, provided herein is a hygiene behavioral modification platform having a system for providing an audiovisual experience for the promotion of hygiene behaviors having a system for facilitating progressive reminders as an individual moves through transits an environment and passes one or more points of reference and for promoting hygiene behavioral modification having Bluetooth Low Energy proximity sensing, passive infrared sensors, and active infrared sensors for detecting the presence of one or more humans and wherein the smart hygiene device is configured as a soap dispenser. In embodiments, provided herein is a hygiene behavioral modification platform having a system for providing an audiovisual experience for the promotion of hygiene behaviors having a system for facilitating progressive reminders as an individual moves through transits an environment and passes one or more points of reference and having a system for detecting activities related to hygiene and reporting a set of indicators of hygiene behaviors. In embodiments, provided herein is a hygiene behavioral modification platform having a system for providing an audiovisual experience for the promotion of hygiene behaviors having a system for facilitating progressive reminders as an individual moves through transits an environment and passes one or more points of reference and having a system for detecting handwashing activity. In embodiments, provided herein is a hygiene behavioral modification platform having a system for providing an audiovisual experience for the promotion of hygiene behaviors having a system for facilitating progressive reminders as an individual moves through transits an environment and passes one or more points of reference and having a system for detecting handwashing activity and producing a measure of duration and timing of the handwashing activity. In embodiments, provided herein is a hygiene behavioral modification platform having a system for providing an audiovisual experience for the promotion of hygiene behaviors having a system for facilitating progressive reminders as an individual moves through transits an environment and passes one or more points of reference and having a sensor fusion system configured to combine data from sensors of at least two types, wherein the fused sensor data is processed to produce an indicator related to hygiene behavior activity. In embodiments, provided herein is a hygiene behavioral modification platform having a system for providing an audiovisual experience for the promotion of hygiene behaviors having a system for facilitating progressive reminders as an individual moves through transits an environment and passes one or more points of reference and having a machine learning and/or artificial intelligence system configured to classify humans as employees or customers. In embodiments, provided herein is a hygiene behavioral modification platform having a system for providing an audiovisual experience for the promotion of hygiene behaviors having a system for facilitating progressive reminders as an individual moves through transits an environment and passes one or more points of reference and having a system for integrating a set of detected indicators of hygiene behavior for a location and/or entity with an online rating/review system for the location and/or entity. In embodiments, provided herein is a hygiene behavioral modification platform having a system for providing an audiovisual experience for the promotion of hygiene behaviors having a system for facilitating progressive reminders as an individual moves through transits an environment and passes one or more points of reference and having a machine learning and/or artificial intelligence system configured to generate a recommendation related to washing hands and/or hand sanitizing. In embodiments, provided herein is a hygiene behavioral modification platform having a system for providing an audiovisual experience for the promotion of hygiene behaviors having a system for facilitating progressive reminders as an individual moves through transits an environment and passes one or more points of reference and having a machine learning and/or artificial intelligence system configured to generate a recommendation related to the duration of handwashing. In embodiments, provided herein is a hygiene behavioral modification platform having a system for providing an audiovisual experience for the promotion of hygiene behaviors having a system for facilitating progressive reminders as an individual moves through transits an environment and passes one or more points of reference and having personal profiles with accompanying personal data structures for storing personal information. In embodiments, provided herein is a hygiene behavioral modification platform having a system for providing an audiovisual experience for the promotion of hygiene behaviors having a system for facilitating progressive reminders as an individual moves through transits an environment and passes one or more points of reference and having workforce profiles with accompanying workforce structures for storing workforce information.

In embodiments, provided herein is a hygiene behavioral modification platform having a system for providing an audiovisual experience for the promotion of hygiene behaviors wherein the audiovisual experience includes an advertisement that plays during the recommended duration of a handwashing event. In embodiments, provided herein is a hygiene behavioral modification platform having a system for providing an audiovisual experience for the promotion of hygiene behaviors wherein the audiovisual experience includes an advertisement that plays during the recommended duration of a handwashing event and having a peer-to-peer configuration system for enabling peer-to-peer communication among a set of hygiene-promoting devices. In embodiments, provided herein is a hygiene behavioral modification platform having a system for providing an audiovisual experience for the promotion of hygiene behaviors wherein the audiovisual experience includes an advertisement that plays during the recommended duration of a handwashing event and having a data aggregation system for aggregating hygiene behavioral data across a set of devices, a set of locations and/or a population of individuals. In embodiments, provided herein is a hygiene behavioral modification platform having a system for providing an audiovisual experience for the promotion of hygiene behaviors wherein the audiovisual experience includes an advertisement that plays during the recommended duration of a handwashing event and having an analytics system for performing an analytic operation to produce analytic measures related to hygiene behavior. In embodiments, provided herein is a hygiene behavioral modification platform having a system for providing an audiovisual experience for the promotion of hygiene behaviors wherein the audiovisual experience includes an advertisement that plays during the recommended duration of a handwashing event and having an analytics system for performing an analytic operation to produce an analytic measure related to hygiene behavior and having analytics indicating hygiene performance levels relevant to a particular individual. In embodiments, provided herein is a hygiene behavioral modification platform having a system for providing an audiovisual experience for the promotion of hygiene behaviors wherein the audiovisual experience includes an advertisement that plays during the recommended duration of a handwashing event and having an analytics system for performing an analytic operation to produce an analytic measure related to hygiene behavior and having analytics indicating hygiene performance levels relevant to a population of individuals. In embodiments, provided herein is a hygiene behavioral modification platform having a system for providing an audiovisual experience for the promotion of hygiene behaviors wherein the audiovisual experience includes an advertisement that plays during the recommended duration of a handwashing event and having an analytics system for performing an analytic operation to produce an analytic measure related to hygiene behavior and having analytics indicating hygiene performance levels relevant to a location of a business. In embodiments, provided herein is a hygiene behavioral modification platform having a system for providing an audiovisual experience for the promotion of hygiene behaviors wherein the audiovisual experience includes an advertisement that plays during the recommended duration of a handwashing event and having a community score system for generating a community score based on handwashing behavior compliance in an environment, and wherein the community score is calculated based on the proportion of humans entering the environment that wash their hands. In embodiments, provided herein is a hygiene behavioral modification platform having a system for providing an audiovisual experience for the promotion of hygiene behaviors wherein the audiovisual experience includes an advertisement that plays during the recommended duration of a handwashing event and for promoting hygiene behavioral modification having Bluetooth Low Energy proximity sensing, passive infrared sensors, and active infrared sensors for detecting the presence of one or more humans, and wherein the smart hygiene device is configured to attach to a soap dispenser. In embodiments, provided herein is a hygiene behavioral modification platform having a system for providing an audiovisual experience for the promotion of hygiene behaviors wherein the audiovisual experience includes an advertisement that plays during the recommended duration of a handwashing event and having Bluetooth Low Energy proximity sensing, passive infrared sensors, and active infrared sensors for detecting the presence of one or more humans. In embodiments, provided herein is a hygiene behavioral modification platform having a system for providing an audiovisual experience for the promotion of hygiene behaviors wherein the audiovisual experience includes an advertisement that plays during the recommended duration of a handwashing event and for promoting hygiene behavioral modification having Bluetooth Low Energy proximity sensing, passive infrared sensors, and active infrared sensors for detecting the presence of one or more humans and wherein the smart hygiene device is configured as a soap dispenser. In embodiments, provided herein is a hygiene behavioral modification platform having a system for providing an audiovisual experience for the promotion of hygiene behaviors wherein the audiovisual experience includes an advertisement that plays during the recommended duration of a handwashing event and having a system for detecting activities related to hygiene and reporting a set of indicators of hygiene behaviors. In embodiments, provided herein is a hygiene behavioral modification platform having a system for providing an audiovisual experience for the promotion of hygiene behaviors wherein the audiovisual experience includes an advertisement that plays during the recommended duration of a handwashing event and having a system for detecting handwashing activity. In embodiments, provided herein is a hygiene behavioral modification platform having a system for providing an audiovisual experience for the promotion of hygiene behaviors wherein the audiovisual experience includes an advertisement that plays during the recommended duration of a handwashing event and having a system for detecting handwashing activity and producing a measure of duration and timing of the handwashing activity. In embodiments, provided herein is a hygiene behavioral modification platform having a system for providing an audiovisual experience for the promotion of hygiene behaviors wherein the audiovisual experience includes an advertisement that plays during the recommended duration of a handwashing event and having a sensor fusion system configured to combine data from sensors of at least two types, wherein the fused sensor data is processed to produce an indicator related to hygiene behavior activity. In embodiments, provided herein is a hygiene behavioral modification platform having a system for providing an audiovisual experience for the promotion of hygiene behaviors wherein the audiovisual experience includes an advertisement that plays during the recommended duration of a handwashing event and having a machine learning and/or artificial intelligence system configured to classify humans as employees or customers. In embodiments, provided herein is a hygiene behavioral modification platform having a system for providing an audiovisual experience for the promotion of hygiene behaviors wherein the audiovisual experience includes an advertisement that plays during the recommended duration of a handwashing event and having a system for integrating a set of detected indicators of hygiene behavior for a location and/or entity with an online rating/review system for the location and/or entity. In embodiments, provided herein is a hygiene behavioral modification platform having a system for providing an audiovisual experience for the promotion of hygiene behaviors wherein the audiovisual experience includes an advertisement that plays during the recommended duration of a handwashing event and having a machine learning and/or artificial intelligence system configured to generate a recommendation related to washing hands and/or hand sanitizing. In embodiments, provided herein is a hygiene behavioral modification platform having a system for providing an audiovisual experience for the promotion of hygiene behaviors wherein the audiovisual experience includes an advertisement that plays during the recommended duration of a handwashing event and having a machine learning and/or artificial intelligence system configured to generate a recommendation related to the duration of handwashing. In embodiments, provided herein is a hygiene behavioral modification platform having a system for providing an audiovisual experience for the promotion of hygiene behaviors wherein the audiovisual experience includes an advertisement that plays during the recommended duration of a handwashing event and having personal profiles with accompanying personal data structures for storing personal information. In embodiments, provided herein is a hygiene behavioral modification platform having a system for providing an audiovisual experience for the promotion of hygiene behaviors wherein the audiovisual experience includes an advertisement that plays during the recommended duration of a handwashing event and having workforce profiles with accompanying workforce structures for storing workforce information.

In embodiments, provided herein is a hygiene behavioral modification platform having a peer-to-peer configuration system for enabling peer-to-peer communication among a set of hygiene-promoting devices. In embodiments, provided herein is a hygiene behavioral modification platform having a peer-to-peer configuration system for enabling peer-to-peer communication among a set of hygiene-promoting devices and having a data aggregation system for aggregating hygiene behavioral data across a set of devices, a set of locations and/or a population of individuals. In embodiments, provided herein is a hygiene behavioral modification platform having a peer-to-peer configuration system for enabling peer-to-peer communication among a set of hygiene-promoting devices and having an analytics system for performing an analytic operation to produce analytic measures related to hygiene behavior. In embodiments, provided herein is a hygiene behavioral modification platform having a peer-to-peer configuration system for enabling peer-to-peer communication among a set of hygiene-promoting devices and having an analytics system for performing an analytic operation to produce an analytic measure related to hygiene behavior and having analytics indicating hygiene performance levels relevant to a particular individual. In embodiments, provided herein is a hygiene behavioral modification platform having a peer-to-peer configuration system for enabling peer-to-peer communication among a set of hygiene-promoting devices and having an analytics system for performing an analytic operation to produce an analytic measure related to hygiene behavior and having analytics indicating hygiene performance levels relevant to a population of individuals. In embodiments, provided herein is a hygiene behavioral modification platform having a peer-to-peer configuration system for enabling peer-to-peer communication among a set of hygiene-promoting devices and having an analytics system for performing an analytic operation to produce an analytic measure related to hygiene behavior and having analytics indicating hygiene performance levels relevant to a location of a business. In embodiments, provided herein is a hygiene behavioral modification platform having a peer-to-peer configuration system for enabling peer-to-peer communication among a set of hygiene-promoting devices and having a community score system for generating a community score based on handwashing behavior compliance in an environment, and wherein the community score is calculated based on the proportion of humans entering the environment that wash their hands. In embodiments, provided herein is a hygiene behavioral modification platform having a peer-to-peer configuration system for enabling peer-to-peer communication among a set of hygiene-promoting devices and for promoting hygiene behavioral modification having Bluetooth Low Energy proximity sensing, passive infrared sensors, and active infrared sensors for detecting the presence of one or more humans, and wherein the smart hygiene device is configured to attach to a soap dispenser. In embodiments, provided herein is a hygiene behavioral modification platform having a peer-to-peer configuration system for enabling peer-to-peer communication among a set of hygiene-promoting devices and having Bluetooth Low Energy proximity sensing, passive infrared sensors, and active infrared sensors for detecting the presence of one or more humans. In embodiments, provided herein is a hygiene behavioral modification platform having a peer-to-peer configuration system for enabling peer-to-peer communication among a set of hygiene-promoting devices and for promoting hygiene behavioral modification having Bluetooth Low Energy proximity sensing, passive infrared sensors, and active infrared sensors for detecting the presence of one or more humans and wherein the smart hygiene device is configured as a soap dispenser. In embodiments, provided herein is a hygiene behavioral modification platform having a peer-to-peer configuration system for enabling peer-to-peer communication among a set of hygiene-promoting devices and having a system for detecting activities related to hygiene and reporting a set of indicators of hygiene behaviors. In embodiments, provided herein is a hygiene behavioral modification platform having a peer-to-peer configuration system for enabling peer-to-peer communication among a set of hygiene-promoting devices and having a system for detecting handwashing activity. In embodiments, provided herein is a hygiene behavioral modification platform having a peer-to-peer configuration system for enabling peer-to-peer communication among a set of hygiene-promoting devices and having a system for detecting handwashing activity and producing a measure of duration and timing of the handwashing activity. In embodiments, provided herein is a hygiene behavioral modification platform having a peer-to-peer configuration system for enabling peer-to-peer communication among a set of hygiene-promoting devices and having a sensor fusion system configured to combine data from sensors of at least two types, wherein the fused sensor data is processed to produce an indicator related to hygiene behavior activity. In embodiments, provided herein is a hygiene behavioral modification platform having a peer-to-peer configuration system for enabling peer-to-peer communication among a set of hygiene-promoting devices and having a machine learning and/or artificial intelligence system configured to classify humans as employees or customers. In embodiments, provided herein is a hygiene behavioral modification platform having a peer-to-peer configuration system for enabling peer-to-peer communication among a set of hygiene-promoting devices and having a system for integrating a set of detected indicators of hygiene behavior for a location and/or entity with an online rating/review system for the location and/or entity. In embodiments, provided herein is a hygiene behavioral modification platform having a peer-to-peer configuration system for enabling peer-to-peer communication among a set of hygiene-promoting devices and having a machine learning and/or artificial intelligence system configured to generate a recommendation related to washing hands and/or hand sanitizing. In embodiments, provided herein is a hygiene behavioral modification platform having a peer-to-peer configuration system for enabling peer-to-peer communication among a set of hygiene-promoting devices and having a machine learning and/or artificial intelligence system configured to generate a recommendation related to the duration of handwashing. In embodiments, provided herein is a hygiene behavioral modification platform having a peer-to-peer configuration system for enabling peer-to-peer communication among a set of hygiene-promoting devices and having personal profiles with accompanying personal data structures for storing personal information. In embodiments, provided herein is a hygiene behavioral modification platform having a peer-to-peer configuration system for enabling peer-to-peer communication among a set of hygiene-promoting devices and having workforce profiles with accompanying workforce structures for storing workforce information.

In embodiments, provided herein is a hygiene behavioral modification platform having a data aggregation system for aggregating hygiene behavioral data across a set of devices, a set of locations and/or a population of individuals. In embodiments, provided herein is a hygiene behavioral modification platform having a data aggregation system for aggregating hygiene behavioral data across a set of devices, a set of locations and/or a population of individuals and having an analytics system for performing an analytic operation to produce analytic measures related to hygiene behavior. In embodiments, provided herein is a hygiene behavioral modification platform having a data aggregation system for aggregating hygiene behavioral data across a set of devices, a set of locations and/or a population of individuals and having an analytics system for performing an analytic operation to produce an analytic measure related to hygiene behavior and having analytics indicating hygiene performance levels relevant to a particular individual. In embodiments, provided herein is a hygiene behavioral modification platform having a data aggregation system for aggregating hygiene behavioral data across a set of devices, a set of locations and/or a population of individuals and having an analytics system for performing an analytic operation to produce an analytic measure related to hygiene behavior and having analytics indicating hygiene performance levels relevant to a population of individuals. In embodiments, provided herein is a hygiene behavioral modification platform having a data aggregation system for aggregating hygiene behavioral data across a set of devices, a set of locations and/or a population of individuals and having an analytics system for performing an analytic operation to produce an analytic measure related to hygiene behavior and having analytics indicating hygiene performance levels relevant to a location of a business. In embodiments, provided herein is a hygiene behavioral modification platform having a data aggregation system for aggregating hygiene behavioral data across a set of devices, a set of locations and/or a population of individuals and having a community score system for generating a community score based on handwashing behavior compliance in an environment, and wherein the community score is calculated based on the proportion of humans entering the environment that wash their hands. In embodiments, provided herein is a hygiene behavioral modification platform having a data aggregation system for aggregating hygiene behavioral data across a set of devices, a set of locations and/or a population of individuals and for promoting hygiene behavioral modification having Bluetooth Low Energy proximity sensing, passive infrared sensors, and active infrared sensors for detecting the presence of one or more humans, and wherein the smart hygiene device is configured to attach to a soap dispenser. In embodiments, provided herein is a hygiene behavioral modification platform having a data aggregation system for aggregating hygiene behavioral data across a set of devices, a set of locations and/or a population of individuals and having Bluetooth Low Energy proximity sensing, passive infrared sensors, and active infrared sensors for detecting the presence of one or more humans. In embodiments, provided herein is a hygiene behavioral modification platform having a data aggregation system for aggregating hygiene behavioral data across a set of devices, a set of locations and/or a population of individuals and for promoting hygiene behavioral modification having Bluetooth Low Energy proximity sensing, passive infrared sensors, and active infrared sensors for detecting the presence of one or more humans and wherein the smart hygiene device is configured as a soap dispenser. In embodiments, provided herein is a hygiene behavioral modification platform having a data aggregation system for aggregating hygiene behavioral data across a set of devices, a set of locations and/or a population of individuals and having a system for detecting activities related to hygiene and reporting a set of indicators of hygiene behaviors. In embodiments, provided herein is a hygiene behavioral modification platform having a data aggregation system for aggregating hygiene behavioral data across a set of devices, a set of locations and/or a population of individuals and having a system for detecting handwashing activity. In embodiments, provided herein is a hygiene behavioral modification platform having a data aggregation system for aggregating hygiene behavioral data across a set of devices, a set of locations and/or a population of individuals and having a system for detecting handwashing activity and producing a measure of duration and timing of the handwashing activity. In embodiments, provided herein is a hygiene behavioral modification platform having a data aggregation system for aggregating hygiene behavioral data across a set of devices, a set of locations and/or a population of individuals and having a sensor fusion system configured to combine data from sensors of at least two types, wherein the fused sensor data is processed to produce an indicator related to hygiene behavior activity. In embodiments, provided herein is a hygiene behavioral modification platform having a data aggregation system for aggregating hygiene behavioral data across a set of devices, a set of locations and/or a population of individuals and having a machine learning and/or artificial intelligence system configured to classify humans as employees or customers. In embodiments, provided herein is a hygiene behavioral modification platform having a data aggregation system for aggregating hygiene behavioral data across a set of devices, a set of locations and/or a population of individuals and having a system for integrating a set of detected indicators of hygiene behavior for a location and/or entity with an online rating/review system for the location and/or entity. In embodiments, provided herein is a hygiene behavioral modification platform having a data aggregation system for aggregating hygiene behavioral data across a set of devices, a set of locations and/or a population of individuals and having a machine learning and/or artificial intelligence system configured to generate a recommendation related to washing hands and/or hand sanitizing. In embodiments, provided herein is a hygiene behavioral modification platform having a data aggregation system for aggregating hygiene behavioral data across a set of devices, a set of locations and/or a population of individuals and having a machine learning and/or artificial intelligence system configured to generate a recommendation related to the duration of handwashing. In embodiments, provided herein is a hygiene behavioral modification platform having a data aggregation system for aggregating hygiene behavioral data across a set of devices, a set of locations and/or a population of individuals and having personal profiles with accompanying personal data structures for storing personal information. In embodiments, provided herein is a hygiene behavioral modification platform having a data aggregation system for aggregating hygiene behavioral data across a set of devices, a set of locations and/or a population of individuals and having workforce profiles with accompanying workforce structures for storing workforce information.

In embodiments, provided herein is a hygiene behavioral modification platform having an analytics system for performing an analytic operation to produce analytic measures related to hygiene behavior. In embodiments, provided herein is a hygiene behavioral modification platform having an analytics system for performing an analytic operation to produce analytic measures related to hygiene behavior and having an analytics system for performing an analytic operation to produce an analytic measure related to hygiene behavior and having analytics indicating hygiene performance levels relevant to a particular individual. In embodiments, provided herein is a hygiene behavioral modification platform having an analytics system for performing an analytic operation to produce analytic measures related to hygiene behavior and having an analytics system for performing an analytic operation to produce an analytic measure related to hygiene behavior and having analytics indicating hygiene performance levels relevant to a population of individuals. In embodiments, provided herein is a hygiene behavioral modification platform having an analytics system for performing an analytic operation to produce analytic measures related to hygiene behavior and having an analytics system for performing an analytic operation to produce an analytic measure related to hygiene behavior and having analytics indicating hygiene performance levels relevant to a location of a business. In embodiments, provided herein is a hygiene behavioral modification platform having an analytics system for performing an analytic operation to produce analytic measures related to hygiene behavior and having a community score system for generating a community score based on handwashing behavior compliance in an environment, and wherein the community score is calculated based on the proportion of humans entering the environment that wash their hands. In embodiments, provided herein is a hygiene behavioral modification platform having an analytics system for performing an analytic operation to produce analytic measures related to hygiene behavior and for promoting hygiene behavioral modification having Bluetooth Low Energy proximity sensing, passive infrared sensors, and active infrared sensors for detecting the presence of one or more humans, and wherein the smart hygiene device is configured to attach to a soap dispenser. In embodiments, provided herein is a hygiene behavioral modification platform having an analytics system for performing an analytic operation to produce analytic measures related to hygiene behavior and having Bluetooth Low Energy proximity sensing, passive infrared sensors, and active infrared sensors for detecting the presence of one or more humans. In embodiments, provided herein is a hygiene behavioral modification platform having an analytics system for performing an analytic operation to produce analytic measures related to hygiene behavior and for promoting hygiene behavioral modification having Bluetooth Low Energy proximity sensing, passive infrared sensors, and active infrared sensors for detecting the presence of one or more humans and wherein the smart hygiene device is configured as a soap dispenser. In embodiments, provided herein is a hygiene behavioral modification platform having an analytics system for performing an analytic operation to produce analytic measures related to hygiene behavior and having a system for detecting activities related to hygiene and reporting a set of indicators of hygiene behaviors. In embodiments, provided herein is a hygiene behavioral modification platform having an analytics system for performing an analytic operation to produce analytic measures related to hygiene behavior and having a system for detecting handwashing activity. In embodiments, provided herein is a hygiene behavioral modification platform having an analytics system for performing an analytic operation to produce analytic measures related to hygiene behavior and having a system for detecting handwashing activity and producing a measure of duration and timing of the handwashing activity. In embodiments, provided herein is a hygiene behavioral modification platform having an analytics system for performing an analytic operation to produce analytic measures related to hygiene behavior and having a sensor fusion system configured to combine data from sensors of at least two types, wherein the fused sensor data is processed to produce an indicator related to hygiene behavior activity. In embodiments, provided herein is a hygiene behavioral modification platform having an analytics system for performing an analytic operation to produce analytic measures related to hygiene behavior and having a machine learning and/or artificial intelligence system configured to classify humans as employees or customers. In embodiments, provided herein is a hygiene behavioral modification platform having an analytics system for performing an analytic operation to produce analytic measures related to hygiene behavior and having a system for integrating a set of detected indicators of hygiene behavior for a location and/or entity with an online rating/review system for the location and/or entity. In embodiments, provided herein is a hygiene behavioral modification platform having an analytics system for performing an analytic operation to produce analytic measures related to hygiene behavior and having a machine learning and/or artificial intelligence system configured to generate a recommendation related to washing hands and/or hand sanitizing. In embodiments, provided herein is a hygiene behavioral modification platform having an analytics system for performing an analytic operation to produce analytic measures related to hygiene behavior and having a machine learning and/or artificial intelligence system configured to generate a recommendation related to the duration of handwashing. In embodiments, provided herein is a hygiene behavioral modification platform having an analytics system for performing an analytic operation to produce analytic measures related to hygiene behavior and having personal profiles with accompanying personal data structures for storing personal information. In embodiments, provided herein is a hygiene behavioral modification platform having an analytics system for performing an analytic operation to produce analytic measures related to hygiene behavior and having workforce profiles with accompanying workforce structures for storing workforce information.

In embodiments, provided herein is a hygiene behavioral modification platform having an analytics system for performing an analytic operation to produce an analytic measure related to hygiene behavior and having analytics indicating hygiene performance levels relevant to a particular individual. In embodiments, provided herein is a hygiene behavioral modification platform having an analytics system for performing an analytic operation to produce an analytic measure related to hygiene behavior and having analytics indicating hygiene performance levels relevant to a particular individual and having an analytics system for performing an analytic operation to produce an analytic measure related to hygiene behavior and having analytics indicating hygiene performance levels relevant to a population of individuals. In embodiments, provided herein is a hygiene behavioral modification platform having an analytics system for performing an analytic operation to produce an analytic measure related to hygiene behavior and having analytics indicating hygiene performance levels relevant to a particular individual and having an analytics system for performing an analytic operation to produce an analytic measure related to hygiene behavior and having analytics indicating hygiene performance levels relevant to a location of a business. In embodiments, provided herein is a hygiene behavioral modification platform having an analytics system for performing an analytic operation to produce an analytic measure related to hygiene behavior and having analytics indicating hygiene performance levels relevant to a particular individual and having a community score system for generating a community score based on handwashing behavior compliance in an environment, and wherein the community score is calculated based on the proportion of humans entering the environment that wash their hands. In embodiments, provided herein is a hygiene behavioral modification platform having an analytics system for performing an analytic operation to produce an analytic measure related to hygiene behavior and having analytics indicating hygiene performance levels relevant to a particular individual and for promoting hygiene behavioral modification having Bluetooth Low Energy proximity sensing, passive infrared sensors, and active infrared sensors for detecting the presence of one or more humans, and wherein the smart hygiene device is configured to attach to a soap dispenser. In embodiments, provided herein is a hygiene behavioral modification platform having an analytics system for performing an analytic operation to produce an analytic measure related to hygiene behavior and having analytics indicating hygiene performance levels relevant to a particular individual and having Bluetooth Low Energy proximity sensing, passive infrared sensors, and active infrared sensors for detecting the presence of one or more humans. In embodiments, provided herein is a hygiene behavioral modification platform having an analytics system for performing an analytic operation to produce an analytic measure related to hygiene behavior and having analytics indicating hygiene performance levels relevant to a particular individual and for promoting hygiene behavioral modification having Bluetooth Low Energy proximity sensing, passive infrared sensors, and active infrared sensors for detecting the presence of one or more humans and wherein the smart hygiene device is configured as a soap dispenser. In embodiments, provided herein is a hygiene behavioral modification platform having an analytics system for performing an analytic operation to produce an analytic measure related to hygiene behavior and having analytics indicating hygiene performance levels relevant to a particular individual and having a system for detecting activities related to hygiene and reporting a set of indicators of hygiene behaviors. In embodiments, provided herein is a hygiene behavioral modification platform having an analytics system for performing an analytic operation to produce an analytic measure related to hygiene behavior and having analytics indicating hygiene performance levels relevant to a particular individual and having a system for detecting handwashing activity. In embodiments, provided herein is a hygiene behavioral modification platform having an analytics system for performing an analytic operation to produce an analytic measure related to hygiene behavior and having analytics indicating hygiene performance levels relevant to a particular individual and having a system for detecting handwashing activity and producing a measure of duration and timing of the handwashing activity. In embodiments, provided herein is a hygiene behavioral modification platform having an analytics system for performing an analytic operation to produce an analytic measure related to hygiene behavior and having analytics indicating hygiene performance levels relevant to a particular individual and having a sensor fusion system configured to combine data from sensors of at least two types, wherein the fused sensor data is processed to produce an indicator related to hygiene behavior activity. In embodiments, provided herein is a hygiene behavioral modification platform having an analytics system for performing an analytic operation to produce an analytic measure related to hygiene behavior and having analytics indicating hygiene performance levels relevant to a particular individual and having a machine learning and/or artificial intelligence system configured to classify humans as employees or customers. In embodiments, provided herein is a hygiene behavioral modification platform having an analytics system for performing an analytic operation to produce an analytic measure related to hygiene behavior and having analytics indicating hygiene performance levels relevant to a particular individual and having a system for integrating a set of detected indicators of hygiene behavior for a location and/or entity with an online rating/review system for the location and/or entity. In embodiments, provided herein is a hygiene behavioral modification platform having an analytics system for performing an analytic operation to produce an analytic measure related to hygiene behavior and having analytics indicating hygiene performance levels relevant to a particular individual and having a machine learning and/or artificial intelligence system configured to generate a recommendation related to washing hands and/or hand sanitizing. In embodiments, provided herein is a hygiene behavioral modification platform having an analytics system for performing an analytic operation to produce an analytic measure related to hygiene behavior and having analytics indicating hygiene performance levels relevant to a particular individual and having a machine learning and/or artificial intelligence system configured to generate a recommendation related to the duration of handwashing. In embodiments, provided herein is a hygiene behavioral modification platform having an analytics system for performing an analytic operation to produce an analytic measure related to hygiene behavior and having analytics indicating hygiene performance levels relevant to a particular individual and having personal profiles with accompanying personal data structures for storing personal information. In embodiments, provided herein is a hygiene behavioral modification platform having an analytics system for performing an analytic operation to produce an analytic measure related to hygiene behavior and having analytics indicating hygiene performance levels relevant to a particular individual and having workforce profiles with accompanying workforce structures for storing workforce information.

In embodiments, provided herein is a hygiene behavioral modification platform having an analytics system for performing an analytic operation to produce an analytic measure related to hygiene behavior and having analytics indicating hygiene performance levels relevant to a population of individuals. In embodiments, provided herein is a hygiene behavioral modification platform having an analytics system for performing an analytic operation to produce an analytic measure related to hygiene behavior and having analytics indicating hygiene performance levels relevant to a population of individuals and having an analytics system for performing an analytic operation to produce an analytic measure related to hygiene behavior and having analytics indicating hygiene performance levels relevant to a location of a business. In embodiments, provided herein is a hygiene behavioral modification platform having an analytics system for performing an analytic operation to produce an analytic measure related to hygiene behavior and having analytics indicating hygiene performance levels relevant to a population of individuals and having a community score system for generating a community score based on handwashing behavior compliance in an environment, and wherein the community score is calculated based on the proportion of humans entering the environment that wash their hands. In embodiments, provided herein is a hygiene behavioral modification platform having an analytics system for performing an analytic operation to produce an analytic measure related to hygiene behavior and having analytics indicating hygiene performance levels relevant to a population of individuals and for promoting hygiene behavioral modification having Bluetooth Low Energy proximity sensing, passive infrared sensors, and active infrared sensors for detecting the presence of one or more humans, and wherein the smart hygiene device is configured to attach to a soap dispenser. In embodiments, provided herein is a hygiene behavioral modification platform having an analytics system for performing an analytic operation to produce an analytic measure related to hygiene behavior and having analytics indicating hygiene performance levels relevant to a population of individuals and having Bluetooth Low Energy proximity sensing, passive infrared sensors, and active infrared sensors for detecting the presence of one or more humans. In embodiments, provided herein is a hygiene behavioral modification platform having an analytics system for performing an analytic operation to produce an analytic measure related to hygiene behavior and having analytics indicating hygiene performance levels relevant to a population of individuals and for promoting hygiene behavioral modification having Bluetooth Low Energy proximity sensing, passive infrared sensors, and active infrared sensors for detecting the presence of one or more humans and wherein the smart hygiene device is configured as a soap dispenser. In embodiments, provided herein is a hygiene behavioral modification platform having an analytics system for performing an analytic operation to produce an analytic measure related to hygiene behavior and having analytics indicating hygiene performance levels relevant to a population of individuals and having a system for detecting activities related to hygiene and reporting a set of indicators of hygiene behaviors. In embodiments, provided herein is a hygiene behavioral modification platform having an analytics system for performing an analytic operation to produce an analytic measure related to hygiene behavior and having analytics indicating hygiene performance levels relevant to a population of individuals and having a system for detecting handwashing activity. In embodiments, provided herein is a hygiene behavioral modification platform having an analytics system for performing an analytic operation to produce an analytic measure related to hygiene behavior and having analytics indicating hygiene performance levels relevant to a population of individuals and having a system for detecting handwashing activity and producing a measure of duration and timing of the handwashing activity. In embodiments, provided herein is a hygiene behavioral modification platform having an analytics system for performing an analytic operation to produce an analytic measure related to hygiene behavior and having analytics indicating hygiene performance levels relevant to a population of individuals and having a sensor fusion system configured to combine data from sensors of at least two types, wherein the fused sensor data is processed to produce an indicator related to hygiene behavior activity. In embodiments, provided herein is a hygiene behavioral modification platform having an analytics system for performing an analytic operation to produce an analytic measure related to hygiene behavior and having analytics indicating hygiene performance levels relevant to a population of individuals and having a machine learning and/or artificial intelligence system configured to classify humans as employees or customers. In embodiments, provided herein is a hygiene behavioral modification platform having an analytics system for performing an analytic operation to produce an analytic measure related to hygiene behavior and having analytics indicating hygiene performance levels relevant to a population of individuals and having a system for integrating a set of detected indicators of hygiene behavior for a location and/or entity with an online rating/review system for the location and/or entity. In embodiments, provided herein is a hygiene behavioral modification platform having an analytics system for performing an analytic operation to produce an analytic measure related to hygiene behavior and having analytics indicating hygiene performance levels relevant to a population of individuals and having a machine learning and/or artificial intelligence system configured to generate a recommendation related to washing hands and/or hand sanitizing. In embodiments, provided herein is a hygiene behavioral modification platform having an analytics system for performing an analytic operation to produce an analytic measure related to hygiene behavior and having analytics indicating hygiene performance levels relevant to a population of individuals and having a machine learning and/or artificial intelligence system configured to generate a recommendation related to the duration of handwashing. In embodiments, provided herein is a hygiene behavioral modification platform having an analytics system for performing an analytic operation to produce an analytic measure related to hygiene behavior and having analytics indicating hygiene performance levels relevant to a population of individuals and having personal profiles with accompanying personal data structures for storing personal information. In embodiments, provided herein is a hygiene behavioral modification platform having an analytics system for performing an analytic operation to produce an analytic measure related to hygiene behavior and having analytics indicating hygiene performance levels relevant to a population of individuals and having workforce profiles with accompanying workforce structures for storing workforce information.

In embodiments, provided herein is a hygiene behavioral modification platform having an analytics system for performing an analytic operation to produce an analytic measure related to hygiene behavior and having analytics indicating hygiene performance levels relevant to a location of a business. In embodiments, provided herein is a hygiene behavioral modification platform having an analytics system for performing an analytic operation to produce an analytic measure related to hygiene behavior and having analytics indicating hygiene performance levels relevant to a location of a business and having a community score system for generating a community score based on handwashing behavior compliance in an environment, and wherein the community score is calculated based on the proportion of humans entering the environment that wash their hands. In embodiments, provided herein is a hygiene behavioral modification platform having an analytics system for performing an analytic operation to produce an analytic measure related to hygiene behavior and having analytics indicating hygiene performance levels relevant to a location of a business and for promoting hygiene behavioral modification having Bluetooth Low Energy proximity sensing, passive infrared sensors, and active infrared sensors for detecting the presence of one or more humans, and wherein the smart hygiene device is configured to attach to a soap dispenser. In embodiments, provided herein is a hygiene behavioral modification platform having an analytics system for performing an analytic operation to produce an analytic measure related to hygiene behavior and having analytics indicating hygiene performance levels relevant to a location of a business and having Bluetooth Low Energy proximity sensing, passive infrared sensors, and active infrared sensors for detecting the presence of one or more humans. In embodiments, provided herein is a hygiene behavioral modification platform having an analytics system for performing an analytic operation to produce an analytic measure related to hygiene behavior and having analytics indicating hygiene performance levels relevant to a location of a business and for promoting hygiene behavioral modification having Bluetooth Low Energy proximity sensing, passive infrared sensors, and active infrared sensors for detecting the presence of one or more humans and wherein the smart hygiene device is configured as a soap dispenser. In embodiments, provided herein is a hygiene behavioral modification platform having an analytics system for performing an analytic operation to produce an analytic measure related to hygiene behavior and having analytics indicating hygiene performance levels relevant to a location of a business and having a system for detecting activities related to hygiene and reporting a set of indicators of hygiene behaviors. In embodiments, provided herein is a hygiene behavioral modification platform having an analytics system for performing an analytic operation to produce an analytic measure related to hygiene behavior and having analytics indicating hygiene performance levels relevant to a location of a business and having a system for detecting handwashing activity. In embodiments, provided herein is a hygiene behavioral modification platform having an analytics system for performing an analytic operation to produce an analytic measure related to hygiene behavior and having analytics indicating hygiene performance levels relevant to a location of a business and having a system for detecting handwashing activity and producing a measure of duration and timing of the handwashing activity. In embodiments, provided herein is a hygiene behavioral modification platform having an analytics system for performing an analytic operation to produce an analytic measure related to hygiene behavior and having analytics indicating hygiene performance levels relevant to a location of a business and having a sensor fusion system configured to combine data from sensors of at least two types, wherein the fused sensor data is processed to produce an indicator related to hygiene behavior activity. In embodiments, provided herein is a hygiene behavioral modification platform having an analytics system for performing an analytic operation to produce an analytic measure related to hygiene behavior and having analytics indicating hygiene performance levels relevant to a location of a business and having a machine learning and/or artificial intelligence system configured to classify humans as employees or customers. In embodiments, provided herein is a hygiene behavioral modification platform having an analytics system for performing an analytic operation to produce an analytic measure related to hygiene behavior and having analytics indicating hygiene performance levels relevant to a location of a business and having a system for integrating a set of detected indicators of hygiene behavior for a location and/or entity with an online rating/review system for the location and/or entity. In embodiments, provided herein is a hygiene behavioral modification platform having an analytics system for performing an analytic operation to produce an analytic measure related to hygiene behavior and having analytics indicating hygiene performance levels relevant to a location of a business and having a machine learning and/or artificial intelligence system configured to generate a recommendation related to washing hands and/or hand sanitizing. In embodiments, provided herein is a hygiene behavioral modification platform having an analytics system for performing an analytic operation to produce an analytic measure related to hygiene behavior and having analytics indicating hygiene performance levels relevant to a location of a business and having a machine learning and/or artificial intelligence system configured to generate a recommendation related to the duration of handwashing. In embodiments, provided herein is a hygiene behavioral modification platform having an analytics system for performing an analytic operation to produce an analytic measure related to hygiene behavior and having analytics indicating hygiene performance levels relevant to a location of a business and having personal profiles with accompanying personal data structures for storing personal information. In embodiments, provided herein is a hygiene behavioral modification platform having an analytics system for performing an analytic operation to produce an analytic measure related to hygiene behavior and having analytics indicating hygiene performance levels relevant to a location of a business and having workforce profiles with accompanying workforce structures for storing workforce information.

In embodiments, provided herein is a hygiene behavioral modification platform having a community score system for generating a community score based on handwashing behavior compliance in an environment, and wherein the community score is calculated based on the proportion of humans entering the environment that wash their hands. In embodiments, provided herein is a hygiene behavioral modification platform having a community score system for generating a community score based on handwashing behavior compliance in an environment, and wherein the community score is calculated based on the proportion of humans entering the environment that wash their hands and for promoting hygiene behavioral modification having Bluetooth Low Energy proximity sensing, passive infrared sensors, and active infrared sensors for detecting the presence of one or more humans, and wherein the smart hygiene device is configured to attach to a soap dispenser. In embodiments, provided herein is a hygiene behavioral modification platform having a community score system for generating a community score based on handwashing behavior compliance in an environment, and wherein the community score is calculated based on the proportion of humans entering the environment that wash their hands and having Bluetooth Low Energy proximity sensing, passive infrared sensors, and active infrared sensors for detecting the presence of one or more humans. In embodiments, provided herein is a hygiene behavioral modification platform having a community score system for generating a community score based on handwashing behavior compliance in an environment, and wherein the community score is calculated based on the proportion of humans entering the environment that wash their hands and for promoting hygiene behavioral modification having Bluetooth Low Energy proximity sensing, passive infrared sensors, and active infrared sensors for detecting the presence of one or more humans and wherein the smart hygiene device is configured as a soap dispenser. In embodiments, provided herein is a hygiene behavioral modification platform having a community score system for generating a community score based on handwashing behavior compliance in an environment, and wherein the community score is calculated based on the proportion of humans entering the environment that wash their hands and having a system for detecting activities related to hygiene and reporting a set of indicators of hygiene behaviors. In embodiments, provided herein is a hygiene behavioral modification platform having a community score system for generating a community score based on handwashing behavior compliance in an environment, and wherein the community score is calculated based on the proportion of humans entering the environment that wash their hands and having a system for detecting handwashing activity. In embodiments, provided herein is a hygiene behavioral modification platform having a community score system for generating a community score based on handwashing behavior compliance in an environment, and wherein the community score is calculated based on the proportion of humans entering the environment that wash their hands and having a system for detecting handwashing activity and producing a measure of duration and timing of the handwashing activity. In embodiments, provided herein is a hygiene behavioral modification platform having a community score system for generating a community score based on handwashing behavior compliance in an environment, and wherein the community score is calculated based on the proportion of humans entering the environment that wash their hands and having a sensor fusion system configured to combine data from sensors of at least two types, wherein the fused sensor data is processed to produce an indicator related to hygiene behavior activity. In embodiments, provided herein is a hygiene behavioral modification platform having a community score system for generating a community score based on handwashing behavior compliance in an environment, and wherein the community score is calculated based on the proportion of humans entering the environment that wash their hands and having a machine learning and/or artificial intelligence system configured to classify humans as employees or customers. In embodiments, provided herein is a hygiene behavioral modification platform having a community score system for generating a community score based on handwashing behavior compliance in an environment, and wherein the community score is calculated based on the proportion of humans entering the environment that wash their hands and having a system for integrating a set of detected indicators of hygiene behavior for a location and/or entity with an online rating/review system for the location and/or entity. In embodiments, provided herein is a hygiene behavioral modification platform having a community score system for generating a community score based on handwashing behavior compliance in an environment, and wherein the community score is calculated based on the proportion of humans entering the environment that wash their hands and having a machine learning and/or artificial intelligence system configured to generate a recommendation related to washing hands and/or hand sanitizing. In embodiments, provided herein is a hygiene behavioral modification platform having a community score system for generating a community score based on handwashing behavior compliance in an environment, and wherein the community score is calculated based on the proportion of humans entering the environment that wash their hands and having a machine learning and/or artificial intelligence system configured to generate a recommendation related to the duration of handwashing. In embodiments, provided herein is a hygiene behavioral modification platform having a community score system for generating a community score based on handwashing behavior compliance in an environment, and wherein the community score is calculated based on the proportion of humans entering the environment that wash their hands and having personal profiles with accompanying personal data structures for storing personal information. In embodiments, provided herein is a hygiene behavioral modification platform having a community score system for generating a community score based on handwashing behavior compliance in an environment, and wherein the community score is calculated based on the proportion of humans entering the environment that wash their hands and having workforce profiles with accompanying workforce structures for storing workforce information.

In embodiments, provided herein is a smart hygiene device for promoting hygiene behavioral modification having Bluetooth Low Energy proximity sensing, passive infrared sensors, and active infrared sensors for detecting the presence of one or more humans, and wherein the smart hygiene device is configured to attach to a soap dispenser. In embodiments, provided herein is a smart hygiene device for promoting hygiene behavioral modification having Bluetooth Low Energy proximity sensing, passive infrared sensors, and active infrared sensors for detecting the presence of one or more humans, and wherein the smart hygiene device is configured to attach to a soap dispenser and having Bluetooth Low Energy proximity sensing, passive infrared sensors, and active infrared sensors for detecting the presence of one or more humans. In embodiments, provided herein is a smart hygiene device for promoting hygiene behavioral modification having Bluetooth Low Energy proximity sensing, passive infrared sensors, and active infrared sensors for detecting the presence of one or more humans, and wherein the smart hygiene device is configured to attach to a soap dispenser and for promoting hygiene behavioral modification having Bluetooth Low Energy proximity sensing, passive infrared sensors, and active infrared sensors for detecting the presence of one or more humans and wherein the smart hygiene device is configured as a soap dispenser. In embodiments, provided herein is a smart hygiene device for promoting hygiene behavioral modification having Bluetooth Low Energy proximity sensing, passive infrared sensors, and active infrared sensors for detecting the presence of one or more humans, and wherein the smart hygiene device is configured to attach to a soap dispenser and having a system for detecting activities related to hygiene and reporting a set of indicators of hygiene behaviors. In embodiments, provided herein is a smart hygiene device for promoting hygiene behavioral modification having Bluetooth Low Energy proximity sensing, passive infrared sensors, and active infrared sensors for detecting the presence of one or more humans, and wherein the smart hygiene device is configured to attach to a soap dispenser and having a system for detecting handwashing activity. In embodiments, provided herein is a smart hygiene device for promoting hygiene behavioral modification having Bluetooth Low Energy proximity sensing, passive infrared sensors, and active infrared sensors for detecting the presence of one or more humans, and wherein the smart hygiene device is configured to attach to a soap dispenser and having a system for detecting handwashing activity and producing a measure of duration and timing of the handwashing activity. In embodiments, provided herein is a smart hygiene device for promoting hygiene behavioral modification having Bluetooth Low Energy proximity sensing, passive infrared sensors, and active infrared sensors for detecting the presence of one or more humans, and wherein the smart hygiene device is configured to attach to a soap dispenser and having a sensor fusion system configured to combine data from sensors of at least two types, wherein the fused sensor data is processed to produce an indicator related to hygiene behavior activity. In embodiments, provided herein is a smart hygiene device for promoting hygiene behavioral modification having Bluetooth Low Energy proximity sensing, passive infrared sensors, and active infrared sensors for detecting the presence of one or more humans, and wherein the smart hygiene device is configured to attach to a soap dispenser and having a machine learning and/or artificial intelligence system configured to classify humans as employees or customers. In embodiments, provided herein is a smart hygiene device for promoting hygiene behavioral modification having Bluetooth Low Energy proximity sensing, passive infrared sensors, and active infrared sensors for detecting the presence of one or more humans, and wherein the smart hygiene device is configured to attach to a soap dispenser and having a system for integrating a set of detected indicators of hygiene behavior for a location and/or entity with an online rating/review system for the location and/or entity. In embodiments, provided herein is a smart hygiene device for promoting hygiene behavioral modification having Bluetooth Low Energy proximity sensing, passive infrared sensors, and active infrared sensors for detecting the presence of one or more humans, and wherein the smart hygiene device is configured to attach to a soap dispenser and having a machine learning and/or artificial intelligence system configured to generate a recommendation related to washing hands and/or hand sanitizing. In embodiments, provided herein is a smart hygiene device for promoting hygiene behavioral modification having Bluetooth Low Energy proximity sensing, passive infrared sensors, and active infrared sensors for detecting the presence of one or more humans, and wherein the smart hygiene device is configured to attach to a soap dispenser and having a machine learning and/or artificial intelligence system configured to generate a recommendation related to the duration of handwashing. In embodiments, provided herein is a smart hygiene device for promoting hygiene behavioral modification having Bluetooth Low Energy proximity sensing, passive infrared sensors, and active infrared sensors for detecting the presence of one or more humans, and wherein the smart hygiene device is configured to attach to a soap dispenser and having personal profiles with accompanying personal data structures for storing personal information. In embodiments, provided herein is a smart hygiene device for promoting hygiene behavioral modification having Bluetooth Low Energy proximity sensing, passive infrared sensors, and active infrared sensors for detecting the presence of one or more humans, and wherein the smart hygiene device is configured to attach to a soap dispenser and having workforce profiles with accompanying workforce structures for storing workforce information.

In embodiments, provided herein is a smart sensor for detecting handwashing behavior having Bluetooth Low Energy proximity sensing, passive infrared sensors, and active infrared sensors for detecting the presence of one or more humans. In embodiments, provided herein is a smart sensor for detecting handwashing behavior having Bluetooth Low Energy proximity sensing, passive infrared sensors, and active infrared sensors for detecting the presence of one or more humans and for promoting hygiene behavioral modification having Bluetooth Low Energy proximity sensing, passive infrared sensors, and active infrared sensors for detecting the presence of one or more humans and wherein the smart hygiene device is configured as a soap dispenser. In embodiments, provided herein is a smart sensor for detecting handwashing behavior having Bluetooth Low Energy proximity sensing, passive infrared sensors, and active infrared sensors for detecting the presence of one or more humans and having a system for detecting activities related to hygiene and reporting a set of indicators of hygiene behaviors. In embodiments, provided herein is a smart sensor for detecting handwashing behavior having Bluetooth Low Energy proximity sensing, passive infrared sensors, and active infrared sensors for detecting the presence of one or more humans and having a system for detecting handwashing activity. In embodiments, provided herein is a smart sensor for detecting handwashing behavior having Bluetooth Low Energy proximity sensing, passive infrared sensors, and active infrared sensors for detecting the presence of one or more humans and having a system for detecting handwashing activity and producing a measure of duration and timing of the handwashing activity. In embodiments, provided herein is a smart sensor for detecting handwashing behavior having Bluetooth Low Energy proximity sensing, passive infrared sensors, and active infrared sensors for detecting the presence of one or more humans and having a sensor fusion system configured to combine data from sensors of at least two types, wherein the fused sensor data is processed to produce an indicator related to hygiene behavior activity. In embodiments, provided herein is a smart sensor for detecting handwashing behavior having Bluetooth Low Energy proximity sensing, passive infrared sensors, and active infrared sensors for detecting the presence of one or more humans and having a machine learning and/or artificial intelligence system configured to classify humans as employees or customers. In embodiments, provided herein is a smart sensor for detecting handwashing behavior having Bluetooth Low Energy proximity sensing, passive infrared sensors, and active infrared sensors for detecting the presence of one or more humans and having a system for integrating a set of detected indicators of hygiene behavior for a location and/or entity with an online rating/review system for the location and/or entity. In embodiments, provided herein is a smart sensor for detecting handwashing behavior having Bluetooth Low Energy proximity sensing, passive infrared sensors, and active infrared sensors for detecting the presence of one or more humans and having a machine learning and/or artificial intelligence system configured to generate a recommendation related to washing hands and/or hand sanitizing. In embodiments, provided herein is a smart sensor for detecting handwashing behavior having Bluetooth Low Energy proximity sensing, passive infrared sensors, and active infrared sensors for detecting the presence of one or more humans and having a machine learning and/or artificial intelligence system configured to generate a recommendation related to the duration of handwashing. In embodiments, provided herein is a smart sensor for detecting handwashing behavior having Bluetooth Low Energy proximity sensing, passive infrared sensors, and active infrared sensors for detecting the presence of one or more humans and having personal profiles with accompanying personal data structures for storing personal information. In embodiments, provided herein is a smart sensor for detecting handwashing behavior having Bluetooth Low Energy proximity sensing, passive infrared sensors, and active infrared sensors for detecting the presence of one or more humans and having workforce profiles with accompanying workforce structures for storing workforce information.

In embodiments, provided herein is a smart hygiene device for promoting hygiene behavioral modification having Bluetooth Low Energy proximity sensing, passive infrared sensors, and active infrared sensors for detecting the presence of one or more humans and wherein the smart hygiene device is configured as a soap dispenser. In embodiments, provided herein is a smart hygiene device for promoting hygiene behavioral modification having Bluetooth Low Energy proximity sensing, passive infrared sensors, and active infrared sensors for detecting the presence of one or more humans and wherein the smart hygiene device is configured as a soap dispenser and having a system for detecting activities related to hygiene and reporting a set of indicators of hygiene behaviors. In embodiments, provided herein is a smart hygiene device for promoting hygiene behavioral modification having Bluetooth Low Energy proximity sensing, passive infrared sensors, and active infrared sensors for detecting the presence of one or more humans and wherein the smart hygiene device is configured as a soap dispenser and having a system for detecting handwashing activity. In embodiments, provided herein is a smart hygiene device for promoting hygiene behavioral modification having Bluetooth Low Energy proximity sensing, passive infrared sensors, and active infrared sensors for detecting the presence of one or more humans and wherein the smart hygiene device is configured as a soap dispenser and having a system for detecting handwashing activity and producing a measure of duration and timing of the handwashing activity. In embodiments, provided herein is a smart hygiene device for promoting hygiene behavioral modification having Bluetooth Low Energy proximity sensing, passive infrared sensors, and active infrared sensors for detecting the presence of one or more humans and wherein the smart hygiene device is configured as a soap dispenser and having a sensor fusion system configured to combine data from sensors of at least two types, wherein the fused sensor data is processed to produce an indicator related to hygiene behavior activity. In embodiments, provided herein is a smart hygiene device for promoting hygiene behavioral modification having Bluetooth Low Energy proximity sensing, passive infrared sensors, and active infrared sensors for detecting the presence of one or more humans and wherein the smart hygiene device is configured as a soap dispenser and having a machine learning and/or artificial intelligence system configured to classify humans as employees or customers. In embodiments, provided herein is a smart hygiene device for promoting hygiene behavioral modification having Bluetooth Low Energy proximity sensing, passive infrared sensors, and active infrared sensors for detecting the presence of one or more humans and wherein the smart hygiene device is configured as a soap dispenser and having a system for integrating a set of detected indicators of hygiene behavior for a location and/or entity with an online rating/review system for the location and/or entity. In embodiments, provided herein is a smart hygiene device for promoting hygiene behavioral modification having Bluetooth Low Energy proximity sensing, passive infrared sensors, and active infrared sensors for detecting the presence of one or more humans and wherein the smart hygiene device is configured as a soap dispenser and having a machine learning and/or artificial intelligence system configured to generate a recommendation related to washing hands and/or hand sanitizing. In embodiments, provided herein is a smart hygiene device for promoting hygiene behavioral modification having Bluetooth Low Energy proximity sensing, passive infrared sensors, and active infrared sensors for detecting the presence of one or more humans and wherein the smart hygiene device is configured as a soap dispenser and having a machine learning and/or artificial intelligence system configured to generate a recommendation related to the duration of handwashing. In embodiments, provided herein is a smart hygiene device for promoting hygiene behavioral modification having Bluetooth Low Energy proximity sensing, passive infrared sensors, and active infrared sensors for detecting the presence of one or more humans and wherein the smart hygiene device is configured as a soap dispenser and having personal profiles with accompanying personal data structures for storing personal information. In embodiments, provided herein is a smart hygiene device for promoting hygiene behavioral modification having Bluetooth Low Energy proximity sensing, passive infrared sensors, and active infrared sensors for detecting the presence of one or more humans and wherein the smart hygiene device is configured as a soap dispenser and having workforce profiles with accompanying workforce structures for storing workforce information.

In embodiments, provided herein is a hygiene behavioral modification platform having a system for detecting activities related to hygiene and reporting a set of indicators of hygiene behaviors. In embodiments, provided herein is a hygiene behavioral modification platform having a system for detecting activities related to hygiene and reporting a set of indicators of hygiene behaviors and having a system for detecting handwashing activity. In embodiments, provided herein is a hygiene behavioral modification platform having a system for detecting activities related to hygiene and reporting a set of indicators of hygiene behaviors and having a system for detecting handwashing activity and producing a measure of duration and timing of the handwashing activity. In embodiments, provided herein is a hygiene behavioral modification platform having a system for detecting activities related to hygiene and reporting a set of indicators of hygiene behaviors and having a sensor fusion system configured to combine data from sensors of at least two types, wherein the fused sensor data is processed to produce an indicator related to hygiene behavior activity. In embodiments, provided herein is a hygiene behavioral modification platform having a system for detecting activities related to hygiene and reporting a set of indicators of hygiene behaviors and having a machine learning and/or artificial intelligence system configured to classify humans as employees or customers. In embodiments, provided herein is a hygiene behavioral modification platform having a system for detecting activities related to hygiene and reporting a set of indicators of hygiene behaviors and having a system for integrating a set of detected indicators of hygiene behavior for a location and/or entity with an online rating/review system for the location and/or entity. In embodiments, provided herein is a hygiene behavioral modification platform having a system for detecting activities related to hygiene and reporting a set of indicators of hygiene behaviors and having a machine learning and/or artificial intelligence system configured to generate a recommendation related to washing hands and/or hand sanitizing. In embodiments, provided herein is a hygiene behavioral modification platform having a system for detecting activities related to hygiene and reporting a set of indicators of hygiene behaviors and having a machine learning and/or artificial intelligence system configured to generate a recommendation related to the duration of handwashing. In embodiments, provided herein is a hygiene behavioral modification platform having a system for detecting activities related to hygiene and reporting a set of indicators of hygiene behaviors and having personal profiles with accompanying personal data structures for storing personal information. In embodiments, provided herein is a hygiene behavioral modification platform having a system for detecting activities related to hygiene and reporting a set of indicators of hygiene behaviors and having workforce profiles with accompanying workforce structures for storing workforce information.

In embodiments, provided herein is a hygiene behavioral modification platform having a system for detecting handwashing activity. In embodiments, provided herein is a hygiene behavioral modification platform having a system for detecting handwashing activity and having a system for detecting handwashing activity and producing a measure of duration and timing of the handwashing activity. In embodiments, provided herein is a hygiene behavioral modification platform having a system for detecting handwashing activity and having a sensor fusion system configured to combine data from sensors of at least two types, wherein the fused sensor data is processed to produce an indicator related to hygiene behavior activity. In embodiments, provided herein is a hygiene behavioral modification platform having a system for detecting handwashing activity and having a machine learning and/or artificial intelligence system configured to classify humans as employees or customers. In embodiments, provided herein is a hygiene behavioral modification platform having a system for detecting handwashing activity and having a system for integrating a set of detected indicators of hygiene behavior for a location and/or entity with an online rating/review system for the location and/or entity. In embodiments, provided herein is a hygiene behavioral modification platform having a system for detecting handwashing activity and having a machine learning and/or artificial intelligence system configured to generate a recommendation related to washing hands and/or hand sanitizing. In embodiments, provided herein is a hygiene behavioral modification platform having a system for detecting handwashing activity and having a machine learning and/or artificial intelligence system configured to generate a recommendation related to the duration of handwashing. In embodiments, provided herein is a hygiene behavioral modification platform having a system for detecting handwashing activity and having personal profiles with accompanying personal data structures for storing personal information. In embodiments, provided herein is a hygiene behavioral modification platform having a system for detecting handwashing activity and having workforce profiles with accompanying workforce structures for storing workforce information.

In embodiments, provided herein is a hygiene behavioral modification platform having a system for detecting handwashing activity and producing a measure of duration and timing of the handwashing activity. In embodiments, provided herein is a hygiene behavioral modification platform having a system for detecting handwashing activity and producing a measure of duration and timing of the handwashing activity and having a sensor fusion system configured to combine data from sensors of at least two types, wherein the fused sensor data is processed to produce an indicator related to hygiene behavior activity. In embodiments, provided herein is a hygiene behavioral modification platform having a system for detecting handwashing activity and producing a measure of duration and timing of the handwashing activity and having a machine learning and/or artificial intelligence system configured to classify humans as employees or customers. In embodiments, provided herein is a hygiene behavioral modification platform having a system for detecting handwashing activity and producing a measure of duration and timing of the handwashing activity and having a system for integrating a set of detected indicators of hygiene behavior for a location and/or entity with an online rating/review system for the location and/or entity. In embodiments, provided herein is a hygiene behavioral modification platform having a system for detecting handwashing activity and producing a measure of duration and timing of the handwashing activity and having a machine learning and/or artificial intelligence system configured to generate a recommendation related to washing hands and/or hand sanitizing. In embodiments, provided herein is a hygiene behavioral modification platform having a system for detecting handwashing activity and producing a measure of duration and timing of the handwashing activity and having a machine learning and/or artificial intelligence system configured to generate a recommendation related to the duration of handwashing. In embodiments, provided herein is a hygiene behavioral modification platform having a system for detecting handwashing activity and producing a measure of duration and timing of the handwashing activity and having personal profiles with accompanying personal data structures for storing personal information. In embodiments, provided herein is a hygiene behavioral modification platform having a system for detecting handwashing activity and producing a measure of duration and timing of the handwashing activity and having workforce profiles with accompanying workforce structures for storing workforce information.

In embodiments, provided herein is a hygiene behavioral modification platform having a sensor fusion system configured to combine data from sensors of at least two types, wherein the fused sensor data is processed to produce an indicator related to hygiene behavior activity. In embodiments, provided herein is a hygiene behavioral modification platform having a sensor fusion system configured to combine data from sensors of at least two types, wherein the fused sensor data is processed to produce an indicator related to hygiene behavior activity and having a machine learning and/or artificial intelligence system configured to classify humans as employees or customers. In embodiments, provided herein is a hygiene behavioral modification platform having a sensor fusion system configured to combine data from sensors of at least two types, wherein the fused sensor data is processed to produce an indicator related to hygiene behavior activity and having a system for integrating a set of detected indicators of hygiene behavior for a location and/or entity with an online rating/review system for the location and/or entity. In embodiments, provided herein is a hygiene behavioral modification platform having a sensor fusion system configured to combine data from sensors of at least two types, wherein the fused sensor data is processed to produce an indicator related to hygiene behavior activity and having a machine learning and/or artificial intelligence system configured to generate a recommendation related to washing hands and/or hand sanitizing. In embodiments, provided herein is a hygiene behavioral modification platform having a sensor fusion system configured to combine data from sensors of at least two types, wherein the fused sensor data is processed to produce an indicator related to hygiene behavior activity and having a machine learning and/or artificial intelligence system configured to generate a recommendation related to the duration of handwashing. In embodiments, provided herein is a hygiene behavioral modification platform having a sensor fusion system configured to combine data from sensors of at least two types, wherein the fused sensor data is processed to produce an indicator related to hygiene behavior activity and having personal profiles with accompanying personal data structures for storing personal information. In embodiments, provided herein is a hygiene behavioral modification platform having a sensor fusion system configured to combine data from sensors of at least two types, wherein the fused sensor data is processed to produce an indicator related to hygiene behavior activity and having workforce profiles with accompanying workforce structures for storing workforce information.

In embodiments, provided herein is a hygiene behavioral modification platform having a machine learning and/or artificial intelligence system configured to classify humans as employees or customers. In embodiments, provided herein is a hygiene behavioral modification platform having a machine learning and/or artificial intelligence system configured to classify humans as employees or customers and having a system for integrating a set of detected indicators of hygiene behavior for a location and/or entity with an online rating/review system for the location and/or entity. In embodiments, provided herein is a hygiene behavioral modification platform having a machine learning and/or artificial intelligence system configured to classify humans as employees or customers and having a machine learning and/or artificial intelligence system configured to generate a recommendation related to washing hands and/or hand sanitizing. In embodiments, provided herein is a hygiene behavioral modification platform having a machine learning and/or artificial intelligence system configured to classify humans as employees or customers and having a machine learning and/or artificial intelligence system configured to generate a recommendation related to the duration of handwashing. In embodiments, provided herein is a hygiene behavioral modification platform having a machine learning and/or artificial intelligence system configured to classify humans as employees or customers and having personal profiles with accompanying personal data structures for storing personal information. In embodiments, provided herein is a hygiene behavioral modification platform having a machine learning and/or artificial intelligence system configured to classify humans as employees or customers and having workforce profiles with accompanying workforce structures for storing workforce information.

In embodiments, provided herein is a hygiene behavioral modification platform having a system for integrating a set of detected indicators of hygiene behavior for a location and/or entity with an online rating/review system for the location and/or entity. In embodiments, provided herein is a hygiene behavioral modification platform having a system for integrating a set of detected indicators of hygiene behavior for a location and/or entity with an online rating/review system for the location and/or entity and having a machine learning and/or artificial intelligence system configured to generate a recommendation related to washing hands and/or hand sanitizing. In embodiments, provided herein is a hygiene behavioral modification platform having a system for integrating a set of detected indicators of hygiene behavior for a location and/or entity with an online rating/review system for the location and/or entity and having a machine learning and/or artificial intelligence system configured to generate a recommendation related to the duration of handwashing. In embodiments, provided herein is a hygiene behavioral modification platform having a system for integrating a set of detected indicators of hygiene behavior for a location and/or entity with an online rating/review system for the location and/or entity and having personal profiles with accompanying personal data structures for storing personal information. In embodiments, provided herein is a hygiene behavioral modification platform having a system for integrating a set of detected indicators of hygiene behavior for a location and/or entity with an online rating/review system for the location and/or entity and having workforce profiles with accompanying workforce structures for storing workforce information.

In embodiments, provided herein is a hygiene behavioral modification platform having a machine learning and/or artificial intelligence system configured to generate a recommendation related to washing hands and/or hand sanitizing. In embodiments, provided herein is a hygiene behavioral modification platform having a machine learning and/or artificial intelligence system configured to generate a recommendation related to washing hands and/or hand sanitizing and having a machine learning and/or artificial intelligence system configured to generate a recommendation related to the duration of handwashing. In embodiments, provided herein is a hygiene behavioral modification platform having a machine learning and/or artificial intelligence system configured to generate a recommendation related to washing hands and/or hand sanitizing and having personal profiles with accompanying personal data structures for storing personal information. In embodiments, provided herein is a hygiene behavioral modification platform having a machine learning and/or artificial intelligence system configured to generate a recommendation related to washing hands and/or hand sanitizing and having workforce profiles with accompanying workforce structures for storing workforce information.

In embodiments, provided herein is a hygiene behavioral modification platform having a machine learning and/or artificial intelligence system configured to generate a recommendation related to the duration of handwashing. In embodiments, provided herein is a hygiene behavioral modification platform having a machine learning and/or artificial intelligence system configured to generate a recommendation related to the duration of handwashing and having personal profiles with accompanying personal data structures for storing personal information. In embodiments, provided herein is a hygiene behavioral modification platform having a machine learning and/or artificial intelligence system configured to generate a recommendation related to the duration of handwashing and having workforce profiles with accompanying workforce structures for storing workforce information.

In embodiments, provided herein is a hygiene behavioral modification platform having personal profiles with accompanying personal data structures for storing personal information. In embodiments, provided herein is a hygiene behavioral modification platform having personal profiles with accompanying personal data structures for storing personal information and having workforce profiles with accompanying workforce structures for storing workforce information.

In embodiments, provided herein is a hygiene behavioral modification platform having workforce profiles with accompanying workforce structures for storing workforce information.

The methods and systems described herein may be deployed in part or in whole through a machine that executes computer software, program codes, and/or instructions on a processor. The present disclosure may be implemented as a method on the machine, as a system or apparatus as part of or in relation to the machine, or as a computer program product embodied in a computer readable medium executing on one or more of the machines. In embodiments, the processor may be part of a server, cloud server, client, network infrastructure, mobile computing platform, stationary computing platform, or other computing platforms. A processor may be any kind of computational or processing device capable of executing program instructions, codes, binary instructions and the like, including a central processing unit (CPU), a general processing unit (GPU), a logic board, a chip (e.g., a graphics chip, a video processing chip, a data compression chip, or the like), a chipset, a controller, a system-on-chip (e.g., an RF system on chip, an AI system on chip, a video processing system on chip, or others), an integrated circuit, an application specific integrated circuit (ASIC), a field programmable gate array (FPGA), an approximate computing processor, a quantum computing processor, a parallel computing processor, a neural network processor, or other type of processor. The processor may be or may include a signal processor, digital processor, data processor, embedded processor, microprocessor or any variant such as a co-processor (math co-processor, graphic co-processor, communication co-processor, video co-processor, AI co-processor, and the like) and the like that may directly or indirectly facilitate execution of program code or program instructions stored thereon. In addition, the processor may enable execution of multiple programs, threads, and codes. The threads may be executed simultaneously to enhance the performance of the processor and to facilitate simultaneous operations of the application. By way of implementation, methods, program codes, program instructions and the like described herein may be implemented in one or more threads. The thread may spawn other threads that may have assigned priorities associated with them; the processor may execute these threads based on priority or any other order based on instructions provided in the program code. The processor, or any machine utilizing one, may include non-transitory memory that stores methods, codes, instructions and programs as described herein and elsewhere. The processor may access a non-transitory storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of a CD-ROM, DVD, memory, hard disk, flash drive, RAM, ROM, cache, network-attached storage, server-based storage, and the like.

A processor may include one or more cores that may enhance speed and performance of a multiprocessor. In embodiments, the process may be a dual core processor, quad core processors, other chip-level multiprocessor and the like that combine two or more independent cores (sometimes called a die).

The methods and systems described herein may be deployed in part or in whole through a machine that executes computer software on a server, client, firewall, gateway, hub, router, switch, infrastructure-as-a-service, platform-as-a-service, or other such computer and/or networking hardware or system. The software may be associated with a server that may include a file server, print server, domain server, internet server, intranet server, cloud server, infrastructure-as-a-service server, platform-as-a-service server, web server, and other variants such as secondary server, host server, distributed server, failover server, backup server, server farm, and the like. The server may include one or more of memories, processors, computer readable media, storage media, ports (physical and virtual), communication devices, and interfaces capable of accessing other servers, clients, machines, and devices through a wired or a wireless medium, and the like. The methods, programs, or codes as described herein and elsewhere may be executed by the server. In addition, other devices required for execution of methods as described in this application may be considered as a part of the infrastructure associated with the server.

The server may provide an interface to other devices including, without limitation, clients, other servers, printers, database servers, print servers, file servers, communication servers, distributed servers, social networks, and the like. Additionally, this coupling and/or connection may facilitate remote execution of programs across the network. The networking of some or all of these devices may facilitate parallel processing of a program or method at one or more locations without deviating from the scope of the disclosure. In addition, any of the devices attached to the server through an interface may include at least one storage medium capable of storing methods, programs, code and/or instructions. A central repository may provide program instructions to be executed on different devices. In this implementation, the remote repository may act as a storage medium for program code, instructions, and programs.

The software program may be associated with a client that may include a file client, print client, domain client, internet client, intranet client and other variants such as secondary client, host client, distributed client and the like. The client may include one or more of memories, processors, computer readable media, storage media, ports (physical and virtual), communication devices, and interfaces capable of accessing other clients, servers, machines, and devices through a wired or a wireless medium, and the like. The methods, programs, or codes as described herein and elsewhere may be executed by the client. In addition, other devices required for the execution of methods as described in this application may be considered as a part of the infrastructure associated with the client.

The client may provide an interface to other devices including, without limitation, servers, other clients, printers, database servers, print servers, file servers, communication servers, distributed servers and the like. Additionally, this coupling and/or connection may facilitate remote execution of programs across the network. The networking of some or all of these devices may facilitate parallel processing of a program or method at one or more locations without deviating from the scope of the disclosure. In addition, any of the devices attached to the client through an interface may include at least one storage medium capable of storing methods, programs, applications, code and/or instructions. A central repository may provide program instructions to be executed on different devices. In this implementation, the remote repository may act as a storage medium for program code, instructions, and programs.

The methods and systems described herein may be deployed in part or in whole through network infrastructures. The network infrastructure may include elements such as computing devices, servers, routers, hubs, firewalls, clients, personal computers, communication devices, routing devices and other active and passive devices, modules and/or components as known in the art. The computing and/or non-computing device(s) associated with the network infrastructure may include, apart from other components, a storage medium such as flash memory, buffer, stack, RAM, ROM and the like. The processes, methods, program codes, instructions described herein and elsewhere may be executed by one or more of the network infrastructural elements. The methods and systems described herein may be adapted for use with any kind of private, community, or hybrid cloud computing network or cloud computing environment, including those which involve features of software as a service (SaaS), platform as a service (PaaS), and/or infrastructure as a service (IaaS).

The methods, program codes, and instructions described herein and elsewhere may be implemented on a cellular network with multiple cells. The cellular network may either be frequency division multiple access (FDMA) network or code division multiple access (CDMA) network. The cellular network may include mobile devices, cell sites, base stations, repeaters, antennas, towers, and the like. The cell network may be a GSM, GPRS, 3G, 4G, 5G, LTE, EVDO, mesh, or other network types.

The methods, program codes, and instructions described herein and elsewhere may be implemented on or through mobile devices. The mobile devices may include navigation devices, cell phones, mobile phones, mobile personal digital assistants, laptops, palmtops, netbooks, pagers, electronic book readers, music players and the like. These devices may include, apart from other components, a storage medium such as flash memory, buffer, RAM, ROM and one or more computing devices. The computing devices associated with mobile devices may be enabled to execute program codes, methods, and instructions stored thereon. Alternatively, the mobile devices may be configured to execute instructions in collaboration with other devices. The mobile devices may communicate with base stations interfaced with servers and configured to execute program codes. The mobile devices may communicate on a peer-to-peer network, mesh network, or other communications network. The program code may be stored on the storage medium associated with the server and executed by a computing device embedded within the server. The base station may include a computing device and a storage medium. The storage device may store program codes and instructions executed by the computing devices associated with the base station.

The computer software, program codes, and/or instructions may be stored and/or accessed on machine readable media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g., USB sticks or keys), floppy disks, magnetic tape, paper tape, punch cards, standalone RAM disks, Zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, network-attached storage, network storage, NVME-accessible storage, PCIE connected storage, distributed storage, and the like.

The methods and systems described herein may transform physical and/or intangible items from one state to another.

The methods and systems described herein may also transform data representing physical and/or intangible items from one state to another.

The elements described and depicted herein, including in flow charts and block diagrams throughout the figures, imply logical boundaries between the elements. However, according to software or hardware engineering practices, the depicted elements and the functions thereof may be implemented on machines through computer executable code using a processor capable of executing program instructions stored thereon as a monolithic software structure, as standalone software modules, or as modules that employ external routines, code, services, and so forth, or any combination of these, and all such implementations may be within the scope of the present disclosure. Examples of such machines may include, but may not be limited to, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices, artificial intelligence, computing devices, networking equipment, servers, routers and the like. Furthermore, the elements depicted in the flow chart and block diagrams or any other logical component may be implemented on a machine capable of executing program instructions. Thus, while the foregoing drawings and descriptions set forth functional aspects of the disclosed systems, no particular arrangement of software for implementing these functional aspects should be inferred from these descriptions unless explicitly stated or otherwise clear from the context. Similarly, it will be appreciated that the various steps identified and described above may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The methods and/or processes described above, and steps associated therewith, may be realized in hardware, software or any combination of hardware and software suitable for a particular application. The hardware may include a general-purpose computer and/or dedicated computing device or specific computing device or particular aspect or component of a specific computing device. The processes may be realized in one or more microprocessors, microcontrollers, embedded microcontrollers, programmable digital signal processors or other programmable devices, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine-readable medium.

The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software, or any other machine capable of executing program instructions. Computer software may employ virtualization, virtual machines, containers, dock facilities, portainers, and other capabilities.

Thus, in one aspect, methods described above and combinations thereof may be embodied in computer executable code that, when executing on one or more computing devices, performs the steps thereof. In another aspect, the methods may be embodied in systems that perform the steps thereof and may be distributed across devices in a number of ways, or all of the functionality may be integrated into a dedicated, standalone device or other hardware. In another aspect, the means for performing the steps associated with the processes described above may include any of the hardware and/or software described above. All such permutations and combinations are intended to fall within the scope of the present disclosure.

While the disclosure has been disclosed in connection with the preferred embodiments shown and described in detail, various modifications and improvements thereon will become readily apparent to those skilled in the art. Accordingly, the spirit and scope of the present disclosure is not to be limited by the foregoing examples, but is to be understood in the broadest sense allowable by law.

The use of the terms "a" and "an" and "the" and similar referents in the context of describing the disclosure (especially in the context of the following claims) is to be construed to cover both the singular and the plural, unless otherwise indicated herein or clearly contradicted by context. The terms "comprising," "with," "including," and "containing" are to be construed as open-ended terms (i.e., meaning "including, but not limited to,") unless otherwise noted. Recitations of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. The term "set" may include a set with a single member. No language in the specification should be construed as indicating any non-claimed element as essential to the practice of the disclosure.

While the foregoing written description enables one skilled to make and use what is considered presently to be the best mode thereof, those skilled in the art will understand and appreciate the existence of variations, combinations, and equivalents of the specific embodiment, method, and examples herein. The disclosure should therefore not be limited by the above described embodiment, method, and examples, but by all embodiments and methods within the scope and spirit of the disclosure.

All documents referenced herein are hereby incorporated by reference as if fully set forth herein.

What is claimed is:

1. A system for monitoring hygienic behavior comprising:
a first sensor positioned to detect a presence of humans by either detecting Bluetooth Low Energy (BLE) signals of mobile computing devices of the humans and/or human bodily motion;
a second sensor configured to determine actions of dispensers containing one or more hygienic substances;

a presentation unit configured to present one or more media items perceivable to the humans; and an analytic unit configured to calculate instances of hygienic events as a scored variable based on a fusion of sensor signals including the actions of the dispenser detected by the second sensor and the presence detected by the first sensor, evaluate a temporal proximity between the instances of the actions of the dispenser detected by the second sensor with the presence detected by the first sensor, report the scored variable to a computing platform, and perform machine learning processing of the data from the plurality of sensors to classify hygiene-related activities and encourage hygiene behavior by optimizing the media played via the presentation unit.

2. The system of claim 1, wherein receiving data from the first sensor and receiving data from the second sensor is wireless, wired, or a combination of wired and wireless.

3. The system of claim 1, wherein the action of the dispenser is dispensing one selected from the group including soap, sanitizing liquid, sanitizing mist, a sanitizing cloth.

4. The system of claim 1, wherein the hygienic event is handwashing.

5. The system of claim 1, wherein the first sensor is at least one selected from the group including a motion sensor, a passive infrared proximity sensor, an active infrared proximity sensor, and a Bluetooth Low Energy (BLE) radio.

6. The system of claim 1, wherein the second sensor is at least one selected from the group including a motion sensor and an active infrared proximity sensor.

7. The system of claim 1, wherein the machine learning processing includes evaluating data obtained from the plurality of sensors and the mobile computing devices.

8. The system of claim 1, wherein the mobile computing devices include a tablet computer, a smart phone and a smart watch.

9. The system of claim 1, wherein the media item is at least one selected from the group including an audio file, an audio-visual file, a text file.

10. A method for monitoring hygienic behavior comprising:

receiving data from a first sensor positioned to detect a presence of one or more humans by detecting Bluetooth Low Energy (BLE) signals of mobile computing devices of the humans and human bodily motion;

presenting a media item perceivable to the humans upon detection of the presence of one of the humans by the first sensor, wherein the media item relates to promotion of hygienic behavior;

receiving data from a second sensor configured to determine actions of a dispenser containing a hygienic substance;

analyzing the received data to calculate a scored variable indicating an instance of hygienic events based on a fusion of sensor signals including the actions of the dispenser with the presence of the human detected by the first sensor;

storing the scored variable;

reporting the stored variable to a computing platform; and performing machine learning processing of the data from the plurality of sensors to classify hygiene-related activities and encourage hygiene behavior by optimizing the media played via the presentation unit.

11. The method of claim 10, wherein receiving data from the first sensor and receiving data from the second sensor is wireless, wired, or a combination of wired and wireless.

12. The method of claim 10, wherein the action of the dispenser is at least one selected from the group including dispensing soap, dispensing a sanitizing liquid, dispensing a sanitizing mist, dispensing a sanitizing cloth.

13. The method of claim 10, wherein the hygienic event is handwashing.

14. The method of claim 10, wherein the first sensor is at least one selected from the group including a motion sensor, a passive infrared proximity sensor, an active infrared proximity sensor, and a Bluetooth Low Energy (BLE) radio.

15. The method of claim 10, wherein the second sensor is at least one selected from the group including a motion sensor and an active infrared proximity sensor.

16. The method of claim 10, wherein the computing platform is at least one of a social media website, a company's website, a marketing platform, an email platform and a SMS platform.

17. The method of claim 10, wherein the performing machine learning processing includes evaluating data obtained from the plurality of sensors and the mobile computing devices.

18. The method of claim 10, wherein the mobile computing devices include a tablet computer, a smart phone and a smart watch.

* * * * *